(12) United States Patent
Shimkets

(10) Patent No.: US 6,689,866 B1
(45) Date of Patent: Feb. 10, 2004

(54) POLYNUCLEOTIDES AND PROTEINS ENCODED THEREBY

(75) Inventor: Richard A. Shimkets, West Haven, CT (US)

(73) Assignee: CuraGen Corporation, New Haven, CT (US)

(*) Notice: Subject to any disclaimer, the term of this patent is extended or adjusted under 35 U.S.C. 154(b) by 233 days.

(21) Appl. No.: 09/520,781

(22) Filed: Mar. 8, 2000

Related U.S. Application Data

(60) Provisional application No. 60/123,667, filed on Mar. 9, 1999.

(51) Int. Cl.$^7$ .................................................. C07K 1/00
(52) U.S. Cl. ..................... 530/350; 530/350; 530/300; 435/7.1; 435/6; 435/69.1
(58) Field of Search .............................. 530/300, 350; 435/7.1, 6, 69.1

(56) References Cited

FOREIGN PATENT DOCUMENTS

| EP | 913471 A2 | 5/1999 |
|---|---|---|
| WO | WO 9630406 | 10/1996 |
| WO | WO 98/27205 A2 | 6/1998 |
| WO | WO 98/33910 A1 | 8/1998 |
| WO | WO 98/39441 A1 | 9/1998 |
| WO | WO 99/27094 A2 | 6/1999 |

OTHER PUBLICATIONS

Shirozu et al., 1996. "Characterization of novel secreted and membrane proteins isolated by the signal sequence trap method." Genomics 37: 273–280.

Jacobs et al., 1997. "A genetic selection for isolating cDNAs encoding secreted proteins." Gene 198: 289–296.

Kopczynski et al., 1998. "A high throughput screen to identify secreted and transmembrane proteins involved in Drosophila embryogenesis." Proc. Natl. Acad. Sci. USA 95: 9973–9978.

PCT International Search Report for PCT/US 00/ 06280 (Jul. 20, 2000).

Artigiani et al. (1999). "Plexins, semaphorins, and scatter factor receptors: a common root for cell guidance signals?" *IUBMB Life* 48(5): 477–82.

Chen et al. (2000). "Embryonic expression and extracellular secretion of Xenopus slit." *Neuroscience* 96(1): 231–6.

Nomura et al., (2000) "Prediction of the Coding Sequences of Unidentified Human Genes. I. The Coding Sequences of 40 New Genes (KIAA0001–KIAA0040) Deduced by Analysis of Randomly Sampled cDNA Clones From Human Immature Myeloid Cell Line KG–1" *DNA Res.* 1: 27–35. *GenBank,* Accession No. Q15391, Feb. 15, 2000.

Diarra–Mehrpour et al., (2000) "Human Plasma Inter–Alpha–Trypsin Inhibitor is Encoded by Four Genes on Three Chromosomes." *Eur. J. Biochem* 179: 147–154. *GenBank,* Accession No. X14690, Jul. 14, 1995.

Fortkamp et al., (1986) "DNA Sequence Encoding A Hirudin–Like Protein and Process for Preparing Such Protein" WO 86/03517A1 *GenBank,* Accession No. A00633, Jan. 28, 1993.

MacDonald et al., (1995) "H. sapiens CpG island DNA genomic Mse1 fragment, clone 90b5, reverse read cpg90b5.rtla" *Direct Submission. GenBank,* Accession No. Z63792, Oct. 22, 1995.

MacDonald et al., (1995) "H. sapiens CpG island DNA genomic Mse1 fragment, clone 90b7, reverse read cpg90b7.rtla" *Direct Submission. GenBank,* Accession No. Z63794, Oct. 22, 1995.

Holmes et al., (1998) "Distinct But Overlapping Expression Patterns of Two Vertebrate Slit Homologs Implies Functional Roles in CNS Development and Organogenesis." *Mech. Dev.* 79: 57–72, *GenBank,* Accession No. AAD04309, Mar. 4, 1999.

Oberthur et al., (1982) "Hemoglobins, XLVII. Hemoglobins of the Bar–Headed Goose (Anser Indicus): Primary Structure and Physiology of Respiration, Systematic and Evolution." *Hoppe–Seyler's Z. Physiol. Chem.* 363: 581–590. *GenBank,* Accession Number, HBGSI, Nov. 14, 1997.

Gendler et al., (1988) "A Highly Immunogenic Region of a Human Polymorphic Epithelial Mucin Expressed by Carcinomas is Made Up of Tandem Repeats." *J. Biol. Chem.* 263: 12820–12823. *GenBank,* Accession No. A28938, Jun. 18, 1993.

Arnold, (1989) "nifF protein (AA 1–176) [*Klebsiella pneumoniae*]" *Direct Submission. GenBank,* Accession No. CAA31680, Feb. 10, 1999.

The et al., (1992) "Molecular Characterization and Structural Organization of D–elg, ad Ets Proto–Oncogene–Related gene of Drosophila." *Oncogene* 7: 2471–2478. *GenBank,* Accession No. X68259, Jan. 25, 1993.

Johnson, (1990) "A31R protein—vaccinia virus (strain Copenhagen)" *Direct Submission. GenBank,* Accession No. F42520, Apr. 8, 1994.

(List continued on next page.)

*Primary Examiner*—Christopher S.F. Low
*Assistant Examiner*—Hope A. Robinson
(74) *Attorney, Agent, or Firm*—Ivor R. Elrifi; Naomi S. Biswas; Mintz Levin Cohn Ferris Glovsky & Popeo, PC.

(57) ABSTRACT

The present invention provides novel isolated SECX polynucleotides and the membrane-associated or secreted polypeptides encoded by the SECX polynucleotides. Also provided are the antibodies that immunospecifically bind to a SECX polypeptide or any derivative, variant, mutant or fragment of the SECX polypeptide, polynucleotide or antibody. The invention additionally provides methods in which the SECX polypeptide, polynucleotide and antibody are utilized in the detection and treatment of a broad range of pathological states, as well as to other uses.

4 Claims, 46 Drawing Sheets

OTHER PUBLICATIONS

Kleinschmidt et al., (1989) "The Primary Structure of Pale–Throated Three–Toed Sloth (Bradypus tridactylus, Xenarthra) Hemoglobin." *Biol. Chem. Hoppe–Seyler* 370: 303–308. *GenBank,* Accession Number HBOWP, Nov. 14, 1997.

Ershler et al., (1992) "Identification of New Protein Kinase Genes, Similar to Kinases of the CDC2 Family and Expressed in Murine Hematopoietic Stem Cells." *Dokl. Adad. Nauk.* 324: 893–897. *GenBank,* Accession No. CAA46200, Nov. 14, 1995.

Both et al., (1984) "Nucleotide Sequence of the DSRNA Genomic Segment 7 of Simian 11 Rotavirus." *Nucl. Acids Res.* 12: 1621–1626. *GenBank,* Accession No. MNXR4S, Jul. 16, 1999.

Scherrer, (1991) "Prosomal p27K protein [Homo sapiens]" *Direct Submission. GenBank,* Accession No. CAA42052, Jul. 23, 1993.

Alonso et al., (1987) "CDNA Cloning and Sequence of MAL, a Hydrophobic Protein Associated with Human T–Cell Differentiation." *Proc. Natl. Acad. Sci. USA* 84: 1997–2001. *GenBank,* Accession No. P21145, Feb. 15, 2000.

Yuan et al. (1990). "The mouse SLIT family: secreted ligands for ROBO expressed in patterns that suggest a role in morphogenesis and axon guidance." *Dev Biol* 212(2): 290–306.

ATGACTGCCGCCATAAGAAGACAGAGAGAACTGAGTATCCTCCCAAAGGTGAATTTCAAT

TTTTGTTATTATGAGTGTGCTTGCTTATATAAAAGAATATGCTTAAGGGAAAAAAGGTGC

TTTAAAGTTAATATTCTACAAACCATAGTTTATGAGCATAAGAAATTACATAATTTACAG

CAATCTGATGTATTAGTAATAATAATGTATTATTATCTCTTAAACAGTGTTTTGTTTTAT

GGCTAACAGTAGCACCTGTGAATGAGGCAGAACCTGTTATTTGGATTTCACAAGGATGTG

AAAGTAATGGTACTGTTAAAAGTACCAAAAATGTATTATATGCTTTAAAAATTCTAGCCA

GAAACAGTATTTTCCTTTTCAACACATCTATTGAAAGTGTTGGATAAATGCAGGATGTT

AATATGCTATAAACATAAAGTCTGTTTTTAAAAAATAGCATTTGAAAATCATGAAGGGCT

TTTTGTTTTCTTTTGTTTGTATATATGTTTATTGGTAAAAGGTGACACTGGAAGCAATGA
                                       MetAsn

ACACCACAGTGATGCAAGGCTTCAACAGATCTGAGCGGTGCCCCAGAGACACTCGGATAG
 ThrThrValMetGlnGlyPheAsnArgSerGluArgCysProArgAspThrArgIleVal

TACAGCTGGTATTCCCAGCCCTCTACACAGTGGTTTTCTTGACCGGCATCCTGCTGAATA
 GlnLeuValPheProAlaLeuTyrThrValValPheLeuThrGlyIleLeuLeuAsnThr

CTTTGGCTCTGTGGGTGTTTGTTCACATCCCCAGCTCCTCCACCTTCATCATCTACCTCA
 LeuAlaLeuTrpValPheValHisIleProSerSerSerThrPheIleIleTyrLeuLys

AAAACACTTTGGTGGCCGACTTGATAATGACACTCATGCTTCCTTTCAAAATCCTCTCTG
 AsnThrLeuValAlaAspLeuIleMetThrLeuMetLeuProPheLysIleLeuSerAsp

ACTCACACCTGGCACCCTGGCAGCTCAGAGCTTTTGTGTGTCGTTTTTCTTCGGTGATAT
 SerHisLeuAlaProTrpGlnLeuArgAlaPheValCysArgPheSerSerValIlePhe

TTTATGAGACCATGTATGTGGGCATCGTGCTGTTAGGGCTCATAGCCTTTGACAGATTCC
 TyrGluThrMetTyrValGlyIleValLeuLeuGlyLeuIleAlaPheAspArgPheLeu

TCAAGATCATCAGACCTTTGAGAAATATTTTTCTAAAAAAACCTGTTTTTGCAAAAACGG
 LysIleIleArgProLeuArgAsnIlePheLeuLysLysProValPheAlaLysThrVal

TCTCAATCTTCATCTGGTTCTTTTTGTTCTTCATCTCCCTGCCAAATATGATCTTGAGCA
 SerIlePheIleTrpPhePheLeuPhePheIleSerLeuProAsnMetIleLeuSerAsn

ACAAGGAAGCAACACCATCGTCTGTGAAAAAGTGTGCTTCCTTAAAGGGGCCTCTGGGGC
 LysGluAlaThrProSerSerValLysLysCysAlaSerLeuLysGlyProLeuGlyLeu

TGAAATGGCATCAAATGGTAAATAACATATGCCAGTTTATTTTCTGGACTGTTTTTATCC
 LysTrpHisGlnMetValAsnAsnIleCysGlnPheIlePheTrpThrValPheIleLeu

TAATGCTTGTGTTTTATGTGGTTATTGCAAAAAAAGTATATGATTCTTATAGAAAGTCCA
 MetLeuValPheTyrValValIleAlaLysLysValTyrAspSerTyrArgLysSerLys

AAAGTAAGGACAGAAAAAACAACAAAAAGCTGGAAGGCAAAGTATTTGTTGTCGTGGCTG
 SerLysAspArgLysAsnAsnLysLysLeuGluGlyLysValPheValValValAlaVal

Fig. 1

```
TCTTCTTTGTGTGTTTTGCTCCATTTCATTTTGCCAGAGTTCCATATACTCACAGTCAAA
  PhePheValCysPheAlaProPheHisPheAlaArgValProTyrThrHisSerGlnThr

CCAACAATAAGACTGACTGTAGACTGCAAAATCAACTGTTTATTGCTAAAGAAACAACTC
  AsnAsnLysThrAspCysArgLeuGlnAsnGlnLeuPheIleAlaLysGluThrThrLeu

TCTTTTTGGCAGCAACTAACATTTGTATGGATCCCTTAATATACATATTCTTATGTAAAA
  PheLeuAlaAlaThrAsnIleCysMetAspProLeuIleTyrIlePheLeuCysLysLys

AATTCACAGAAAAGCTACCATGTATGCAAGGGAGAAAGACCACAGCATCAAGCCAAGAAA
  PheThrGluLysLeuProCysMetGlnGlyArgLysThrThrAlaSerSerGlnGluAsn

ATCATAGCAGTCAGACAGACAACATAACCTTAGGCTGACAACTGTACATAGGGTTAACTT
  HisSerSerGlnThrAspAsnIleThrLeuGly

CTATTTATTGATGAGACTTCCGTAGATAATGTGGAAATCAAATTTAACCAAGAAAAAAAG

ATTGGAACAAATGCTCTCTTACATTTTATTATCCTCGTGTACAGAAAAGATTATATAAAA

TTTAAATCCACATAGATCTATTCATAAGCTGAATGAACCATTACTAAGAGAATGCAACAG

GATACAAATGGCCACTAGAGGTCATTATTTCTTTCTTTCTTTATTCAGCGGCCGCTTTTT

TTTTTTTTTTTT
```

Fig. 1
(Continued)

```
GCGACTATTTCCCCCAAAGAGACAAGCACACATGTAGGAATGACAAAGGCTTGCGAAGGA

GAGAGCGCAGCCCGCGGCCCGGAGAGATCCCCTCGATAATGGATTACTAAATGGGATACA

CGCTGTACCAGTTCGCTCCGAGCCCCGGCCGCCTGTCCGTCGATGCACCGAAAAGGGTGA

AGTAGAGAAATAAAGTCTCCCCGCTGAACTACTATGAGGTCAGAAGCCTTGCTGCTATAT
                                   MetArgSerGluAlaLeuLeuLeuTyr

TTCACACTGCTACACTTTGCTGGGGCTGGTTTCCAGAAGATTCTGAGCCAATCAGTATT
PheThrLeuLeuHisPheAlaGlyAlaGlyPheProGluAspSerGluProIleSerIle

TCGCATGGCAACTATACAAAACAGTATCCGGTGTTTGTGGGCCACAAGCCAGGACGGAAC
SerHisGlyAsnTyrThrLysGlnTyrProValPheValGlyHisLysProGlyArgAsn

ACCACACAGAGGCACAGGCTGGACATCCAGATGATTATGATCATGAACGGAACCCTCTAC
ThrThrGlnArgHisArgLeuAspIleGlnMetIleMetIleMetAsnGlyThrLeuTyr

ATTGCTGCTAGGGACCATATTTATACTGTTGATATAGACACATCACACACGGAAGAAATT
IleAlaAlaArgAspHisIleTyrThrValAspIleAspThrSerHisThrGluGluIle

TATTGTAGCAAAAAACTGACATGGAAATCTAGACAGGCCGATGTAGACACATGCAGAATG
TyrCysSerLysLysLeuThrTrpLysSerArgGlnAlaAspValAspThrCysArgMet

AAGGGAAAACATAAGGATGAGTGCCACAACTTTATTAAAGTTCTTCTAAAGAAAAACGAT
LysGlyLysHisLysAspGluCysHisAsnPheIleLysValLeuLeuLysLysAsnAsp

GATGCATTGTTTGTCTGTGGAACTAATGCCTTCAACCCTTCCTGCAGAAACTATAAGATG
AspAlaLeuPheValCysGlyThrAsnAlaPheAsnProSerCysArgAsnTyrLysMet

GATACATTGGAACCATTCGGGGATGAATTCAGCGGAATGGCCAGATGCCCATATGATGCC
AspThrLeuGluProPheGlyAspGluPheSerGlyMetAlaArgCysProTyrAspAla

AAACATGCCAACGTTGCACTGTTTGCAGATGGAAAACTATACTCAGCCACAGTGACTGAC
LysHisAlaAsnValAlaLeuPheAlaAspGlyLysLeuTyrSerAlaThrValThrAsp

TTCCTTGCCATTGACGCAGTCATTTACCGGAGTCTTGGAGAAAGCCCTACCCTGCGGACC
PheLeuAlaIleAspAlaValIleTyrArgSerLeuGlyGluSerProThrLeuArgThr

GTCAAGCACGATTCAAAATGGTTGAAAGAACCATACTTTGTTCAAGCCGTGGATTACGGA
ValLysHisAspSerLysTrpLeuLysGluProTyrPheValGlnAlaValAspTyrGly

GATTATATCTACTTCTTCTTCAGGGAAATAGCAGTGGAGTATAACACCATGGGAAAGGTA
AspTyrIleTyrPhePheArgGluIleAlaValGluTyrAsnThrMetGlyLysVal

GTTTTCCCAAGAGTGGCTCAGGTTTGTAAGAATGATATGGGAGGATCTCAAAGAGTCCTG
ValPheProArgValAlaGlnValCysLysAsnAspMetGlyGlySerGlnArgValLeu

GAGAAACAGTGGACGTCGTTCCTGAAGGCGCGCTTGAACTGCTCAGTTCCTGGAGACTCT
GluLysGlnTrpThrSerPheLeuLysAlaArgLeuAsnCysSerValProGlyAspSer

CATTTTTATTTCAACATTCTCCAGGCAGTTACAGATGTGATTCGTATCAACGGCCGTGAT
HisPheTyrPheAsnIleLeuGlnAlaValThrAspValIleArgIleAsnGlyArgAsp
```

Fig. 2

```
GTTGTCCTGGCAACGTTTTCTACACCTTATAACAGCATCCCTGGGTCTGCAGTCTGTGCC
ValValLeuAlaThrPheSerThrProTyrAsnSerIleProGlySerAlaValCysAla

TATGACATGCTTGACATTGCCAGTGTTTTTACTGGGAGATTCAAGGAACAGAAGTCTCCT
TyrAspMetLeuAspIleAlaSerValPheThrGlyArgPheLysGluGlnLysSerPro

GATTCCACCTGGACACCAGTTCCTGATGAACGAGTTCCTAAGCCCAGGCCAGGTTGCTGT
AspSerThrTrpThrProValProAspGluArgValProLysProArgProGlyCysCys

GCTGGCTCATCCTCCTTAGAAAGATATGCAACCTCCAATGAGTTCCCTGATGATACCCTG
AlaGlySerSerSerLeuGluArgTyrAlaThrSerAsnGluPheProAspAspThrLeu

AACTTCATCAAGACGCACCCGCTCATGGATGAGGCAGTGCCCTCCATCTTCAACAGGCCA
AsnPheIleLysThrHisProLeuMetAspGluAlaValProSerIlePheAsnArgPro

TGGTTCCTGAGAACAATGGTCAGATACCGCCTTACCAAAATTGCAGTGGACACAGCTGCT
TrpPheLeuArgThrMetValArgTyrArgLeuThrLysIleAlaValAspThrAlaAla

GGGCCATATCAGAATCACACTGTGGTTTTTCTGGGATCAGAGAAGGGAATCATCTTGAAG
GlyProTyrGlnAsnHisThrValValPheLeuGlySerGluLysGlyIleIleLeuLys

TTTTTGGCCAGAATAGGAAATAGTGGTTTTCTAAATGACAGCCTTTTCCTGGAGGAGATG
PheLeuAlaArgIleGlyAsnSerGlyPheLeuAsnAspSerLeuPheLeuGluGluMet

AGTGTTTACAACTCTGAAAAATGCAGCTATGATGGAGTCGAAGACAAAAGGATCATGGGC
SerValTyrAsnSerGluLysCysSerTyrAspGlyValGluAspLysArgIleMetGly

ATGCAGCTGGACAGAGCAAGCAGCTCTCTGTATGTTGCGTTCTCTACCTGTGTGATAAAG
MetGlnLeuAspArgAlaSerSerSerLeuTyrValAlaPheSerThrCysValIleLys

GTTCCCCTTGGCCGGTGTGAACGACATGGGAAGTGTAAAAAAACCTGTATTGCCTCCAGA
ValProLeuGlyArgCysGluArgHisGlyLysCysLysLysThrCysIleAlaSerArg

GACCCATATTGTGGATGGATAAAGGAAGGTGGTGCCTGCAGCCATTTATCACCCAACAGC
AspProTyrCysGlyTrpIleLysGluGlyGlyAlaCysSerHisLeuSerProAsnSer

AGACTGACTTTTGAGCAGGACATAGAGCGTGGCAATACAGATGGTCTGGGGGACTGTCAC
ArgLeuThrPheGluGlnAspIleGluArgGlyAsnThrAspGlyLeuGlyAspCysHis

AATTCCTTTGTGGCACTGAATGGGCATTCCAGTTCCCTCTTGCCCAGCACAACCACATCA
AsnSerPheValAlaLeuAsnGlyHisSerSerSerLeuLeuProSerThrThrThrSer

GATTCGACGGCTCAAGAGGGGTATGAGTCTAGGGGAGGAATGCTGGACTGGAAGCATCTG
AspSerThrAlaGlnGluGlyTyrGluSerArgGlyGlyMetLeuAspTrpLysHisLeu

CTTGACTCACCTGACAGCACAGACCCTTTGGGGGCAGTGTCTTCCCATAATCACCAAGAC
LeuAspSerProAspSerThrAspProLeuGlyAlaValSerSerHisAsnHisGlnAsp

AAGAAGGGAGTGATTCGGGAAAGTTACCTCAAAGGCCACGACCAGCTGGTTCCCGTCACC
LysLysGlyValIleArgGluSerTyrLeuLysGlyHisAspGlnLeuValProValThr

CTCTTGGCCATTGCAGTCATCCTGGCTTTCGTCATGGGGGCCGTCTTCTCGGGCATCACC
LeuLeuAlaIleAlaValIleLeuAlaPheValMetGlyAlaValPheSerGlyIleThr
```

Fig. 2
(Continued)

```
GTCTACTGCGTCTGTGATCATCGGCGCAAAGACGTGGCTGTGGTGCAGCGCAAGGAGAAG
ValTyrCysValCysAspHisArgArgLysAspValAlaValValGlnArgLysGluLys

GAGCTCACCCACTCGCGCCGGGGCTCCATGAGCAGCGTCACCAAGCTCAGCGGCCTCTTT
GluLeuThrHisSerArgArgGlySerMetSerSerValThrLysLeuSerGlyLeuPhe

GGGGACACTCAATCCAAAGACCCAAAGCCGGAGGCCATCCTCACGCCACTCATGCACAAC
GlyAspThrGlnSerLysAspProLysProGluAlaIleLeuThrProLeuMetHisAsn

GGCAAGCTCGCCACTCCCGGCAACACGGCCAAGATGCTCATTAAAGCAGACCAGCACCAC
GlyLysLeuAlaThrProGlyAsnThrAlaLysMetLeuIleLysAlaAspGlnHisHis

CTGGACCTGACGGCCCTCCCCACCCCAGAGTCAACCCCAACGCTGCAGCAGAAGCGGGAA
LeuAspLeuThrAlaLeuProThrProGluSerThrProThrLeuGlnGlnLysArgGlu

CCCAGCCGCGGCACCCGCGAGTGGGAGAGGAACCAGAACCCTCATCAATGCCTGCACAAAG
ProSerArgGlyThrArgGluTrpGluArgAsnGlnAsnLeuIleAsnAlaCysThrLys

GACATGCCCCCCATGGGCTCCCCTGTGATTCCCACGGACCTGCCCCTGCGGGCCTCCCCC
AspMetProProMetGlySerProValIleProThrAspLeuProLeuArgAlaSerPro

AGCCACATCCCCAGCGTGGTGGTCCTGCCCATCACGCAGCAGGGCTACCAGCATGAGTAC
SerHisIleProSerValValValLeuProIleThrGlnGlnGlyTyrGlnHisGluTyr

GTGGACCAGCCCAAAATGAGCGAGGTGGCCCAGATGGCGCTGGAGGACCAGGCCGCCACA
ValAspGlnProLysMetSerGluValAlaGlnMetAlaLeuGluAspGlnAlaAlaThr

CTGGAGTATAAGACCATCAAGGAACATCTCAGCAGCAAGAGTCCCAACCATGGGGTGAAC
LeuGluTyrLysThrIleLysGluHisLeuSerSerLysSerProAsnHisGlyValAsn

CTTGTGGAGAACCTGGACAGCCTGCCCCCCAAAGTTCCACAGCGGGAGGCCTCCCTGGGT
LeuValGluAsnLeuAspSerLeuProProLysValProGlnArgGluAlaSerLeuGly

CCCCCGGGAGCCTCCCTGTCTCAGACCGGTCTAAGCAAGCGGCTGGAAATGCACCACTCC
ProProGlyAlaSerLeuSerGlnThrGlyLeuSerLysArgLeuGluMetHisHisSer

TCTTCCTACGGGGTTGACTATAAGAGGAGCTACCCCACGAACTCGCTCACGAGAAGCCAC
SerSerTyrGlyValAspTyrLysArgSerTyrProThrAsnSerLeuThrArgSerHis

CTGACCACCTACTCTCATCAGAAGCAACACTAACCCCGACAATTCAHCTCTGACTTCAAA
LeuThrThrTyrSerHisGlnLysGlnHis

GGGACCAGAGCTTTGGCAGGGGAGACAACCCGCCGCCCGCCCCGCAGAGGGTGGACTCCA

TCCAGGTGCACAGCTCCCAGCCATCTGGCCAGGCCGTGACTGTCTCGAGGCAGCCCAGCC

TCAACGCCTACAACTCACTGACAAGGTCGGGGCTGAAGCGTACGCCCTCGCTAAAGCCGG

ACGTACCCCCCAAACCATCCTTTGCTCCCCTTTCCACATCCATGAAGCCCAATGATGCGT

GTACATAATCCCAGGGGGAGGGGGTCAGGTGTCGAACCAGCAGGCAAGGCGAGGTGTCCG

CTCAGCTCAGCAAGGTTCTCAACTGCCTCGAGTACCCACCAAACCAAAAAGGCCTGCGGC

AGAACCGAGGGACGCTGGGTCCTCCTCTCTGGGACACAGGGGTACTCACGAAAACTGGGC

CGCGTGGTTTGGTGAAAG
```

Fig. 2
(Continued)

```
GCGACTATTTCCCCCAAAGAGACAAGCACACATGTAGGAATGACAAAGGCTTGCGAAGGA

GAGAGCGCAGCCCGCGGCCCGGAGAGATCCCCTCGATAATGGATTACTAAATGGGATACA

CGCTGTACCAGTTCGCTCCGAGCCCCGGCCGCCTGTCCGTCGATGCACCGAAAAGGGTGA

AGTAGAGAAATAAAGTCTCCCCGCTGAACTACTATGAGGTCAGAAGCCTTGCTGCTATAT
                                     MetArgSerGluAlaLeuLeuLeuTyr

TTCACACTGCTACACTTTGCTGGGGCTGGTTTCCCAGAAGATTCTGAGCCAATCAGTATT
PheThrLeuLeuHisPheAlaGlyAlaGlyPheProGluAspSerGluProIleSerIle

TCGCATGGCAACTATACAAAACAGTATCCGGTGTTTGTGGGCCACAAGCCAGGACGGAAC
SerHisGlyAsnTyrThrLysGlnTyrProValPheValGlyHisLysProGlyArgAsn

ACCACACAGAGGCACAGGCTGGACATCCAGATGATTATGATCATGAACGGAACCCTCTAC
ThrThrGlnArgHisArgLeuAspIleGlnMetIleMetIleMetAsnGlyThrLeuTyr

ATTGCTGCTAGGGACCATATTTATACTGTTGATATAGACACATCACACACGGAAGAAATT
IleAlaAlaArgAspHisIleTyrThrValAspIleAspThrSerHisThrGluGluIle

TATTGTAGCAAAAAACTGACATGGAAATCTAGACAGGCCGATGTAGACACATGCAGAATG
TyrCysSerLysLysLeuThrTrpLysSerArgGlnAlaAspValAspThrCysArgMet

AAGGGAAAACATAAGGATGAGTGCCACAACTTTATTAAAGTTCTTCTAAAGAAAAACGAT
LysGlyLysHisLysAspGluCysHisAsnPheIleLysValLeuLeuLysLysAsnAsp

GATGCATTGTTTGTCTGTGGAACTAATGCCTTCAACCCTTCCTGCAGAAACTATAAGATG
AspAlaLeuPheValCysGlyThrAsnAlaPheAsnProSerCysArgAsnTyrLysMet

GATACATTGGAACCATTCGGGGATGAATTCAGCGGAATGGCCAGATGCCCATATGATGCC
AspThrLeuGluProPheGlyAspGluPheSerGlyMetAlaArgCysProTyrAspAla

AAACATGCCAACGTTGCACTGTTTGCAGATGGAAAACTATACTCAGCCACAGTGACTGAC
LysHisAlaAsnValAlaLeuPheAlaAspGlyLysLeuTyrSerAlaThrValThrAsp

TTCCTTGCCATTGACGCAGTCATTTACCGGAGTCTTGGAGAAAGCCCTACCCTGCGGACC
PheLeuAlaIleAspAlaValIleTyrArgSerLeuGlyGluSerProThrLeuArgThr

GTCAAGCACGATTCAAAATGGTTGAAAGAACCATACTTTGTTCAAGCCGTGGATTACGGA
ValLysHisAspSerLysTrpLeuLysGluProTyrPheValGlnAlaValAspTyrGly

GATTATATCTACTTCTTCTTCAGGGAAATAGCAGTGGAGTATAACACCATGGGAAAGGTA
AspTyrIleTyrPhePhePheArgGluIleAlaValGluTyrAsnThrMetGlyLysVal

GTTTTCCCAAGAGTGGCTCAGGTTTGTAAGAATGATATGGGAGGATCTCAAAGAGTCCTG
ValPheProArgValAlaGlnValCysLysAsnAspMetGlyGlySerGlnArgValLeu

GAGAAACAGTGGACGTCGTTCCTGAAGGCGCGCTTGAACTGCTCAGTTCCTGGAGACTCT
GluLysGlnTrpThrSerPheLeuLysAlaArgLeuAsnCysSerValProGlyAspSer

CATTTTTATTTCAACATTCTCCAGGCAGTTACAGATGTGATTCGTATCAACGGGCGTGAT
HisPheTyrPheAsnIleLeuGlnAlaValThrAspValIleArgIleAsnGlyArgAsp

GTTGTCCTGGCAACGTTTTCTACACCTTATAACAGCATCCCTGGGTCTGCAGTCTGTGCC
ValValLeuAlaThrPheSerThrProTyrAsnSerIleProGlySerAlaValCysAla
```

Fig. 3

```
TATGACATGCTTGACATTGCCAGTGTTTTTACTGGGAGATTCAAGGAACAGAAGTCTCCT
TyrAspMetLeuAspIleAlaSerValPheThrGlyArgPheLysGluGlnLysSerPro

GATTCCACCTGGACACCAGTTCCTGATGAACGAGTTCCTAAGCCCAGGCCAGGTTGCTGT
AspSerThrTrpThrProValProAspGluArgValProLysProArgProGlyCysCys

GCTGGCTCATCCTCCTTAGAAAGATATGCAACCTCCAATGAGTTCCCTGATGATACCCTG
AlaGlySerSerSerLeuGluArgTyrAlaThrSerAsnGluPheProAspAspThrLeu

AACTTCATCAAGACGCACCCGCTCATGGATGAGGCAGTGCCCTCCATCTTCAACAGGCCA
AsnPheIleLysThrHisProLeuMetAspGluAlaValProSerIlePheAsnArgPro

TGGTTCCTGAGAACAATGGTCAGATACCGCCTTACCAAAATTGCAGTGGACACAGCTGCT
TrpPheLeuArgThrMetValArgTyrArgLeuThrLysIleAlaValAspThrAlaAla

GGGCCATATCAGAATCACACTGTGGTTTTTCTGGGATCAGAGAAGGGAATCATCTTGAAG
GlyProTyrGlnAsnHisThrValValPheLeuGlySerGluLysGlyIleIleLeuLys

TTTTTGGCCAGAATAGGAAATAGTGGTTTTCTAAATGACAGCCTTTTCCTGGAGGAGATG
PheLeuAlaArgIleGlyAsnSerGlyPheLeuAsnAspSerLeuPheLeuGluGluMet

AGTGTTTACAACTCTGAAAAATGCAGCTATGATGGAGTCGAAGACAAAAGGATCATGGGC
SerValTyrAsnSerGluLysCysSerTyrAspGlyValGluAspLysArgIleMetGly

ATGCAGCTGGACAGAGCAAGCAGCTCTCTGTATGTTGCGTTCTCTACCTGTGTGATAAAG
MetGlnLeuAspArgAlaSerSerSerLeuTyrValAlaPheSerThrCysValIleLys

GTTCCCCTTGGCCGGTGTGAACGACATGGGAAGTGTAAAAAAACCTGTATTGCCTCCAGA
ValProLeuGlyArgCysGluArgHisGlyLysCysLysLysThrCysIleAlaSerArg

GACCCATATTGTGGATGGATAAAGGAAGGTGGTGCCTGCAGCCATTTATCACCCAACAGC
AspProTyrCysGlyTrpIleLysGluGlyGlyAlaCysSerHisLeuSerProAsnSer

AGACTGACTTTTGAGCAGGACATAGAGCGTGGCAATACAGATGGTCTGGGGGACTGTCAC
ArgLeuThrPheGluGlnAspIleGluArgGlyAsnThrAspGlyLeuGlyAspCysHis

AATTCCTTTGTGGCACTGAATGGAGTGATTCGGGAAAGTTACCTCAAAGGCCACGACCAG
AsnSerPheValAlaLeuAsnGlyValIleArgGluSerTyrLeuLysGlyHisAspGln

CTGGTTCCCGTCACCCTCTTGGCCATTGCAGTCATCCTGGCTTTCGTCATGGGGGCCGTC
LeuValProValThrLeuLeuAlaIleAlaValIleLeuAlaPheValMetGlyAlaVal

TTCTCGGGCATCACCGTCTACTGCGTCTGTGATCATCGGCGCAAAGACGTGGCTGTGGTG
PheSerGlyIleThrValTyrCysValCysAspHisArgArgLysAspValAlaValVal

CAGCGCAAGGAGAAGGAGCTCACCCACTCGCGCCGGGGCTCCATGAGCAGCGTCACCAAG
GlnArgLysGluLysGluLeuThrHisSerArgArgGlySerMetSerSerValThrLys

CTCAGCGGCCTCTTTGGGGACACTCAATCCAAAGACCCAAAGCCGGAGGCCATCCTCACG
LeuSerGlyLeuPheGlyAspThrGlnSerLysAspProLysProGluAlaIleLeuThr

CCACTCATGCACAACGGCAAGCTCGCCACTCCCGGCAACACGGCCAAGATGCTCATTAAA
ProLeuMetHisAsnGlyLysLeuAlaThrProGlyAsnThrAlaLysMetLeuIleLys
```

Fig. 3
(Continued)

```
GCAGACCAGCACCACCTGGACCTGACGGCCCTCCCCACCCCAGAGTCAACCCCAACGCTG
AlaAspGlnHisHisLeuAspLeuThrAlaLeuProThrProGluSerThrProThrLeu

CAGCAGAAGCGGGAACCCAGCCGCGGCACCCGCGAGTGGGAGAGGAACCAGAACCTCATC
GlnGlnLysArgGluProSerArgGlyThrArgGluTrpGluArgAsnGlnAsnLeuIle

AATGCCTGCACAAAGGACATGCCCCCATGGGCTCCCCTGTGATTCCCACGGACCTGCCC
AsnAlaCysThrLysAspMetProProMetGlySerProValIleProThrAspLeuPro

CTGCGGGCCTCCCCCAGCCACATCCCCAGCGTGGTGGTCCTGCCCATCACGCAGCAGGGC
LeuArgAlaSerProSerHisIleProSerValValValLeuProIleThrGlnGlnGly

TACCAGCATGAGTACGTGGACCAGCCCAAAATGAGCGAGGTGGCCCAGATGGCGCTGGAG
TyrGlnHisGluTyrValAspGlnProLysMetSerGluValAlaGlnMetAlaLeuGlu

GACCAGGCCGCCACACTGGAGTATAAGACCATCAAGGAACATCTCAGCAGCAAGAGTCCC
AspGlnAlaAlaThrLeuGluTyrLysThrIleLysGluHisLeuSerSerLysSerPro

AACCATGGGGTGAACCTTGTGGAGAACCTGGACAGCCTGCCCCCCAAAGTTCCACAGCGG
AsnHisGlyValAsnLeuValGluAsnLeuAspSerLeuProProLysValProGlnArg

GAGGCCTCCCTGGGTCCCCCGGGAGCCTCCCTGTCTCAGACCGGTCTAAGCAAGCGGCTG
GluAlaSerLeuGlyProProGlyAlaSerLeuSerGlnThrGlyLeuSerLysArgLeu

GAAATGCACCACTCCTCTTCCTACGGGGTTGACTATAAGAGGAGCTACCCCACGAACTCG
GluMetHisHisSerSerSerTyrGlyValAspTyrLysArgSerTyrProThrAsnSer

CTCACGAGAAGCCACCTGACCACCTACTCTCATCAGAAGCAACACTAACCCCGACAATTC
LeuThrArgSerHisLeuThrThrTyrSerHisGlnLysGlnHis

ANCTCTGACTTCAAAGGGACCAGAGCTTTGGCAGGGGAGACAACCCGCCGCCCGCCCCGC

AGAGGGTGGACTCCATCCAGGTGCACAGCTCCCAGCCATCTGGCCAGGCCGTGACTGTCT

CGAGGCAGCCCAGCCTCAACGCCTACAACTCACTGACAAGGTCGGGGCTGAAGCGTACGC

CCTCGCTAAAGCCGGACGTACCCCCCAAACCATCCTTTGCTCCCCTTTCCACATCCATGA

AGCCCAATGATGCGTGTACATAATCCCAGGGGGAGGGGGTCAGGTGTCGAACCAGCAGGC

AAGGCGAGGTGTCCGCTCAGCTCAGCAAGGTTCTCAACTGCCTCGAGTACCCACCAAACC

AAAAAGGCCTGCGGCAGAACCGAGGGACGCTGGGTCCTCCTCTCTGGGACACAGGGGTAC

TCACGAAAACTGGGCCGCGTGGTTTGGTGAAAG
```

Fig. 3
(Countinued)

```
TCTCCCCTTTCCAGCTGAAAGGCTATTGTTCATGAGATTAGAATTCCAGTCAACACTGGT

ATTGGAAACTATTTTGCAGTAGTAGACAAGGGAGTTCGCAATCATTCATATCATTACATT

TCTGTGTTTTCTCTGTGATGATCATGAACATTGCTCAGAGCAATGCTGTGATATCACAGT
              MetIleMetAsnIleAlaGlnSerAsnAlaValIleSerGlnTrp

GGCTATTTATGATTAGATCATTTCATTGCATGCTTACACTTTTCATGGAAAAATGTAACA
 LeuPheMetIleArgSerPheHisCysMetLeuThrLeuPheMetGluLysCysAsnLys

AATGTCAAAATATAAATCAGAAATTCTTGCTCCAAATAATTGCAAAGAACTTGTTTTCAA
 CysGlnAsnIleAsnGlnLysPheLeuLeuGlnIleIleAlaLysAsnLeuPheSerThr

CCCCACTTTTGGAATATTCAAAAAAGTTTAGGGTAATTACCAGGTTTGGTGTGTGTCACT
 ProLeuLeuGluTyrSerLysLysPheArgValIleThrArgPheGlyValCysHisPhe

TCTGGGCTGAGAGGGATTTTAGGTTTCAGAGAAATAAATTGTGTTTTACCGGGAGCCGGT
 TrpAlaGluArgAspPheArgPheGlnArgAsnLysLeuCysPheThrGlySerArgCys

GTTGTCCATGTAGGTTCAGGGCTTTTAGAAATTTTAGGTGTAATTGTTCCGGCACTTGTG
 CysProCysArgPheArgAlaPheArgAsnPheArgCysAsnCysSerGlyThrCysGly

GTTCTTTCAGGTTTGGTTCTTGGCGGTTTGGGCCGGGGGCGTCGTTTAGGTGTAGAAGGG
 SerPheArgPheGlySerTrpArgPheGlyProGlyAlaSerPheArgCysArgArgAsp

ATAGATGTAGTTTGCTGGGGAGCAGGTGTCGTAGGCTGCATTTCTGGACTGGTAAAGATT
 ArgCysSerLeuLeuGlySerArgCysArgArgLeuHisPheTrpThrGlyLysAspPhe

TCCAGTTTTTGAGGAACAAATGGTGTTTCACTTGGAGCCAGTGTTGCCCTTGGCTGTTCA
 GlnPheLeuArgAsnLysTrpCysPheThrTrpSerGlnCysCysProTrpLeuPheLys

AGAGTTCTAGAAGTTTTAGGTGGGATAGAATCCAGAATACGATCACTTGTTGCTGGGTAG
 SerSerArgSerPheArgTrpAspArgIleGlnAsnThrIleThrCysCysTrpValGly

GAATCTGATATCTCAGGCTCATCTAATGTTGTAGGGCTTGAGAAAACATCATAAGTTGCA
 Ile

GTTTGAGGCTGCAGAACTTTGGAATCTTTCCAGAATTTCCTGAGGCAAAAACACCCTTCC

CTTTTGAAAAACCTAG
```

Fig. 4

```
CACTTCCCCCTTTTGTTAATTAAAACTAAGAAGTCGGAATGGGAACGAGGTGCCCAGCTC

CCGTGGAGAAAGCTTAAGGACACCACGCCAGTGCTTTCCTGCCTTCCTTCCGAGATGGAA

AGAGGAGCTCCTAGCTCACTTAAGCCGGGGTAGGGCTGGTTCTCCTTTCCGAGCCAAAAT

CCCAGGCGATGGTGAATTATGAACGTGCCACACCATGAAGCTCTTGTGGCAGGTAACTGT
                              MetLysLeuLeuTrpGlnValThrVal

GCACCACCACACCTGGAATGCCATCCTGCTCCCGTTCGTCTACCTCACGGCGCAAGTGTG
HisHisHisThrTrpAsnAlaIleLeuLeuProPheValTyrLeuThrAlaGlnValTrp

GATTCTGTGTGCAGCCATCGCTGCTGCCGCCTCAGCCGGGCCCCAGAACTGCCCCTCCGT
IleLeuCysAlaAlaIleAlaAlaAlaAlaSerAlaGlyProGlnAsnCysProSerVal

CTGCTCGTGCAGTAACCAGTTCAGCAAGGTGGTGTGCACGCGCCGGGGCCTCTCCGAGGT
CysSerCysSerAsnGlnPheSerLysValValCysThrArgArgGlyLeuSerGluVal

CCCGCAGGGTATTCCCTCGAACACCCGGTACCTCAACCTCATGGAGAACAACATCCAGAT
ProGlnGlyIleProSerAsnThrArgTyrLeuAsnLeuMetGluAsnAsnIleGlnMet

GATCCAGGCCGACACCTTCCGCCACCTCCACCACCTGGAGGTCCTGCAGTTGGGCAGGAA
IleGlnAlaAspThrPheArgHisLeuHisHisLeuGluValLeuGlnLeuGlyArgAsn

CTCCATCCGGCAGATTGAGGTGGGGGCCTTCAACGGCCTGGCCAGCCTCAGCACCCTGGA
SerIleArgGlnIleGluValGlyAlaPheAsnGlyLeuAlaSerLeuSerThrLeuGlu

GCTGTTCGACAACTGGCTGACAGTCATCCCTAGCGGGGCCTTTGAATACCTGTCCAAGCT
LeuPheAspAsnTrpLeuThrValIleProSerGlyAlaPheGluTyrLeuSerLysLeu

GCGGGAGCTCTGGCTTCGCAACAACCCCATCGAAAGCATCCCCTCTTACGCCTTCAACCG
ArgGluLeuTrpLeuArgAsnAsnProIleGluSerIleProSerTyrAlaPheAsnArg

GGTGCCCTCCCTCATGCGCCTGGACTTGGGGGAGCTCAAGAAGCTGGAGTATATCTCTGA
ValProSerLeuMetArgLeuAspLeuGlyGluLeuLysLysLeuGluTyrIleSerGlu

GGGAGCTTTTGAGGGGCTGTTCAACCTCAAGTATCTGAACTTGGGCATGTGCAACATTAA
GlyAlaPheGluGlyLeuPheAsnLeuLysTyrLeuAsnLeuGlyMetCysAsnIleLys

AGACATGCCCAATCTCACCCCCCTGGTGGGGCTGGAGGAGCTGGAGATGTCAGGGAACCA
AspMetProAsnLeuThrProLeuValGlyLeuGluGluLeuGluMetSerGlyAsnHis

CTTCCCTGAGATCAGGCCTGGCTCCTTCCATGGCCTGAGCTCCCTCAAGAAGCTCTGGGT
PheProGluIleArgProGlySerPheHisGlyLeuSerSerLeuLysLysLeuTrpVal

CATGAACTCACAGGTCAGCCTGATTGAGCGGAATGCTTTTGACGGGCTGGCTTCACTTGT
MetAsnSerGlnValSerLeuIleGluArgAsnAlaPheAspGlyLeuAlaSerLeuVal

GGAACTCAACTTGGCCCACAATAACCTCTCTTCTTTGCCCCATGACCTCTTTACCCCGCT
GluLeuAsnLeuAlaHisAsnAsnLeuSerSerLeuProHisAspLeuPheThrProLeu

GAGGTACCTGGTGGAGTTGCATCTACACCACAACCCTTGGAACTGTGATTGTGACATTCT
ArgTyrLeuValGluLeuHisLeuHisHisAsnProTrpAsnCysAspCysAspIleLeu

GTGGCTAGCCTGGTGGCTTCGAGAGTATATACCCACCAATTCCACCTGCTGTGGCCGCTG
TrpLeuAlaTrpTrpLeuArgGluTyrIleProThrAsnSerThrCysCysGlyArgCys
```

Fig. 5

```
TCATGCTCCCATGCACATGCGAGGCCGCTACCTCGTGGAGGTGGACCAGGCCTCCTTCCA
 HisAlaProMetHisMetArgGlyArgTyrLeuValGluValAspGlnAlaSerPheGln

GTGCTCTGCCCCCTTCATCATGGACGCACCTCGAGACCTCAACATTTCTGAGGGTCGGAT
 CysSerAlaProPheIleMetAspAlaProArgAspLeuAsnIleSerGluGlyArgMet

GGCAGAACTTAAGTGTCGGACTCCCCCTATGTCCTCCGTGAAGTGGTTGCTGCCCAATGG
 AlaGluLeuLysCysArgThrProProMetSerSerValLysTrpLeuLeuProAsnGly

GACAGTGCTCAGCCACGCCTCCCGCCACCCAAGGATCTCTGTCCTCAACGACGGCACCTT
 ThrValLeuSerHisAlaSerArgHisProArgIleSerValLeuAsnAspGlyThrLeu

GAACTTTTCCCACGTGCTGCTTTCAGACACTGGGGTGTACACATGCATGGGGACCAATGT
 AsnPheSerHisValLeuLeuSerAspThrGlyValTyrThrCysMetGlyThrAsnVal

TGCAGGCAACTCCAACGCCTCGGCCTACCTCAATGGGAGCACGGCTGAGCTTAACACCTC
 AlaGlyAsnSerAsnAlaSerAlaTyrLeuAsnGlySerThrAlaGluLeuAsnThrSer

CAACTACAGCTTCTTCACCACAGGAACAGGGGAGACCACGGAGATCTCGCCTGAGGACAC
 AsnTyrSerPhePheThrThrGlyThrGlyGluThrThrGluIleSerProGluAspThr

AACGCGAAAGTACAAGCCTGTTCCTACCACGTCCACTGGTTACCAGCCGGCATATACCAC
 ThrArgLysTyrLysProValProThrThrSerThrGlyTyrGlnProAlaTyrThrThr

CTCTACCACGGTGCTCATTCAGACTACCCGTGTGCCCAAGCAGGTGGCAGTACCCGCGAC
 SerThrThrValLeuIleGlnThrThrArgValProLysGlnValAlaValProAlaThr

AGACACCACTGACAAGATGCAGACCAGCCTGGATGAAGTCATGAAGACCACCAAGATCAT
 AspThrThrAspLysMetGlnThrSerLeuAspGluValMetLysThrThrLysIleIle

CATTGGCTGCTTTGTGGCAGTGACTCTGCTAGCTGCCGCCATGTTGATTGTCTTCTATAA
 IleGlyCysPheValAlaValThrLeuLeuAlaAlaAlaMetLeuIleValPheTyrLys

ACTTCGTAAGCGGCACCAGCAGCGGAGTACAGTCACAGCCGCCCGGACTGTTGAGATAAT
 LeuArgLysArgHisGlnGlnArgSerThrValThrAlaAlaArgThrValGluIleIle

CCAGGTGGACGAAGACATCCCAGCAGCAACATCCGCAGCAGCAACAGCAGCTCCGTCCGG
 GlnValAspGluAspIleProAlaAlaThrSerAlaAlaAlaThrAlaAlaProSerGly

TGTATCAGGTGAAGGGGCAGTAGTGCTGCCCACAATTCATGACCATATTAACTACAACAC
 ValSerGlyGluGlyAlaValValLeuProThrIleHisAspHisIleAsnTyrAsnThr

CTACAAACCAGCACATGGGGCCCACTGGACAGAAAACAGCCTGGGGAACTCTCTGCACCC
 TyrLysProAlaHisGlyAlaHisTrpThrGluAsnSerLeuGlyAsnSerLeuHisPro

CACAGTCACCACTATCTCTGAACCTTATATAATTCAGACCCATACCAAGGACAAGGTACA
 ThrValThrThrIleSerGluProTyrIleIleGlnThrHisThrLysAspLysValGln

GGAAACTCAAATATGACTCCCCTCCCCCAAAAAACTTATAAAATGCAATAGAATGCACAC
 GluThrGlnIle

AAAGACAGCAACTTTTGTACAGAGTGGGGAGAGACTTTTTCTTGTATATGCTTATATATT

AAGTCTATGGGCTGGTTAAAAAAAAACAGATTATATTAAAATTTAAAGACAAAAAGTCAAA

CACTTCCCCCTTTTGTTAATTAAAACTAAGAAGTCGGAATGGGAACGAGGTGCCCAGCTC

CCGTGGAGAAAGCTTAAGGACACCACGCCAGTGCTTTCCTGCCTTCCTTCCGAGATGGAA

AGAGGAGCTCCTAGCTCACTTAAGCCGGGGTAGGGCTGGTTCTCCTTTCCGAGCCAAAAT

CCCAGGCGATGGTGAATTATGAACGTGCCACACCATGAAGCTCTTGTGGCAGGTAACTGT
                              MetLysLeuLeuTrpGlnValThrVal

GCACCACCACACCTGGAATGCCATCCTGCTCCCGTTCGTCTACCTCACGGCGCAAGTGTG
HisHisHisThrTrpAsnAlaIleLeuLeuProPheValTyrLeuThrAlaGlnValTrp

GATTCTGTGTGCAGCCATCGCTGCTGCCGCCTCAGCCGGGCCCCAGAACTGCCCCTCCGT
IleLeuCysAlaAlaIleAlaAlaAlaAlaSerAlaGlyProGlnAsnCysProSerVal

CTGCTCGTGCAGTAACCAGTTCAGCAAGGTGGTGTGCACGCGCCGGGGCCTCTCCGAGGT
CysSerCysSerAsnGlnPheSerLysValValCysThrArgArgGlyLeuSerGluVal

CCCGCAGGGTATTCCCTCGAACACCCGGTACCTCAACCTCATGGAGAACAACATCCAGAT
ProGlnGlyIleProSerAsnThrArgTyrLeuAsnLeuMetGluAsnAsnIleGlnMet

GATCCAGGCCGACACCTTCCGCCACCTCCACCACCTGGAGGTCCTGCAGTTGGGCAGGAA
IleGlnAlaAspThrPheArgHisLeuHisHisLeuGluValLeuGlnLeuGlyArgAsn

CTCCATCCGGCAGATTGAGGTGGGGGCCTTCAACGGCCTGGCCAGCCTCAGCACCCTGGA
SerIleArgGlnIleGluValGlyAlaPheAsnGlyLeuAlaSerLeuSerThrLeuGlu

GCTGTTCGACAACTGGCTGACAGTCATCCCTAGCGGGGCCTTTGAATACCTGTCCAAGCT
LeuPheAspAsnTrpLeuThrValIleProSerGlyAlaPheGluTyrLeuSerLysLeu

GCGGGAGCTCTGGCTTCGCAACAACCCCATCGAAAGCATCCCCTCTTACGCCTTCAACCG
ArgGluLeuTrpLeuArgAsnAsnProIleGluSerIleProSerTyrAlaPheAsnArg

GGTGCCCTCCCTCATGCGCCTGGACTTGGGGGAGCTCAAGAAGCTGGAGTATATCTCTGA
ValProSerLeuMetArgLeuAspLeuGlyGluLeuLysLysLeuGluTyrIleSerGlu

GGGAGCTTTTGAGGGGCTGTTCAACCTCAAGTATCTGAACTTGGGCATGTGCAACATTAA
GlyAlaPheGluGlyLeuPheAsnLeuLysTyrLeuAsnLeuGlyMetCysAsnIleLys

AGACATGCCCAATCTCACCCCCCTGGTGGGGCTGGAGGAGCTGGAGATGTCAGGGAACCA
AspMetProAsnLeuThrProLeuValGlyLeuGluGluLeuGluMetSerGlyAsnHis

CTTCCCTGAGATCAGGCCTGGCTCCTTCCATGGCCTGAGCTCCCTCAAGAAGCTCTGGGT
PheProGluIleArgProGlySerPheHisGlyLeuSerSerLeuLysLysLeuTrpVal

CATGAACTCACAGGTCAGCCTGATTGAGCGGAATGCTTTTGACGGGCTGGCTTCACTTGT
MetAsnSerGlnValSerLeuIleGluArgAsnAlaPheAspGlyLeuAlaSerLeuVal

GGAACTCAACTTGGCCCACAATAACCTCTCTTCTTTGCCCCATGACCTCTTTACCCCGCT
GluLeuAsnLeuAlaHisAsnAsnLeuSerSerLeuProHisAspLeuPheThrProLeu

GAGGTACCTGGTGGAGTTGCATCTACACCACAACCCTTGGAACTGTGATTGTGACATTCT
ArgTyrLeuValGluLeuHisLeuHisHisAsnProTrpAsnCysAspCysAspIleLeu

GTGGCTAGCCTGGTGGCTTCGAGAGTATATACCCACCAATTCCACCTGCTGTGGCCGCTG
TrpLeuAlaTrpTrpLeuArgGluTyrIleProThrAsnSerThrCysCysGlyArgCys

TCATGCTCCCATGCACATGCGAGGCCGCTACCTCGTGGAGGTGGACCAGGCCTCCTTCCA
HisAlaProM tHisMetArgGlyArgTyrLeuValGluValAspGlnAlaSerPheGln

Fig. 6

```
GTGCTCTGCCCCCTTCATCATGGACGCACCTCGAGACCTCAACATTTCTGAGGGTCGGAT
CysSerAlaProPheIleMetAspAlaProArgAspLeuAsnIleSerGluGlyArgMet

GGCAGAACTTAAGTGTCGGACTCCCCCTATGTCCTCCGTGAAGTGGTTGCTGCCCAATGG
AlaGluLeuLysCysArgThrProProMetSerSerValLysTrpLeuLeuProAsnGly

GACAGTGCTCAGCCACGCCTCCCGCCACCCAAGGATCTCTGTCCTCAACGACGGCACCTT
ThrValLeuSerHisAlaSerArgHisProArgIleSerValLeuAsnAspGlyThrLeu

GAACTTTTCCCACGTGCTGCTTTCAGACACTGGGGTGTACACATGCATGGGGACCAATGT
AsnPheSerHisValLeuLeuSerAspThrGlyValTyrThrCysMetGlyThrAsnVal

TGCAGGCAACTCCAACGCCTCGGCCTACCTCAATGGGAGCACGGCTGAGCTTAACACCTC
AlaGlyAsnSerAsnAlaSerAlaTyrLeuAsnGlySerThrAlaGluLeuAsnThrSer

CAACTACAGCTTCTTCACCACAGGAACAGGGGAGACCACGGAGATCTCGCCTGAGGACAC
AsnTyrSerPhePheThrThrGlyThrGlyGluThrThrGluIleSerProGluAspThr

AACGCGAAAGTACAAGCCTGTTCCTACCACGTCCACTGGTTACCAGCCGGCATATACCAC
ThrArgLysTyrLysProValProThrThrSerThrGlyTyrGlnProAlaTyrThrThr

CTCTACCACGGTGCTCATTCAGACTACCCGTGTGCCCAAGCAGGTGGCAGTACCCGCGAC
SerThrThrValLeuIleGlnThrThrArgValProLysGlnValAlaValProAlaThr

AGACACCACTGACAAGATGCAGACCAGCCTGGATGAAGTCATGAAGACCACCAAGATCAT
AspThrThrAspLysMetGlnThrSerLeuAspGluValMetLysThrThrLysIleIle

CATTGGCTGCTTTGTGGCAGTGACTCTGCTAGCTGCCGCCATGTTGATTGTCTTCTATAA
IleGlyCysPheValAlaValThrLeuLeuAlaAlaAlaMetLeuIleValPheTyrLys

ACTTCGTAAGCGGCACCAGCAGCGGAGTACAGTCACAGCCGCCCCCACACTGGAGAGAAA
LeuArgLysArgHisGlnGlnArgSerThrValThrAlaAlaProThrLeuGluArgLys

ACACAGGGACAAAAACACACCACAACAAAAACACCCACAACAAAAACAACAGCCCCCCCC
HisArgAspLysAsnThrProGlnGlnLysHisProGlnGlnLysGlnGlnProProPro

GGTATAACAGGAAAGGGCACAATAGCGCCCCACAAAACACAACAACATAAAAAACAAAAC
Val

ACACACAAACCAGCACATGGGGCCCACTGGACAGAAAACAGCCTGGGGAACTCTGTGCAC
CCCACAGTCACCACTATCTCTGAACCTTATATAATTCAGACCCATACCAAGGACAAGGTA
CAGGAAACTCAAATATGACTCCCCTCCCCCAAAAAACTTATAAAATGCAATAGAATGCAC
ACAAAGACAGCAACTTTTGTACAGAGTGGGAGAGACTTTTTCTTGTATATGCTTATATA
TTAAGTCTATGGGCTGGTTAAAAAAAACAGATTATATTAAAATTTAAAGACAAAAAGTCA
AAACAAAAATATTTTCTAACTTGTAAGTTCTATTTAAAGGGGGTGGGGGGAATCTTGGG
AACGTTGTGGGGTACAAGCCACAAGTTAACTTGCTATGCTGCCAGAAGGGATTTCTGGTA
TAAGGTTGAAATTGCTGAGATAAAATAAACTAAAACAACAAACATCCTTAAAGAGGTAGG
GTGTGGGCTGCTGAAGGGGCAAGAGGGATAGACTGAATCTGTCATTTTTAGAAGATGCTT
CATAGGACACAGGACTATCCATTTCTA
```

Fig. 6
(Countinued)

```
GGCGTTTGTGGCCGTCCGGCTNCCCTGACATGCAGATTTCCACCCAGAAGACAGAGAAGG
AGCCAGTGGTCATGGAATGGGCTGGGGTCAAAGACTGGGTGCCTGGGAGCTGAGGCAGCC
ACCGTTTCAGCCTGGCCAGCCCTCTGGACCCCGAGGTTGGACCCTACTGTGACACACCTA
CCATGCGGACACTCTTCAACCTCCTCTGGCTTGCCCTGGCCTGCAGCCCTGTTCACACTA
CCCTGTCAAAGTCAGATGCCAAAAAAGCCGCCTCAAAGACGCTGCTGGAGAAGAGTCAGT
TTTCAGATAAGCCGGTGCAAGACCGGGGTTTGGTGGTGACGGACCTCAAAGCTGAGAGTG
TGGTTCTTGAGCATCGCAGCTACTGCTCGGCAAAGGCCCGGGACAGACACTTTGCTGGGG
ATGTACTGGGCTATGTCACTCCACCAGTGGAACAGCCATGGCTACGATGTCACCAAGGTC
MetTyrTrpAlaMetSerLeuHisGlnTrpAsnSerHisGlyTyrAspValThrLysVal

TTTGGGAGCAAGTTCACACAGATCTCACCCGTCTGGCTGCAGCTGAAGAGACGTGGCCGT
PheGlySerLysPheThrGlnIleSerProValTrpLeuGlnLeuLysArgArgGlyArg

GAGATGTTTGAGGTCACGGGCCTCCACGACGTGGACCAAGGGTGGATGCGAGCTGTCAGG
GluMetPheGluValThrGlyLeuHisAspValAspGlnGlyTrpMetArgAlaValArg

AAGCATGCCAAGGGCCTGCACATAGTGCCTCGGCTCCTGTTTGAGGACTGGACTTACGAT
LysHisAlaLysGlyLeuHisIleValProArgLeuLeuPheGluAspTrpThrTyrAsp

GATTTCCGGAACGTCTTAGACAGTGAGGATGAGATAGAGGAGCTGAGCAAGACCGTGGTC
AspPheArgAsnValLeuAspSerGluAspGluIleGluGluLeuSerLysThrValVal

CAGGTGGCAAAGAACCAGCATTTCGATGGCTTCGTGGTGGAGGTCTGGAACCAGCTGCTA
GlnValAlaLysAsnGlnHisPheAspGlyPheValValGluValTrpAsnGlnLeuLeu

AGCCAGAAGCGCGTGGGCCTCATCCACATGCTCACCCACTTGGCCGAGGCTCTGCACCAG
SerGlnLysArgValGlyLeuIleHisMetLeuThrHisLeuAlaGluAlaLeuHisGln

GCCCGGCTGCTGGCCCTCCTGGTCATCCCGCCTGCCATCACCCCCGGGACCGACCAGCTG
AlaArgLeuLeuAlaLeuLeuValIleProProAlaIleThrProGlyThrAspGlnLeu

GGCATGTTCACGCACAAGGAGTTTGAGCAGCTGGCCCCCGTGCTGGATGGTTTCAGCCTC
GlyMetPheThrHisLysGluPheGluGlnLeuAlaProValLeuAspGlyPheSerLeu

ATGACCTACGACTACTCTACAGCGCATCAGCCTGGCCCTAATGCACCCCTGTCCTGGGTT
MetThrTyrAspTyrSerThrAlaHisGlnProGlyProAsnAlaProLeuSerTrpVal

CGAGCCTGCGTCCAGGTCCTGGACCCGAAAGTCCAAGTGGCGAAGCAAAATCCTCCTGGGG
ArgAlaCysValGlnValLeuAspProLysSerLysTrpArgSerLysIleLeuLeuGly

CTCAACTTCTATGGTATGGACTACGCGACCTCCAAGGATGCCCGTGAGCCTGTTGTCGGG
LeuAsnPheTyrGlyMetAspTyrAlaThrSerLysAspAlaArgGluProValValGly

GCCAGGTACATGCAGACACTGAAGTCTGCATTCGTACTCTTAGCAAACTTGGAAAATTTG
AlaArgTyrMetGlnThrLeuLysSerAlaPheValLeuLeuAlaAsnLeuGluAsnLeu

AGGCGAAATTCTTCAAATAAAAAAAAAAAAAAAAAAAATTTTTTCTGTTTCTTCTCTTCT
ArgArgAsnSerSerAsnLysLysLysLysLysLysAsnPhePheCysPhePheSerSer

GTCTTCTCGTTTGGAGACCACAAACACTAGATCCATTGAATTTGTCCCACAGCTCACGAA
ValPheSerPheGlyAspHisLysHis

TACACCTTTTACCTTTTGGA
```

Fig. 7A

```
  1 GCCTCCCTGACATGCAGCCCTCTGGACCCCGAGGTTGGACCCTAC
    AlaSerLeuThrCysSerProLeuAspProGluValGlyProTyr

46 TGTGACACACCTACCATGCGGACACTCTTCAACCTCCTCTGGCTT
    CysAspThrProThrMetArgThrLeuPheAsnLeuLeuTrpLeu

91 GCCCTGGCCTGCAGCCCTGTTCACACTACCCTGTCAAAGTCAGAT
    AlaLeuAlaCysSerProValHisThrThrLeuSerLysSerAsp

136 GCCAAAAAGCCGCCTCAAAGACGCTGCTGGAGAAGAGTCAGTTT
    AlaLysLysAlaAlaSerLysThrLeuLeuGluLysSerGlnPhe

181 TCAGATAAGCCGGTGCAAGACCGGGGTTTGGTGGTGACGGACCTC
    SerAspLysProValGlnAspArgGlyLeuValValThrAspLeu

226 AAAGCTGAGAGTGTGGTTCTTGAGCATCGCAGCTACTGCTCGGCA
    LysAlaGluSerValValLeuGluHisArgSerTyrCysSerAla

271 AAGGCCCGGGACAGACACTTTGCTGGGGATGTACTGGGCTATGTC
    LysAlaArgAspArgHisPheAlaGlyAspValLeuGlyTyrVal

316 ACTCCATGGAACAGCCATGGCTACGATGTCACCAAGGTCTTTGGG
    ThrProTrpAsnSerHisGlyTyrAspValThrLysValPheGly

361 AGCAAGTTCACACAGATCTCACCCGTCTGGCTGCAGCTGAAGAGA
    SerLysPheThrGlnIleSerProValTrpLeuGlnLeuLysArg

406 CGTGGCCGTGAGATGTTTGAGGTCACGGGCCTCCACGACGTGGAC
    ArgGlyArgGluMetPheGluValThrGlyLeuHisAspValAsp

451 CAAGGGTGGATGCGAGCTGTCAGGAAGCATGCCAAGGGCCTGCAC
    GlnGlyTrpMetArgAlaValArgLysHisAlaLysGlyLeuHis

496 ATAGTGCCTCGGCTCCTGTTTGAGGACTGGACTTACGATGATTTC
    IleValProArgLeuLeuPheGluAspTrpThrTyrAspAspPhe

541 CGGAACGTCTTAGACAGTGAGGATGAGATAGAGGAGCTGAGCAAG
    ArgAsnValLeuAspSerGluAspGluIleGluGluLeuSerLys

586 ACCGTGGTCCAGGTGGCAAAGAACCAGCATTTCGATGGCTTCGTG
    ThrValValGlnValAlaLysAsnGlnHisPheAspGlyPheVal

631 GTGGAGGTCTGGAACCAGCTGCTAAGCCAGAAGCGCGTGGGCCTC
    ValGluValTrpAsnGlnLeuLeuSerGlnLysArgValGlyLeu

676 ATCCACATGCTCACCCACTTGGCCGAGGCTCTGCACCAGGCCCGG
    IleHisMetLeuThrHisLeuAlaGluAlaLeuHisGlnAlaArg

721 CTGCTGGCCCTCCTGGTCATCCCGCCTGCCATCACCCCCGGGACC
    LeuLeuAlaLeuLeuValIleProProAlaIleThrProGlyThr

766 GACCAGCTGGGCATGTTCACGCACAAGGAGTTTGAGCAGCTGGCC
    AspGlnLeuGlyMetPheThrHisLysGluPheGluGlnLeuAla

811 CCCGTGCTGGATGGTTTCAGCCTCATGACCTACGACTACGCAACA
    ProValLeuAspGlyPheSerLeuMetThrTyrAspTyrAlaThr
```

Fig. 7B

```
 856  CTGTCCTGGGTTCGAGCCTGCGTCCAGGTCCTGGATCCCTGGGGC
      LeuSerTrpValArgAlaCysValGlnValLeuAspProTrpGly

901  TCAACTTCTATGGTATGGACTACGCGACCTCCAAGGATGCCCGTG
      SerThrSerMetValTrpThrThrArgProProArgMetProVal

946  AGCCTGTTGTCGGGGCCAGGTACATCCAGACACTGAAGGACCACA
      SerLeuLeuSerGlyProGlyThrSerArgHis
 991  GGCCCCGGATGGTGTGGGACGGCCAGGCCTCAGAGCACTTCTTCG
1036  AGTACAAGAAGAGCCGCAGTGGGAGGCACGTCGTCTTCTACCCAA
1081  CCCTGAAGTCCCTGCAGGTGCGGCTGGAGCTGGCCCGGGAGCTGG
1126  GCGTTGGGGTCTCNATNTGGAGCTGGCCAGGGCCTGGACTACT
1171  TNTACGACCTGCTCTAGGTGGGCATTGCGGCCTCCGCGGTGGACG
1216  TGTTCTTTTCTAAGCCATGGAGTGAGTGAGCAGGTGTGAAATACA
1261  GGCCTCCACTCCGTTTACAAAAAAAAA
```

Fig. 7B
(Continued)

```
  1  GCCTCCCTGACATGCAGCCCTCTGGACCCCGAGGTTGGACCCTAC
 46  TGTGACACACCTACCATGCGGACACTCTTCAACCTCCTCTGGCTT
 91  GCCCTGGCCTGCAGCCCTGTTCACACTACCCTGTCAAAGTCAGAT
136  GCCAAAAAAGCCGCCTCAAAGACGCTGCTGGAGAAGAGTCAGTTT
181  TCAGATAAGCCGGTGCAAGACCGGGGTTTGGTGGTGACGGACCTC
226  AAAGCTGAGAGTGTGGTTCTTGAGCATCGCAGCTACTGCTCGGCA
271  AAGGCCCGGGACAGACACTTTGCTGGGGATGTACTGGGCTATGTC
                                     MetTyrTrpAlaMetSe
316  ACTCCACCAGTGGAACAGCCATGGCTACGATGTCACCAAGGTCTT
     rLeuHisGlnTrpAsnSerHisGlyTyrAspValThrLysValPh
361  TGGGAGCAAGTTCACACAGATCTCACCCGTCTGGCTGCAGCTGAA
     eGlySerLysPheThrGlnIleSerProValTrpLeuGlnLeuLy
406  GAGACGTGGCCGTGAGATGTTTGAGGTCACGGGCCTCCACGACGT
     sArgArgGlyArgGluMetPheGluValThrGlyLeuHisAspVa
451  GGACCAAGGGTGGATGCGAGCTGTCAGGAAGCATGCCAAGGGCCT
     lAspGlnGlyTrpMetArgAlaValArgLysHisAlaLysGlyLe
496  GCACATAGTGCCTCGGCTCCTGTTTGAGGACTGGACTTACGATGA
     uHisIleValProArgLeuLeuPheGluAspTrpThrTyrAspAs
541  TTTCCGGAACGTCTTAGACAGTGAGGATGAGATAGAGGAGCTGAG
     pPheArgAsnValLeuAspSerGluAspGluIleGluGluLeuSe
586  CAAGACCGTGGTCCAGGTGGCAAAGAACCAGCATTTCGATGGCTT
     rLysThrValValGlnValAlaLysAsnGlnHisPheAspGlyPh
631  CGTGGTGGAGGTCTGGAACCAGCTGCTAAGCCAGAAGCGCGTGGG
     eValValGluValTrpAsnGlnLeuLeuSerGlnLysArgValGl
676  CCTCATCCACATGCTCACCCACTTGGCCGAGGCTCTGCACCAGGC
     yLeuIleHisMetLeuThrHisLeuAlaGluAlaLeuHisGlnAl
721  CCGGCTGCTGGCCCTCCTGGTCATCCCGCCTGCCATCACCCCCGG
     aArgLeuLeuAlaLeuLeuValIleProProAlaIleThrProGl
766  GACCGACCAGCTGGGCATGTTCACGCACAAGGAGTTTGAGCAGCT
     yThrAspGlnLeuGlyMetPheThrHisLysGluPheGluGlnLe
811  GGCCCCCGTGCTGGATGGTTTCAGCCTCATGACCTACGACTACGC
     uAlaProValLeuAspGlyPheSerLeuMetThrTyrAspTyrAl
856  AACACTGTCCTGGGTTCGAGCCTGCGTCCAGGTCCTGGATCCCTG
     aThrLeuSerTrpValArgAlaCysValGlnValLeuAspProTr
901  GGGCTCAACTTCTATGGTATGGACTACGCGACCTCCAAGGATGCC
     pGlySerThrSerMetValTrpThrThrArgProProArgMetPr
946  CGTGAGCCTGTTGTCGGGGCCAGGTACATCCAGACACTGAAGGAC
     oValSerLeuLeuSerGlyProGlyThrSerArgHis
```

Fig. 7C

```
 991 CACAGGCCCCGGATGGTGTGGGACGGCCAGGCCTCAGAGCACTTC
1036 TTCGAGTACAAGAAGAGCCGCAGTGGGAGGCACGTCGTCTTCTAC
1081 CCAACCCTGAAGTCCCTGCAGGTGCGGCTGGAGCTGGCCCCGGGAG
1126 CTGGGCGTTGGGGTCTCNATNTGGGAGCTGGGCCAGGGCCTGGAC
1171 TACTTNTACGACCTGCTCTAGGTGGGCATTGCGGCCTCCGCGGTG
1216 GACGTGTTCTTTTCTAAGCCATGGAGTGAGTGAGCAGGTGTGAAA
1261 TACAGGCCTCCACTCCGTTTACAAAAAAAAA
```

Fig. 7C
(Continued)

```
ACGCGTGCAGGTGGCGGAACTTGCTCTAACTTCCTCGGCCGAGCCGGGCCGCGCCGCCGC
TGCCGCCGCCGCGCGGATTCTGCTTCTCAGAAGATGCACTATTATAGATACTCTAACG
                                MetHisTyrTyrArgTyrSerAsnAla
CCAAGGTCAGCTGCTGGTACAAGTACCTCCTTTTCAGCTACAACATCATCTTCTGGTTGG
  LysValSerCysTrpTyrLysTyrLeuLeuPheSerTyrAsnIleIlePheTrpLeuAla
CTGGAGTTGTCTTCCTTGGAGTCGGGTTGTGGCATGGAGCGAAAAGGGTGTGCTGTCCG
  GlyValValPheLeuGlyValGlyLeuTrpAlaTrpSerGluLysGlyValLeuSerAsp
ACCTCACCAAAGTGACCCGGATGCATGGAATCGACCCTGCGGTGCTGGTCCTGATGGTGG
  LeuThrLysValThrArgMetHisGlyIleAspProAlaValLeuValLeuMetValGly
GCGCGGTGATGTTCACCCTGGGGTTCGCCGGCCGCGTGGGGGCGCGCAGGGAGAATATCT
  AlaValMetPheThrLeuGlyPheAlaGlyArgValGlyAlaArgArgGluAsnIleCys
GCTTGCTCAACTTTTTCTGTGGCACCATCGTGCTCATCTTCTTCCTGGAGCTGGCTGTGG
  LeuLeuAsnPhePheCysGlyThrIleValLeuIlePhePheLeuGluLeuAlaValAla
CCGTGCTGGCCTTCCTGTTCCAGGACTGGGTGAGGGACCGGTTCCGGGAGTTCTTCGAGA
  ValLeuAlaPheLeuPheGlnAspTrpValArgAspArgPheArgGluPhePheGluSer
GCAACATCAAGTCCTACCGGGACGATATCGATCTGCAAAACCTCATCGACTCCCTTCAGA
  AsnIleLysSerTyrArgAspAspIleAspLeuGlnAsnLeuIleAspSerLeuGlnLys
AAGCTAACCAGTGCTGTGGCGCATATGGCCCTGAAGACTGGGACCTCAACGTCTACTTCA
  AlaAsnGlnCysCysGlyAlaTyrGlyProGluAspTrpAspLeuAsnValTyrPheAsn
ATTGCAGCGGTGCCAGCTACAGCCGAGAGAAGTGCGGGGTCCCCTTCTCCTGCTGCGTGC
  CysSerGlyAlaSerTyrSerArgGluLysCysGlyValProPheSerCysCysValPro
CAGATCCTGCGCAAAAAGTTGTGAACACACAGTGTGGATATGATGTCAGGATTCAGCTGA
  AspProAlaGlnLysValValAsnThrGlnCysGlyTyrAspValArgIleGlnLeuLys
AGAGCAAGTGGGATGAGTCCATCTTCACGAAAGGCTGCATCCAGGCGCTGGAAAGCTGGC
  SerLysTrpAspGluSerIlePheThrLysGlyCysIleGlnAlaLeuGluSerTrpLeu
TCCCGCGGAACATTTACATTGTGGCTGGCGTCTTCATCGCCATCTCGCTGTTGCAGATAT
  ProArgAsnIleTyrIleValAlaGlyValPheIleAlaIleSerLeuLeuGlnIlePhe
TTGGCATCTTCCTGGCAAGGACGCTGATCTCAGACATCGAGGCAGTGAAGACCGGCCATC
  GlyIlePheLeuAlaArgThrLeuIleSerAspIleGluAlaValLysThrGlyHisHis
ACTTCTGAGGAGCAGAGTTGAGGGAGCCGAGCTGAGCCACGCTGGGAGGCCAGAGCCTTT
  Phe
CTCTGCCATCAGCCCTACGTCCAGAGGGAGAGGAGCCGACACCCCCAGAGCCAGTGCCCC
ATCTTAAGCATCAGCGTGACGTGACCTCTCTGTTTCTGCTTGCTGGTGCTGAAGACCAAG
GGTCCCCCTTGATACCCTGCCCAAACTTGTGACTGCATCCCTCTGGAGTCTACCCAGAGAC
AGAGAATGTGTCTTTATGTGGGAGTGGTGACTCTGAAAGACAGAGAGGGCTCCTGTGGCT
GCCAGGAGGGCTTGACTCAGACCCCCTGCAGCTCAAGCATGTCTGCAGGACACCCTGGTC
CCCTCTCCACTGGCATCCAGACATCTGCTTTGGGTCATCCACATCTGTGGGTGGGCCGTG
GGTAGAGGGACCCACAGGCGTGGACAGGGCATCTCTCTCCATCAAGCAAAGCAGCATGGG
GGCCTGCCCGTAACGGGAGGCGGACGTGGCCCCGCTGGGCCTCTCCGA
```

Fig. 8A

```
  1 CCGCGTGCTGGTCCTGATGGTGGGCGCGGTGATGTTCACCCGGGG
    ArgValLeuValLeuMetValGlyAlaValMetPheThrArgGl

46 TTCGCCGGCCGCGTGGGGGCGCGCCAGGGAGAATATCTGCTTGCT
    ySerProAlaAlaTrpGlyArgAlaArgGluAsnIleCysLeuLe

91 CAACTTTTTCTGTGGCACCATCGTGCTCATCTTCTTCCTGGAGCT
    uAsnPhePheCysGlyThrIleValLeuIlePhePheLeuGluLe

136 GGCTGTGGCCGTGCTGGCCTTCCTGTTCCAGGACTGGGTGAGGGA
    uAlaValAlaValLeuAlaPheLeuPheGlnAspTrpValArgAs

181 CCGGTTCCGGGAGTTCTTCGAGAGCAACATCAAGTCCTACCGGGA
    pArgPheArgGluPhePheGluSerAsnIleLysSerTyrArgAs

226 CGATATCGATCTGCAAAACCTCATCGACTCCCTTCAGAAAGCTAA
    pAspIleAspLeuGlnAsnLeuIleAspSerLeuGlnLysAlaAs

271 CCAGTGCTGTGGCGCATATGGCCCTGAAGACTGGGACCTCAACGT
    nGlnCysCysGlyAlaTyrGlyProGluAspTrpAspLeuAsnVa

316 CTACTTCAATTGCAGCGGTGCCAGCTACAGCCGAGAGAAGTGCGG
    lTyrPheAsnCysSerGlyAlaSerTyrSerArgGluLysCysGl

361 GGTCCCCTTCTCCTGCTGCGTGCCAGATCCTGCGCAAAAAGTTGT
    yValProPheSerCysCysValProAspProAlaGlnLysValVa

406 GAACACACAGTGTGGATATGATGTCAGGATTCAGCTGAAGAGCAA
    lAsnThrGlnCysGlyTyrAspValArgIleGlnLeuLysSerLy

451 GTGGGATGAGTCCATCTTCACGAAAGGCTGCATCCAGGCGCTGGA
    sTrpAspGluSerIlePheThrLysGlyCysIleGlnAlaLeuGl

496 AAGCTGGCTCCCGCGGAACATTTACATTGTGGCTGGCGTCTTCAT
    uSerTrpLeuProArgAsnIleTyrIleValAlaGlyValPheIl

541 CGCCATCTCGCTGTTGCAGATATTTGGCATCTTCCTGGCAAGGAC
    eAlaIleSerLeuLeuGlnIlePheGlyIlePheLeuAlaArgTh

586 GCTGATCTCAGACATCGAGGCAGTGAAGGCCGGCCATCACTTCTG
    rLeuIleSerAspIleGluAlaValLysAlaGlyHisHisPhe
631 AGGAGCAGAGTTGAGGGAGCCGAGCTGAGCCACGCTGGGAGGCCA
676 GAGCCTTTCTCTGCCATCAGCCCTACGTCCAGAGGGAGAGGAGCC
721 GACACCCCAGAGCCAGTGCCCCATCTTAAGCATCAGCGTGACGT
766 GACCTCTCTGTTTCTGCTTGCTGGTGCTGAAGACCAAGGGTCCCC
811 CTTGTT
```

Fig. 8B

```
AACGGCGCAGGTCCCAGCAGCTGGGGTTCCCCCTCAGCCCGTGAGCAGCCATGTCCAACC
                                                 MetSerAsnPro

CCAGCGCCCCACCACCATATGAAGACCGCAACCCCCTGTACCCAGGCCCTCTGCCCCCTG
 SerAlaProProProTyrGluAspArgAsnProLeuTyrProGlyProLeuProProGly

GGGGCTATGGGCAGCCATCTGTCCTGCCAGGAGGGTATCCTGCCTACCCTGGCTACCCGC
  GlyTyrGlyGlnProSerValLeuProGlyGlyTyrProAlaTyrProGlyTyrProGln

AGCCTGGCTACGGTCACCCTGCTGGCTACCCACAGCCCATGCCCCCCACCCACCCGATGC
  ProGlyTyrGlyHisProAlaGlyTyrProGlnProMetProProThrHisProMetPro

CCATGAACTACGGCCCAGGCCATGGCTATGATGGGGAGGAGAGAGCGGTGAGTGATAGCT
  MetAsnTyrGlyProGlyHisGlyTyrAspGlyGluGluArgAlaValSerAspSerPhe

TCGGGCCTGGAGAATGGGATGACCGGAAAGTGCGACACACTTTTATCCGAAAGGTTTACT
  GlyProGlyGluTrpAspAspArgLysValArgHisThrPheIleArgLysValTyrSer

CCATCATCTCCGGGCAGCTGCTCATCACTGGGGCCATCATTGCTATCTTCACCTTTGGGG
  IleIleSerGlyGlnLeuLeuIleThrGlyAlaIleIleAlaIlePheThrPheGlyGlu

AACCTGTCAGCGCCTTTGGCAGGAGAAATGTGGCTGTCTACTACGTGTCCTATGCTGTCT
  ProValSerAlaPheGlyArgArgAsnValAlaValTyrTyrValSerTyrAlaValPhe

TCAGTGTCACCTACCTGATCCTTGCCTGCTGCCAGGGACCCAGACGCCGTTTCCCATGGA
  SerValThrTyrLeuIleLeuAlaCysCysGlnGlyProArgArgArgPheProTrpAsn

ACATCATTCTGCTGACCCTTTTTACTTTTGCCATGGGCTTCATGACGGGCACCATTTCCA
  IleIleLeuLeuThrLeuPheThrPheAlaMetGlyPheMetThrGlyThrIleSerSer

GTATGTACCAAACCAAAGCCGTCATCATTGCAATGATCATCACTGCGGTGGTATCCATTT
  MetTyrGlnThrLysAlaValIleIleAlaMetIleIleThrAlaValValSerIleSer

CAGTCACCATCTTCTGCTTTCAGACCAAGGTGGACTTCACCTCGTGCACAGGCCTCTTCT
  ValThrIlePheCysPheGlnThrLysValAspPheThrSerCysThrGlyLeuPheCys

GTGTCCTGGGAATTGTGCTCCTGGTGACTGGGATTGTCACTAGCATTGTGCTCTACTTCC
  ValLeuGlyIleValLeuLeuValThrGlyIleValThrSerIleValLeuTyrPheGln

AATACGTTTACTGGCTCCACATGCTCTATGCTGCTCTGGGGGCCATTTGTTTCACCCTGT
  TyrValTyrTrpLeuHisMetLeuTyrAlaAlaLeuGlyAlaIleCysPheThrLeuPhe

TCCTGGCTTACGACACACAGCTGGTCCTGGGGAACCGGAAGCACACCATCAGCCCCGAGG
  LeuAlaTyrAspThrGlnLeuValLeuGlyAsnArgLysHisThrIleSerProGluAsp

ACTACATCACTGGCGCCCTGCAGATTTACACAGACATCATCTACATCTTCACCTTTGTGC
  TyrIleThrGlyAlaLeuGlnIleTyrThrAspIleIleTyrIlePheThrPheValLeu

TGCAGCTGATGGGGGATCGCAATTAAGGAGCAAGCCCCCATTTTCACCCGATCCTGGCT
  GlnLeuMetGlyAspArgAsn
```

Fig. 9A

```
CTCCCTTCCAAGCTAGAGGGCTGGGCCCTATGACTGTGGTCTGGGCTTTAGGCCCCTTTC
CTTCCCCTTGAGTAACATGCCCAGTTTCCTTTCTGTCCTGGAGACAGGTGGCCTCTCTGG
CTATGGATGTGTGGGTACTTGGTGGGGACGGAGGAGCTAGGGACTAACTGTTGCTCTTGG
TGGGCTTGGCAGGGACTAGGCTGAAGATGTGTCTTCTCCCCGCCACCTACTGTATGACAC
CACATTCTTCCTAACAGCTGGGGTTGTGAGGAATATGAAAAGAGCCTATTCGATAGCTAG
AAGGGAATATGAAAGGTAGAAGTGACTTCAAGGTCACGAGGTTCCCCTCCCACCTCTGTC
ACAGGCTTCTTGACTACGTAGTTGGAGCTATTTCTTCCCCCAGCAAAGCCAGAGAGCTTT
GTCCCCGGCCTCCTGGACACATAGGCCATTATCCTGTATTCCTTTGGCTTGGCATCTTTT
AGCTCAGGAAGGTAGAAGAGATCTGTGCCCATGGGTCTCCTTGCTTCAATCCCTTCTTGT
TTCAGTGACATATGTATTGTTTATCTGGGTTAGGGATGGGGGACAGATAATAGAACGAGC
AAAGTAACCTATACAGGCCAGCATGGAACAGCATCTCCCCTGGGCTTGCTCCTGGCTTGT
GACGCTATAAGACAGAGCAGGCCACATGTGGCCATCTGCTCCCCATTCTTGAAAGCTGCT
GGGGCCTCCTTGCAGGCTTCTGGATCC
```

Fig. 9A
(Continued)

```
  1  CGCTCCGTCTGGAACGGCGCAGGTCCCAGCAGCTGGGGTTCCCCC

46  TCAGCCCGTGAGCAGCCATGTCCAACCCCAGCGCCCCACCACCAT
                     MetSerAsnProSerAlaProProT

91  ATGAAGACCGCAACCCCCTGTACCCAGGCCCTCTGCCCCCTGGGG
     yrGluAspArgAsnProLeuTyrProGlyProLeuProProGlyG

136  GCTATGGGCAGCCATCTGTCCTGCCAGGAGGGTATCCTGCCTACC
     lyTyrGlyGlnProSerValLeuProGlyGlyTyrProAlaTyrP

181  CTGGCTACCCGCAGCCTGGCTACGGTCACCCTGCTGGCTACCCAC
     roGlyTyrProGlnProGlyTyrGlyHisProAlaGlyTyrProG

226  AGCCCATGCCCCCACTCACCCGATGCCCATGAACTACGGCCCAG
     lnProMetProProThrHisProMetProMetAsnTyrGlyProG

271  GCCATGGCTATGATGGGGAGGAGAGAGCGGTGAGTGATAGCTTCG
     lyHisGlyTyrAspGlyGluGluArgAlaValSerAspSerPheG

316  GGCCTGGAGAGTGGGATGACCGGAAAGTGCGACACACTTTTATCC
     lyProGlyGluTrpAspAspArgLysValArgHisThrPheIleA

361  GAAAGGTTTACTCCATCATCTCCGTGCAGCTGCTCATCACTGTGG
     rgLysValTyrSerIleIleSerValGlnLeuLeuIleThrValA

406  CCATCATTGCTATCTTCACCTTTGTGGAACCTGTCAGCGCCTTTG
     laIleIleAlaIlePheThrPheValGluProValSerAlaPheV

451  TGAGGAGAAATGTGGCTGTCTACTACGTGTCCTATGCTGTCTTCG
     alArgArgAsnValAlaValTyrTyrValSerTyrAlaValPheV

496  TTGTCACCTACCTGATCCTTGCCTGCTGCCAGGGACCCAGACGCC
     alValThrTyrLeuIleLeuAlaCysCysGlnGlyProArgArgA

541  GTTTCCCATGGAACATCATTCTGCTGACCCTTTTTACTTTTGCCA
     rgPheProTrpAsnIleIleLeuLeuThrLeuPheThrPheAlaM

586  TGGGCTTCATGACGGGCACCATTTCCAGTATGTACCAAACCAAAG
     etGlyPheMetThrGlyThrIleSerSerMetTyrGlnThrLysA

631  CCGTCATCATTGCAATGATCATCACTGCGGTGGTATCCATTTCAG
     laValIleIleAlaMetIleIleThrAlaValValSerIleSerV

676  TCACCATCTTCTGCTTTCAGACCAAGGTGAGGGCATGGAGGGCCC
     alThrIlePheCysPheGlnThrLysValArgAlaTrpArgAlaL

721  TTCCCTGGCCCCCCGACTCCCCTTTCTTATCAGGCCCGGACCCCG
     euProTrpProProAspSerProPheLeuSerGlyProAspProG

766  GTACACTAGGGATGTTCCCTAGAGACCTGATCCCCTTCTCCTCAT
     lyThrLeuGlyMetPheProArgAspLeuIleProPheSerSerS

811  CCGCACCTACAAAACTGTGTCCTGTTTCTGTCCTTAGAATGTTGT
     erAlaProThrLysLeuCysProValSerValLeuArgMetLeuT

856  GGACATTCCCATACCCCCTAGGAGGCAGCACTGGGACTCCCTGGC
     rpThrPheProTyrProLeuGlyGlyS rThrGlyThrProTrpG
```

Fig. 9B

```
 901 AGGGCCAGTCTGACTGGGCTGGTTGTCACAGCCATCTGACAGGTG
     lnGlyGlnSerAspTrpAlaGlyCysHisSerHisLeuThrGlyA

946 CCTCTTTCTTGCTTCCTGGCAGGTGGACTTCACCTCGTGCACAGG
     laSerPheLeuLeuProGlyArgTrpThrSerProArgAlaGlnA

991 CCTCTTCTGTGTCCTGGGAATTGTGCTCCTGGTGACTGGGATTGT
     laSerSerValSerTrpGluLeuCysSerTrp

1036 CACTAGCATTGTGCTCTTAGCATTGTGCTCTACTTCCAATACGTT
1081 TACTGGCTCCACATGCTCTATGCTGCTCTGGGGGCCATTTGTTTC
1126 ACCCTGTTCCTGGCTTACGACACACAGCTGGTCCTGGGGAACCGG
1171 AAGCACACCATCAGCCCCGAGGACTACATCACTGGCGCCCTGCAG
1216 ATTTACACAGACATCATCTACATCTTCACCTTTGTGCTGCAGCTG
1261 ATGGGGGATCGCAATTAAGGAGCAAGCCCCCATTTTCACCCGATC
1306 CTGGGCTCTCCCTTCCAAGCTAGAGGGCTGGGCTCAATGACTGTG
1351 GTCTGGGCTTTAGGCCCCTTTCCTTCCCCTTGAGTAACATGCCCA
1396 GTTTCCTTTCTGTCCTGGAGACAGGTGGCCTCTCTGGCTATGGAT
1441 GTGTGGGTACTTGGTGGGGACGGAGGAGCTAGGGACTAACTGTTG
1486 CTCTTGGTGGGCTTGGCAGGGACTAGGCTGAAGATGTGTCTTCTC
1531 CCCGCCACCTACTGTATGACACCACATTCTTCCTAACAGCTGGGG
1576 TTGTGAGGAATATGAAAAGAGCCTATTCGATAGCTAGAAGGGAAT
1621 ATGAAAGGTAGAAGTGACTTCAAGGTCACGAGGTTCCCCTCCCAC
1666 CTCTGTCACAGGCTTCTTGACTACGTAGTTGGAGCTATTTCTTCC
1711 CCCAGCAAAGCCAGAGAGCTTTGTCCCCGGCCTCCTGGACACATA
1756 GGCCATTATCCTGTATTCCTTTGGCTTGGCATCTTTTAGCTCAGG
1801 AAGGTAGAAGAGATCTGTGCCCATGGGTCTCCTTGCTTCAATCCC
1846 TTCTTGTTTCAGTGACATATGTATTGTTTATCTGGGTTAGGGATG
1891 GGGGACAGATAATAGAACGAGCAAAGTAACCTATACAGGCCAGCA
1936 TGGAACAGCATCTCCCCTGGGCTTGCTCCTGGCTTGTGACGCTAT
1981 AAGACAGAGCAGGCCACATGTGGCCATTCTGCTCCCATTCTTGA
2026 AAGCTGCTGGGCCTCCTTGCAGGCTTCTGGATCTCTGGTCAGAG
2071 TGAACTCTTGCTTCCTGTATTCAGGCAGCTCAGAGCAGAAAGTAA
2116 GGGGCAGAGTCATACGTGTGGCCAGGAAGTAGCCAGGGTGAAGAG
2161 AGACTCGGTGCGGGCAGGGAGAATGCCTGGGGGTCCCTCACCTGG
2206 CTAGGGAGATACCGAAGCCTACTGTGGTACTGAAGACTTCTGGGT
2251 TCTTTCCTTCTGCTAACCCAGGGAGGGTCCTAAGAGGAAGGTGAC
2296 TTCTCTCTGTTTGTCTTAAGTTGCACTGGGGATTTCTGACTTGA
2341 GGCCCATCTCTCCAGCCAGCCACTGCCTTCTTTGTAATATTAAGT
2386 GCCTTGAGCTGGAATGGGGAAGGGGGACAAGGGTCAGTCTGTCGG
2431 GTGGGGGCAGAAATCAAATCAGCCCAAGGATATAGTTAGGATTAA
2476 TTACTTAATAGAGAAATCCTAACTATATCACACAAAGGGATACAA
2521 CTATAAATGTAATAAAATTTATGTCTAGAAGTTAAAAAAAAAAAA
2566 AAAAAAGT
```

Fig. 9B
(Continued)

TTCATAACAAAAATCCAGGCCAGGCACGGTGGCTCATTTTTAAAAGTCAAAAGAAAAAAT
AGTACTTAAAAAATAGAAAAATAAAATACTGTACACCAAAATAAGCTAGAAAAATGGAAC
TAAGAAATAATATTTGAAATTAATATAAAATGAAGCTACAGAAGGCATAAGTAAGTCCAA
ATGTTGGCTCTTTGAAAGACTATTAAATAATTACACAGAAAGTCTAATAAAGAGAAAAGA
GAGAAAAAAACTGTCAGAATGCTACCGAACTGTACTGCTTCTACAGTGAGAACACGGATC
TGACTTGTCGGCAGCCCAAGTGTGACAAGTGCAATGCTGCCTATCCTCACCTGGCTCACC
TGCCATCTGCCATGGCAGACTCATCCTTCCGGTTTCCTCGCACATGGTGGCAGTCTGCGG
          MetAlaAspSerSerPheArgPheProArgThrTrpTrpGlnSerAlaGlu
AGGATGTGCACAGAGAAAAGATCCAGTTAGACCTGGAAGCTGAATTCTACTTCACTCACC
  AspValHisArgGluLysIleGlnLeuAspLeuGluAlaGluPheTyrPheThrHisLeu
TAATTGTGATGTTCAAGTCCCCCAGGCCGGCTGCCATGGTGCTGGACCGCTCCCAGGACT
  IleValMetPheLysSerProArgProAlaAlaMetValLeuAspArgSerGlnAspPhe
TTGGGAAAACATGGAAGCCTTATAAGTACTTTGCGACTAACTGCTCCGCTACATTTGGCC
  GlyLysThrTrpLysProTyrLysTyrPheAlaThrAsnCysSerAlaThrPheGlyLeu
TGGAAGATGATGTTGTCAAGAAGGGCGCTATTTGTACTTCTAAATACTCCAGTCCTTTTC
  GluAspAspValValLysLysGlyAlaIleCysThrSerLysTyrSerSerProPhePro
CATGCACTGGAGGAGAGGTTATTTTCAAAGCTTTGTCACCACCATACGATACAGAGAACC
  CysThrGlyGlyGluValIlePheLysAlaLeuSerProProTyrAspThrGluAsnPro
CTTACAGTGCCAAAGTTCAGGAGCAGCTGAAGATCACCAACCTTCGCGTGCAGCTGCTGA
  TyrSerAlaLysValGlnGluGlnLeuLysIleThrAsnLeuArgValGlnLeuLeuLys
AACGACAGTCTTGTCCCTGTCAGAGAAATGACCTGAACGAAGAGCCTCAACATTTTACAC
  ArgGlnSerCysProCysGlnArgAsnAspLeuAsnGluGluProGlnHisPheThrHis
ACTATGCAATCTATGATTTCATTGTCAAGGGCAGCTGCTTCTGCAATGGCCACGCTGATC
  TyrAlaIleTyrAspPheIleValLysGlySerCysPheCysAsnGlyHisAlaAspGln
AATGCATACCTGTTCATGGCTTCAGACCTGTCAAGGCCCCAGGAACATTCCACATGGTCC
  CysIleProValHisGlyPheArgProValLysAlaProGlyThrPheHisMetValHis
ATGGAAGTGTATGTGTAAGCACAACACAGCAGGCAGCCACTGCCAGCACTGTGCCCCGT
  GlyLysCysMetCysLysHisAsnThrAlaGlySerHisCysGlnHisCysAlaProLeu
TATACAATGACCGGCCATGGGAGGCAGCTGATGGCAAAACGGGGCTCCCAACGAGTGCA
  TyrAsnAspArgProTrpGluAlaAlaAspGlyLysThrGlyAlaProAsnGluCysArg
GAACCTGCAAGTGTAATGGGCATGCTGATACCTGTCACTTCGACGTTAATGTGTGGGAGG
  ThrCysLysCysAsnGlyHisAlaAspThrCysHisPheAspValAsnValTrpGluAla
CATCAGGGAATCGTAGTGGTGGTGTCTGTGATGACTGTCAGCACAACACAGAAGGACAGT
  SerGlyAsnArgSerGlyGlyValCysAspAspCysGlnHisAsnThrGluGlyGlnTyr

Fig. 10

```
ATTGCCAGAGGTGCAAGCCAGGCTTCTATCGTGACCTGCGGAGACCCTTCTCAGCTCCAG
   CysGlnArgCysLysProGlyPheTyrArgAspLeuArgArgProPheSerAlaProAsp
ATGCTTGCAAACGTAAGTAACCTGTGGTTTCCAGAAAATAGGCTGATTTGTACAAGAGAT
   AlaCysLysArgLys
GAATCTCTTTATCCCTCATTCTGCTAACCCAAGAGAAGGAGGTCATTGAGGTTCTGAGAT
AACACACTTACAGATATCGGTTAATTTCTTCATTGATAAGAAGCAAGAATTTTCAACCAT
TGGGTGAAAACAGTATAATATTCATCAAAAGTAATTTCCTTTCTCATTCTNCATAAAGTA
AAAATTATTCCCTATACGCTGCATTTTGGTAAACAGGATGACTAATAGAAAAAAAAATGA
TGAANAAGGAGACTATTTAAGAACTTAAGACTACTTGGGAGTAGAAGGTAGACAATAATG
GACTCANCTGATGAAATAAAGGTAAGTACTGGACTTGGAATATCTTTACCTTACAGGGAA
CTTAAC
```

Fig. 10
(Continued)

```
GCTCCGCGACTCGGCCTCTCCACCCCCTCCCCAGCCTTTCTCTCGCCCTCTTCTCCCACA

CTCCCGGCCGGCGCCTCGGCTTTGTGCGAGGAGATGGTGTAGCCCCCTGGCCGCCGAAGA

GGAGCCGGACACTTGTCTCCCGTCTCCGAGCTGCTCCCCACCCCTGGAGGAGAGACCCCC

CCCTCGGCTCGGCGCCTTCTGCGTCTCCCGGCTGGTGGGAAGCCTCTGCGCCGCCGGCA

CCATGAGTGAACAGAGTATCTGTCAGGCAAGAGCTGCTGTGATGGTTTATGATGATGCCA
  MetSerGluGlnSerIleCysGlnAlaArgAlaAlaValMetValTyrAspAspAlaAsn

ATAAGAAGTGGGTGCCAGCTGGTGGCTCAACTGGATTCAGCAGAGTTCATATCTATCACC
  LysLysTrpValProAlaGlyGlySerThrGlyPheSerArgValHisIleTyrHisHis

ATACAGGCAACAACACATTCAGAGTGGTGGGCAGGAAGATTCAGGACCATCAGGTCGTGA
  ThrGlyAsnAsnThrPheArgValValGlyArgLysIleGlnAspHisGlnValValIle

TAAACTGTGCCATTCCTAAAGGGTTGAAGTACAATCAAGCTACACAGACCTTCCACCAGT
  AsnCysAlaIleProLysGlyLeuLysTyrAsnGlnAlaThrGlnThrPheHisGlnTrp

GGCGAGATGCTAGACAGGTGTATGGTCTCAACTTTGGCAGCAAAGAGGATGCCAATGTCT
  ArgAspAlaArgGlnValTyrGlyLeuAsnPheGlySerLysGluAspAlaAsnValPhe

TCGCAAGTGCCATGATGCATGCCTTAGAAGTGTTAAATTCACAGGAAACAGGGCCAACAT
  AlaSerAlaMetMetHisAlaLeuGluValLeuAsnSerGlnGluThrGlyProThrLeu

TGCCTAGACAAAACTCACAACTACCTGCTCAAGTTCAAAATGGCCCATCCCAAGAAGAAT
  ProArgGlnAsnSerGlnLeuProAlaGlnValGlnAsnGlyProSerGlnGluGluLeu

TGGAAATTCAAAGAAGACAACTACAAGAACAGCAACGGCAAAAGGAGCTGGAGCGGGAAA
  GluIleGlnArgArgGlnLeuGlnGluGlnGlnArgGlnLysGluLeuGluArgGluArg

GGCTGAAGCGAGAAAGAATGGAAAGAGAAAGGAAGAAGAGAGAGAGGTTAGAAAGGGAAA
  LeuLysArgGluArgMetGluArgGluArgLysLysArgGluArgLeuGluArgGluArg

GGCTGGAGAGGGAGCGACTGGAACAAGAACAGCTGGAGAGAGAGAGACAAGAACGGGAAC
  LeuGluArgGluArgLeuGluGlnGluGlnLeuGluArgGluArgGlnGluArgGluArg

GGCAGGAACGCCTGGAGCGGCAGGAACGCCTGGAGCGGCAGGAACGCCTGGAGCGGCAGG
  GlnGluArgLeuGluArgGlnGluArgLeuGluArgGlnGluArgLeuGluArgGlnGln

AACGCCTGGATCGGGAGAGGCAAGAAAGACAAGAACGAGAGAGGCTGGAGAGACTGGAAC
  ArgLeuAspArgGluArgGlnGluArgGlnGluArgGluArgLeuGluArgLeuGluArg

GGGAGAGGCAAGAAAGGGAGCGACAAGAGCAGTTAGAAAGGGAACAGCTGGAATGGGAGA
  GluArgGlnGluArgGluArgGlnGluGlnLeuGluArgGluGlnLeuGluTrpGluArg

GAGAGCGCAGAATATCAAGTGCTGCTGCCCCTGCCTCTGTTGAGACTCCTCTAAACTCTG
  GluArgArgIleSerSerAlaAlaAlaProAlaSerValGluThrProLeuAsnSerVal

TGCTGGGAGACTCTTCTGCTTCTGAGCCAGGCTTGCAGGCAGCCTCTCAGCCGGCCGAGA
  LeuGlyAspSerSerAlaSerGluProGlyLeuGlnAlaAlaSerGlnProAlaGluThr
```

Fig. 11

```
CTCCATCCCAACAGGAAGACAATCGCCCTTTAACTGGACTTGCAGCTGCAATTGCCGGAG
  ProSerGlnGlnGluAspAsnArgProLeuThrGlyLeuAlaAlaAlaIleAlaGlyAla

CAAAACTTAGGAAAGTGTCACGGATGGAGGATACCTCTTTCCCAAGTGGAGGGAATGCTA
  LysLeuArgLysValSerArgMetGluAspThrSerPheProSerGlyGlyAsnAlaIle

TTGGTGTGAACTCCGCCTCATCTAAAACAGATACAGGCCGTGGAAATGGACCCCTTCCTT
  GlyValAsnSerAlaSerSerLysThrAspThrGlyArgGlyAsnGlyProLeuProLeu

TAGGGGGTAGTGGTTTAATGGAAGAAATGAGTGCCCTGCTGGCCACGAGGAGAAGAATTG
  GlyGlySerGlyLeuMetGluGluMetSerAlaLeuLeuAlaThrArgArgArgIleAla

CTGAAAAGGGATCAACAATAGAAACAGAACAAAAGAGGACAAAGGTGAAGATTCAGAGC
  GluLysGlySerThrIleGluThrGluGlnLysGluAspLysGlyGluAspSerGluPro

CTGTAACTTCTAAGGCCTCTTCAACAAGTACACCTGAACCAACAAGAAAACCTTGGGAAA
  ValThrSerLysAlaSerSerThrSerThrProGluProThrArgLysProTrpGluArg

GAACAAATACAATGAATGGCAGCAAGTCACCTGTTATCTCCAGACCTCCAAGGAAAAATC
  ThrAsnThrMetAsnGlySerLysSerProValIleSerArgProProArgLysAsnGln

AGATTGTTTTTGACAACAGGTCCTATGATTCATTACACAGACCAAAATCCACACCCGTTA
  IleValPheAspAsnArgSerTyrAspSerLeuHisArgProLysSerThrProValIle

TCACAGCCCAGTGCCAATGGAGTCCAGACGGAAGGACTTGACTATGACAGGCTGAAGCAG
  ThrAlaGlnCysGlnTrpSerProAspGlyArgThr

GACATTTTAGATGAAATGAGAAAAGAATTAACAAAGCTAAAAGAAGAGCTCATTGATGCA

ATCAGGCAGGAACTGAGCAAGTCAAATACTGCATAGAGGAACAGACTAAGGAGAGATAGG

ACTTTAATCTGGAGGAAAAATATCCTACAAACAACAACTGTTCACAACAGCAAACCCCTA

CATTTATGAGCTGTAAGAAGAAAATGGAGACAAACAGAAGGAGGGAAAAACCAACCTACT

CTGAAAGCCTTCAGACATTATGACTCTGGTGATAAGCTCTTTCCCTCTCCGTTTGCTGCT

TTTTTCTGGCCAACATCAGAATGGTAACAC
```

Fig. 11
(Continued)

```
CTCCATCCCAACAGGAAGACAATCGCCCTTTAACTGGACTTGCAGCTGCAATTGCCGGAG
  ProSerGlnGlnGluAspAsnArgProLeuThrGlyLeuAlaAlaAlaIleAlaGlyAla

CAAAACTTAGGAAAGTGTCACGGATGGAGGATACCTCTTTCCCAAGTGGAGGGAATGCTA
  LysLeuArgLysValSerArgMetGluAspThrSerPheProSerGlyGlyAsnAlaIle

TTGGTGTGAACTCCGCCTCATCTAAAACAGATACAGGCCGTGGAAATGGACCCCTTCCTT
  GlyValAsnSerAlaSerSerLysThrAspThrGlyArgGlyAsnGlyProLeuProLeu

TAGGGGGTAGTGGTTTAATGGAAGAAATGAGTGCCCTGCTGGCCACGAGGAGAAGAATTG
  GlyGlySerGlyLeuMetGluGluMetSerAlaLeuLeuAlaThrArgArgArgIleAla

CTGAAAAGGGATCAACAATAGAAACAGAACAAAAAGAGGACAAAGGTGAAGATTCAGAGC
  GluLysGlySerThrIleGluThrGluGlnLysGluAspLysGlyGluAspSerGluPro

CTGTAACTTCTAAGGCCTCTTCAACAAGTACACCTGAACCAACAAGAAAACCTTGGGAAA
  ValThrSerLysAlaSerSerThrSerThrProGluProThrArgLysProTrpGluArg

GAACAAATACAATGAATGGCAGCAAGTCACCTGTTATCTCCAGACCTCCAAGGAAAAATC
  ThrAsnThrMetAsnGlySerLysSerProValIleSerArgProProArgLysAsnGln

AGATTGTTTTTGACAACAGGTCCTATGATTCATTACACAGACCAAAATCCACACCCGTTA
  IleValPheAspAsnArgSerTyrAspSerLeuHisArgProLysSerThrProValIle

TCACAGCCCAGTGCCAATGGAGTCCAGACGGAAGGACTTGACTATGACAGGCTGAAGCAG
  ThrAlaGlnCysGlnTrpSerProAspGlyArgThr

GACATTTTAGATGAAATGAGAAAAGAATTAACAAAGCTAAAAGAAGAGCTCATTGATGCA

ATCAGGCAGGAACTGAGCAAGTCAAATACTGCATAGAGGAACAGACTAAGGAGAGATAGG

ACTTTAATCTGGAGGAAAAATATCCTACAAACAACAACTGTTCACAACAGCAAACCCCTA

CATTTATGAGCTGTAAGAAGAAAATGGAGACAAACAGAAGGAGGGAAAAACCAACCTACT

CTGAAAGCCTTCAGACATTATGACTCTGGTGATAAGCTCTTTCCCTCTCCGTTTGCTGCT

TTTTTCTGGCCAACATCAGAATGGTAACAC
```

Fig. 11
(Contiued)

```
GCTCCGCGACTCGGCCTCTCCACCCCCTCCCCAGCCTTTCTCTCGCCCTCTTCTCCCACA

CTCCCGGCCGGCGCCTCGGCTTTGTGCGAGGAGATGGTGTAGCCCCCTGGCCGCCGAAGA

GGAGCCGGACACTTGTCTCCCGTCTCCGAGCTGCTCCCCACCCCTGGAGGAGAGACCCCC

CCCTCGGCTCGGCGCCTTCTGCGTCTCCCGGCTGGTGGGGAAGCCTCTGCGCCGCCGGCA

CCATGAGTGAACAGAGTATCTGTCAGGCAAGAGCTGCTGTGATGGTTTATGATGATGCCA
   MetSerGluGlnSerIleCysGlnAlaArgAlaAlaValMetValTyrAspAspAlaAsn

ATAAGAAGTGGGTGCCAGCTGGTGGCTCAACTGGATTCAGCAGAGTTCATATCTATCACC
   LysLysTrpValProAlaGlyGlySerThrGlyPheSerArgValHisIleTyrHisHis

ATACAGGCAACAACACATTCAGAGTGGTGGGCAGGAAGATTCAGGACCATCAGGTCGTGA
   ThrGlyAsnAsnThrPheArgValValGlyArgLysIleGlnAspHisGlnValValIle

TAAACTGTGCCATTCCTAAAGGGTTGAAGTACAATCAAGCTACACAGACCTTCCACCAGT
   AsnCysAlaIleProLysGlyLeuLysTyrAsnGlnAlaThrGlnThrPheHisGlnTrp

GGCGAGATGCTAGACAGGTGTATGGTCTCAACTTTGGCAGCAAAGAGGATGCCAATGTCT
   ArgAspAlaArgGlnValTyrGlyLeuAsnPheGlySerLysGluAspAlaAsnValPhe

TCGCAAGTGCCATGATGCATGCCTTAGAAGTGTTAAATTCACAGGAAACAGGGCCAACAT
   AlaSerAlaMetMetHisAlaLeuGluValLeuAsnSerGlnGluThrGlyProThrLeu

TGCCTAGACAAAACTCACAACTACCTGCTCAAGTTCAAAATGGCCCATCCCAAGAAGAAT
   ProArgGlnAsnSerGlnLeuProAlaGlnValGlnAsnGlyProSerGlnGluGluLeu

TGGAAATTCAAAGAAGACAACTACAAGAACAGCAACGGCAAAAGGAGCTGGAGCGGGAAA
   GluIleGlnArgArgGlnLeuGlnGluGlnGlnArgGlnLysGluLeuGluArgGluArg

GGCTGAAGCGAGAAAGAATGGAAAGAGAAAGGAAGAAGAGAGAGAGGTTAGAAAGGGAAA
   LeuLysArgGluArgMetGluArgGluArgLysLysArgGluArgLeuGluArgGluArg

GGCTGGAGAGGGAGCGACTGGAACAAGAACAGCTGGAGAGAGAGAGACAAGAACGGGAAC
   LeuGluArgGluArgLeuGluGlnGluGlnLeuGluArgGluArgGlnGluArgGluArg

GGCAGGAACGCCTGGAGCGGCAGGAACGCCTGGAGCGGCAGGAACGCCTGGAGCGGCAGG
   GlnGluArgLeuGluArgGlnGluArgLeuGluArgGlnGluArgLeuGluArgGlnGlu

AACGCCTGGATCGGGAGAGGCAAGAAAGACAAGAACGAGAGAGGCTGGAGAGACTGGAAC
   ArgLeuAspArgGluArgGlnGluArgGlnGluArgGluArgLeuGluArgLeuGluArg

GGGAGAGGCAAGAAAGGGAGCGACAAGAGCAGTTAGAAAGGGAACAGCTGGAATGGGAGA
   GluArgGlnGluArgGluArgGlnGluGlnLeuGluArgGluGlnLeuGluTrpGluArg

GAGAGCGCAGAATATCAAGTGCTGCTGCCCCTGCCTCTGTTGAGACTCCTCTAAACTCTG
   GluArgArgIleSerSerAlaAlaAlaProAlaSerValGluThrProLeuAsnSerVal

TGCTGGGAGACTCTTCTGCTTCTGAGCCAGGCTTGCAGGCAGCCTCTCAGCCGGCCGAGA
   LeuGlyAspSerSerAlaSerGluProGlyLeuGlnAlaAlaSerGlnProAlaGluThr
```

Fig. 12

```
CTCCATCCCAACAGGAAGACAATCGCCCTTTAACTGGACTTGCAGCTGCAATTGCCGGAG
    ProSerGlnGlnGluAspAsnArgProLeuThrGlyLeuAlaAlaAlaIleAlaGlyAla

CAAAACTTAGGAAAGTGTCACGGATGGAGGATACCTCTTTCCCAAGTGGAGGGAATGCTA
    LysLeuArgLysValSerArgMetGluAspThrSerPheProSerGlyGlyAsnAlaIle

TTGGTGTGAACTCCGCCTCATCTAAAACAGATACAGGCCGTGGAAATGGACCCCTTCCTT
    GlyValAsnSerAlaSerSerLysThrAspThrGlyArgGlyAsnGlyProLeuProLeu

TAGGGGGTAGTGGTTTAATGGAAGAAATGAGTGCCCTGCTGGCCACGAGGAGAAGAATTG
    GlyGlySerGlyLeuMetGluGluMetSerAlaLeuLeuAlaThrArgArgArgIleAla

CTGAAAAGGGATCAACAATAGAAACAGAACAAAAAGAGGACAAAGGTGAAGATTCAGAGC
    GluLysGlySerThrIleGluThrGluGlnLysGluAspLysGlyGluAspSerGluPro

CTGTAACTTCTAAGGCCTCTTCAACAAGTACACCTGAACCAACAAGAAAACCTTGGGAAA
    ValThrSerLysAlaSerSerThrSerThrProGluProThrArgLysProTrpGluArg

GAACAAATACAATGAATGGCAGCAAGTCACCTGTTATCTCCAGACCAAAATCCACACCCT
    ThrAsnThrMetAsnGlySerLysSerProValIleSerArgProLysSerThrProLeu

TATCACAGCCCAGTGCCAATGGAGTCCAGACGGAAGGACTTGACTATGACAGGCTGAAGC
    SerGlnProSerAlaAsnGlyValGlnThrGluGlyLeuAspTyrAspArgLeuLysGln

AGGACATTTTAGATGAAATGAGAAAAGAATTAACAAAGCTAAAAGAAGAGCTCATTGATG
    AspIleLeuAspGluMetArgLysGluLeuThrLysLeuLysGluGluLeuIleAspAla

CAATCAGGCAGGAACTGAGCAAGTCAAATACTGCATAGAGGAACAGACTAAGGAGAGATA
    IleArgGlnGluLeuSerLysSerAsnThrAla

GGACTTTAATCTGGAGGAAAAATATCCTACAAACAACAACTGTTCACAACAGCAAACCCC

TACATTTATGAGCTGTAAGAAGAAAATGGAGACAAACAGAAGGAGGGAAAAACCAACCTA

CTCTGAAAGCCTTCAGACATTATGACTCTGGTGATAAGCTCTTTCCCTCTCCGTTTGCTG

CTTTTTTCTGGCCAACATCAGAATGGTAACAC
```

Fig. 12
(Continued)

```
GAATTCGAGCGCAGGAGCTCCGCTTCTCCACCTGCTCCCGGGGAGCTAGTGGGATCCAGA
GAATCACCCGCTGATGGTTTTTGCCCAGGCCTGAAACAACCAGAGAGCTACGGGAAAGGA
AGGGCTTGGCTTGCCAGAGGAATTTTCCAAGTGCTCAAACGCCAGGCTTACGGCGCCTGT
GATCCGTCCAGGAGGACAAAGTGGGATTTGAGGATCCACTCCACTTCTGCTCATGGCGCG
                                                        M  A  R
CCAGGGCCTGCCCCTGCACGTGGCCACACTGCTGACTGGGCTGCTGGAATGCCTGGGCTT
 Q  G  L  P  L  H  V  A  T  L  L  T  G  L  L  E  C  L  G  F
TGCTGGCGTCCTCTTTGGCTGGCCTTCACTAGTGTTTGTCTTCAAGAATGAAGATTACTT
 A  G  V  L  F  G  W  P  S  L  V  F  V  F  K  N  E  D  Y  F
TAAGGATCTGTGTGGACCAGATGCTGGGCCGATTGGCAATGCCACAGGGCAGGCTGACTG
 K  D  L  C  G  P  D  A  G  P  I  G  N  A  T  G  Q  A  D  C
CAAAGCCCAGGATGAGAGGTTCTCACTCATCTTCACCCTGGGGTCCTTCATGAACAACTT
 K  A  Q  D  E  R  F  S  L  I  F  T  L  G  S  F  M  N  N  F
CATGACATTCCCCACTGGCTACATCTTTGACCGGTTCAAGACCACCGTGGCACGCCTCAT
 M  T  F  P  T  G  Y  I  F  D  R  F  K  T  T  V  A  R  L  I
AGCCATATTTTTCTACACCACCGCCACACTCATCATAGCCTTCACCTCTGCAGCTTCTTT
 A  I  F  F  Y  T  T  A  T  L  I  I  A  F  T  S  A  A  S  L
ATGAAAAAGGCATCAGCCTCAGGGCCTCCTTCATCTTCATCTCTGTCTGCAAGTACCTGG
CATGTAGCACGCACTTTCCTCCTGATGCCCCGGGGGCACATCCCATACCCACTGCCCCCC
AACTACAGCTATGGCCTGTGCCCTGGGAATGGCACCACAAAGGAAGAGAAGGAAACAGCT
GAGCATGAAAACAGGGAGCTACAGTCAAAGGAGTTCCTTTCAGCGAA
```

Fig. 13

```
CTTTTTTCAGATAACATCTTCTGAGTCATAACCAGCCTGGGTCCCCCATGATCGTGGGGTCCCCTCGGGCCCTGACACAG
                                            MetIleValGlySerProArgAlaLeuThrGln

CCCCTGGGTCTCCTTCGCCTGCTGCAGCTGGTGTCTACCTGCGTGGCCTTCTCGCTGGTGGCTAGCGTGGGCGCCTGGAC
ProLeuGlyLeuLeuArgLeuLeuGlnLeuValSerThrCysValAlaPheSerLeuValAlaSerValGlyAlaTrpTh

GGGGTCCATGGGCAACTGGTCCATGTTCACCTGGTGCTTCTGCTTCTCCGTGACCCTGATCATCCTCATCGTGGAGCTGT
rGlySerMetGlyAsnTrpSerMetPheThrTrpCysPheCysPheSerValThrLeuIleIleLeuIleValGluLeuC

GCGGGCTCCAGGCCCGCTTCCCCCTGTCTTGGCGCAACTTCCCCATCACCTTCGCCTGCTATGCGGCCCTCTTCTGCCTC
ysGlyLeuGlnAlaArgPheProLeuSerTrpArgAsnPheProIleThrPheAlaCysTyrAlaAlaLeuPheCysLeu

TCGGCCTCCATCATCTACCCCACCACCTATGTCCAGTTCCTGTCCCACGGCCGTTCGCGGGACCACGCCATCGCCGCCAC
SerAlaSerIleIleTyrProThrThrTyrValGlnPheLeuSerHisGlyArgSerArgAspHisAlaIleAlaAlaTh

CTTCTTCTCCTGCATCGCGTGTGTGGCTTACGCCACCGAAGTGGCCTGGACCCGGGCCCGGCCCGGCGAGATCACTGGCT
rPhePheSerCysIleAlaCysValAlaTyrAlaThrGluValAlaTrpThrArgAlaArgProGlyGluIleThrGlyT

ATATGGCCACCGTACCCGGGCTGCTGAAGGTGCTGGAGACCTTCGTTGCCTGCATCATCTTCGCGTTCATCAGCGACCCC
yrMetAlaThrValProGlyLeuLeuLysValLeuGluThrPheValAlaCysIleIlePheAlaPheIleSerAspPro

AACCTGTACCAGCACCAGCCGGCCCTGGAGTGGTGCGTGGCGGTGTACGCCATCTGCTTCATCCTAGCGGCCATCGCCAT
AsnLeuTyrGlnHisGlnProAlaLeuGluTrpCysValAlaValTyrAlaIleCysPheIleLeuAlaAlaIleAlaIl

CCTGCTGAACCTGGGGGAGTGCACCAACGTGCTACCCATCCCCTTCCCCAGCTTCCTGTCGGGGCTGGCCTTGCTGTCTG
eLeuLeuAsnLeuGlyGluCysThrAsnValLeuProIleProPheProSerPheLeuSerGlyLeuAlaLeuLeuSerV

TCCTCCTCTATGCCACCGCCCTTGTTCTCTGGCCCCTCTACCAGTTCGATGAGAAGTATGGCGGCCAGCCTCGGCGCTCG
alLeuLeuTyrAlaThrAlaLeuValLeuTrpProLeuTyrGlnPheAspGluLysTyrGlyGlyGlnProArgArgSer

AGAGATGTAAGCTGCAGCCGCAGCCATGCCTACTACGTGTGTGCCTGGGACCGCCGACTGGCTGTGGCCATCCTGACGGC
ArgAspValSerCysSerArgSerHisAlaTyrTyrValCysAlaTrpAspArgArgLeuAlaValAlaIleLeuThrAl

CATCAACCTACTGGCGTATGTGGCTGACCTGGTGCACTCTGCCCACCTGGTTTTTGTCAAGGTCTAAGACTCTCCCAAGA
aIleAsnLeuLeuAlaTyrValAlaAspLeuValHisSerAlaHisLeuValPheValLysVal

GGCTCCCGTTCCCTCTCCAACCTCTTTGTTCTTCTTGCCCGAGTTTTCTTTATGGAGTACTTCTTTCCTCCGCCTTTCCT

CTGTTTTCCTCTTCCTGTCTCCC
```

Fig. 14

```
1    GGATCCGGTTTCCCAGAAGATTCTGAGCCAATCAGTATTTCGCAT
     GlySerGlyPheProGluAspSerGluProIleSerIleSerHis

46   GGCAACTATACAAAACAGTATCCGGTGTTTGTGGGCCACAAGCCA
     GlyAsnTyrThrLysGlnTyrProValPheValGlyHisLysPro

91   GGACGGAACACCACACAGAGGCACAGGCTGGACATCCAGATGATT
     GlyArgAsnThrThrGlnArgHisArgLeuAspIleGlnMetIle

136  ATGATCATGAACGGAACCCTCTACATTGCTGCTAGGGACCATATT
     MetIleMetAsnGlyThrLeuTyrIleAlaAlaArgAspHisIle

181  TATACTGTTGATATAGACACATCACACACGGAAGAAATTTATTGT
     TyrThrValAspIleAspThrSerHisThrGluGluIleTyrCys

226  AGCAAAAAACTGACATGGAAATCTAGACAGGCCGATGTAGACACA
     SerLysLysLeuThrTrpLysSerArgGlnAlaAspValAspThr

271  TGCAGAATGAAGGGAAAACATAAGGATGAGTGCCACAACTTTATT
     CysArgMetLysGlyLysHisLysAspGluCysHisAsnPheIle

316  AAAGTTCTTCTAAAGAAAAACGATGATGCATTGTTTGTCTGTGGA
     LysValLeuLeuLysLysAsnAspAspAlaLeuPheValCysGly

361  ACTAATGCCTTCAACCCTTCCTGCAGAAACTATAAGATGGATACA
     ThrAsnAlaPheAsnProSerCysArgAsnTyrLysMetAspThr

406  TTGGAACCATTCGGGGATGAATTCAGCGGAATGGCCAGATGCCCA
     LeuGluProPheGlyAspGluPheSerGlyMetAlaArgCysPro

451  TATGATGCCAAACATGCCAACGTTGCACTGTTTGCAGATGGAAAA
     TyrAspAlaLysHisAlaAsnValAlaLeuPheAlaAspGlyLys

496  CTATACTCAGCCACAGTGACTGACTTCCTTGCCATTGACGCAGTC
     LeuTyrSerAlaThrValThrAspPheLeuAlaIleAspAlaVal

541  ATTTACCGGAGTCTTGGAGAAAGCCCTACCCTGCGGACCGTCAAG
     IleTyrArgSerLeuGlyGluSerProThrLeuArgThrValLys

586  CACGATTCAAAATGGTTGAAAGAACCATACTTTGTTCAAGCCGTG
     HisAspSerLysTrpLeuLysGluProTyrPheValGlnAlaVal

631  GATTACGGAGATTATATCTACTTCTTCTTCAGGGAAATAGCAGTG
     AspTyrGlyAspTyrIleTyrPhePhePheArgGluIleAlaVal

676  GAGTATAACACCATGGGAAAGGTAGTTTTCCCAAGAGTGGCTCAG
     GluTyrAsnThrMetGlyLysValValPheProArgValAlaGln

721  GTTTGTAAGAATGATATGGGAGGATCTCAAAGAGTCCTGGAGAAA
     ValCysLysAsnAspMetGlyGlySerGlnArgValLeuGluLys

766  CAGTGGACGTCGTTCCTGAAGGCGCGCTTGAACTGCTCAGTTCCT
     GlnTrpThrSerPh LeuLysAlaArgLeuAsnCysSerValPro
```

Fig. 15

```
811  GGAGACTCTCATTTTTATTTCAACATTCTCCAGGCAGTTACAGAT
     GlyAspSerHisPheTyrPheAsnIleLeuGlnAlaValThrAsp

856  GTGATTCGTATCAACGGGCGTGATGTTGTCCTGGCAACGTTTTCT
     ValIleArgIleAsnGlyArgAspValValLeuAlaThrPheSer

901  ACACCTTATAACAGCATCCCTGGGTCTGCAGTCTGTGCCTATGAC
     ThrProTyrAsnSerIleProGlySerAlaValCysAlaTyrAsp

946  ATGCTTGACATTGCCAGTGTTTTTACTGGGAGATTCAAGGAACAG
     MetLeuAspIleAlaSerValPheThrGlyArgPheLysGluGln

991  AAGTCTCCTGATTCCACCTGGACACCAGTTCCTGATGAACGAGTT
     LysSerProAspSerThrTrpThrProValProAspGluArgVal

1036 CCTAAGCCCAGGCCAGGTTGCTGTGCTGGCTCATCCTCCTTAGAA
     ProLysProArgProGlyCysCysAlaGlySerSerSerLeuGlu

1081 AGATATGCAACCTCCAATGAGTTCCCTGATGATACCCTGAACTTC
     ArgTyrAlaThrSerAsnGluPheProAspAspThrLeuAsnPhe

1126 ATCAAGACGCACCCGCTCATGGATGAGGCAGTGCCCTCCATCTTC
     IleLysThrHisProLeuMetAspGluAlaValProSerIlePhe

1171 AACAGGCCATGGTTCCTGAGAACAATGGTCAGATACCGCCTTACC
     AsnArgProTrpPheLeuArgThrMetValArgTyrArgLeuThr

1216 AAAATTGCAGTGGACACAGCTGCTGGGCCATATCAGAATCACACT
     LysIleAlaValAspThrAlaAlaGlyProTyrGlnAsnHisThr

1261 GTGGTTTTTCTGGGATCAGAGAAGGGAATCATCTTGAAGTTTTTG
     ValValPheLeuGlySerGluLysGlyIleIleLeuLysPheLeu

1306 GCCAGAATAGGAAATAGTGGTTTTCTAAATGACAGCCTTTTCCTG
     AlaArgIleGlyAsnSerGlyPheLeuAsnAspSerLeuPheLeu

1351 GAGGAGATGAGTGTTTACAACTCTGAAAAATGCAGCTATGATGGA
     GluGluMetSerValTyrAsnSerGluLysCysSerTyrAspGly

1396 GTCGAAGACAAAAGGATCATGGGCATGCAGCTGGACAGAGCAAGC
     ValGluAspLysArgIleMetGlyMetGlnLeuAspArgAlaSer

1441 AGCTCTCTGTATGTTGCGTTCTCTACCTGTGTGATAAAGGTTCCC
     SerSerLeuTyrValAlaPheSerThrCysValIleLysValPro

1486 CTTGGCCGGTGTGAACGACATGGAAGTGTAAAAAAACCTGTATT
     LeuGlyArgCysGluArgHisGlyLysCysLysLysThrCysIle

1531 GCCTCCAGAGACCCATATTGTGGATGGATAAAGGAAGGTGGTGCC
     AlaSerArgAspProTyrCysGlyTrpIleLysGluGlyGlyAla

1576 TGCAGCCATTTATCACCCAACAGCAGACTGACTTTTGAGCAGGAC
     CysSerHisLeuSerProAsnSerArgLeuThrPheGluGlnAsp

1621 ATAGAGCGTGGCAATACAGATGGTCTGGGGGACTGTCACAATTCC
     IleGluArgGlyAsnThrAspGlyLeuGlyAspCysHisAsnSer
```

Fig. 15 Cont.

```
1666 TTTGTGGCACTGAATGGGCATTCCAGTTCCCTCTTGCCCAGCACA
     PheValAlaLeuAsnGlyHisSerSerSerLeuLeuProSerThr

1711 ACCACATCAGATTCGACGGCTCAAGAGGGGTATGAGTCTAGGGGA
     ThrThrSerAspSerThrAlaGlnGluGlyTyrGluSerArgGly

1756 GGAATGCTGGACTGGAAGCATCTGCTTGACTCACCTGACAGCACA
     GlyMetLeuAspTrpLysHisLeuLeuAspSerProAspSerThr

1801 GACCCTTTGGGGGCAGTGTCTTCCCATAATCACCAAGACAAGAAG
     AspProLeuGlyAlaValSerSerHisAsnHisGlnAspLysLys

1846 GGAGTGATTCGGGAAAGTTACCTCAAAGGCCACGACCAGCTCGAG
     GlyValIleArgGluSerTyrLeuLysGlyHisAspGlnLeuGlu
```

Fig. 15
(Continued)

```
GGATCC AACTGCCCCTCCGTCTGCTCGTGCAGTAACCAGTTCAG
CAAGGTGGTGTGCACGCGCCGGGGCCTCTCCGAGGTCCCGCAGGGTATTCCCTCGAACACCCGGTACCTCAACCTCATGG
AGAACAACATCCAGATGATCCAGGCCGACACCTTCCGCCACCTCCACCACCTGGAGGTCCTGCAGTTGGGCAGGAACTCC
ATCCGGCAGATTGAGGTGGGGGCCTTCAACGGCCTGGCCAGCCTCAACACCCTGGAGCTGTTCGACAACTGGCTGACAGT
CATCCCTAGCGGGGCCTTTGAATACCTGTCCAAGCTGCGGGAGCTCTGGCTTCGCAACAACCCCATCGAAAGCATCCCCT
CTTACGTCTTCAACCGGGTGCCCTCCCTCATGCGCCTGGACTTGGGGGAGCTCAAGAAGCTGGAGTATATCTCTGAGGGA
GCTTTTGAGGGCTGTTCAACCTCAAGTATCTGAACTTGGGCATGTGCAACATTAAAGACATGCCCAATCTCACCCCCCT
GGTGGGGCTGGAGGAGCTGGAGATGTCAGGGAACCACTTCCCTGAGATCAGGCCTGGCTCCTTCCATGCCTGAGCTCCC
TCAAGAAGCTCTGGGTCATGAACTCACAGGTCAGCCTGATTGAGCGGAATGCTTTTGACGGGCTGGCTTCACTTGTGGAA
CTCAACTTGGCCCACAATAACCTCTCTTCTTTGCCCCATGACCTCTTTACCCCGCTGAGGTACCTGGTGGAGTTGCATCT
ACACCACAACCCTTGGAACTGTGATTGTGACATTCTGTGGCTAGCCTGGTGGCTTCGAGAGTATATACCCACCAATTCCA
CCTGCTGTGGCCGCTGTCATGCTCCCATGCACATGCGAGGCCGCTACCTCGTGGAGGTGGACCAGGCCTCCTTCCAGTGC
TCTGCCCCCTTCATCATGGACGCACCTCGAGACCCTCAACATTTCTGAGGGTCGGATGGCAGAACTTAAGTGTCGGACTCC
CCCTATGTCCTCCGTGAAGTGGTTGCTGCCCAATGGGACAGTGCTCAGCCATGCCTCCCGCCACCCAAGGATCTCTGTCC
TCAACGACGGCACCTTGAACTTTTCCCACGTGCTGCTTTCAGACACCGGGTGTACACATGCATGGTGACCAATGTTGCA
GGCAACTCCAACGCCTCGGCCTACCTCAATGTGAGCACGGCTGAGCTTAACACCTCCAACTACAGCTTCTTCACCACAGT
AACAGTGGAGACCACGGAGATCTCGCCTGAGGACACAACGCGAAAGTACAAGCCTGTTCCTACCACGTCCACTGGTTACC
AGCCGGCATATACCACCTCTACCACGGTCGAG
```

Fig. 17A

```
NCPSVCSCSNQFSKVVCTRRGLSEVPQGIPSNTRYLNLMENNIQMIQADTFRHLHHLEVLQLGRNSIRQIEVGAFNG
LASLNTLELFDNWLTVIPSGAFEYLSKLRELWLRNNPIESIPSYAFNRVPSLMRLDLGELKKLEYISEGAFEGLFNL
KYLNLGMCNIKDMPNLTPLVGLEELEMSGNHFPEIRPGSFHGLSSLKKLWVMNSQVSLIERNAFDGLASLVELHLAH
NNLSSLPHDLFTPLRYLVELHLHHNPWNCDCDILWLAWWLREYIPTNSTCCGRCHAPMHMRGRYLVEVDQASFQCSA
PFIMDAPRDLNISEGRMAELKCRTPPMSSVKWLLPNGTVLSHASRHPRISVLNDGTLNFSHVLLSDTGVYTCMYTNV
AGNSNASAYLNVSTAELNTSNYSPFTTVTVETTEISPEDTTRKYKPVPTTSTGYQPAYTTSTT
```

Fig. 17B

POLYNUCLEOTIDES AND PROTEINS ENCODED THEREBY

RELATED APPLICATIONS

This application claims priority to U.S. Ser. No. 60/123,667, filed March 9, 1999, which is incorporated herein by reference in its entirety.

FIELD OF THE INVENTION

The invention relates to polynucleotides and secreted or membrane-associated polypeptides encoded by such polynucleotides, as well as vectors, host cells, antibodies and recombinant methods for producing the polypeptides and polynucleotides.

BACKGROUND OF THE INVENTION

Eukaryotic cells are subdivided by membranes into multiple functionally distinct compartments that are referred to as organelles. Each organelle includes proteins essential for its proper function. These proteins can include sequence motifs often referred to as sorting signals. The sorting signals can aid in targeting the proteins to their appropriate cellular organelle(s). In addition, sorting signals can direct some proteins to be exported, or secreted, from the cell.

One type of sorting sequence is a signal sequence (also referred to as a signal peptide or leader sequence). The signal sequence is present as an amino-terminal extension on a newly synthesized polypeptide chain A signal sequence targets proteins to an intracellular organelle called the endoplasmic reticulum (ER).

The signal peptide takes part in an array of protein-protein and protein-lipid interactions that result in translocation of a polypeptide containing the signal sequence through a channel in the ER. After translocation, a membrane-bound enzyme (signal peptidase) liberates the mature protein from the signal sequence.

The ER functions to separate membrane-bound proteins and secreted proteins from proteins that remain in the cytoplasm. Once targeted to the ER, both secreted and membrane-bound proteins can be further distributed to another cellular organelle called the Golgi apparatus. The Golgi directs the proteins to vesicles, lysosomes, the plasma membrane, mitochondria and other cellular organelles.

Only a limited number of genes encoding human membrane-bound and secreted proteins have been identified. Examples of known secreted proteins include human insulin, interferon, interleukins, transforming growth factor-beta, human growth hormone, erythropoietin, lymphokines. A need exists for identifying and characterizing additional novel human secreted proteins and the genes that encode them.

SUMMARY OF THE INVENTION

The present invention is based, in part, upon the discovery of novel human polynucleotide sequences and the membrane-bound or secreted polypeptides encoded by these sequences. Polypeptides of the invention include a chemokine receptor-like protein (clone 2777610), semaphorin protein-like splice variants (assembled clones 2864933-1 and 2864933-2, and the pCEP4/Sec-2864933 vector and cDNA clone pCR2.1-2864933), a putative mitochondrial protein (clone 2982339), SLIT protein-like splice variants (assembled clones 3352358-1 and 3352358-2 and the cDNA clone 3352358-S153A), a putative microbody (peroxisome) associated protein (clones 3884846, 3884846-1 and 3884846-2), a tetraspanin-like protein (clones 3911675 and 3911675-2), a putative proline-rich membrane protein (clones 4004056 and 4004056.0.143u), a laminin β-chain precursor-like protein (clone 4004731-1), AVENA protein-like splice variants (clones 4009334-1 and 4009334-2), a fetal lung-associated protein (clone 4035508) and a myeloid upregulated protein (clone 4339264). These polynucleotides and the polypeptides encoded thereby are collectively referred to as the SECX gene set, the sequences of which are disclosed in SEQ ID NOs:1–32.

In one aspect, the invention includes an isolated SECX nucleic acid molecule which includes a nucleotide sequence encoding a polypeptide that includes the amino acid sequence of one or more of SEQ ID NOs:2, 4, 6, 8, 10, 12, 14, 16, 18, 20, 22, 24, 26, 28, 30, 32, 75, 77, 79 and 81. For example, in various embodiments, the nucleic acid can include a nucleotide sequence that includes SEQ ID NOs:1, 3, 5, 7, 9, 11, 13, 15, 17, 19, 21, 23, 25, 27, 29, 31, 74, 76, 78 and 80. Alternatively, the encoded SECX polypeptide may have a variant amino acid sequence, e.g., have an identity or similarity less than 100% to the disclosed amino acid sequences, as described herein.

The invention also includes an isolated polypeptide that includes the amino acid sequence of one or more of SEQ ID NOs 2, 4, 6, 8, 10, 12, 14, 16, 20, 22, 24, 26, 28, 30, 32, 34, 36, 38, 40, 42, 44, 46, or 48: or a fragment having at least 15 amino acids of these amino acid sequences. Also included is a naturally occurring polypeptide variant of a SECX polypeptide, wherein the polypeptide is encoded by a nucleic acid molecule which hybridizes under stringent conditions to a nucleic acid molecule consisting of a SECX nucleic acid molecule.

Also included in the invention is an antibody which selectively binds to a SECX polypeptide.

The invention further includes a method for producing a SECX polypeptide by culturing a host cell expressing one of the herein described SECX nucleic acids under conditions in which the nucleic acid molecule is expressed.

The invention also includes methods for detecting the presence of a SECX polypeptide or nucleic acid in a sample from a mammal, e.g., a human, by contacting a sample from the mammal with an antibody which selectively binds to one of the herein described polypeptides, and detecting the formation of reaction complexes including the antibody and the polypeptide in the sample. Detecting the formation of complexes in the sample indicates the presence of the polypeptide in the sample.

The invention further includes a method for detecting or diagnosing the presence of a disease, e.g., a pathological condition, associated with altered levels of a polypeptide having an amino acid sequence at least 80% identical to a SECX polypeptide in a sample. The method includes measuring the level of the polypeptide in a biological sample from the mammalian subject, e.g., a human, and comparing the level detected to a level of the polypeptide present in normal subjects, or in the same subject at a different time, e.g., prior to onset of a condition. An increase or decrease in the level of the polypeptide as compared to normal levels indicates a disease condition.

Also included in the invention is a method of detecting the presence of a SECX nucleic acid molecule in a sample from a mammal, e.g., a human. The method includes contacting the sample with a nucleic acid probe or primer which selectively hybridizes to the nucleic acid molecule and determining whether the nucleic acid probe or primer binds to a nucleic acid molecule in the sample. Binding of the nucleic acid probe or primer indicates the nucleic acid molecule is present in the sample.

The invention further includes a method for detecting or diagnosing the presence of a disease associated with altered levels of a SECX nucleic acid in a sample from a mammal, e.g,. a human. The method includes measuring the level of the nucleic acid in a biological sample from the mammalian subject and comparing the level detected to a level of the nucleic acid present in normal subjects, or in the same subject at a different time. An increase or decrease in the level of the nucleic acid as compared to normal levels indicates a disease condition.

The invention also includes a method of treating a pathological state in a mammal, e.g,. a human, by administering to the subject a SECX polypeptide to the subject in an amount sufficient to alleviate the pathological condition. The polypeptide has an amino acid sequence at least 80% identical to a SECX polypeptide.

Alternatively, the mammal may be treated by administering an antibody as herein described in an amount sufficient to alleviate the pathological condition.

Pathological states for which the methods of treatment of the invention are envisioned include a cancer, e.g. colorectal carcinoma, a prostate cancer a benign tumor, an immune disorder, an immune deficiency, an autoimmune disease, acquired immune deficiency syndrome, transplant rejection, allergy, an infection by a pathological organism or agent, an inflammatory disorder, arthritis, a hematopoietic disorder, a skin disorder, atherosclerosis, restenosis, a neurological disease, Alzheimer's disease, trauma, a surgical or traumatic wound, a spinal cord injury, and a skeletal disorder.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In the case of conflict, the present specification, including definitions, will control. In addition, the materials, methods, and examples are illustrative only and not intended to be limiting.

Other features and advantages of the invention will be apparent from the following detailed description and claims.

BRIEF DESCRIPTION OF THE DRAWINGS

FIG. 1 is a representation of the nucleotide and encoded polypeptide sequences of clone 2777610.

FIG. 2 is a representation of the nucleotide and encoded polypeptide sequences of clone 2864933-1.

FIG. 3 is a representation of the nucleotide and encoded polypeptide sequences of clone 2864933-2.

FIG. 4 is a representation of the nucleotide and encoded polypeptide sequences of clone 2982339.

FIG. 5 is a representation of the nucleotide and encoded polypeptide sequences of clone 3352358-1.

FIG. 6 is a representation of the nucleotide and encoded polypeptide sequences of clone 3352358-2.

FIG. 7 is a representation of the nucleotide and encoded polypeptide sequences of clone 3884846 (FIG. 7A), clone 3884846-1 (FIG. 7B), and clone 3884846-2 (FIG. 7C).

FIG. 8 is a representation of the nucleotide and encoded polypeptide sequences of clone 3911675 (FIG. 8A) and clone 3911675-2 (FIG. 8B).

FIG. 9 is a representation of the nucleotide and encoded polypeptide sequences of clone 4004056 (FIG. 9A) and clone 4004056.0.143u (FIG. 9B).

FIG. 10 is a representation of the nucleotide and encoded polypeptide sequences of clone 4004731-1.

FIG. 11 is a representation of the nucleotide and encoded polypeptide sequences of clone 4009334-1.

FIG. 12 is a representation of the nucleotide and encoded polypeptide sequences of clone 4009334-2.

FIG. 13 is a representation of the nucleotide and encoded polypeptide sequences of clone 4035508.

FIG. 14 is a representation of the nucleotide and encoded polypeptide sequences of clone 4339264.

FIG. 15 is a representation of the nucleotide and encoded polypeptide sequences of the cDNA clone pCR2.1-2864933.

FIG. 17 depicts the nucleotide (panel A) and amino acid (panel B) sequences obtained for the cDNA clone 3352358-S153A, which comprises the extracellular domain of 3352358-1, wherein the underlined sequences depict flanking sequence.

DETAILED DESCRIPTION OF THE INVENTION

Figure 16:
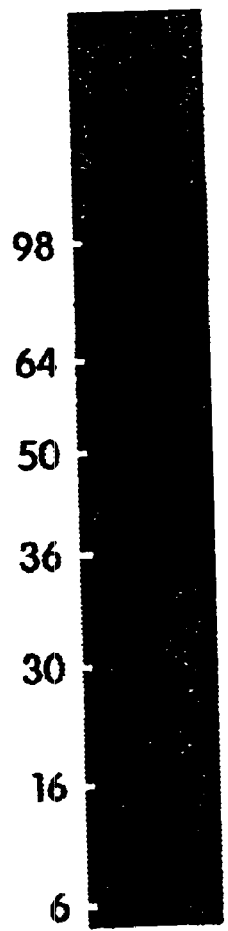
FIG. 16 depicts the Western blot after reducing SDS-PAGE of expression of the pCEP4/Sec-2864933 vector in 293 cells.

The present invention is based, in part, upon the discovery of novel polynucleotide sequences and the membrane-bound or secreted polypeptides encoded by these sequences. Polypeptides encoded by nucleotides of the invention include clone 2777610 (a chemokine receptor-like protein, SEQ ID NOS:1–2); assembled clones 2864933-1 and 2864933-2 and the pCEP4/Sec-2864933 vector and cDNA clone pCR2.1-2864933 (semaphorin protein-like splice variants, SEQ ID NOS:3–6, 29–30); clone 2982339 (a putative mitochondrial protein, SEQ ID NOS:7–8), assembled clones 3352358-1 and 3352358-2 and the cDNA clone 3352358-S153A (SLIT protein-like splice variants, SEQ ID NOS:9–12, 31–32); clones 3884846, 3884846-1 and 3884846-2 (putative microbody/peroxisome associated protein splice variants, SEQ ID NOS:13–14 and 74–77), clones 3911675 and 3911675-2 (tetraspanin-like protein splice variants SEQ ID NOS:15–16 and 78–79); clones 4004056 and 4004056.0.143u (putative proline-rich membrane protein splice variants, SEQ ID NOS:17–18 and 80–81); clone 4004731-1 (a laminin β-chain precursor-like protein, SEQ ID NOS:19–20); clones 4009334-1 and 4009334-2 (AVENA protein-like splice variants, SEQ ID NOS:21–24); clone 4035508 (a novel fetal lung-associated protein, SEQ ID NOS:25–26); and clone 4339264 (a myeloid upregulated protein, SEQ ID NOS:27–28). These genes are collectively referred to as the SECX gene set. The polynucleotides and polypeptides are set forth in Table 1. Table 1 lists the SEQ ID NOs for each nucleotide and amino acid sequence of the invention, as well as SEQ ID NOs for the primers specific to the clones of this invention that were employed in various aspects and embodiments described herein.

TABLE 1

Sequences and Corresponding SEQ ID Numbers

| Clone or Primer No. | FIG. | Nucleic acid SEQ ID NO: | Protein SEQ ID NO: |
|---|---|---|---|
| 2777610 | 1 | 1 | 2 |
| 2864933-1 | 2 | 3 | 4 |
| 2864933-2 | 3 | 5 | 6 |
| 2982339 | 4 | 7 | 8 |
| 3352358-1 | 5 | 9 | 10 |
| 3352358-2 | 6 | 11 | 12 |
| 3884846 | 7A | 13 | 14 |
| 3884846-1 | 7B | 74 | 75 |
| 3884846-2 | 7C | 76 | 77 |
| 3911675 | 8A | 15 | 16 |
| 3911675-2 | 8B | 78 | 79 |
| 4004056 | 9A | 17 | 18 |
| 4004056.0.143u | 9B | 80 | 81 |
| 4004731-1 | 10 | 19 | 20 |
| 4009334-1 | 11 | 21 | 22 |
| 4009334-2 | 12 | 23 | 24 |
| 4035508 | 13 | 25 | 26 |
| 4339264 | 14 | 27 | 28 |
| pCR2.1-2864933 | 15 | 29 | 30 |
| 3352358-S153A | 17A, 17B | 31 | 32 |
| 2864933 MatF | | 33 | |
| 2864933 F-TOPO-Reverse | | 34 | |
| 2864933-Seq-0 | | 35 | |
| 2864933-Seq-1 | | 36 | |
| 2864933-Seq-2 | | 37 | |
| 2864933-Seq-3 | | 38 | |
| 2864933-Seq-4 | | 39 | |
| 2864933-Seq-5 | | 40 | |
| 2864933-Seq-6 | | 41 | |
| pSec-V5-His Forward | | 42 | |
| pSec-V5-His Reverse | | 43 | |
| 3352358CForward | | 44 | |
| 3352358CReverse | | 45 | |
| 3352358 Seq-1 | | 46 | |
| 3352358 Seq-2 | | 47 | |
| 3352358 Seq-3 | | 48 | |
| 3352358 Seq-4 | | 49 | |
| Ag 111 (F) | | 50 | |
| Ag 111 (R) | | 51 | |
| Ag 111 (P) | | 52 | |
| Ag 88 (F) | | 53 | |
| Ag 88 (R) | | 54 | |
| Ag 88 (P) | | 55 | |
| Ag 291 (F) | | 56 | |
| Ag 291 (R) | | 57 | |
| Ag 291 (P) | | 58 | |
| Ag 341 (F) | | 59 | |
| Ag 341 (R) | | 60 | |
| Ag 341 (P) | | 61 | |
| Ag 42 (F) | | 62 | |
| Ag 42 (R) | | 63 | |
| Ag 42 (P) | | 64 | |
| Ag 115 (F) | | 65 | |
| Ag 115 (R) | | 66 | |
| Ag 115 (P) | | 67 | |
| Ag 118 (F) | | 68 | |
| Ag 118 (R) | | 69 | |
| Ag 118 (P) | | 70 | |
| Ag 120 (F) | | 71 | |
| Ag 120 (R) | | 72 | |
| Ag 120 (P) | | 73 | |

1. Clone 2777610

Clone 2777610 is a 1812 bp nucleic acid sequence (SEQ ID NO:1) that was originally identified in bone tissue, which includes bone marrow. The full length clone (FIG. 1) was further assembled from sequences expressed in bone tissues. An open reading frame ("ORF") encoding a polypeptide (SEQ ID NO:2) having 333 amino acid residues is found at nucleotides 537–1535 (FIG. 1). The nucleotide sequence includes a Kozak sequence. The stop codon TGA is found at nucleotides 1536–1538. The results of a PSORT analysis predict that the protein is localized in the plasma membrane with a certainty of 0.6000. The SignalP program predicts that a signal sequence occurs with a most likely cleavage site between residues 44 and 45, represented by the dash between the amino acids TLA-LW (i.e., ThrLeuAla-LeuTrp).

The protein of clone 2777610 has 332 of 333 residues both (99%) identical and positive to a human seven transmembrane receptor protein designated HNEAA81 (European Patent number 913471-A2). As used herein, "identical" residues correspond to those residues in a comparison between two sequences where the equivalent nucleotide base or amino acid residue in an alignment of two sequences is the same residue. Residues are "positive" when the comparisons between two sequences in an alignment show that residues in an equivalent position in a comparison are either the same amino acid or a conserved amino acid as defined below. Clone 2777610 was also found to have 328 of 333 residues both (98%) identical and positive to a human chemokine receptor-like protein (PCT Publication WO9839441-A1). A weaker similarity was also detected for a 338 residue human probable G protein-coupled receptor KIAA0001 (GenBank Accession number Q15391).

Members of the G protein-coupled receptor (GPCR) superfamily contain seven transmembrane domains and transduce extracellular signals through heterotrimeric G proteins. G-protein-coupled receptors (GPCRs) are integral membrane proteins of great pharmacological importance owing to their central role in the regulation of cellular responses to external stimuli. See, for example, Marchese et al., 1999 *Trends Pharmacol Sci* 20(9): 370–5; and Rozengurt 1998 *J Cell Physiol* 177(4):507–17.

GPCR receptors specifically bind select neurotransmitters and peptide hormones, and are likely to underlie the recognition and G-protein-mediated transduction of various signals. These signals activated by ligand-bound GPCRs have been implicated in a variety of normal and abnormal processes, including development, inflammation, and malignant transformation (matrix invasion, motility, chemotaxis, adhesion, growth and survival signaling). These signaling peptides exert their characteristic effects on cellular processes by binding to specific GPCRs on the surface of their target cells. Typically, the binding of a neuropeptide to its cognate GPCR triggers the activation of multiple signal transduction pathways that act in a synergistic and combinatorial fashion to relay the mitogenic signal to the nucleus and promote cell proliferation. A rapid increase in the synthesis of lipid-derived second messengers with subsequent activation of protein phosphorylation cascades is an important early response to neuropeptides. An emerging theme in signal transduction is that these agonists also induce rapid and coordinate tyrosine phosphorylation of cellular proteins including the nonreceptor tyrosine kinase p125fak and the adaptor proteins p130cas and paxillin. This tyrosine phosphorylation pathway depends on the integrity of the actin cytoskeleton and requires functional Rho.

The Clone 2777610 protein is a seven transmembrane receptor protein with chemokine receptor-like properties.

Clone 2777610 is a G protein coupled receptor (GPCR) that is a likely gamma-aminobutyric acid receptor, in the class of P2Y-like GPCRs. As such, Clone 2777610 is useful in diagnosing and/or treating pathologies and disorders associated with G-protein coupled receptor metabolism, e.g., bacterial disease; asthma; fungal disease; viral disease; HIV-1; HIV-2; cancer; anorexia; Parkinson's disease; hypertension; osteoporosis; myocardial infarction; manic depression; schizophrenia; Gilles dela Tourett's syndrome; inflammatory disorder; and viral infection.

Based on the roles of other GPCRs and the high expression of 2777610 in lymphoid tissue such as the spleen, bone marrow, lymph node (see Example 6), the inventor anticipates that successful therapeutic targeting of 2777610, using either small molecules that inhibit transmembrane signaling by 2777610 or monoclonal antibodies designed to block the interaction of 2777610 with ligand(s), might have utility in modulating lymphoproliferative disorders (myeloma, myeloid leukemia, non-Hodgkin's lymphoma, etc.) or autoimmune diseases (SLE, etc.) or both. Likewise, with respect to the high expression of 2777610 in whole adult human brain, hippocampus, substantia nigra and spinal cord, modulation of 2777610 signaling using the approaches described above will have clinical utility to modulate certain neurodegenerative disorders affecting motor function.

2. Clone 2864933-1

Clone 2864933-1 includes a nucleic acid sequence (SEQ ID NO:3) including 3498 nucleotides (FIG. 2). This clone is similar to clone 2864933-2 (below) with the exception that 2864933-1 has an insert of 164 nucleotides at positions 1942–2106. The gene fragment giving rise to this clone was found in mainly in heart tissue. Fragments included in this gene were also found in lymph node, pancreas, thalamus, brain, salivary gland and adrenal gland. Clone 2864933-1 includes a Kozak sequence, a start codon at nucleotides 214–216, and a TAA termination codon at nucleotides 3031–3033. The nucleotide residues between 214–3030 define an ORF encoding a protein (SEQ ID NO:4) of 939 amino acid residues (FIG. 2). Molecular cloning and expression of a fragment corresponding to the putative mature extracellular domain of 2864933-1 is given in Examples 2 and 3. The PSORT program predicts that the 2864933-1 protein localizes to the plasma membrane with a certainty of 0.4600. The protein is a likely Type I transmembrane protein, with the predicted transmembrane domain between residues 645–661 of SEQ ID NO:4. The SignalP program predicts that the protein has a signal peptide cleavage site between residues 18 and 19, represented by the dash between the amino acids AGA-GF (i.e., AlaGlyAla-Gly Phe).

The 2864933-1 protein is 94% identical, and 97% similar, to a murine semaphorin polypeptide having 888 amino acid residues (GenBank Accession Number AAB86408). In addition, it shows 35% identity and 53% similarity to human semaphorin III (GenBank Accession Number AAA65938). For these reasons the 2864933-1 polypeptide is believed to be a cytokine-like growth factor.

The semaphorin (a.k.a. collapsin) family of molecules plays a critical role in the guidance of nerve growth cones during neuronal development. The family is characterized by the presence of a conserved semaphorin domain at the amino terminus. Mutational analysis of human semaphorin A(V) revealed mutations (germline in 1 case) in 3 of 40 lung cancers. Semaphorin E is responsible for a non-MDR drug resistance in human cancers including ovarian cancer and is overexpressed in CDDP-resistant cell lines as well as induced by diverse chemotherapeutic drugs and by X-ray and UV irradiation. Yamada et al. 1997 *Proc. Nat. Acad. Sci.* 94: 14713–14718. Human semaphorin E mRNA is up-regulated in synovial fibroblasts of rheumatoid arthritis patients. Mangasser-Stephan et al. 1997 *Biochem. Biophys. Res. Commun.* 234: 153–156. Human neuropilin-1, a receptor for the collapsin/semaphorin family that mediates neuronal cell guidance, is expressed by endothelial and tumor cells as an isoform-specific receptor for vascular endothelial growth factor and is believed to regulate VEGF-induced angiogenesis. Soker et al. 1998 *Cell* 92: 735–745.

Semaphorins, the plexin family of semaphorin receptors, and scatter factor receptors share evolutionarily conserved protein modules, e.g., the semaphorin domain and Met Related Sequences (MRS). Artigiani et al., 1999, *IUBMB Life* 48(5):477–82. These proteins have a common role of mediating cell guidance cues. During development, scatter factor receptors control cell migration, epithelial tubulogenesis, and neurite extension. Semaphorins and their receptors are known signals for axon guidance. They are also believed to regulate developmental processes involving cell migration and morphogenesis, and have been implicated in immune function and tumor progression. Scatter factors and secreted semaphorins are diffusible ligands, whereas membrane-bound semaphorins signal by cell-cell interaction. Cell guidance control by semaphorins requires plexins, alone or in a receptor complex with neurophilins. Semaphorins, besides their role in axon guidance, are expected to have multiple functions in morphogenesis and tissue remodeling by mediating cell-repelling cues through plexin receptors.

The potential roles of the 2864933 protein in tumorgenesis include development of chemoresistance, radiotherapy resistance, survival in trophic factor limited secondary tissue site microenvironments, potential involvement in enhancing VEGF-induced angiogenesis.

Based on the reported roles of semaphorins summarized herein it is anticipated that successful therapeutic targeting of 2864933 and/or its splice variants will result in significant anti-tumor activity in combination with established cytotoxic/genotoxic therapies (i.e. chemosensitization, radiosensitization). Additionally, the semaphorins play roles in axon outgrowth and neuronal cell migration. In this regard successful therapeutic targeting of 2864933-1 and/or 2864933-2 might also limit the extent (frequency) of metastatic dissemination (tumor burden) and potentially limit tumor angiogenesis. Therapeutic targeting of 2864933 and its splice variants is also provided via the generation of human or humanized monoclonal antibodies that block the ability of 2864933-1 or 2864933-2 to interact with cognate ligand(s) and elicit a transmembrane signal(s). Equally, the generation of small molecules (synthetics, cell permeable peptides, other) than specifically interfere with one or more of the downstream signaling components in the pathway(s) activated by ligand-bound 2864933-1 and/or 2864933-2 would be expected to have significant anti-tumor activity as described above. Likewise, the introduction of antisense constructs (naked DNA, adenoviral constructs), ribozymes to inhibit the expression of 2864933-1 and/or 2864933-1 would be expected to have significant anti-tumor activity as described above.

Figure 19A:
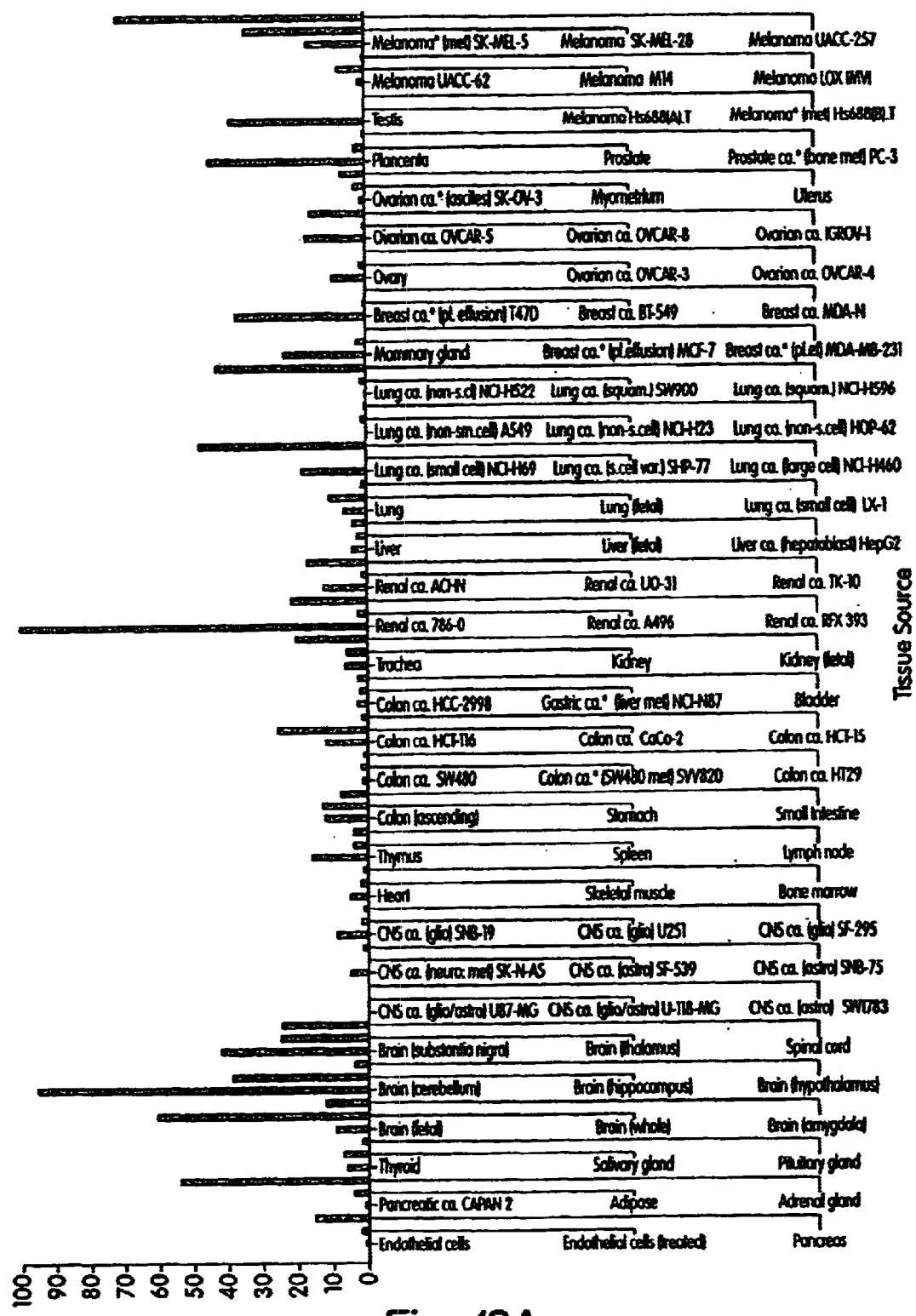
FIG. 19 depicts real time quantitative PCR (TaqMan™) analysis of the expression of clone 2864933 utilizing primer-probe set 88 (Panel A), primer-probe set 291 (Panel B), and primer-probe set 341 (Panel C).
Figure 19B:
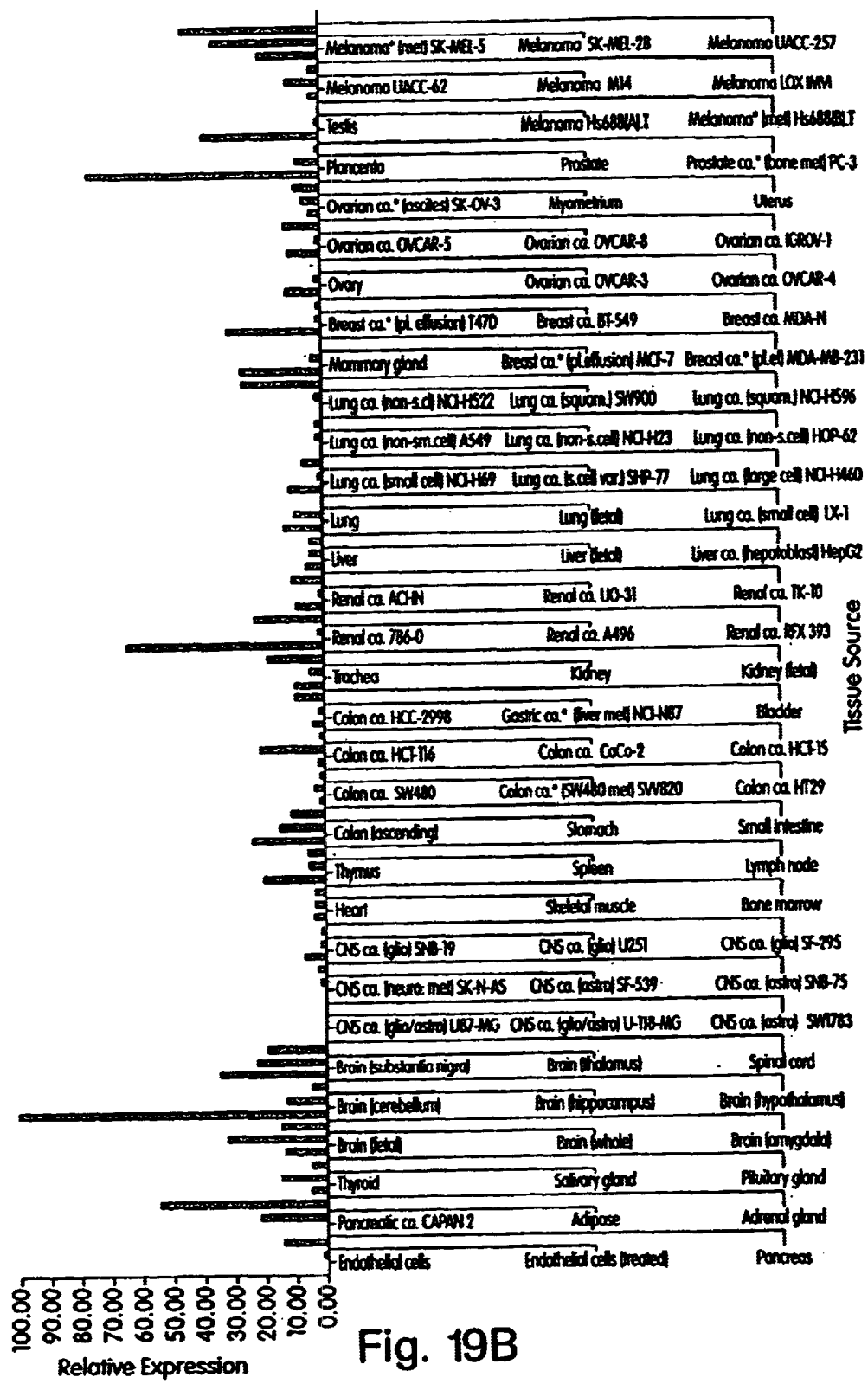
Figure 19C:
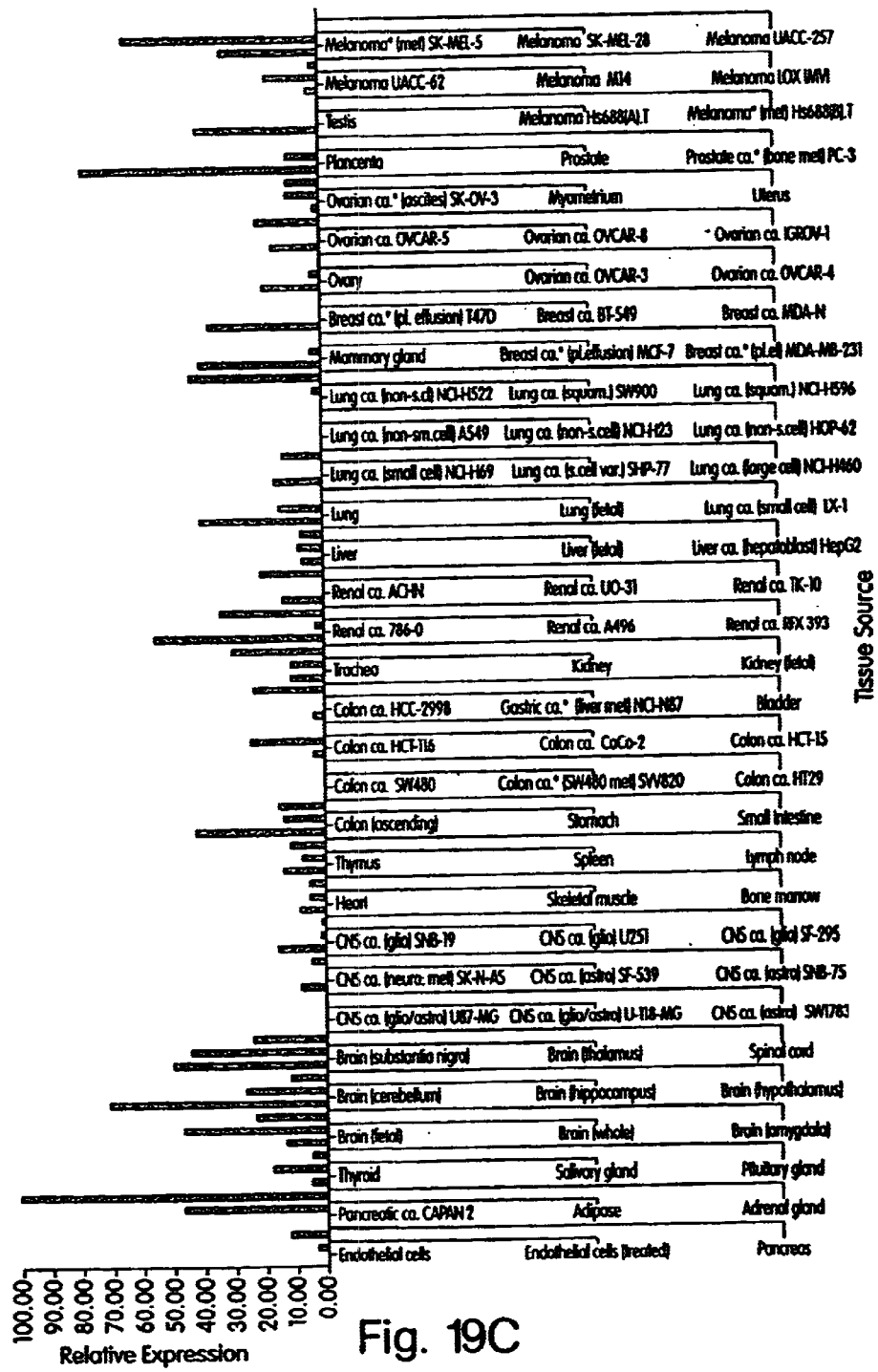

Based on the expression profiles of the 2864933-1 and 2864933-2 transcripts set forth in Example 7 and FIGS. 19A, 19B and 19C, therapeutic indications for targeting 2864933-1 and 2864933-2include renal cell carcinomas, small cell lung cancers, large cell variants of small cell lung cancer, breast adenocarcinomas, and malignant melanomas. Clones 2864933-1 and 2864933-2 are useful in diagnosing and/or treating pathologies related to developmental malfunction, especially in the nervous system, and in treatment of CNS pathologies, e.g., Alzheimer's disease and parkinsonism.

3. Clone 2864933-2

Clone 2864933-2 has a nucleic acid sequence (SEQ ID NO:5) of 3333 nucleotides (FIG. 3). This clone is similar to clone 2864933-1 (above; FIG. 2) with the exception that 2864933-1 has an insert of 164 nucleotides at positions 1942-2106(according to the SEQ ID NO:3 numbering for clone 2864933-1). This difference appears to be an RNA splicing variation. The gene fragment giving rise to this clone 2864933-2 was found mainly in heart tissue. Transcribed sequences from this gene are also found in lymph node, pancreas, thalamus, brain, salivary gland and adrenal gland. Clone 2864933-1 includes a Kozak sequence, a start codon at nucleotides 214–216, and a TAA termination codon at nucleotides 2866–2868. The nucleotides between 214 and 2865 thus define an ORF encoding a protein (SEQ ID NO:6) of 884 amino acid residues (FIG. 3). The PSORT program predicts that the 2864933-1 protein localizes to the plasma membrane with a certainty of 0.4600. The SignalP program predicts that the protein most likely has a signal peptide cleavage site between residues 18 and 19, represented by the dash between the amino acids AGA-GF (i.e., AlaGlyAla-GlyPhe).

The 2864933-2 protein is 95% identical, and 97% similar to murine semaphorin having 888 amino acid residues (GenBank Accession number AAB86408). In addition, it shows 38% identity and 55% similarity to human semaphorin III (GenBank Accession number AAA65938).

The 2864933-2 protein was also found to have 869 of 877 residues (99%) identical, and 871 of 877 residues (99%) positive, to the 974 residue human secreted protein from a clone designated CJ145-1 (PCT Publication WO9827205-A2). The 2864933-2 sequence was isolated from a human fetal brain cDNA library and is a novel secreted protein distinct from clone CJ145-1 in both size and sequence. Clone 2864933-2 is useful for cytokine and cell proliferation/differentiation activity, immune stimulating or suppressing activity, hematopoiesis regulating activity, tissue growth activity, activin/inhibin activity, chemotactic/chemokinetic activity, hemostatic and thrombotic activity, receptor/ligand activity, anti-inflammatory activity, cadherin/tumor invasion suppressor activity, tumor inhibition activity and other activities. The Clone 2864933-2 is also useful in diagnosing and/or treating pathologies related to developmental malfunction, especially in the nervous system, and in the treatment of CNS pathologies, e.g., Alzheimer's disease and parkinsonism.

4. Clone 2982339

Clone 2982339 has a sequence (SEQ ID NO:7) of 856 nucleotides (FIG. 4), including a Kozak sequence, an initiation codon at positions 138–140 and a TGA stopcodon at positions 726–728. This sequence between residues 138 to 725 defines an open reading frame encoding a protein (SEQ ID NO:8) of 196 amino acid residues (FIG. 4). The clone originated from fetal brain and was assembled using 65 sequences from fetal thymus and placenta. Fragments for this clone are also found in human placenta, thymus gland, thyroid gland, and bone, including osteosarcomas. The PSORT predicts that the 2982339 protein localizes to the mitochondrial matrix space with a certainty of 0.7077. SignalP suggests that the protein may have no known N-terminal signal sequence.

The 2982339 protein has 16 of 54 residues (29%) identical to, and 24 of 54 residues (44%) positive with, an artificial sequence of 109 residues that is an aprotinin analogue precursor (GenBank Accession numbers AAB54954 and AAB54956). Aprotinin, also known as pancreatic trypsin inhibitor precursor or basic protease inhibitor, is an intracellular polypeptide found in many tissues, and is a known inhibitor of trypsin, kallikrein, chymotrypsin, and plasmin. GenBank Accession number P00974; Creighton and Charles, 1987 *J. Mol. Biol.* 194 (1): 11–22.

5. Clone 3352358-1

Clone 3352358-1 includes a 2341 nucleotide sequence (SEQ ID NO:9) (FIG. 5) with an initiation codon at nucleotides 215–217 and a TAA stop codon at nucleotides 2174–2176. This sequence between residues 215 to 2173 defines an ORF encoding a protein (SEQ ID NO:10) of 653 residues (FIG. 5). The clone was identified by a polynucleotide fragment originating in fetal liver. Expressed sequences are also found in liver, including fetal liver, kidney, including fetal kidney, and thalamus. The PSORT program predicts that the 3352358-1 protein localizes to the plasma membrane with a certainty of 0.46. The SignalP program predicts that the protein has a signal peptide, with the most likely cleavage site between residues 38 and 39, represented by the dash between the amino acids AAA-AS (i.e., AlaAlaAla-AlaSer), or between residues 41 and 42, represented by the dash between the amino acids ASA-GP (i.e., AlaSerAla-GlyPro). The protein is predicted to be a Type I transmembrane protein with the transmembrane domain located between residues 522 and 551.

The 3352358-1 protein has 35% of its residues identical, and 48% of its residues similar to, human slit-1 protein, a protein of 1534 residues (GenBank Accession number BAA35184). 3352358-1 protein is also 39% identical and 46% similar to human slit-3 protein, a protein of 1523 residues (GenBank Accession number BAA35186); and 40% identical and 48% similar to the human neurogenic extracellular slit protein slit-2 having 1521 residues (GenBank Accession number AAD04309). The 3352358-1 protein has an overall 53% identity to a hypothetical 45.1 kDa protein (GenBank Accession number CAB70473).

The slit genes encode proteins with a conserved chemorepulsive activity for axons in invertebrates and vertebrates. Chen et al., 2000, *Neuroscience* 96: 231–236; Yuan et al., 1999 *Dev Biol* 212: 290–306. For example, the binding of Slit to Roundabout, expressed on the cell surface, is implicated in neuronal guidance activity. Thus, Slit proteins may guide axon projections in multiple regions of the embryo.

By analogy, Clone 3352358-1 has diagnostic and therapeutic utility in pathologies related to neural development and in CNS pathologies, e.g., Alzheimer's disease and parkinsonism.

Molecular cloning and expression of the putative mature extracellular domain of 3352358-1 is described in Examples 4 and 5. This cloned fragment originated from cDNA samples obtained from human testis and fetal brain. The resulting clone, designated clone 3352358-S153A, differs in sequence from that shown in FIG. 5. The respective 3352358-S153A nucleotide sequence is disclosed in FIG. 17A (SEQ ID NO:31) and polypeptide sequence is disclosed in FIG. 17B (SEQ ID NO: 32). One reason for the sequence difference between the 3352358-1 clone and 3352358-S153A cDNA is likely the tissue or organ sources of the cDNAs. If so, this finding represents a tissue-specific or organ-specific basis for allelic variants (also known as isoforms) of proteins, e.g., the disclosed 3352358-1 slit-like protein. The 3352358-1 and 3352358-S153A clones will thus have utility in identifying those tissue or cell types that express these allelic or splice variants.

The 3352358 sequence is related to MEGF (multiple epidermal growth factor-like domains)/Slit family and roundabout. The domain that characterizes epidermal growth factor consists of approximately 50 amino acids with 3 disulfide bonds. EGF-like domains are believed to play a critical role in a number of extracellular events, including cell adhesion and receptor-ligand interactions. Proteins with EGF-like domains often consist of more than 1,000 amino acids, have multiple copies of the EGF-like domain, and contain additional domains known to be involved in specific protein-protein interactions.

Important members of this family include fat tumor suppressor, (Drosophila, homolog of, 2; fat2). The Drosophila fat gene is a tumor suppressor gene whose product controls cell proliferation and morphogenesis in the imaginal discs in a contact-dependent manner. Another relative of 3352358 is Slit1 (also known as MEGF4), a Drosophila gene involved in the formation and maintenance of the nervous and endocrine systems. Another relative of 3352358 is roundabout, a Drosophila gene that controls axon crossing of the CNS midline and defines a novel subfamily of evolutionarily conserved guidance receptors. Kidd et al. 1998 *Cell* 92: 205–215; Nakayama et al. 1998 *Genomics* 51: 27–34.

The potential role(s) of 3352358 in Tumorgenesis include chemoresistance, radiotherapy resistance, survival in trophic factor limited secondary tissue site microenvironments, potential involvement in angiogenesis.

Based on the reported roles of MEGFs/SLITs/Roundabout described herein it is anticipated that successful therapeutic targeting of 3352358 and/or its splice variants will result in significant anti-tumor activity in combination with established cytotoxic/genotoxic therapies (i.e. chemosensitization, radiosensitization). Additionally, the semaphorins play roles in axon outgrowth and neuronal cell migration. In this regard successful therapeutic targeting of 3352358 might also limit the extent (frequency) of metastatic dissemination (tumor burden) and potentially limit tumor angiogenesis. Therapeutic targeting of 3352358 and its splice variants will also be provided via the generation of human or humanized monoclonal antibodies that block the ability of 3352358 to interact with cognate ligand(s) and elicit a transmembrane signal(s). Equally, the generation of small molecules (synthetics, cell permeable peptides, other) than specifically interfere with one or more of the downstream signaling components in the pathway(s) activated by ligand-bound 3352358 will have significant anti-tumor activity as described above. Likewise, the introduction of antisense constructs (naked DNA, adenoviral constructs), ribozymes to inhibit the expression of 3352358 will have significant anti-tumor activity as described above.

Figure 20:
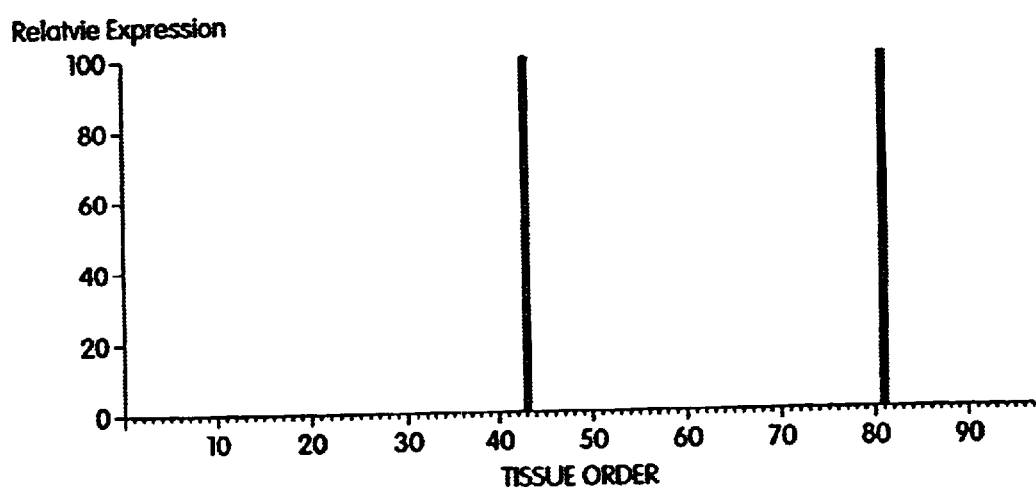
FIG. 20 depicts real time quantitative PCR (TaqMan™) analysis of the expression of 3352358.

Based on the expression profiles of the 3352358 transcripts presented in Example 8 and FIG. 20, the therapeutic indications for targeting 3352358 include select hepatomas/hepatocellular carcinomas and renal cell carcinomas.

6. Clone 3352358-2

Clone 3352358-2 of 2607 nucleotides (SEQ ID NO:11) includes a Kozak sequence, an initiation codon at nucleotides 215–217 and a TAA termination codon at nucleotides 1985–1987 (FIG. 6). This sequence between residues 215 to 1984 defines an ORF encoding a protein (SEQ ID NO:12) of 590 residues (FIG. 6). The PSORT program predicts that the 3352358-2 localizes in the plasma membrane. The SignalP program predicts that the protein has a signal peptide, with the most likely cleavage site between residues 38 and 39, represented by the dash between the amino acids AAA-AS (ie., AlaAlaAla-AlaSer). This clone originates in human liver, including adult and fetal liver. Transcribed sequences from this gene are found in liver, including fetal liver, bone, including bone marrow, brain, and the pituitary gland.

Similarity searches indicate that the 3352358-2 protein is 35% identical and 48% similar with human slit-1 protein (GenBank Accession number BAA35184) having 1534 residues. The slit genes encode proteins with a conserved chemorepulsive activity that affects axons from both invertebrates and vertebrates. Chen et al., 2000, *Neuroscience* 96(1):231–236; Yuan et al., 1999 *Dev Biol* 212(2):290–306. Binding of Slit to the Roundabout protein expressed on a cell surface is implicated in this neuronal guidance activity. Thus Slit proteins guide axon projections in multiple regions of the developing embryo.

Clone 3352358-2 will have diagnostic and therapeutic utility in pathologies related to neural development and CNS pathologies, e.g., Alzheimer's disease and parkinsonism.

7. Clone 3884846

Clone 3884846 includes a polynucleotide (SEQ ID NO:13) of 1340 nucleotides (FIG. 7A) having a Kozak sequence, an initiation codon at nucleotides 421–423 and a TAG stop codon at nucleotides 1288–1290. This sequence between residues 421 through 1287 defines an ORF encoding a protein (SEQ ID NO:14) of 289 amino acid residues (FIG. 7A). Transcribed sequences from this gene are found in pituitary gland, testis, kidney, including fetal kidney, brain, including fetal brain, pituitary gland, placenta, pancreas, testis, spleen kidney, including fetal kidney, fetal liver, skeletal muscle, heart, OVCAR-3 cells and lung. The PSORT program predicts that the 3884846 protein localizes to the microbody (peroxisome) with a certainty of 0.7480. There appears to be no known signal peptide in the protein.

Clone 3884846-1 does not have an initiation codon at the beginning of the nucleotide sequence (SEQ ID NO:74), so it is believed that the disclosed clone represents an incomplete ORF. It is assumed that an initiation codon is found upstream from the sequence shown, such that the cDNA sequence extends further 5' from that shown in FIG. 7B. A stop codon of TGA is located at nucleotides 979–981. The 3884846-1 nucleotide sequence between residues 1 to 978 defines an ORF encoding a protein (SEQ ID NO:75) of 326 amino acid residues (FIG. 7B).

A full length Clone 3884846-2 includes the nucleic acid sequence (SEQ ID NO:76) shown in FIG. 7C. Clone 3884846-2 has an initiation codon at nucleotides 299–301 and a TGA stop codon at nucleotides 983–985. This sequence between residues 299 to 982 defines an ORF encoding a protein (SEQ ID NO:77) of 228 amino acid residues (FIG. 7C).

8. Clone 3911675

Clone 3911675 is a polynucleotide (SEQ ID NO:15) of 1428 nucleotides (FIG. 8A). The nucleotide sequence includes a Kozak sequence, a start codon at positions 96–98, and a TGA stop codon at nucleotides 906–908. This sequence between residues 96 through 905 define an ORF encoding a protein (SEQ ID NO:16) having 270 amino acid residues (FIG. 8A). The clone originates in DNA isolated from spleen cells. The PSORT program predicts that the protein is localized in the plasma membrane. According to the SignalP program, the protein is predicted to have a signal peptide with the most probable cleavage site between 42 and 43, represented by the dash between the amino acids AWS-EK (i.e., AlaTrpSer-GluLys).

Clone 3911675-2 does not have an initiation codon at the beginning of the nucleotide sequence (SEQ ID NO:78), so it is believed that the disclosed clone represents an incomplete ORF. It is assumed that an initiation codon is found upstream from the sequence shown, such that the cDNA sequence extends further 5' from that shown in FIG. 8B. A stop codon of TGA is located at nucleotides 629–631. The 3911675-2 nucleotide sequence between residues 2 to 628 defines an ORF encoding a 3911675-2 protein (SEQ ID NO:79) of 209 amino acid residues (FIG. 8B).

In database searches for similarity, the 3911675 protein is 57% identical to, and 75% positive with, human tetraspan NET-4 protein of 268 residues (GenBank Accession Number AAC17120), and is 57% identical to, and 74% positive with, human tetraspanin TSPAN-5 having 264 residues (GenBank Accession Number NP005714).

TM4SF4 (transmembrane 4 superfamily member 4), is an integral membrane glycoprotein found to regulate the adhesive and proliferative status of intestinal epithelial cells through a density-dependent mechanism. Members of the 'transmembrane 4 superfamily' (TM4SF) are cell-surface proteins presumed to have 4 transmembrane domains. Many tetraspan proteins are considered "promiscuous" interactors by virtue of their associations with other molecules, including lineage-specific proteins, integrins, and other tetraspanins. Tetraspan proteins are involved in diverse processes, e.g., cell activation and proliferation, adhesion and motility, differentiation, and cancer. Maecker et al. 1997 *FASEB J* 11(6): 428–42. The tetraspan family proteins function as "molecular facilitators, grouping specific cell-surface proteins and thus increasing the formation and stability of functional signaling complexes" and so aid in the formation of plasma membrane signaling complexes. Maecker et al. 1997 *FASEB J* 11(6): 428–42; Birling et al, 1999 *J. Neurochem* 73(6): 2600–2008. Neuronal tetraspanin family members are implicated in axon growth and target recognition. Perron and Bixby 1999 *FEBS Lett* 461(1–2): 86–90.

Based on the reported roles of tetraspan-related proteins described herein it is anticipated that successful therapeutic targeting of 3911675 and/or its splice variants will result in significant anti-tumor activity (tumor growth inhibition) especially in combination with established cytotoxic/ genotoxic therapies (i.e. chemosensitization, radiosensitization). In this regard successful therapeutic targeting of 3911675 might also limit the extent (frequency) of metastatic dissemination (tumor burden) and potentially limit tumor angiogenesis. Therapeutic targeting of 3911675 and its splice variants will also be provided via the generation of human or humanized monoclonal antibodies that block the ability of 3911675 to interact with specific cognate ligand(s) and elicit a transmembrane signal(s). Equally, the generation of small molecules (e.g., synthetics, cell permeable peptides) that specifically interfere with one or more of the downstream signaling components in the pathway(s) activated by ligand-bound 3911675 will have significant anti-tumor activity as described above. Likewise, the introduction of antisense constructs (naked DNA, adenoviral constructs), ribozymes to inhibit the expression of 3911675 will have significant anti-tumor activity as described above.

Clone 3911675 will thus have diagnostic and therapeutic utility in pathologies related to cell signaling and neural development and in CNS pathologies, e.g., Alzheimer's disease and parkinsonism. Based on the ubiquitous expression profiles of the 3911675 gene (see Example 9 and FIG. 21), one specific therapeutic indication for targeting 3911675 is for malignant melanoma.

9. Clone 4004056

Clone 4004056 includes a nucleic acid sequence (SEQ ID NO:17) of 1767 nucleotides (FIG. 9). There is an initiation codon at positions 51–53 and a TAA stop codon at positions 984–986. Nucleotides from 51 to 983 therefore define an ORF encoding a protein (SEQ ID NO:18) of 311 amino acid residues (FIG. 9). The clone was originally identified in salivary gland. Transcribed sequences from this gene are found in total RNA libraries from adrenal gland, placenta, mammary tissue, prostate, testis, uterus, spleen, fetal thymus (CRL7046), osteogenic sarcoma cells (HTB96), fetal lung, thalamus, fetal kidney and Burkitt's lymphoma (i.e., Raji cells), and in mRNA libraries from bone marrow, melanoma, pituitary, thyroid. The PSORT program predicts that the 4004056 protein is localized in the plasma membrane. SignalP predicts no known signal peptide for this protein, however.

FIG. 9B shows the nucleotide sequence (SEQ ID NO:80) and translated protein sequence (SEQ ID NO:81) for clone 4004056.0.143u. Clone 4004056.0.143u has an initiation codon at nucleotides 63–65 and a TGA stop codon at nucleotides 1023–1025. This sequence between residues 63 and 1022 defines an ORF encoding a protein (SEQ ID NO:81) of 320 amino acid residues (FIG. 9B).

Database searches indicate that the 4004056 protein has 306 of 311 residues (98%) both identical to and positive with a 311 residue human transmembrane domain containing protein from clone HP01862, thought to control cell proliferation and differentiation. (PCT Publication WO9927094-A2). Similarly, the protein has 306 of 311 residues (98%) identical to and positive with a 311 residue human protein (SEQ ID NO:10 from PCT Publication WO9927094-A2). Clone 4004056 furthermore has 305 of 311 residues (98%) both identical to and positive with the human 311 residue proline-rich membrane protein (PCT Publication WO9833910-A1). In other searches it was found that the 4004056 protein has 153 of 284 residues identicdal to (53%), and 196 of 284 residues positive with (69%), the 316 residue neural membrane protein 35 (GenBank Accession Number AAC32463). In addition, the protein is 42% identical to, and 65% positive with, a 208 residue fragment of human NMDA receptor glutamate-binding chain (GenBank Accession Number AAB94292).

The novel 4004056 clone has a range of activities including cytokine and cell differentiation, immune stimulation/ suppression, hematopoiesis regulation, tissue growth, activin/inhibin activities, chemostatic/chemokinetic activities, hemostatic/thrombolytic activities, receptor/ ligand activities, tumor inhibitor, anti-inflammatory and additional undefined activities. The 4004056 cDNAs has utility as a probes for gene diagnosis and as gene sources for gene therapy. These cDNAs are also useful for large scale expression of proteins. Cells transformed with various 4004056 nucleotides are useful for detection of the corresponding ligands and for screening of novel low-molecular weight pharmaceuticals.

The 4004056 protein is a likely human proline-rich membrane protein (PRMP). PRMP is similar to rat NMDA receptor glutamic acid binding subunit. PRMP is involved in cell signaling, protein trafficking and subcellular localization, control of cell architecture, cell-cell interactions, cell growth and development, and modulation of immune and inflammatory responses. The PRMP and agonists can be used to promote tissue or organ regeneration. The antagonists or inhibitors of PRMP is useful for treating or preventing disorders associated with expression of PRMP, e.g. inflammatory and allergic conditions such as rheumatoid and osteoarthritis, asthma, allergic rhinitis, atopic dermatitis, autoimmune conditions such as Sjogren's syndrome, scleroderma, hyperthyroidism (Grave's disease), systemic lupus, myasthenia gravis, autoimmune thyroiditis, diabetes mellitus, pancreatitis, ulcerative colitis, Crohn's disease, atrophic gastritis, and graft versus host disease, disorders relating to abnormal cellular differentiation, proliferation, or degeneration, including arteriosclerosis, atherosclerosis, hyperaldosteronism, hypocortisolism (Addison's disease), hypothyroidism, colorectal polyps, gastric and duodenal ulcers, cancers of hematopoietic cells and lymphoid tissues including leukemias, lymphomas (including Hodgkin's disease), lymphosarcomas and myelomas, and carcinomas of glands, tissues, and organs involved in secretion or absorption, and organs of the gastrointestinal tract.

10. Clone 4004731-1

Clone 4004731-1 is a polynucleotide (SEQ ID NO:19) comprising 1686 nucleotides (FIG. 10). The clone has a Kozak sequence, an initiation codon at positions 372–374 and a TAA termination codon at nucleotides 1278–1280. The nucleotide residues between 372 and 1277 thus define an ORF encoding a protein (SEQ ID NO:20) having 302 amino acid residues (FIG. 10). The PSORT predicts that the protein localizes to the mitochondrial matrix space with a low certainty of 0.3600. The program SignalP predicts that no known signal peptide is present. Transcribed sequences from this gene are found in brain, pituitary, heart, breast and spleen.

In similarity searches it was found that the 4004731-1 protein has 50% identity and 67% similarity with the human laminin beta-1 chain precursor (laminin B1 chain), a protein having 1786 residues (GenBank Accession Number P07942). Laminins are a major component of the basement membrane and have several biologically active sites that regulate angiogenesis and tumor growth. Grant et al., 1994 *Pathol Res Pract.* 190(9–10): 854–863. Laminins strongly stimulate axon outgrowth in vitro, and are transiently expressed in embryonic development and after CNS injury. Luebke et al., 1995 *J. Neurobiol* 27(1): 1–14. In addition, Laminin B1 expression is greatly disturbed in severely diseased patients with severe childhood autosomal recessive muscular dystrophy. Yamada et al., 1995 *Lab Invest.* 72(6): 715–722. Clone 4004731-1 thus has diagnostic and therapeutic utility in pathologies related to muscular dystrophy, cell outgrowth, cell proliferation, angiogenesis, and neural development and in CNS pathologies, e.g., CNS injury, Alzheimer's disease and parkinsonism.

11. Clone 4009334-1

Clone 4009334-1 includes a polynucleotide (SEQ ID NO:21) having 2010 nucleotides (FIG. 11). This clone is similar to clone 4009334-2 (below), but is longer than the latter because of inserts at nucleotides 1361–1440 and 1541–1597 in SEQ ID NO:21. These differences are thought to arise from splicing variations of the mRNA. Clone 4009334-1 has a start codon at positions 243–245 and a TGA termination codon at nucleotides 1659–1661. Residues between 243 and 1658 therefore define an ORF encoding a protein (SEQ ID NO:22) of 472 residues (FIG. 11). The PSORT software program affords a weak prediction that the 4009334-1 protein localizes to the microbody (certainty =0.30). The SignalP software program predicts that the protein lacks a known signal peptide. Transcribed sequences from this gene are found in OVCAR-3 cells, MCF-7 cells, mammary gland, lung, including fetal lung, brain, including thalamus, adrenal gland, salivary gland, pancreas, heart, white blood cells and Raji cells.

The 4009334-1 protein has 272 of 304 residues (89%) identical to, and 278 of 304 residues (91%) positive with, the 550 residue AVENA protein from *Gallus gallus* (chicken) (GenBank Accession Numbers AB017437 and BAA33016). It also has 218 of 251 residues (86%) identical to, and 228 of 251 residues (90%) positive with, a murine 783 residue enabled homolog (neural variant MENA+ protein) (GenBank Accession Number AAC52864). The 4009334-1 protein additionally has 94 of 146 residues (64%) identical to, and 107 of 146 residues (73%) positive with, the 380 residue human vasodilator-stimulated phosphoprotein (VASP) (GenBank Accession Number P50552).

Clone 4009334-1 thus has diagnostic and therapeutic utility in pathologies related to cellular control, cell proliferation, cell development and cell differentiation. Clone 4009334-1 is also useful in angiogenesis, carcinogenesis, and in body and organ homeostasis.

12. Clone 4009334-2

Clone 4009334-2 includes a polynucleotide (SEQ ID NO:23) of 1952 nucleotides (FIG. 12) that appears to be a shorter splice variant of clone 4009334-1 (SEQ ID NO:21, above). The 4009334-2 nucleic acid sequence includes a Kozak sequence, an initiation codon at nucleotides 243–245 and a stop codon at positions 1716–1718. Residues between 243 and 1715 define an ORF encoding a protein (SEQ ID NO:24) having 491 amino acid residues (FIG. 12). The PSORT program affords a weak prediction that the 4009334-1 protein localizes to the microbody (certainty= 0.30). The SignalP program predicts that the protein lacks a signal peptide. Transcribed sequences from this gene are found in OVCAR-3 cells, MCF-7 cells, mammary gland, lung, including fetal lung, brain, including thalamus, adrenal gland, salivary gland, pancreas, heart, white blood cells and Raji cells.

The 4009334-2 protein has 272 of 304 residues (89%) identical to, and 278 of 304 residues (91%) positive with, the 550 residue d1033982 (GenBank Accession Number AB017437) AVENA protein from *Gallus gallus* (chicken) (GenBank Accession Number BAA33016). It also has 218 of 251 residues (86%) identical to, and 228 of 251 residues (90%) positive with, a murine 783 residue enabled homolog (neural variant MENA+ protein) (GenBank Accession Number AAC52864). The 4009334-2 protein additionally has 94 of 146 residues (64%) identical to, and 107 of 146 residues (73%) positive with, the 380 residue human vasodilator-stimulated phosphoprotein (VASP) (GenBank Accession Number P50552).

Clone 4009334-2 thus has diagnostic and therapeutic utility in pathologies related to cellular control, cell proliferation, cell development and cell differentiation. Clone 4009334-2 is also useful in angiogenesis, carcinogenesis, pathologies related to neoplasia, and body and organ homeostasis.

13. Clone 4035508

Clone 4035508 includes a polynucleotide sequence (SEQ ID NO:25) of 827 nucleotides (FIG. 13). The clone includes a Kozak sequence, a start codon at positions 233–235 and a TGA stop codon at nucleotides 602–604, thus setting forth an ORF between residues 233 and 601 encoding a polypeptide(SEQ ID NO:26) having 123 residues (FIG. 13). The PSORT program predicts that the 4035508 protein localizes to the plasma membrane. The SignalP program predicts that the 4035508 polypeptide has a signal peptide whose most probable cleavage site occurs between residues 29 and 30, represented by the dash between the amino acids LFG-WP (i.e., LeuPheGly-TrpPro). Transcribed sequences from this gene are found in fetal lung tissue, and in multiple adult tissue types, including lymph node tissues.

Similarity searching reveals that the 4035508 protein has 37 of 108 residues (34%) identical to, and 55 of 108 residues (50%) positive with, a 559 residue human protein PB39 (POV1; GenBank Accession Number AAC33004), a predicted secreted protein upregulated and alternatively spliced in prostate cancer. Cole et al., 1998 *Genomics* 51(2): 282–287.

PB39 plays a role in the development of human prostate cancer. By analogy, successful therapeutic targeting of 4035508 and/or its splice variants to a mammalian subject will result in provide significant anti-tumor activity, especially in combination with established cytotoxic/genotoxic therapies (i.e. chemosensitization and radiosensitization). Moreover successful therapeutic targeting of 4035508 will also limit the extent, frequency, or both of metastatic dissemination (tumor burden). 4035508 will also limit tumor angiogenesis since 4035508 is highly expressed in activated endothelial cells, such as human umbilical vein endothelial cells (HUVECs).

Therapeutic targeting of 4035508 and its splice variants will also be provided via generation of human or humanized monoclonal antibodies that block the ability of 4035508 to interact with cognate receptor(s) and elicit a transmembrane signal(s). Equally, the generation of small molecules (synthetics, cell permeable peptides, other) than specifically interfere with one or more of the downstream signaling components in the pathway(s) activated by 4035508 bound to cognate receptor(s) will have significant anti-tumor activity as described above. Likewise, the introduction of antisense constructs (naked DNA, adenoviral constructs), ribozymes to inhibit the expression of 4035508 in select human malignancies will have significant anti-tumor activity as described above.

Clone 4035508 has diagnostic and therapeutic utility in pathologies related to neoplasias, cell proliferation and cellular control. Based on the expression profile of the 4035508 gene (see Example 10 and FIG. 22) the therapeutic indications for targeting 4035508 include metastatic colon carcinomas (up regulation in SW620 metastatic variant of SW480), breast adenocarcinomas, glioma/astrocytomas, small cell lung cancers and malignant melanomas.

14. Clone 4339264

Clone 4339264 includes a polynucleotide (SEQ ID NO:27) of 1063 nucleotides (FIG. 14). The clone includes an initiation codon at positions 48–50 and TAA termination codon at positions 945–947. This clone includes an ORF from residues 48 to 944 encoding a protein (SEQ ID NO:28) of 299 amino acid residues (FIG. 14). The PSORT program predicts that the 4339264 protein localizes in the plasma membrane with a certainty of 0.6000. The SignalP program predicts that there is a signal peptide whose cleavage site most likely occurs between residues 69 and 70, represented by the dash between the amino acids LQA-RF (i.e., LeuGlnAla-ArgPhe). The clone originates in DNA isolated from lymph node. Transcribed sequences from this gene are found in MCF-7 cells, OVCAR-3 cells, heart, prostate, uterus, mammary gland, salivary gland, thalamus, bone marrow, lymph node, spleen, fetal liver, fetal thymus-CRL7046, and 10 human total RNA libraries from Clontech, Inc. (Palo Alto, Calif.; brain, fetal brain, liver, fetal liver, skeletal muscle, pancreas, kidney, heart, lung and placenta).

In a similarity search, it was found that the 4339264 protein has 194 of 219 residues (88%) identical to, and 207 of 219 residues (94%) positive with the 296 residue myeloid upregulated protein of mouse (GenBank Accession Number O35682). In addition, the protein has 39 of 125 residues (31%) identical to, and 58 of 125 residues (46%) positive with the 153 residue human four transmembrane domain MAL T-lymphocyte maturation-associated protein (GenBank Accession Number P21145). The MAL protein is believed to act as a signaling receptor and transporter of water-soluble molecules and ions across the lipid bilayer. Alonso and Weissman 1987 Proc Natl Acad Sci U.S.A. 84(7): 1997–2000.

The breadth of expression of 4339264 transcript among a wide range of normal and cancerous tissues identified using quantitative real-time PCR (Example 11 and FIG. 23) suggests that the protein encoded by the 4339264 gene has a generalized role in cell homeostasis. Expression of 4339264 is elevated in select human cancer cell lines relative to the tissue of origin and elevated in some fetal tissue relative to the adult tissue, indicating a role in organogenesis and tissue repair. Overexpression of 4339264 should therefore contribute to tumor genesis. In addition, high expression of 4339264 in fetal kidney relative to the adult kidney suggests a likely role of 4339264 in organogenesis.

Successful therapeutic targeting and downregulation of 4339264 and/or its splice variants will result in significant anti-tumor activity, especially in combination with established cytotoxic/genotoxic therapies (i.e. chemosensitization, radiosensitization). Moreover successful therapeutic targeting of 4339264 will also limit the extent and frequency of metastatic dissemination (i.e., tumor burden) and potentially limit tumor angiogenesis.

Therapeutic targeting of 4339264 and its splice variants will also be provided by generation of human or humanized monoclonal antibodies that block the ability of 4339264 to interact with cognate receptor(s) and elicit a transmembrane signal(s). Equally, the generation of small molecules (i.e., synthetics, cell permeable peptides, other) that specifically interfere with one or more of the downstream signaling components in the pathway(s) activated by 4339264 when bound to specific cognate receptor(s) will have significant anti-tumor activity as described above. Likewise, the introduction of antisense constructs (i.e., naked DNA, adenoviral constructs) or ribozymes to inhibit the expression of 4339264 in select human malignancies will also have significant anti-tumor activity as described above.

Clone 4339264 thus has diagnostic and therapeutic utility in pathologies related to cell signaling, regulation and development. Based on the expression profile of the 4339264 gene (Example 11 and FIG. 23) the therapeutic indications for targeting 4339264 include malignant melanomas, small cell lung carcinomas and renal cell carcinoma.

Nucleic Acids

One aspect of the invention pertains to isolated nucleic acid molecules (i.e., SEQ ID NOs:1, 3, 5, 7, 9, 11, 13, 15, 17, 19, 21, 23, 25, 27, 74, 76, 78 and 80, plus 29 and 31) that encode the SECX polypeptides of the invention, wherein the SECX polypeptides are selected from the group comprising clone 2777610, clone 2864933-1, clone 2864933-2, clone 2982339, clone 3352358-1, clone 3352358-2, clone 3884846, clone 3884846-1, clone 3884846-2, clone 3911675, clone 3911675-2, clone 4004056, clone 4004056.0.143u, clone 4004731-1, clone 4009334-1, clone 4009334-2, clone 4035508, and clone 4339264 polypeptides, (i.e., SEQ ID NOs:2, 4, 6, 8, 10, 12, 14, 16, 18, 20, 22, 24, 26, 28, 75, 77, 79 and 81, plus 30 and 32; see Table 1 and FIGS. 1–17), or biologically active portions thereof, as well as nucleic acid fragments sufficient for use as hybridization probes to identify SECX-encoding nucleic acids (e.g., SECX mRNA) and fragments for use as PCR primers for the amplification or mutation of SECX nucleic acid molecules. As used herein, the term "nucleic acid molecule" is intended to include DNA molecules (e.g., cDNA or genomic DNA), RNA molecules (e.g., mRNA), analogs of the DNA or RNA generated using nucleotide analogs, and derivatives, fragments and homologs thereof. The nucleic acid molecule can be single-stranded or double-stranded, but preferably is double-stranded DNA. SECX nucleic acids of the invention include SEQ ID NOs:1, 3, 5, 7, 9, 11, 13, 15., 17, 19, 21, 23, 25, 27, 74, 76, 78 and 80, plus 29 and 31 (Table 1 and FIGS. 1–17), and fragments, homologs, and derivatives thereof.

"Probes" refer to nucleic acid sequences of variable length, preferably between at least about 10 nucleotides (nt), 100 nt, or as many as about, e.g., 6,000 nt, depending on use. Probes are used in the detection of identical, similar, or complementary nucleic acid sequences. Longer length probes are usually obtained from a natural or recombinant source, are highly specific and much slower to hybridize than oligomers. Probes may be single- or double-stranded and designed to have specificity in PCR, membrane-based hybridization technologies, or ELISA-like technologies.

An "isolated" nucleic acid molecule is one that is separated from other nucleic acid molecules which are present in the natural source of the nucleic acid. Preferably, an "isolated" nucleic acid is free of sequences which naturally flank the nucleic acid (i.e., sequences located at the 5' and 3' ends of the nucleic acid) in the genomic DNA of the organism from which the nucleic acid is derived. For example, in various embodiments, an isolated nucleic acid molecule encoding any one of the SECX polypeptides, including chemokine receptor-like protein, semaphorin protein-like splice variants, a putative mitochondrial protein (clone 2982339), SLIT protein-like splice variants, a putative microbody (peroxisome) associated protein (clone 3884846), a tetraspanin-like protein, a putative proline-rich membrane protein (clone 4004056), a laminin β-chain precursor-like protein, AVENA protein-like splice variants (clones 4009334-1 and 4009334-2), a fetal lung-associated protein (clone 4035508) and a myeloid upregulated protein (clone 4339264), can contain less than about 5 kb, 4 kb, 3 kb, 2 kb, 1 kb, 0.5 kb or 0.1 kb of nucleotide sequences which naturally flank the nucleic acid molecule in genomic DNA of the cell from which the nucleic acid is derived (e.g., adult and fetal cells from tissues including bone tissue (including bone marrow), heart, lymph node, pancreas, spleen, thymus, placenta, kidney, liver, thalamus, brain, pituitary, breast, lung, salivary gland and adrenal gland). Moreover, an "isolated" nucleic acid molecule, e.g., a cDNA molecule, can be substantially free of other cellular material or culture medium when produced by recombinant techniques, or of chemical precursors or other chemicals when chemically synthesized.

A nucleic acid molecule of the present invention, e.g., a SECX nucleic acid molecule having the nucleotide sequence of SEQ ID NOs:1, 3, 5, 7, 9, 11, 13, 15, 17, 19, 21, 23 25 or 27, plus 29 or 31, or a complement of any of these nucleotide sequences, can be isolated using standard molecular biology techniques and the sequence information provided herein. Using all or a portion of the SECX nucleic acid sequences of SEQ ID NOs:1, 3, 5, 7, 9, 11, 13, 15, 17, 19, 21, 23, 25 or 27, plus 29 or 31, or a complement of any of these nucleotide sequences, as a hybridization probe, said SECX molecules can be isolated using standard hybridization and cloning techniques (e.g., as described in Sambrook et al., (eds.), Molecular Cloning: A Laboratory Manual $2^{nd}$ Ed., Cold Spring Harbor Laboratory Press, Cold Spring Harbor, N.Y., 1989; and Ausubel, et al., (eds.), Current Protocols in Molecular Biology, John Wiley & Sons, New York, N.Y., 1993.)

A nucleic acid of the invention can be amplified using cDNA, mRNA or alternatively, genomic DNA, as a template and appropriate oligonucleotide primers according to standard PCR amplification techniques. The nucleic acid so amplified can be cloned into an appropriate vector and characterized by DNA sequence analysis. Furthermore, oligonucleotides corresponding to SECX nucleotide sequences can be prepared by standard synthetic techniques, e.g., using an automated DNA synthesizer.

As used herein, the term "oligonucleotide" refers to a series of linked nucleotide residues, which oligonucleotide has a sufficient number of nucleotide bases to be used in a PCR reaction. A short oligonucleotide sequence may be based on, or designed from, a genomic or cDNA sequence and is used to amplify, confirm, or reveal the presence of an identical, similar or complementary DNA or RNA in a particular cell or tissue. Oligonucleotides comprise portions of a nucleic acid sequence having about 10 nt, 50 nt, or 100 nucleotides in length, preferably about 15 nucleotides to 30 nucleotides in length. In one embodiment, an oligonucleotide comprising a nucleic acid molecule less than 100 nucleotides in length would further comprise at lease 6 contiguous nucleotides of SEQ ID NOs:1, 3, 5, 7, 9, 11, 13, 15, 17, 19, 21, 23, 25, 27, 74, 76, 78 and 80, plus 29 and 31, or a complement thereof. Oligonucleotides may be chemically synthesized and may be used as probes.

In an embodiment, an isolated nucleic acid molecule of the invention comprises a SECX nucleic acid molecule that is a complement of the nucleotide sequence shown in SEQ ID NOs:1, 3, 5, 7, 9, 11, 13, 15, 17, 19, 21, 23, 25, 27, 74, 76, 78 and 80, plus 29 and 31, or a portion of this nucleotide sequence. A nucleic acid molecule that is complementary to said SECX nucleotide sequences is one that is sufficiently complementary to the nucleotide sequence shown in SEQ ID NOs:1, 3, 5, 7, 9, 11, 13, 15, 17, 19, 21, 23, 25, 27, 74, 76, 78 and 80, plus 29 and 31, or a portion of this nucleotide sequence, that it can hydrogen bond with little or no mismatches to the given SECX nucleotide sequence, thereby forming a stable duplex.

As used herein, the term "complementary" refers to Watson-Crick or Hoogsteen base pairing between nucleotides units of a nucleic acid molecule, and the term "binding" means the physical or chemical interaction between two polypeptides or compounds or associated polypeptides or compounds or combinations thereof. Binding includes ionic, non-ionic, Von der Waals, hydrophobic interactions, etc. A physical interaction can be either direct or indirect. Indirect interactions may be through or due to the effects of another polypeptide or compound. Direct binding refers to interactions that do not take place through, or due to, the effect of another polypeptide or compound, but instead are without other substantial chemical intermediates.

Moreover, the nucleic acid molecule of the invention can comprise only a portion of the nucleic acid sequence of SEQ ID NOs:1, 3, 5, 7, 9, 11, 13, 15, 17, 19, 21, 23, 25, 27, 74, 76, 78 and 80, plus 29 and 31, or the nucleotide sequence of the DNA insert of the plasmid, e.g., e.g., the pSecTag2 B and pSecV5His vectors described in Example 3, wherein e.g., a fragment that can be used as a probe or primer or a fragment encoding a biologically active portion of SECX. Fragments provided herein are defined as sequences of at least 6 (contiguous) nucleic acids or at least 4 (contiguous) amino acids, a length sufficient to allow for specific hybridization in the case of nucleic acids or for specific recognition of an epitope in the case of amino acids, respectively, and are at most some portion less than a full length sequence. Fragments may be derived from any contiguous portion of a nucleic acid or amino acid sequence of choice. Derivatives are nucleic acid sequences or amino acid sequences formed from the native compounds either directly or by modification or partial substitution. Analogs are nucleic acid sequences or amino acid sequences that have a structure similar to, but not identical to, the native compound but differs from it in respect to certain components or side chains. Analogs may be synthetic or from a different evolutionary origin and may have a similar or opposite metabolic activity compared to wild type. Homologs are nucleic acid sequences or amino acid sequences of a particular gene that are derived from different species.

Derivatives and analogs may be full length or other than full length, if the derivative or analog contains a modified nucleic acid or amino acid, as described below. Derivatives or analogs of the nucleic acids or proteins of the invention include, but are not limited to, molecules comprising regions that are substantially homologous to the nucleic acids or proteins of the invention, in various embodiments, by at least about 30%, 50%, 70%, 80%, or 95% identity (with a preferred identity of 80–95%) over a nucleic acid or amino acid sequence of identical size or when compared to an aligned sequence in which the alignment is done by a computer homology program known in the art (e.g., see below), or whose encoding nucleic acid is capable of hybridizing to the complement of a sequence encoding the aforementioned proteins under stringent, moderately stringent, or low stringent conditions. See e.g. Ausubel, et al., Current Protocols in Molecular Biology, John Wiley & Sons, New York, N.Y., 1993, and below.

A "homologous nucleic acid sequence" or "homologous amino acid sequence," or variations thereof, refer to sequences characterized by a homology at the nucleotide level or amino acid level as discussed above. Homologous nucleotide sequences encode those sequences coding for isoforms of SECX polypeptide. Isoforms can be expressed in different tissues of the same organism as a result of, for example, alternative splicing of RNA. Alternatively, isoforms can be encoded by different genes. In the present invention, homologous nucleotide sequences include nucleotide sequences encoding for a SECX polypeptide of species other than humans, including, but not limited to, mammals, and thus can include, e.g., mouse, rat, rabbit, dog, cat cow, horse, and other organisms. Homologous nucleotide sequences also include, but are not limited to, naturally occurring allelic variations and mutations of the nucleotide sequences set forth herein. A homologous nucleotide sequence does not, however, include the nucleotide sequence encoding human SECX protein. Homologous nucleic acid sequences include those nucleic acid sequences that encode conservative amino acid substitutions (see below) in SEQ ID NOs:1, 3, 5, 7, 9, 11, 13, 15, 17, 19, 21, 23, 25, 27, 74, 76, 78 and 80, plus 29 and 31, as well as a polypeptide having SECX activity. Biological activities of the individual SECX proteins are described above. A homologous amino acid sequence does not encode the amino acid sequence of a human SECX polypeptide.

A SECX polypeptide is encoded by the open reading frame ("ORF") of a SECX nucleic acid. The invention includes the nucleic acid sequence comprising the stretch of nucleic acid sequences of SEQ ID NOs:1, 3, 5, 7, 9, 11, 13, 15, 17, 19, 21, 23, 25, 27, 74, 76, 78 and 80, plus 29 and 31, that comprises the ORF of that nucleic acid sequence and encodes a polypeptide of SEQ ID NOs:2, 4, 6, 8, 10, 12, 14, 16, 18, 20, 22, 24, 26, 28, 75, 77, 79 and 81, plus 30 and 32.

An "open reading frame" ("ORF") corresponds to a nucleotide sequence that could potentially be translated into a polypeptide. A stretch of nucleic acids comprising an ORF is uninterrupted by a stop codon. An ORF that represents the coding sequence for a full protein begins with an ATG "start" codon and terminates with one of the three "stop" codons, namely, TAA, TAG, or TGA. For the purposes of this invention, an ORF may be any part of a coding sequence, with or without a start codon, a stop codon, or both. For an ORF to be considered as a good candidate for coding for a bona fide cellular protein, a minimum size requirement is often set, for example, a stretch of DNA that would encode a protein of 50 amino acids or more.

The nucleotide sequence determined from the cloning of the human SECX gene allows for the generation of probes and primers designed for use in identifying and/or cloning SECX homologues in other cell types, e.g. from other tissues, as well as SECX homologues from other mammals. The probe/primer typically comprises substantially purified oligonucleotide. The oligonucleotide typically comprises a region of nucleotide sequence that hybridizes under stringent conditions to at least about 12, 25, 50, 100, 150, 200, 250, 300, 350 or 400 consecutive sense strand nucleotide sequence of SEQ ID NOs:1, 3, 5, 7, 9, 11, 13, 15, 17, 19, 21, 23, 25, 27, 74, 76, 78 and 80, plus 29 and 31, or the nucleotide of the DNA insert of the plasmid such as, e.g., the pSecTag2 B and pSecV5His vectors described in Example 3; or an anti-sense strand nucleotide sequence of a SECX nucleotide or the anti-sense strand SECX nucleotide sequence of the DNA insert of the plasmid known in the art; or of a naturally occurring mutant of a SECX nucleotide, or the naturally occurring mutant of the DNA insert of the plasmid vector known in the art.

Probes based on the human SECX nucleotide sequence can be used to detect transcripts or genomic sequences encoding the same or homologous proteins. In various embodiments, the probe further comprises a label group attached thereto, e.g. the label group can be a radioisotope, a fluorescent compound, an enzyme, or an enzyme co-factor. Such probes can be used as a part of a diagnostic test kit for identifying cells or tissue which misexpress a SECX protein, e.g., by measuring a level of a SECX-encoding nucleic acid in a sample of cells from a subject e.g., detecting SECX mRNA levels or determining whether a genomic SECX gene has been mutated or deleted.

"A polypeptide having a biologically active portion of SECX" refers to polypeptides exhibiting activity similar, but not necessarily identical to, an activity of a polypeptide of the present invention, including mature forms, as measured in a particular biological assay, with or without dose dependency. A nucleic acid fragment encoding a "biologically active portion of SECX" can be prepared by isolating a portion of a SECX nucleotide that encodes a polypeptide having a SECX biological activity (wherein the biological activities of the SECX proteins are described above), expressing the encoded portion of SECX protein (e.g., by recombinant expression in vitro) and assessing the activity of the encoded portion of SECX. For example, a nucleic acid fragment encoding a biologically active portion of SECX includes an extracellular domain, e.g., the clone 2864933-1 amino acid residues 19 to 644 of SEQ ID NO:4. In another embodiment, a nucleic acid fragment encoding a biologically active portion of SECX that includes an extracellular domain includes the DNA encoding such domains, e.g., at least the nucleic acids of SEQ ID NO:9 that encodes the human clone 3352358-1 extracellular domain represented by amino acid residues 42 to 486 of SEQ ID NO:10.

SECX variants

The invention further encompasses any one or more nucleic acid molecules that differ from the SECX nucleotide sequence shown in at least one of SEQ ID NOs:1, 3, 5, 7, 9, 11, 13, 15, 17, 19, 21, 23, 25, 27, 74, 76, 78 and 80, plus 29 and 31, due to degeneracy of the genetic code and thus encode the same SECX protein as that encoded by any of the above nucleotide sequences. In another embodiment, an isolated SECX nucleic acid molecule of the invention has a nucleotide sequence encoding a protein having any one amino acid sequence shown in SEQ ID NOs:2, 4, 6, 8, 10, 12, 14, 16, 18, 20, 22, 24, 26, 28, 75, 77, 79 and 81, plus 30 and 32.

In addition to these human SECX nucleotide sequences, or the SECX nucleotide sequence of the DNA insert of a plasmid or vector, it will be appreciated by those skilled in the art that DNA sequence polymorphisms that lead to changes in the amino acid sequences of a SECX may exist within a population (e.g., the human population). Such genetic polymorphism in a SECX gene may exist among individuals within a population due to natural allelic variation. As used herein, the terms "gene" and "recombinant gene" refer to nucleic acid molecules comprising an open reading frame encoding a SECX protein, preferably a mammalian SECX protein. Such natural allelic variations can typically result in 1–5% variance in the nucleotide sequence of the SECX gene. Any and all such nucleotide variations and resulting amino acid polymorphisms in SECX that are the result of natural allelic variation and that do not alter the functional activity of SECX are intended to be within the scope of the invention.

Moreover, nucleic acid molecules encoding SECX proteins from other species, and thus that have a nucleotide sequence that differs from the human sequence disclosed herein, are intended to be within the scope of the invention. Nucleic acid molecules corresponding to natural allelic variants and homologues of a SECX cDNAs of the invention can be isolated based on their homology to the human SECX nucleic acids disclosed herein using the human cDNAs, or a portion thereof, as a hybridization probe according to standard hybridization techniques under stringent hybridization conditions. For example, a soluble human SECX cDNA can be isolated based on its homology to human membrane-bound SECX. Likewise, a membrane-bound human SECX cDNA can be isolated based on its homology to soluble human SECX.

Accordingly, in another embodiment, an isolated nucleic acid molecule of the invention is at least 6 nucleotides in length and hybridizes under stringent conditions to the nucleic acid molecule comprising at least one SECX nucleotide sequence. In another embodiment, the nucleic acid is at least 10, 25, 50, 100, 250, 500 or 2000 nucleotides in length. In another embodiment, an isolated nucleic acid molecule of the invention hybridizes to the coding region. As used herein, the term "hybridizes under stringent conditions" is intended to describe conditions for hybridization and washing under which nucleotide sequences at least 60% homologous to each other typically remain hybridized to each other.

Homologs (i.e., nucleic acids encoding SECX proteins derived from species other than human) or other related sequences (e.g., paralogs) can be obtained by low, moderate or high stringency hybridization with all or a portion of the particular human sequence as a probe using methods well known in the art for nucleic acid hybridization and cloning.

As used herein, the phrase "stringent hybridization conditions" refers to conditions under which a probe, primer or oligonucleotide will hybridize to its target sequence, but to no other sequences. Stringent conditions are sequence-dependent and will be different in different circumstances. Longer sequences hybridize specifically at higher temperatures than shorter sequences. Generally, stringent conditions are selected to be about 5° C. lower than the thermal melting point (Tm) for the specific sequence at a defined ionic strength and pH. The Tm is the temperature (under defined ionic strength, pH and nucleic acid concentration) at which 50% of the probes complementary to the target sequence hybridize to the target sequence at equilibrium. Since the target sequences are generally present at excess, at Tm, 50% of the probes are occupied at equilibrium. Typically, stringent conditions will be those in which the salt concentration is less than about 1.0 M sodium ion, typically about 0.01 to 1.0 M sodium ion (or other salts) at pH 7.0 to 8.3 and the temperature is at least about 30° C. for short probes, primers or oligonucleotides (e.g., 10 nt to 50 nt) and at least about 60° C. for longer probes, primers and oligonucleotides. Stringent conditions may also be achieved with the addition of destabilizing agents, such as formamide.

Stringent conditions are known to those skilled in the art and can be found in Ausubel et al., (eds.), Current Protocols in Molecular Biology, John Wiley & Sons, N.Y. (1989), 6.3.1–6.3.6. Preferably, the conditions are such that sequences at least about 65%, 70%, 75%, 85%, 90%, 95%, 98%, or 99% homologous to each other typically remain hybridized to each other. A non-limiting example of stringent hybridization conditions are hybridization in a high salt buffer comprising 6×SSC, 50 mM Tris-HCl (pH 7.5), 1 mM EDTA, 0.02% PVP, 0.02% Ficoll, 0.02% BSA, and 500 mg/ml denatured salmon sperm DNA at 65° C., followed by one or more washes in 0.2×SSC, 0.01% BSA at 50° C. An isolated nucleic acid molecule of the invention that hybridizes under stringent conditions to a SECX nucleotide sequence corresponds to a naturally-occurring nucleic acid molecule. As used herein, a "naturally-occurring" nucleic acid molecule refers to an RNA or DNA molecule having a nucleotide sequence that occurs in nature (e.g., encodes a natural protein).

In a second embodiment, a nucleic acid sequence that is hybridizable to at least one SECX nucleic acid molecule, or fragments, analogs or derivatives thereof, under conditions of moderate stringency is provided. A non-limiting example of moderate stringency hybridization conditions are hybridization in 6×SSC, 5×Denhardt's solution, 0.5% SDS and 100 mg/ml denatured salmon sperm DNA at 55° C., followed by one or more washes in 1×SSC, 0.1% SDS at 37° C. Other conditions of moderate stringency that may be used are well-known in the art. See, e.g., Ausubel et al. (eds.), 1993, Current Protocols in Molecular Biology, John Wiley & Sons, NY, and Kriegler, 1990, Gene Transfer and Expression, A Laboratory Manual, Stockton Press, NY.

In a third embodiment, a nucleic acid that is hybridizable to at least one SECX nucleic acid molecule, or fragments, analogs or derivatives thereof, under conditions of low stringency, is provided. A non-limiting example of low stringency hybridization conditions are hybridization in 35% formamide, 5×SSC, 50 mM Tris-HCl (pH 7.5), 5 mM EDTA, 0.02% PVP, 0.02% Ficoll, 0.2% BSA, 100 mg/ml denatured salmon sperm DNA, 10% (wt/vol) dextran sulfate at 40° C., followed by one or more washes in 2×SSC, 25 mM Tris-HCl (pH 7.4), 5 mM EDTA, and 0.1% SDS at 50° C. Other conditions of low stringency that may be used are well known in the art (e.g., as employed for cross-species hybridizations). See, e.g., Ausubel et al. (eds.), 1993, Current Protocols in Molecular Biology, John Wiley & Sons, NY, and Kriegler, 1990, Gene Transfer and Expression, A Laboratory Manual, Stockton Press, NY; Shilo and Weinberg, 1981, *Proc Natl Acad Sci USA* 78: 6789–6792.

Conservative mutations

In addition to naturally-occurring allelic variants of the SECX sequence that may exist in the population, the skilled artisan will further appreciate that changes can be introduced by mutation into at least one SECX nucleotide sequence of SEQ ID NOs:1, 3, 5, 7, 9, 11, 13, 15, 17, 19, 21, 23, 25, 27, 74, 76, 78 and 80, plus 29 and 31, thereby leading to changes in the amino acid sequence of the encoded SECX protein, without altering the functional ability of the SECX protein. For example, nucleotide substitutions leading to amino acid substitutions at "non-essential" amino acid residues can be made in the sequence of SEQ ID NOs:2, 4, 6, 8, 10, 12, 14, 16, 18, 20, 22, 24, 26, 28, 75, 77, 79 and 81, plus 30 and 32, or the SECX nucleotide sequence of the DNA insert of the plasmid or vector known in the art. A "non-essential" amino acid residue is a residue that can be altered from the wild-type sequence of SECX without altering the biological activity, whereas an "essential" amino acid residue is required for biological activity. For example, amino acid residues that are conserved among the SECX proteins of the present invention, are predicted to be particularly unamenable to alteration.

Another aspect of the invention pertains to nucleic acid molecules encoding SECX proteins that contain changes in amino acid residues that are not essential for activity. Such SECX proteins differ in amino acid sequence from SEQ ID NOs:2, 4, 6, 8, 10, 12, 14, 16, 18, 20, 22, 24, 26, 28, 75, 77, 79 and 81, plus 30 and 32, yet retain biological activity. In one embodiment, the isolated nucleic acid molecule comprises a nucleotide sequence encoding a protein, wherein the protein comprises an amino acid sequence at least about 45% homologous to at least one SECX amino acid sequence. Preferably, the protein encoded by the nucleic acid molecule is at least about 60% homologous to at least one SECX polypeptide, more preferably at least about 70% homologous, at least about 80% homologous, at least about 90% homologous, and most preferably at least about 95% homologous to that given SECX polypeptide.

An isolated nucleic acid molecule encoding a SECX protein homologous to a given SECX protein can be created by introducing one or more nucleotide substitutions, additions or deletions into the corresponding SECX nucleotide sequence, such that one or more amino acid substitutions, additions or deletions are introduced into the encoded protein.

Mutations can be introduced into SEQ ID NOs:1, 3, 5, 7, 9, 11, 13, 15, 17, 19, 21, 23, 25, 27, 74, 76, 78 and 80, plus 29 and 31, by standard techniques, e.g., site-directed mutagenesis and PCR-mediated mutagenesis. Preferably, conservative amino acid substitutions are made at one or more predicted non-essential amino acid residues. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted non-essential amino acid residue in SECX is replaced with another amino acid residue from the same side chain family. Alternatively, in another embodiment, mutations can be introduced randomly along all or part of a SECX coding sequence, e.g., by saturation mutagenesis, and the resultant mutants can be screened for SECX biological activity to identify mutants that retain activity. Following mutagenesis, the encoded SECX protein can be expressed by any recombinant technology known in the art and the activity of the protein can be determined.

In one embodiment, a mutant SECX protein can be assayed for (1) the ability to form protein:protein interactions with other SECX proteins, other cell-surface proteins, or biologically active portions thereof, (2) complex formation between a mutant SECX protein and a SECX ligand; (3) the ability of a mutant SECX protein to bind to an intracellular target protein or biologically active portion thereof; (e.g. avidin proteins).

Antisense

Another aspect of the invention pertains to isolated antisense nucleic acid molecules that are hybridizable to or complementary to a SECX nucleic acid molecule, or fragments, analogs or derivatives thereof. An "antisense" nucleic acid comprises a nucleotide sequence that is complementary to a "sense" nucleic acid encoding a protein, e.g., complementary to the coding strand of a double-stranded cDNA molecule or complementary to an mRNA sequence. In specific aspects, antisense nucleic acid molecules are provided that comprise a sequence complementary to at least about 10, 25, 50, 100, 250 or 500 nucleotides or an entire SECX coding strand, or to only a portion thereof. Nucleic acid molecules encoding fragments, homologs, derivatives and analogs of a SECX protein, or antisense nucleic acids complementary to a SECX nucleic acid sequence, are additionally provided.

In one embodiment, an antisense nucleic acid molecule is antisense to a "coding region" of the coding strand of a nucleotide sequence encoding SECX. The term "coding region" refers to the region of the nucleotide sequence comprising codons which are translated into amino acid residues (e.g., ORFs shown in FIGS. 1–17). In another embodiment, the antisense nucleic acid molecule is antisense to a "noncoding region" of the coding strand of a nucleotide sequence encoding SECX. The term "noncoding region" refers to 5' and 3' sequences which flank the coding region that are not translated into amino acids (i.e., also referred to as 5' and 3' untranslated regions).

Given the coding strand sequences encoding SECX disclosed herein (e.g., SEQ ID NOs:1, 3, 5, 7, 9, 11, 13, 15, 17, 19, 21, 23, 25, 27, 74, 76, 78 and 80, plus 29 and 31), antisense nucleic acids of the invention can be designed according to the rules of Watson and Crick or Hoogsteen base pairing. The antisense nucleic acid molecule can be complementary to the entire coding region of SECX mRNA, but more preferably is an oligonucleotide that is antisense to only a portion of the coding or noncoding region of SECX mRNA. For example, the antisense oligonucleotide can be complementary to the region surrounding the translation start site of SECX mRNA. An antisense oligonucleotide can be, for example, about 5, 10, 15, 20, 25, 30, 35, 40, 45 or 50 nucleotides in length. An antisense nucleic acid of the invention can be constructed using chemical synthesis or enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used.

Examples of modified nucleotides that can be used to generate the antisense nucleic acid include: 5-fluorouracil, 5-bromouracil, 5-chlorouracil, 5-iodouracil, hypoxanthine, xanthine, 4-acetylcytosine, 5-(carboxyhydroxylmethyl)uraci 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracl, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl)uracil, (acp3) w, and 2,6-diaminopurine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

The antisense nucleic acid molecules of the invention are typically administered to a subject or generated in situ such that they hybridize with or bind to cellular mRNA and/or genomic DNA encoding a SECX protein to thereby inhibit expression of the protein, e.g., by inhibiting transcription and/or translation. The hybridization can be by conventional nucleotide complementarity to form a stable duplex, or, for example, in the case of an antisense nucleic acid molecule that binds to DNA duplexes, through specific interactions in the major groove of the double helix. An example of a route of administration of antisense nucleic acid molecules of the invention includes direct injection at a tissue site. Alternatively, antisense nucleic acid molecules can be modified to target selected cells and then administered systemically. For example, for systemic administration, antisense molecules can be modified such that they specifically bind to receptors or antigens expressed on a selected cell surface, e.g., by linking the antisense nucleic acid molecules to peptides or antibodies that bind to cell surface receptors or antigens. The antisense nucleic acid molecules can also be delivered to cells using the vectors described herein. To achieve sufficient intracellular concentrations of antisense molecules, vector constructs in which the antisense nucleic acid molecule is placed under the control of a strong pol II or pol III promoter are preferred.

In yet another embodiment, the antisense nucleic acid molecule of the invention is an α-anomeric nucleic acid molecule. An ox-anomeric nucleic acid molecule forms specific double-stranded hybrids with complementary RNA in which, contrary to the usual β-units, the strands run parallel to each other (Gaultier et al. (1987) *Nucleic Acids Res* 15: 6625–6641). The antisense nucleic acid molecule can also comprise a 2'-o-methylribonucleotide (Inoue et al. (1987) *Nucleic Acids Res* 15: 6131–6148) or a chimeric RNA-DNA analogue (Inoue et al. (1987) *FEBS Lett* 215: 327–330).

Ribozymes and PNA moieties

Nucleic acid modifications include, by way of nonlimiting example, modified bases, and nucleic acids whose sugar phosphate backbones are modified or derivatized. These modifications are carried out at least in part to enhance the chemical stability of the modified nucleic acid, such that they may be used, for example, as antisense binding nucleic acids in therapeutic applications in a subject.

In one embodiment, an antisense nucleic acid of the invention is a ribozyme. Ribozymes are catalytic RNA molecules with ribonuclease activity that are capable of cleaving a single-stranded nucleic acid, e.g., an mRNA, to which they have a complementary region. Thus, ribozymes (e.g., hammerhead ribozymes (described in Haselhoff and Gerlach (1988) *Nature* 334:585–591)) can be used to catalytically cleave SECX mRNA transcripts to thereby inhibit translation of SECX mRNA. A ribozyme having specificity for a SECX-encoding nucleic acid can be designed based upon the nucleotide sequence of a SECX cDNA disclosed herein (ie., SEQ ID NOs:1, 3, 5, 7, 9, 11, 13, 15, 17, 19, 21, 23, 25, 27, 74, 76, 78 and 80, plus 29 and 31). For example, a derivative of a Tetrahymena L-19 IVS RNA can be constructed in which the nucleotide sequence of the active site is complementary to the nucleotide sequence to be cleaved in a SECX-encoding mRNA. See, e.g., Cech et al. U.S. Pat. No. 4,987,071; and Cech et al. U.S. Pat. No. 5,116,742. Alternatively, SECX mRNA can be used to select a catalytic RNA having a specific ribonuclease activity from a pool of RNA molecules. See, e.g., Bartel et al., (1993) *Science* 261:1411–1418.

Alternatively, SECX gene expression can be inhibited by targeting nucleotide sequences complementary to the regulatory region of a SECX gene (e.g., the SECX promoter and/or enhancers) to form triple helical structures that prevent transcription of the SECX gene in target cells. See generally, Helene. (1991) *Anticancer Drug Des.* 6: 569–84; Helene. et al. (1992) *Ann. N.Y. Acad. Sci.* 660:27–36; and Maher (1992) *Bioassays* 14: 807–15.

In various embodiments, the nucleic acids of SECX can be modified at the base moiety, sugar moiety or phosphate backbone to improve, e.g., the stability, hybridization, or solubility of the molecule. For example, the deoxyribose phosphate backbone of the nucleic acids can be modified to generate peptide nucleic acids (see Hyrup et al. (1996) *Bioorg Med Chem* 4: 5–23). As used herein, the terms "peptide nucleic acids" or "PNAs" refer to nucleic acid mimics, e.g., DNA mimics, in which the deoxyribose phosphate backbone is replaced by a pseudopeptide backbone and only the four natural nucleobases are retained. The neutral backbone of PNAs has been shown to allow for specific hybridization to DNA and RNA under conditions of low ionic strength. The synthesis of PNA oligomers can be performed using standard solid phase peptide synthesis protocols as described in Hyrup et al. (1996) above; Perry-O'Keefe et al. (1996) *PNAS* 93: 14670–675.

PNAs of SECX can be used in therapeutic and diagnostic applications. For example, PNAs can be used as antisense or antigene agents for sequence-specific modulation of gene expression by, e.g., inducing transcription or translation arrest or inhibiting replication. PNAs of SECX can also be used, e.g., in the analysis of single base pair mutations in a gene by, e.g., PNA directed PCR clamping; as artificial restriction enzymes when used in combination with other enzymes, e.g., SI nucleases (Hyrup B. (1996) above); or as probes or primers for DNA sequence and hybridization (Hyrup et al. (1996), above; Perry-O'Keefe (1996), above).

In another embodiment, PNAs of SECX can be modified, e.g., to enhance their stability or cellular uptake, by attaching lipophilic or other helper groups to PNA, by the formation of PNA-DNA chimeras, or by the use of liposomes or other techniques of drug delivery known in the art. For example, PNA-DNA chimeras of SECX can be generated that may combine the advantageous properties of PNA and DNA. Such chimeras allow DNA recognition enzymes, e.g., RNase H and DNA polymerases, to interact with the DNA portion while the PNA portion would provide high binding affinity and specificity. PNA-DNA chimeras can be linked using linkers of appropriate lengths selected in terms of base stacking, number of bonds between the nucleobases, and orientation (Hyrup (1996) above). The synthesis of PNA-DNA chimeras can be performed as described in Hyrup (1996) above and Finn et al. (1996) *Nucl Acids Res* 24: 3357–63. For example, a DNA chain can be synthesized on a solid support using standard phosphoramidite coupling chemistry, and modified nucleoside analogs, e.g., 5'-(4-methoxytrityl)amino-5'-deoxy-thymidine phosphoramidite, can be used between the PNA and the 5' end of DNA (Mag et al. (1989) *Nucl Acid Res* 17: 5973–88). PNA monomers are then coupled in a stepwise manner to produce a chimeric molecule with a 5' PNA segment and a 3' DNA segment (Finn et al. (1 996) above). Alternatively, chimeric molecules can be synthesized with a 5' DNA segment and a 3' PNA segment. See, Petersen et al. (1975) *Bioorg Med Chem Lett* 5: 1119–11124.

In other embodiments, the oligonucleotide may include other appended groups such as peptides (e.g., for targeting host cell receptors in vivo), or agents facilitating transport across the cell membrane (see, e.g., Letsinger et al., 1989, *Proc. Natl. Acad. Sci. U.S.A.* 86:6553–6556; Lemaitre et al., 1987, *Proc. Natl. Acad. Sci.* 84:648–652; PCT Publication No. WO88/09810) or the blood-brain barrier (see, e.g., PCT Publication No. WO89/10134). In addition, oligonucleotides can be modified with hybridization triggered cleavage agents (See, e.g., Krol et al., 1988, *BioTechniques* 6:958–976) or intercalating agents. (See, e.g., Zon, 1988, *Pharm. Res.* 5: 539–549). To this end, the oligonucleotide may be conjugated to another molecule, e.g., a peptide, a hybridization triggered cross-linking agent, a transport agent, a hybridization-triggered cleavage agent, etc.

SECX proteins

The novel protein of the invention includes the SECX proteins whose sequences are provided in FIGS. 1–15 and 17 (SEQ IDNOs:2, 4, 6, 8, 10, 12, 14, 16, 18, 20, 22, 24, 26, 28, 75, 77, 79 and 81, plus 30 and 32). The invention also includes a mutant or variant protein, any of whose residues may be changed from the corresponding residue shown in FIGS. 1–15 and 17 while still encoding a protein that maintains its SECX activities and physiological functions, or a functional fragment thereof. In the mutant or variant protein, up to 20% or more of the residues may be so changed.

In general, an SECX variant that preserves SECX-like function includes any variant in which residues at a particular position in the sequence have been substituted by other amino acids, and further include the possibility of inserting an additional residue or residues between two residues of the parent protein as well as the possibility of deleting one or more residues from the parent sequence. Any amino acid substitution, insertion, or deletion is encompassed by the invention. In favorable circumstances, the substitution is a conservative substitution as defined above.

One aspect of the invention pertains to isolated SECX proteins, and biologically active portions thereof, or derivatives, fragments, analogs or homologs thereof. Also provided are polypeptide fragments suitable for use as immunogens to raise anti-SECX antibodies. In one embodiment, native SECX proteins can be isolated from cells or tissue sources by an appropriate purification scheme using standard protein purification techniques. In another embodiment, SECX proteins are produced by recombinant DNA techniques. Alternative to recombinant expression, a SECX protein or polypeptide can be synthesized chemically using standard peptide synthesis techniques.

An "isolated" or "purified" protein or biologically active portion thereof is substantially free of cellular material or other contaminating proteins from the cell or tissue source from which the SECX protein is derived, or substantially free from chemical precursors or other chemicals when chemically synthesized. The language "substantially free of cellular material" includes preparations of SECX protein in which the protein is separated from cellular components of the cells from which it is isolated or recombinantly produced. In one embodiment, the language "substantially free of cellular material" includes preparations of SECX protein having less than about 30% (by dry weight) of non-SECX protein (also referred to herein as a "contaminating protein"), more preferably less than about 20% of non-SECX protein, still more preferably less than about 10% of non-SECX protein, and most preferably less than about 5% non-SECX protein. When the SECX protein or biologically active portion thereof is recombinantly produced, it is also preferably substantially free of culture medium, i.e., culture medium represents less than about 20%, more preferably less than about 10%, and most preferably less than about 5% of the volume of the protein preparation.

The language "substantially free of chemical precursors or other chemicals" includes preparations of SECX protein in which the protein is separated from chemical precursors or other chemicals that are involved in the synthesis of the protein. In one embodiment, the language "substantially free of chemical precursors or other chemicals" includes preparations of SECX protein having less than about 30% (by dry weight) of chemical precursors or non-SECX chemicals, more preferably less than about 20% chemical precursors or non-SECX chemicals, still more preferably less than about 10% chemical precursors or non-SECX chemicals, and most preferably less than about 5% chemical precursors or non-SECX chemicals.

Biologically active portions of a SECX protein include peptides comprising amino acid sequences sufficiently homologous to or derived from the amino acid sequence of the SECX protein, e.g., the amino acid sequence shown in SEQ ID NOs:2, 4, 6, 8, 10, 12, 14, 16, 18, 20, 22, 24, 26, 28, 75, 77, 79 and 81, plus 30 and 32, that include fewer amino acids than the full length SECX proteins, and exhibit at least one activity of a SECX protein. Typically, biologically active portions comprise a domain or motif with at least one activity of the SECX protein. A biologically active portion of a SECX protein can be a polypeptide which is, for example, 10, 25, 50, 100 or more amino acids in length.

It is to be understood that a biologically active portion of a SECX protein of the present invention may contain at least one of the structural domains identified in Sections 1–14, above. An alternative biologically active portion of a SECX protein may contain an extracellular domain of the SECX protein. Another biologically active portion of a SECX protein may contain the transmembrane domain of the SECX protein. Yet another biologically active portion of a SECX protein of the present invention may contain the intracellular domain of the SECX protein.

Moreover, other biologically active portions, in which other regions of the protein are deleted, can be prepared by recombinant techniques and evaluated for one or more of the functional activities of a native SECX protein.

In an embodiment, the SECX protein has any one or more amino acid sequences shown in SEQ ID NOs:2, 4, 6, 8, 10, 12, 14, 16, 18, 20, 22, 24, 26, 28, 75, 77, 79 and 81, plus 30 and 32. In other embodiments, the SECX protein is substantially homologous to any one of SEQ ID NOs:2, 4, 6, 8, 10, 12, 14, 16, 18, 20, 22, 24, 26, 28, 75, 77, 79 and 81, plus 30 and 32, and retains the functional activity of that given SECX protein yet differs in amino acid sequence due to natural allelic variation or mutagenesis, as described in detail below. Accordingly, in another embodiment, the SECX protein is a protein that comprises an amino acid sequence at least about 75% homologous to any one amino acid sequence of SEQ ID NOs:2, 4, 6, 8, 10, 12, 14, 16, 18, 20, 22, 24, 26, 28, 75, 77, 79 and 81, plus 30 and 32, and retains the functional activity of that SECX protein.

This invention further features isolated SECX protein, or derivatives, fragments, analogs or homologs thereof, that is encoded by a nucleic acid molecule having a nucleotide sequence that hybridizes under stringent hybridization conditions to a nucleic acid molecule comprising the nucleotide sequence of any one or more of SEQ ID NOs:1, 3, 5, 7, 9, 11, 13, 15, 17, 19, 21, 23, 25, 27, 74, 76, 78 and 80, plus 29 and 31.

Determining homology between two or more sequences

To determine the percent homology of two amino acid sequences or of two nucleic acids, the sequences are aligned for optimal comparison purposes (e.g., gaps can be introduced in the sequence of a first amino acid or nucleic acid sequence for optimal alignment with a second amino or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are homologous at that position (i.e., as used herein amino acid or nucleic acid "homology" is equivalent to amino acid or nucleic acid "identity").

The nucleic acid sequence homology may be determined as the degree of identity between two sequences. The homology may be determined using computer programs known in the art, such as GAP software provided in the GCG program package. See, Needleman and Wunsch 1970 *J Mol Biol* 48: 443–453. Using GCG GAP software with the following settings for nucleic acid sequence comparison: GAP creation penalty of 5.0 and GAP extension penalty of 0.3, the coding region of the analogous nucleic acid sequences referred to above exhibits a degree of identity preferably of at least 70%, 75%, 80%, 85%, 90%, 95%, 98%, or 99%, with the CDS (i.e., encoding) part of the DNA sequence shown in any one or more of SEQ ID NOs:1, 3, 5, 7, 9, 11, 13, 15, 17, 19, 21, 23, 25, 27, 74, 76, 78 and 80, plus 29 and 31.

The term "sequence identity" refers to the degree to which two polynucleotide or polypeptide sequences are identical on a residue-by-residue basis over a particular region of comparison. The term "percentage of sequence identity" is calculated by comparing two optimally aligned sequences over that region of comparison, determining the number of positions at which the identical nucleic acid base (e.g., A, T, C, G, U, or I, in the case of nucleic acids) occurs in both sequences to yield the number of matched positions, dividing the number of matched positions by the total number of positions in the region of comparison (i.e., the window size), and multiplying the result by 100 to yield the percentage of sequence identity. The term "substantial identity" as used herein denotes a characteristic of a polynucleotide sequence, wherein the polynucleotide comprises a sequence that has at least 80 percent sequence identity, preferably at least 85 percent identity and often 90 to 95 percent sequence identity, more usually at least 99 percent sequence identity as compared to a reference sequence over a comparison region. Similar calculation are used when comparing amino acid residues in polypeptide sequences.

Chimeric and fusion proteins

The invention also provides SECX chimeric or fusion proteins. As used herein, a SECX "chimeric protein" or "fusion protein" comprises a SECX polypeptide operatively linked to a non-SECX polypeptide. A "SECX polypeptide" refers to a polypeptide having an amino acid sequence corresponding to SECX, whereas a "non-SECX polypeptide" refers to a polypeptide having an amino acid sequence corresponding to a protein that is not substantially homologous to the SECX protein, e.g., a protein that is different from the SECX protein and that is derived from the same or a different organism. Within a SECX fusion protein the SECX polypeptide can correspond to all or a portion of a SECX protein. In one embodiment, a SECX fusion protein comprises at least one biologically active portion of a SECX protein. In another embodiment, a SECX fusion protein comprises at least two biologically active portions of a SECX protein. In yet another embodiment, a SECX fusion protein comprises at least three biologically active portions of a SECX protein. Within the fusion protein, the term "operatively linked" is intended to indicate that the SECX polypeptide and the non-SECX polypeptide are fused in-frame to each other. The non-SECX polypeptide can be fused to the N-terminus or C-terminus of the SECX polypeptide.

For example, in one embodiment a SECX fusion protein comprises a SECX domain operably linked to the extracellular domain of a second protein known to be involved in an activity of interest. Such fusion proteins can be further utilized in screening assays for compounds which modulate SECX activity (such assays are described in detail below).

In one embodiment, the fusion protein is a GST-SECX fusion protein in which the SECX sequences are fused to the C-terminus of the GST (i.e., glutathione S-transferase) sequences. Such fusion proteins can facilitate the purification of recombinant SECX.

In another embodiment, the fusion protein is a SECX protein containing a heterologous signal sequence at its N-terminus. For example, the native SECX signal sequence (i.e., about amino acids 1 to 26, or as described in Sections 1–14 above) can be removed and replaced with a signal sequence from another protein. In certain host cells (e.g., mammalian host cells), expression and/or secretion of SECX can be increased through use of a heterologous signal sequence.

In yet another embodiment, the fusion protein is a SECX-immunoglobulin fusion protein in which the SECX sequences comprising primarily the extracellular domains are fused to sequences derived from a member of the immunoglobulin protein family. The SECX-immunoglobulin fusion proteins of the invention can be incorporated into pharmaceutical compositions and administered to a subject to inhibit an interaction between a SECX ligand and a SECX protein on the surface of a cell, to thereby suppress SECX-mediated signal transduction in vivo. The SECX-immunoglobulin fusion proteins can be used to affect the bioavailability of a SECX cognate ligand. Inhibition of the SECX ligand/SECX interaction may be useful therapeutically for both the treatment of proliferative and differentiative disorders, as well as modulating (e.g. promoting or inhibiting) cell survival. Moreover, the SECX-immunoglobulin fusion proteins of the invention can be used as immunogens to produce anti-SECX antibodies in a subject, to purify SECX ligands, and in screening assays to identify molecules that inhibit the interaction of SECX with a SECX ligand.

A SECX chimeric or fusion protein of the invention can be produced by standard recombinant DNA techniques. For example, DNA fragments coding for the different polypeptide sequences are ligated together in-frame in accordance with conventional techniques, e.g., by employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers that give rise to complementary overhangs between two consecutive gene fragments that can subsequently be annealed and reamplified to generate a chimeric gene sequence (see, for example, Ausubel et al. (eds.) Current Protocols in Molecular Biology, John Wiley & Sons, 1992). Moreover, many expression vectors are commercially available that already encode a fusion moiety (e.g., a GST polypeptide). A SECX-encoding nucleic acid can be cloned into such an expression vector such that the fusion moiety is linked in-frame to the SECX protein.

The invention also provides signal sequences derived from various SECX polypeptides. The signal sequences include, e.g., polypeptides including the signal peptides identified for the SECX polypeptides as predicted by the SignalP software program for the SECX polypeptides described above. These signal sequences are useful for directing a linked polypeptide sequence to a desired intracellular or extracellular (if secretion from the cell is desired) location. In some embodiments, the signal sequence includes a portion of a SECX signal sequence that is sufficient to direct a linked polypeptide to a desired cellular compartment.

SECX agonists and antagonists

The present invention also pertains to variants of the SECX proteins that function as either SECX agonists (mimetics) or as SECX antagonists. Variants of the SECX protein can be generated by mutagenesis, e.g., discrete point mutation or truncation of the SECX protein. An agonist of the SECX protein can retain substantially the same, or a subset of, the biological activities of the naturally occurring form of the SECX protein. An antagonist of the SECX protein can inhibit one or more of the activities of the naturally occurring form of the SECX protein by, for example, competitively binding to a downstream or upstream member of a cellular signaling cascade which includes the SECX protein. Thus, specific biological effects can be elicited by treatment with a variant of limited function. In one embodiment, treatment of a subject with a variant having a subset of the biological activities of the naturally occurring form of the protein has fewer side effects in a subject relative to treatment with the naturally occurring form of the SECX proteins.

Variants of the SECX protein that function as either SECX agonists (mimetics) or as SECX antagonists can be identified by screening combinatorial libraries of mutants, e.g., truncation mutants, of the SECX protein for SECX protein agonist or antagonist activity. In one embodiment, a variegated library of SECX variants is generated by combinatorial mutagenesis at the nucleic acid level and is encoded by a variegated gene library. A variegated library of SECX variants can be produced by, for example, enzymatically ligating a mixture of synthetic oligonucleotides into gene sequences such that a degenerate set of potential SECX sequences is expressible as individual polypeptides, or alternatively, as a set of larger fusion proteins (e.g., for phage display) containing the set of SECX sequences therein. There are a variety of methods which can be used to produce libraries of potential SECX variants from a degenerate oligonucleotide sequence. Chemical synthesis of a degenerate gene sequence can be performed in an automatic DNA synthesizer, and the synthetic gene then ligated into an appropriate expression vector. Use of a degenerate set of genes allows for the provision, in one mixture, of all of the sequences encoding the desired set of potential SECX sequences. Methods for synthesizing degenerate oligonucleotides are known in the art (see, e.g., Narang (1983) *Tetrahedron* 39:3; Itakura et al. (1984) *Annu Rev Biochem* 53:323; Itakura et al. (1984) *Science* 198:1056; Ike et al. (1983) *Nucl Acid Res* 11:477.

Polypeptide libraries

In addition, libraries of fragments of the SECX protein coding sequence can be used to generate a variegated population of SECX fragments for screening and subsequent selection of variants of a SECX protein. In one embodiment, a library of coding sequence fragments can be generated by treating a double stranded PCR fragment of a SECX coding sequence with a nuclease under conditions wherein nicking occurs only about once per molecule, denaturing the double stranded DNA, renaturing the DNA to form double stranded DNA that can include sense/antisense pairs from different nicked products, removing single stranded portions from reformed duplexes by treatment with SI nuclease, and ligating the resulting fragment library into an expression vector. By this method, an expression library can be derived which encodes N-terminal and internal fragments of various sizes of the SECX protein.

Several techniques are known in the art for screening gene products of combinatorial libraries made by point mutations or truncation, and for screening cDNA libraries for gene products having a selected property. Such techniques are adaptable for rapid screening of the gene libraries generated by the combinatorial mutagenesis of SECX proteins. The most widely used techniques, which are amenable to high throughput analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recrusive ensemble mutagenesis (REM), a new technique that enhances the frequency of functional mutants in the libraries, can be used in combination with the screening assays to identify SECX variants (Arkin and Yourvan (1992) *PNAS* 89:7811–7815; Delgrave et al. (1993) *Protein Engineering* 6:327–331).

In one embodiment, cell based assays can be exploited to analyze a variegated SECX library, e.g., a library of mutant SECX polypeptides. For example, a library of expression vectors can be transfected into a cell line that ordinarily responds to a particular ligand or receptor in a SECX-dependent manner, e.g., through a signaling complex. The transfected cells are then contacted with the putative SECX interactant and the effect of expression of the mutant SECX on signaling by the signaling complex can be detected, e.g. by measuring a cellular activity or cell survival. Plasmid DNA can then be recovered from the cells which score for inhibition, or alternatively, potentiation of, e.g., cytokine induction, and the individual clones further characterized.

Anti-SECX antibodies

The invention encompasses antibodies and antibody fragments, such as $F_{ab}$ or $(F_{ab})_2$, that bind immunospecifically to any of the polypeptides of the invention.

An isolated SECX protein, or a portion or fragment thereof, can be used as an immunogen to generate antibodies that bind SECX using standard techniques for polyclonal and monoclonal antibody preparation. The full-length SECX protein can be used or, alternatively, the invention provides antigenic peptide fragments of SECX for use as immunogens. The antigenic peptide of SECX comprises at least 4 amino acid residues of the amino acid sequence shown in SEQ ID NOs:2, 4, 6, 8, 10, 12, 14, 16, 18, 20, 22, 24, 26, 28, 75, 77, 79 and 81, plus 30 and 32 and encompasses an epitope of SECX such that an antibody raised against the peptide forms a specific immune complex with SECX. Preferably, the antigenic peptide comprises at least 6, 8, 10, 15, 20, or 30 amino acid residues. Longer antigenic peptides are sometimes preferable over shorter antigenic peptides, depending on use and according to methods well known to someone skilled in the art.

In certain embodiments of the invention, at least one epitope encompassed by the antigenic peptide is a region of SECX that is located on the surface of the protein, e.g., a hydrophilic region. A hydrophobicity analysis of the human SECX protein sequence will indicate which regions of a SECX polypeptide are particularly hydrophilic and, therefore, are likely to encode surface residues useful for targeting antibody production. As a means for targeting antibody production, hydropathy plots showing regions of hydrophilicity and hydrophobicity may be generated by any method well known in the art, including, for example, the Kyte Doolittle or the Hopp Woods methods, either with or without Fourier transformation. See, e.g., Hopp and Woods, 1981, *Proc. Nat. Acad. Sci. USA* 78: 3824–3828; Kyte and Doolittle 1982, *J. Mol. Biol.* 157: 105–142, each incorporated herein by reference in their entirety.

As disclosed herein, SECX protein sequence of SEQ ID NOs:2, 4, 6, 8, 10, 12, 14, 16, 18, 20, 22, 24, 26, 28, 75, 77, 79 and 81, plus 30 and 32, or derivatives, fragments, analogs or homologs thereof, may be utilized as immunogens in the generation of antibodies that immunospecifically-bind these protein components. The term "antibody" as used herein refers to immunoglobulin molecules and immunologically active portions of immunoglobulin molecules, i.e., molecules that contain an antigen binding site that specifically binds (immunoreacts with) an antigen, such as SECX. Such antibodies include, but are not limited to, polyclonal, monoclonal, chimeric, single chain, $F_{ab}$ and $F_{(ab')2}$ fragments, and an $F_{ab}$ expression library. In a specific embodiment, antibodies to human SECX proteins are disclosed. Various procedures known within the art may be used for the production of polyclonal or monoclonal antibodies to a SECX protein sequence, or derivative, fragment, analog or homolog thereof. Some of these proteins are discussed below.

For the production of polyclonal antibodies, various suitable host animals (e.g., rabbit, goat, mouse or other mammal) may be immunized by injection with the native protein, or a synthetic variant thereof, or a derivative of the foregoing. An appropriate immunogenic preparation can contain, for example, recombinantly expressed SECX protein or a chemically synthesized SECX polypeptide. The preparation can further include an adjuvant. Various adjuvants used to increase the immunological response include, but are not limited to, Freund's (complete and incomplete), mineral gels (e.g., aluminum hydroxide), surface active substances (e.g., lysolecithin, pluronic polyols, polyanions, peptides, oil emulsions, dinitrophenol, etc.), human adjuvants such as *Bacille Calmette-Guerin* and *Corynebacterium parvum*, or similar immunostimulatory agents. If desired, the antibody molecules directed against SECX can be isolated from the mammal (e.g., from the blood) and further purified by well known techniques, such as protein A chromatography to obtain the IgG fraction.

The term "monoclonal antibody" or "monoclonal antibody composition", as used herein, refers to a population of antibody molecules that contain only one species of an antigen binding site capable of immunoreacting with a particular epitope of SECX. A monoclonal antibody composition thus typically displays a single binding affinity for a particular SECX protein with which it immunoreacts. For preparation of monoclonal antibodies directed towards a particular SECX protein, or derivatives, fragments, analogs or homologs thereof, any technique that provides for the production of antibody molecules by continuous cell line culture may be utilized. Such techniques include, but are not limited to, the hybridoma technique (see Kohler & Milstein, 1975 *Nature* 256: 495–497); the trioma technique; the human B-cell hybridoma technique (see Kozbor, et al., 1983 *Immunol Today* 4: 72) and the EBV hybridoma technique to produce human monoclonal antibodies (see Cole, et al., 1985 In: Monoclonal Antibodies and Cancer Therapy, Alan R. Liss, Inc., pp. 77–96). Human monoclonal antibodies may be utilized in the practice of the present invention and may be produced by using human hybridomas (see Cote, et al., 1983. *Proc Natl Acad Sci USA* 80: 2026–2030) or by transforming human B-cells with Epstein Barr Virus in vitro (see Cole, et al., 1985 In: Monoclonal Antibodies and Cancer Therapy, Alan R. Liss, Inc., pp. 77–96). Each of the above citations are incorporated herein by reference in their entirety.

According to the invention, techniques can be adapted for the production of single-chain antibodies specific to a SECX protein (see e.g., U.S. Pat. No. 4,946,778). In addition, methodologies can be adapted for the construction of $F_{ab}$ expression libraries (see e.g., Huse, et al., 1989 *Science* 246: 1275–1281) to allow rapid and effective identification of monoclonal $F_{ab}$ fragments with the desired specificity for a SECX protein or derivatives, fragments, analogs or homologs thereof. Non-human antibodies can be "humanized" by techniques well known in the art. See e.g., U.S. Pat. No. 5,225,539. Antibody fragments that contain the idiotypes to a SECX protein may be produced by techniques known in the art including, but not limited to: (i) an $F_{(ab')2}$ fragment produced by pepsin digestion of an antibody molecule; (ii) an $F_{ab}$ fragment generated by reducing the disulfide bridges of an $F_{(ab')2}$ fragment; (iii) an $F_{ab}$ fragment generated by the treatment of the antibody molecule with papain and a reducing agent and (iv) $F_v$ fragments.

Additionally, recombinant anti-SECX antibodies, such as chimeric and humanized monoclonal antibodies, comprising both human and non-human portions, which can be made using standard recombinant DNA techniques, are within the scope of the invention. Such chimeric and humanized monoclonal antibodies can be produced by recombinant DNA techniques known in the art, for example using methods described in International Application No. PCT/US86/02269; European Patent Application No. 184,187; European Patent Application No. 171,496; European Patent Application No. 173,494; PCT International Publication No. WO 86/01533; U.S. Pat. No. 4,816,567; U.S. Pat. No. 5,225,539; European Patent Application No. 125,023; Better et al. (1988) *Science* 240:1041–1043; Liu et al. (1987) *PNAS*

84:3439–3443; Liu et al. (1987) *J Immunol.* 139:3521–3526; Sun et al. (1987) *PNAS* 84:214–218; Nishimura et al. (1987) *Cancer Res* 47:999–1005; Wood et al. (1985) *Nature* 314:446–449; Shaw et al. (1988) *J Natl Cancer Inst* 80:1553–1559); Morrison(1985) *Science* 229:1202–1207; Oi et al. (1986) *BioTechniques* 4:214; Jones et al. (1986) *Nature* 321:552–525; Verhoeyan et al. (1988) *Science* 239:1534; and Beidler et al. (1988) *J Immunol* 141:4053–4060. Each of the above citations are incorporated herein by reference in their entirety.

In one embodiment, methodologies for the screening of antibodies that possess the desired specificity include, but are not limited to, enzyme-linked immunosorbent assay (ELISA) and other immunologically-mediated techniques known within the art. In a specific embodiment, selection of antibodies that are specific to a particular domain of a SECX protein is facilitated by generation of hybridomas that bind to the fragment of a SECX protein possessing such a domain. Antibodies that are specific for an above-described domain within a SECX protein, or derivatives, fragments, analogs or homologs thereof, are also provided herein.

Anti-SECX antibodies may be used in methods known within the art relating to the localization and/or quantitation of a SECX protein (e.g., for use in measuring levels of the SECX protein within appropriate physiological samples, for use in diagnostic methods, for use in imaging the protein, and the like). In a given embodiment, antibodies for SECX proteins, or derivatives, fragments, analogs or homologs thereof, that contain the antibody derived binding domain, are utilized as pharmacologically-active compounds [hereinafter "Therapeutics"].

An anti-SECX antibody (e.g., monoclonal antibody) can be used to isolate SECX by standard techniques, such as affinity chromatography or immunoprecipitation. An anti-SECX antibody can facilitate the purification of natural SECX from cells and of recombinantly produced SECX expressed in host cells. Moreover, an anti-SECX antibody can be used to detect SECX protein (e.g., in a cellular lysate or cell supernatant) in order to evaluate the abundance and pattern of expression of the SECX protein. Anti-SECX antibodies can be used diagnostically to monitor protein levels in tissue as part of a clinical testing procedure, e.g., to, for example, determine the efficacy of a given treatment regimen. Detection can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}I$, $^{131}I$, $^{35}S$ or $^{3}H$.

SECX Recombinant Expression Vectors and Host Cells

Another aspect of the invention pertains to vectors, preferably expression vectors, containing a nucleic acid encoding SECX protein, or derivatives, fragments, analogs or homologs thereof. As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors". In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The recombinant expression vectors of the invention comprise a nucleic acid of the invention in a form suitable for expression of the nucleic acid in a host cell, which means that the recombinant expression vectors include one or more regulatory sequences, selected on the basis of the host cells to be used for expression, that is operatively linked to the nucleic acid sequence to be expressed. Within a recombinant expression vector, "operably linked" is intended to mean that the nucleotide sequence of interest is linked to the regulatory sequence(s) in a manner that allows for expression of the nucleotide sequence (e.g., in an in vitro transcription/translation system or in a host cell when the vector is introduced into the host cell). The term "regulatory sequence" is intended to includes promoters, enhancers and other expression control elements (e.g., polyadenylation signals). Such regulatory sequences are described, for example, in Goeddel; Gene Expression Technology: Methods in Enzymology 185, Academic Press, San Diego, Calif. (1990). Regulatory sequences include those that direct constitutive expression of a nucleotide sequence in many types of host cell and those that direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, etc. The expression vectors of the invention can be introduced into host cells to thereby produce proteins or peptides, including fusion proteins or peptides, encoded by nucleic acids as described herein (e.g., SECX proteins, mutant forms of SECX, fusion proteins, etc.).

The recombinant expression vectors of the invention can be designed for expression of SECX in prokaryotic or eukaryotic cells. For example, SECX can be expressed in bacterial cells such as *E. coli,* insect cells (using baculovirus expression vectors) yeast cells or mammalian cells. Suitable host cells are discussed further in Goeddel, Gene Expression Technology: Methods in Enzymology 185, Academic Press, San Diego, Calif. (1990). Alternatively, the recombinant expression vector can be transcribed and translated in vitro, for example using T7 promoter regulatory sequences and T7 polymerase.

Expression of proteins in prokaryotes is most often carried out in *E. coli* with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: (1) to increase expression of recombinant protein; (2) to increase the solubility of the recombinant protein; and (3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc.; Smith and Johnson (1988) *Gene* 67:31–40), pMAL (New England Biolabs, Beverly, Mass.) and pRIT5 (Pharmacia, Piscataway, N.J.) that fuse glutathione S-transferase (GST), maltose E binding protein, or protein A, respectively, to the target recombinant protein.

Examples of suitable inducible non-fusion *E. coli* expression vectors include pTrc (Amrann et al., (1988) *Gene* 69:301–315) and pET 11d (Studier et al., Gene Expression Technology: Methods in Enzymology 185, Academic Press, San Diego, Calif. (1990) 60–89).

One strategy to maximize recombinant protein expression in *E. coli* is to express the protein in a host bacteria with an impaired capacity to proteolytically cleave the recombinant protein. See, Gottesman, Gene Expression Technology: Methods in Enzymology 185, Academic Press, San Diego, Calif. (1990) 119–128. Another strategy is to alter the nucleic acid sequence of the nucleic acid to be inserted into an expression vector so that the individual codons for each amino acid are those preferentially utilized in *E. coli* (Wada et al., (1992) *Nucleic Acids Res.* 20:2111–2118). Such alteration of nucleic acid sequences of the invention can be carried out by standard DNA synthesis techniques.

In another embodiment, the SECX expression vector is a yeast expression vector. Examples of vectors for expression in yeast *S. cerivisae* include pYepSec1 (Baldari, et al., (1987) *EMBO J* 6:229–234), pMFa (Kurjan and Herskowitz, (1982) *Cell* 30:933–943), pJRY88 (Schultz et al., (1987) *Gene* 54:113–123), pYES2 (Invitrogen Corporation, San Diego, Calif.), and picZ (InVitrogen Corp., San Diego, Calif.).

Alternatively, SECX can be expressed in insect cells using baculovirus expression vectors. Baculovirus vectors available for expression of proteins in cultured insect cells (e.g., SF9 cells) include the pAc series (Smith et al. (1983) *Mol Cell Biol* 3:2156–2165) and the pVL series (Lucklow and Summers (1989) *Virology* 170:31–39).

In yet another embodiment, a nucleic acid of the invention is expressed in mammalian cells using a mammalian expression vector. Examples of mammalian expression vectors include pCDM8 (Seed (1987) *Nature* 329:840) and pMT2PC (Kaufman et al. (1987) *EMBO J* 6: 187–195). When used in mammalian cells, the expression vector's control functions are often provided by viral regulatory elements. For example, commonly used promoters are derived from polyoma, Adenovirus 2, cytomegalovirus and Simian Virus 40. For other suitable expression systems for both prokaryotic and eukaryotic cells. See, e.g., Chapters 16 and 17 of Sambrook et al., Molecular Cloning: A Laboratory Manual. 2nd ed., Cold Spring Harbor Laboratory, Cold Spring Harbor Laboratory Press, Cold Spring Harbor, N.Y., 1989.

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert et al. (1987) *Genes Dev* 1:268–277), lymphoid-specific promoters (Calame and Eaton (1988) *Adv Immunol* 43:235–275), in particular promoters of T cell receptors (Winoto and Baltimore (1989) *EMBO J* 8:729–733) and immunoglobulins (Banerji et al. (1983) *Cell* 33:729–740; Queen and Baltimore (1983) *Cell* 33:741–748), neuron-specific promoters (e.g., the neurofilament promoter; Byrne and Ruddle (1989) *PNAS* 86:5473–5477), pancreas-specific promoters (Edlund et al. (1985) *Science* 230:912–916), and mammary gland-specific promoters (e.g., milk whey promoter; U.S. Pat. No. 4,873,316 and European Application Publication No. 264,166). Developmentally-regulated promoters are also encompassed, e.g., the murine hox promoters (Kessel and Gruss (1990) *Science* 249:374–379) and the α-fetoprotein promoter (Campes and Tilghman (1989) *Genes Dev* 3:537–546).

The invention further provides a recombinant expression vector comprising a DNA molecule of the invention cloned into the expression vector in an antisense orientation. That is, the DNA molecule is operatively linked to a regulatory sequence in a manner that allows for expression (by transcription of the DNA molecule) of an RNA molecule that is antisense to SECX mRNA. Regulatory sequences operatively linked to a nucleic acid cloned in the antisense orientation can be chosen that direct the continuous expression of the antisense RNA molecule in a variety of cell types, for instance viral promoters and/or enhancers, or regulatory sequences can be chosen that direct constitutive, tissue specific or cell type specific expression of antisense RNA. The antisense expression vector can be in the form of a recombinant plasmid, phagemid or attenuated virus in which antisense nucleic acids are produced under the control of a high efficiency regulatory region, the activity of which can be determined by the cell type into which the vector is introduced. For a discussion of the regulation of gene expression using antisense genes see Weintraub et al., "Antisense RNA as a molecular tool for genetic analysis," Reviews—Trends in Genetics, Vol. 1(1) 1986.

Another aspect of the invention pertains to host cells into which a recombinant expression vector of the invention has been introduced. The terms "host cell" and "recombinant host cell" are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, SECX protein can be expressed in bacterial cells such as *E. coli*, insect cells, yeast or mammalian cells (such as Chinese hamster ovary cells (CHO) or COS cells). Other suitable host cells are known to those skilled in the art.

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook, et al. (Molecular Cloning: A Laboratory Manual. 2nd ed., Cold Spring Harbor Laboratory, Cold Spring Harbor Laboratory Press, Cold Spring Harbor, N.Y., 1989), and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., resistance to antibiotics) is generally introduced into the host cells along with the gene of interest. Various selectable markers include those that confer resistance to drugs, such as G418, hygromycin and methotrexate. Nucleic acid encoding a selectable marker can be introduced into a host cell on the same vector as that encoding SECX or can be introduced on a separate vector. Cells stably transfected with the introduced nucleic acid can be identified by drug selection (e.g., cells that have incorporated the selectable marker gene will survive, while the other cells die).

A host cell of the invention, such as a prokaryotic or eukaryotic host cell in culture, can be used to produce (i.e., express) SECX protein. Accordingly, the invention further provides methods for producing SECX protein using the host cells of the invention. In one embodiment, the method comprises culturing the host cell of invention (into which a recombinant expression vector encoding SECX has been introduced) in a suitable medium such that SECX protein is produced. In another embodiment, the method further comprises isolating SECX from the medium or the host cell.

Transgenic animals

The host cells of the invention can also be used to produce nonhuman transgenic animals. For example, in one embodiment, a host cell of the invention is a fertilized oocyte or an embryonic stem cell into which SECX-coding sequences have been introduced. Such host cells can then be used to create non-human transgenic animals in which exogenous SECX sequences have been introduced into their genome or homologous recombinant animals in which endogenous SECX sequences have been altered. Such animals are useful for studying the function and/or activity of SECX and for identifying and/or evaluating modulators of SECX activity. As used herein, a "transgenic animal" is a non-human animal, preferably a mammal, more preferably a rodent such as a rat or mouse, in which one or more of the cells of the animal includes a transgene. Other examples of transgenic animals include non-human primates, sheep, dogs, cows, goats, chickens, amphibians, etc. A transgene is exogenous DNA that is integrated into the genome of a cell from which a transgenic animal develops and that remains in the genome of the mature animal, thereby directing the expression of an encoded gene product in one or more cell types or tissues of the transgenic animal. As used herein, a "homologous recombinant animal" is a non-human animal, preferably a mammal, more preferably a mouse, in which an endogenous SECX gene has been altered by homologous recombination between the endogenous gene and an exogenous DNA molecule introduced into a cell of the animal, e.g., an embryonic cell of the animal, prior to development of the animal.

A transgenic animal of the invention can be created by introducing SECX-encoding nucleic acid into the male pronuclei of a fertilized oocyte, e.g., by microinjection, retroviral infection, and allowing the oocyte to develop in a pseudopregnant female foster animal. The human SECX cDNA can be introduced as a transgene into the genome of a non-human animal. Alternatively, a nonhuman homologue of the human SECX gene, such as a mouse SECX gene, can be isolated based on hybridization to the human SECX cDNA (described further above) and used as a transgene. Intronic sequences and polyadenylation signals can also be included in the transgene to increase the efficiency of expression of the transgene. A tissue-specific regulatory sequence(s) can be operably linked to the SECX transgene to direct expression of SECX protein to particular cells. Methods for generating transgenic animals via embryo manipulation and microinjection, particularly animals such as mice, have become conventional in the art and are described, for example, in U.S. Pat. Nos. 4,736,866; 4,870,009; and 4,873,191; and Hogan 1986, In: Manipulating the Mouse Embryo, Cold Spring Harbor Laboratory Press, Cold Spring Harbor, N.Y. Similar methods are used for production of other transgenic animals. A transgenic founder animal can be identified based upon the presence of the SECX transgene in its genome and/or expression of SECX mRNA in tissues or cells of the animals. A transgenic founder animal can then be used to breed additional animals carrying the transgene. Moreover, transgenic animals carrying a transgene encoding SECX can further be bred to other transgenic animals carrying other transgenes.

To create a homologous recombinant animal, a vector is prepared which contains at least a portion of a SECX gene into which a deletion, addition or substitution has been introduced to thereby alter, e.g., functionally disrupt, the SECX gene. The SECX gene can be a human gene (e.g., the cDNA of SEQ ID NOs:1, 3, 5, 7, 9, 11, 13, 15, 17, 19, 21, 23, 25, 27, 74, 76, 78 and 80, plus 29 and 31), but more preferably, is a non-human homologue of a human SECX gene. For example, a mouse homologue of human SECX gene of, e.g., SEQ ID NO:29, can be used to construct a homologous recombination vector suitable for altering an endogenous SECX gene in the mouse genome. In one embodiment, the vector is designed such that, upon homologous recombination, the endogenous SECX gene is functionally disrupted (i.e., no longer encodes a functional protein; also referred to as a "knock out" vector).

Alternatively, the vector can be designed such that, upon homologous recombination, the endogenous SECX gene is mutated or otherwise altered but still encodes functional protein (e.g., the upstream regulatory region can be altered to thereby alter the expression of the endogenous SECX protein). In the homologous recombination vector, the altered portion of the SECX gene is flanked at its 5' and 3' ends by additional nucleic acid of the SECX gene to allow for homologous recombination to occur between the exogenous SECX gene carried by the vector and an endogenous SECX gene in an embryonic stem cell. The additional flanking SECX nucleic acid is of sufficient length for successful homologous recombination with the endogenous gene. Typically, several kilobases of flanking DNA (both at the 5' and 3' ends) are included in the vector. See e.g., Thomas et al. (1987) Cell 51:503 for a description of homologous recombination vectors. The vector is introduced into an embryonic stem cell line (e.g., by electroporation) and cells in which the introduced SECX gene has homologously recombined with the endogenous SECX gene are selected (see e.g., Li et al. (1992) Cell 69:915).

The selected cells are then injected into a blastocyst of an animal (e.g., a mouse) to form aggregation chimeras. See e.g., Bradley 1987, In: Teratocarcinomas and Embryonic Stem Cells: A Practical Approach, Robertson, ed. IRL, Oxford, pp. 113–152. A chimeric embryo can then be implanted into a suitable pseudopregnant female foster animal and the embryo brought to term. Progeny harboring the homologously recombined DNA in their germ cells can be used to breed animals in which all cells of the animal contain the homologously recombined DNA by germline transmission of the transgene. Methods for constructing homologous recombination vectors and homologous recombinant animals are described further in Bradley (1991) *Curr Opin Biotechnol* 2:823–829; PCT International Publication Nos.: WO 90/11354; WO 91/01140; WO 92/0968; and WO 93/04169.

In another embodiment, transgenic non-humans animals can be produced that contain selected systems that allow for regulated expression of the transgene. One example of such a system is the cre/loxP recombinase system of bacteriophage P1. For a description of the cre/loxP recombinase system, see, e.g., Lakso et al. (1992) *PNAS* 89:6232–6236. Another example of a recombinase system is the FLP recombinase system of *Saccharomyces cerevisiae* (O'Gorman et al. (1991) *Science* 251:1351–1355. If a cre/loxP recombinase system is used to regulate expression of the transgene, animals containing transgenes encoding both the Cre recombinase and a selected protein are required. Such animals can be provided through the construction of "double" transgenic animals, e.g., by mating two transgenic animals, one containing a transgene encoding a selected protein and the other containing a transgene encoding a recombinase.

Clones of the non-human transgenic animals described herein can also be produced according to the methods described in Wilmut et al. (1997) *Nature* 385:810–813. In brief, a cell, e.g., a somatic cell, from the transgenic animal can be isolated and induced to exit the growth cycle and enter $G_0$ phase. The quiescent cell can then be fused, e.g., through the use of electrical pulses, to an enucleated oocyte from an animal of the same species from which the quiescent cell is isolated. The reconstructed oocyte is then cultured such that it develops to morula or blastocyte and then transferred to pseudopregnant female foster animal. The offspring borne of this female foster animal will be a clone of the animal from which the cell, e.g., the somatic cell, is isolated.

Pharmaceutical Compositions

The SECX nucleic acid molecules, SECX proteins, and anti-SECX antibodies (also referred to herein as "active compounds") of the invention, and derivatives, fragments, analogs and homologs thereof, can be incorporated into pharmaceutical compositions suitable for administration. Such compositions typically comprise the nucleic acid molecule, protein, or antibody and a pharmaceutically acceptable carrier. As used herein, "pharmaceutically acceptable carrier" is intended to include any and all solvents, dispersion media, coatings, antibacterial and antifungal agents, isotonic and absorption delaying agents, and the like, compatible with pharmaceutical administration. Suitable carriers are described in the most recent edition of Remington's Pharmaceutical Sciences, a standard reference text in the field, which is incorporated herein by reference. Preferred examples of such carriers or diluents include, but are not limited to, water, saline, finger's solutions, dextrose solution, and 5% human serum albumin. Liposomes and non-aqueous vehicles such as fixed oils may also be used. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., a SECX protein or anti-SECX antibody) in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

The nucleic acid molecules of the invention can be inserted into vectors and used as gene therapy vectors. Gene therapy vectors can be delivered to a subject by, for example, intravenous injection, local administration (see U.S. Pat. No. 5,328,470) or by stereotactic injection (see e.g., Chen et al. (1994) *PNAS* 91:3054–3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells that produce the gene delivery system.

The pharmaceutical compositions can be included in a container, pack, or dispenser together with instructions for administration.

Uses and Methods of the Invention

The nucleic acid molecules, proteins, protein homologues, and antibodies described herein that include extracellular and transmembrane domains and, therefore, can be used in one or more of the following methods: (a) screening assays; (b) detection assays (e.g., chromosomal mapping, tissue typing, forensic biology), (c) predictive medicine (e.g., diagnostic assays, prognostic assays, monitoring clinical trials, and pharmacogenomics); and (d) methods of treatment (e.g., therapeutic and prophylactic). A SECX protein interacting with other cellular proteins can thus be used to.(i) modulate that respective protein activity; (ii) regulate cellular proliferation; (iii) regulate cellular differentiation; and (iv) regulate cell survival.

The isolated nucleic acid molecules of the invention can be used to express SECX protein (e.g., via a recombinant expression vector in a host cell in gene therapy applications), to detect SECX mRNA (e.g., in a biological sample) or a genetic lesion in a SECX gene, and to modulate SECX activity, as described further below. In addition, the SECX proteins can be used to screen drugs or compounds that modulate the SECX activity or expression as well as to treat disorders characterized by insufficient or excessive production of SECX protein or production of SECX protein forms that have decreased or aberrant activity compared to SECX wild type protein (e.g. proliferative disorders such as cancer or preclampsia, or any disease or disorder described in Sections 1–14 above). In addition, the anti-SECX antibodies of the invention can be used to detect and isolate SECX proteins and modulate SECX activity.

This invention further pertains to novel agents identified by the above described screening assays and uses thereof for treatments as described herein.

Screening Assays

The invention provides a method (also referred to herein as a "screening assay") for identifying modulators, i.e., candidate or test compounds or agents (e.g., peptides, peptidomimetics, small molecules or other drugs) that bind to SECX proteins or have a stimulatory or inhibitory effect on, for example, SECX expression or SECX activity.

In one embodiment, the invention provides assays for screening candidate or test compounds which bind to or modulate the activity of the membrane-bound form of a SECX protein or polypeptide or biologically active portion thereof. The test compounds of the present invention can be obtained using any of the numerous approaches in combinatorial library methods known in the art, including: biological libraries; spatially addressable parallel solid phase or solution phase libraries; synthetic library methods requiring deconvolution; the "one-bead one-compound" library method; and synthetic library methods using affinity chromatography selection. The biological library approach is limited to peptide libraries, while the other four approaches are applicable to peptide, non-peptide oligomer or small molecule libraries of compounds (Lam (1997) *Anticancer Drug Des* 12:145).

Examples of methods for the synthesis of molecular libraries can be found in the art, for example in: DeWitt et al. (1993) *Proc Natl Acad Sci U.S.A.* 90:6909; Erb et al. (1994) *Proc Natl Acad Sci U.S.A.* 91:11422; Zuckermann et al. (1994) *J Med Chem* 37:2678; Cho et al. (1993) *Science* 261:1303; Carrell et al. (1994) *Angew Chem Int Ed Engl* 33:2059; Carell et al. (1994) *Angew Chem Int Ed Engl* 33:2061; and Gallop et al. (1994) *J Med Chem* 37:1233.

Libraries of compounds may be presented in solution (e.g., Houghten (1992) *BioTechniques* 13:412–421), or on beads (Lam (1991) *Nature* 354:82–84), on chips (Fodor (1993) *Nature* 364:555–556), bacteria (Ladner U.S. Pat. No. 5,223,409), spores (Ladner U.S. Pat. No. '409), plasmids (Cull et al. (1992) *Proc Natl Acad Sci USA* 89: 1865–1869) or on phage (Scott and Smith (1990) *Science* 249:386–390; Devlin (1990) *Science* 249:404–406; Cwirla et al. (1990) *Proc Natl Acad Sci U.S.A.* 87:6378–6382; Felici (1991) *J Mol Biol* 222:301–310; Ladner above.).

In one embodiment, an assay is a cell-based assay in which a cell which expresses a membrane-bound form of SECX protein, or a biologically active portion thereof, on the cell surface is contacted with a test compound and the ability of the test compound to bind to a SECX protein determined. The cell, for example, can of mammalian origin or a yeast cell. Determining the ability of the test compound to bind to the SECX protein can be accomplished, for example, by coupling the test compound with a radioisotope or enzymatic label such that binding of the test compound to the SECX protein or biologically active portion thereof can be determined by detecting the labeled compound in a complex. For example, test compounds can be labeled with $^{125}I$, $^{35}S$, $^{14}C$, or $^3H$, either directly or indirectly, and the radioisotope detected by direct counting of radioemission or by scintillation counting. Alternatively, test compounds can be enzymatically labeled with, for example, horseradish peroxidase, alkaline phosphatase, or luciferase, and the enzymatic label detected by determination of conversion of an appropriate substrate to product. In one embodiment, the assay comprises contacting a cell which expresses a membrane-bound form of SECX protein, or a biologically active portion thereof, on the cell surface with a known compound which binds SECX to form an assay mixture, contacting the assay mixture with a test compound, and determining the ability of the test compound to interact with a SECX protein, wherein determining the ability of the test compound to interact with a SECX protein comprises determining the ability of the test compound to preferentially bind to SECX or a biologically active portion thereof as compared to the known compound.

In another embodiment, an assay is a cell-based assay comprising contacting a cell expressing a membrane-bound form of SECX protein, or a biologically active portion thereof, on the cell surface with a test compound and determining the ability of the test compound to modulate (e.g., stimulate or inhibit) the activity of the SECX protein or biologically active portion thereof. Determining the ability of the test compound to modulate the activity of SECX or a biologically active portion thereof can be accomplished, for example, by determining the ability of the SECX protein to bind to or interact with a SECX target molecule. As used herein, a "target molecule" is a molecule with which a SECX protein binds or interacts in nature, for example, a molecule on the surface of a cell which expresses a SECX interacting protein, a molecule on the surface of a second cell, a molecule in the extracellular milieu, a molecule associated with the internal surface of a cell membrane or a cytoplasmic molecule. A SECX target molecule can be a non-SECX molecule or a SECX protein or polypeptide of the present invention. In one embodiment, a SECX target molecule is a component of a signal transduction pathway that facilitates transduction of an extracellular signal (e.g. a signal generated by binding of a compound to a membrane-bound SECX molecule) through the cell membrane and into the cell. The target, for example, can be a second intercellular protein that has catalytic activity or a protein that facilitates the association of downstream signaling molecules with SECX.

Determining the ability of the SECX protein to bind to or interact with a SECX target molecule can be accomplished by one of the methods described above for determining direct binding. In one embodiment, determining the ability of the SECX protein to bind to or interact with a SECX target molecule can be accomplished by determining the activity of the target molecule. For example, the activity of the target molecule can be determined by detecting induction of a cellular second messenger of the target (i.e. intracellular $Ca^{2+}$, diacylglycerol, $IP_3$, etc.), detecting catalytic/enzymatic activity of the target an appropriate substrate, detecting the induction of a reporter gene (comprising a SECX-responsive regulatory element operatively linked to a nucleic acid encoding a detectable marker, e.g., luciferase), or detecting a cellular response, for example, cell survival, cellular differentiation, or cell proliferation.

In yet another embodiment, an assay of the present invention is a cell-free assay comprising contacting a SECX protein or biologically active portion thereof with a test compound and determining the ability of the test compound to bind to the SECX protein or biologically active portion thereof. Binding of the test compound to the SECX protein can be determined either directly or indirectly as described above. In one embodiment, the assay comprises contacting the SECX protein or biologically active portion thereof with a known compound which binds SECX to form an assay mixture, contacting the assay mixture with a test compound, and determining the ability of the test compound to interact with a SECX protein, wherein determining the ability of the test compound to interact with a SECX protein comprises determining the ability of the test compound to preferentially bind to SECX or biologically active portion thereof as compared to the known compound.

In another embodiment, an assay is a cell-free assay comprising contacting SECX protein or biologically active portion thereof with a test compound and determining the ability of the test compound to modulate (e.g. stimulate or inhibit) the activity of the SECX protein or biologically active portion thereof. Determining the ability of the test compound to modulate the activity of SECX can be accomplished, for example, by determining the ability of the SECX protein to bind to a SECX target molecule by one of the methods described above for determining direct binding. In an alternative embodiment, determining the ability of the test compound to modulate the activity of SECX can be accomplished by determining the ability of the SECX protein further modulate a SECX target molecule. For example, the catalytic/enzymatic activity of the target molecule on an appropriate substrate can be determined as previously described.

In yet another embodiment, the cell-free assay comprises contacting the SECX protein or biologically active portion thereof with a known compound which binds SECX to form an assay mixture, contacting the assay mixture with a test compound, and determining the ability of the test compound to interact with a SECX protein, wherein determining the ability of the test compound to interact with a SECX protein comprises determining the ability of the SECX protein to preferentially bind to or modulate the activity of a SECX target molecule.

The cell-free assays of the present invention are amenable to use of both the soluble form or the membrane-bound form of SECX. In the case of cell-free assays comprising the membrane-bound form of SECX, it may be desirable to utilize a solubilizing agent such that the membrane-bound form of SECX is maintained in solution. Examples of such solubilizing agents include non-ionic detergents such as n-octylglucoside, n-dodecylglucoside, n-dodecylmaltoside, octanoyl-N-methylglucamide, decanoyl-N-methylglucamide, Triton® X-100, Triton® X-114, Thesit®, Isotridecypoly(ethylene glycol ether)$_n$, N-dodecyl-N,N-dimethyl-3-ammonio-1-propane sulfonate, 3-(3-cholamidopropyl)dimethylamminiol-1-propane sulfonate (CHAPS), or 3-(3-cholamidopropyl)dimethylamminiol-2-hydroxy-1-propane sulfonate (CHAPSO).

In more than one embodiment of the above assay methods of the present invention, it may be desirable to immobilize either SECX or its target molecule to facilitate separation of complexed from uncomplexed forms of one or both of the proteins, as well as to accommodate automation of the assay. Binding of a test compound to SECX, or interaction of SECX with a target molecule in the presence and absence of a candidate compound, can be accomplished in any vessel suitable for containing the reactants. Examples of such vessels include microtiter plates, test tubes, and microcentrifuge tubes. In one embodiment, a fusion protein can be provided that adds a domain that allows one or both of the proteins to be bound to a matrix. For example, GST-SECX fusion proteins or GST-target fusion proteins can be adsorbed onto glutathione sepharose beads (Sigma Chemical, St. Louis, Mo.) or glutathione derivatized microtiter plates, that are then combined with the test compound or the test compound and either the non-adsorbed target protein or SECX protein, and the mixture is incubated under conditions conducive to complex formation (e.g., at physiological conditions for salt and pH). Following incubation, the beads or microtiter plate wells are washed to remove any unbound components, the matrix immobilized in the case of beads, complex determined either directly or indirectly, for example, as described above. Alternatively, the complexes can be dissociated from the matrix, and the level of SECX binding or activity determined using standard techniques.

Other techniques for immobilizing proteins on matrices can also be used in the screening assays of the invention. For example, either SECX or its target molecule can be immobilized utilizing conjugation of biotin and streptavidin. Biotinylated SECX or target molecules can be prepared from biotin-NHS (N-hydroxy-succinimide) using techniques well known in the art (e.g., biotinylation kit, Pierce Chemicals, Rockford, Ill.), and immobilized in the wells of streptavidin-coated 96 well plates (Pierce Chemical). Alternatively, antibodies reactive with SECX or target molecules, but which do not interfere with binding of the SECX protein to its target molecule, can be derivatized to the wells of the plate, and unbound target or SECX trapped in the wells by antibody conjugation. Methods for detecting such complexes, in addition to those described above for the GST-immobilized complexes, include immunodetection of complexes using antibodies reactive with the SECX or target molecule, as well as enzyme-linked assays that rely on detecting an enzymatic activity associated with the SECX or target molecule.

In another embodiment, modulators of SECX expression are identified in a method wherein a cell is contacted with a candidate compound and the expression of SECX mRNA or protein in the cell is determined. The level of expression of SECX mRNA or protein in the presence of the candidate compound is compared to the level of expression of SECX mRNA or protein in the absence of the candidate compound. The candidate compound can then be identified as a modulator of SECX expression based on this comparison. For example, when expression of SECX mRNA or protein is greater (statistically significantly greater) in the presence of the candidate compound than in its absence, the candidate compound is identified as a stimulator of SECX mRNA or protein expression. Alternatively, when expression of SECX mRNA or protein is less (statistically significantly less) in the presence of the candidate compound than in its absence, the candidate compound is identified as an inhibitor of SECX mRNA or protein expression. The level of SECX mRNA or protein expression in the cells can be determined by methods described herein for detecting SECX mRNA or protein.

In yet another aspect of the invention, the SECX proteins can be used as "bait proteins" in a two-hybrid assay or three hybrid assay (see, e.g., U.S. Pat. No. 5,283,317; Zervos et al. (1993) Cell 72:223–232; Madura et al. (1993) J Biol Chem 268:12046–12054; Bartel et al. (1993) BioTechniques 14:920–924; Iwabuchi et al. (1993) Oncogene 8:1693–1696; and Brent WO94/10300), to identify other proteins that bind to or interact with SECX ("SECX-binding proteins" or "SECX-bp") and modulate SECX activity. Such SECX-binding proteins are also likely to be involved in the propagation of signals by the SECX proteins as, for example, upstream or downstream elements of the SECX pathway.

The two-hybrid system is based on the modular nature of most transcription factors, which consist of separable DNA-binding and activation domains. Briefly, the assay utilizes two different DNA constructs. In one construct, the gene that codes for SECX is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. If the "bait" and the "prey" proteins are able to interact, in vivo, forming a SECX-dependent complex, the DNA-binding and activation domains of the transcription factor are brought into close proximity. This proximity allows transcription of a reporter gene (e.g., LacZ) that is operably linked to a transcriptional regulatory site responsive to the transcription factor. Expression of the reporter gene can be detected and cell colonies containing the functional transcription factor can be isolated and used to obtain the cloned gene that encodes the protein which interacts with SECX.

This invention further pertains to novel agents identified by the above-described screening assays and uses thereof for treatments as described herein.

Detection Assays

Portions or fragments of the cDNA sequences identified herein (and the corresponding complete gene sequences) can be used in numerous ways as polynucleotide reagents. For example, these sequences can be used to: (i) map their respective genes on a chromosome; and, thus, locate gene regions associated with genetic disease; (ii) identify an individual from a minute biological sample (tissue typing); and (iii) aid in forensic identification of a biological sample. These applications are described in the subsections below.

Chromosome Mapping

Once the sequence (or a portion of the sequence) of a gene has been isolated, this sequence can be used to map the location of the gene on a chromosome. This process is called chromosome mapping. Accordingly, portions or fragments of the SECX, sequences, described herein, can be used to map the location of the SECX genes, respectively, on a chromosome. The mapping of the SECX sequences to chromosomes is an important first step in correlating these sequences with genes associated with disease.

Briefly, SECX genes can be mapped to chromosomes by preparing PCR primers (preferably 15–25 bp in length) from the SECX sequences. Computer analysis of the SECX, sequences can be used to rapidly select primers that do not span more than one exon in the genomic DNA, thus complicating the amplification process. These primers can then be used for PCR screening of somatic cell hybrids containing individual human chromosomes. Only those hybrids containing the human gene corresponding to the SECX sequences will yield an amplified fragment.

Somatic cell hybrids are prepared by fusing somatic cells from different mammals (e.g., human and mouse cells). As hybrids of human and mouse cells grow and divide, they gradually lose human chromosomes in random order, but retain the mouse chromosomes. By using media in which mouse cells cannot grow, because they lack a particular enzyme, but in which human cells can, the one human chromosome that contains the gene encoding the needed enzyme will be retained. By using various media, panels of hybrid cell lines can be established. Each cell line in a panel contains either a single human chromosome or a small number of human chromosomes, and a full set of mouse chromosomes, allowing easy mapping of individual genes to specific human chromosomes. (D'Eustachio et al. (1983) Science 220:919–924). Somatic cell hybrids containing only fragments of human chromosomes can also be produced by using human chromosomes with translocations and deletions.

PCR mapping of somatic cell hybrids is a rapid procedure for assigning a particular sequence to a particular chromosome. Three or more sequences can be assigned per day using a single thermal cycler. Using the SECX sequences to design oligonucleotide primers, sublocalization can be achieved with panels of fragments from specific chromosomes.

Fluorescence in situ hybridization (FISH) of a DNA sequence to a metaphase chromosomal spread can further be used to provide a precise chromosomal location in one step. Chromosome spreads can be made using cells whose division has been blocked in metaphase by a chemical like colcemid that disrupts the mitotic spindle. The chromosomes can be treated briefly with trypsin, and then stained with Giemsa. A pattern of light and dark bands develops on each chromosome, so that the chromosomes can be identified individually. The FISH technique can be used with a DNA sequence as short as 500 or 600 bases. However, clones larger than 1,000 bases have a higher likelihood of binding to a unique chromosomal location with sufficient signal intensity for simple detection. Preferably 1,000 bases, and more preferably 2,000 bases, will suffice to get good results at a reasonable amount of time. For a review of this technique, see Vermna et al., Human Chromosomes: A Manual of Basic Techniques (Pergamon Press, New York 1988).

Reagents for chromosome mapping can be used individually to mark a single chromosome or a single site on that chromosome, or panels of reagents can be used for marking multiple sites and/or multiple chromosomes. Reagents corresponding to noncoding regions of the genes actually are preferred for mapping purposes. Coding sequences are more likely to be conserved within gene families, thus increasing the chance of cross hybridizations during chromosomal mapping.

Once a sequence has been mapped to a precise chromosomal location, the physical position of the sequence on the chromosome can be correlated with genetic map data. Such data are found, for example, in McKusick, Mendelian Inheritance in Man, available on-line through Johns Hopkins University Welch Medical Library). The relationship between genes and disease, mapped to the same chromosomal region, can then be identified through linkage analysis (co-inheritance of physically adjacent genes), described in, for example, Egeland et al. (1987) Nature, 325:783–787.

Moreover, differences in the DNA sequences between individuals affected and unaffected with a disease associated with the SECX gene, can be determined. If a mutation is observed in some or all of the affected individuals but not in any unaffected individuals, then the mutation is likely to be the causative agent of the particular disease. Comparison of affected and unaffected individuals generally involves first looking for structural alterations in the chromosomes, such as deletions or translocations that are visible from chromosome spreads or detectable using PCR based on that DNA sequence. Ultimately, complete sequencing of genes from several individuals can be performed to confirm the presence of a mutation and to distinguish mutations from polymorphisms.

Tissue Typing

The SECX sequences of the present invention can also be used to identify individuals from minute biological samples. In this technique, an individual's genomic DNA is digested with one or more restriction enzymes, and probed on a Southern blot to yield unique bands for identification. The sequences of the present invention are useful as additional DNA markers for RFLP ("restriction fragment length polymorphisms," described in U.S. Pat. No. 5,272,057).

Furthermore, the sequences of the present invention can be used to provide an alternative technique that determines the actual base-by-base DNA sequence of selected portions of an individual's genome. Thus, the SECX sequences described herein can be used to prepare two PCR primers from the 5' and 3' ends of the sequences. These primers can then be used to amplify an individual's DNA and subsequently sequence it.

Panels of corresponding DNA sequences from individuals, prepared in this manner, can provide unique individual identifications, as each individual will have a unique set of such DNA sequences due to allelic differences. The sequences of the present invention can be used to obtain such identification sequences from individuals and from tissue. The SECX sequences of the invention uniquely represent portions of the human genome. Allelic variation occurs to some degree in the coding regions of these sequences, and to a greater degree in the noncoding regions. It is estimated that allelic variation between individual humans occurs with a frequency of about once per each 500 bases. Much of the allelic variation is due to single nucleotide polymorphisms (SNPs), which include restriction fragment length polymorphisms (RFLPs).

Each of the sequences described herein can be used as a standard against which DNA from an individual can be compared for identification purposes. Because greater numbers of polymorphisms occur in the noncoding regions, fewer sequences are necessary to differentiate individuals. The noncoding sequences of any one or more of SEQ ID NOs:1, 3, 5, 7, 9, 11, 13, 15, 17, 19, 21, 23, 25, 27, 74, 76, 78 and 80, plus 29 and 31 can comfortably provide positive individual identification with a panel of perhaps 10 to 1,000 primers that each yield a noncoding amplified sequence of 100 bases. If predicted coding sequences are used, a more appropriate number of primers for positive individual identification would be 500–2,000.

A further use of the SECX sequences is to identify a cell or tissue type in a biological sample. As discussed above, various SECX genes are expressed in one or more cell types. Thus, a cell type can be identified based on the presence of RNA molecules from one or more SECX genes. Tissue distribution of various SECX genes are shown and discussed in FIGS. 19–23 and Examples 6–11, below.

Use of SECX Sequences in Forensic Biology

DNA-based identification techniques can also be used in forensic biology. Forensic biology is a scientific field employing genetic typing of biological evidence found at a crime scene as a means for positively identifying, for example, a perpetrator of a crime. To make such an identification, PCR technology can be used to amplify DNA sequences taken from very small biological samples such as tissues, e.g., hair or skin, or body fluids, e.g., blood, saliva, or semen found at a crime scene. The amplified sequence can then be compared to a standard, thereby allowing identification of the origin of the biological sample.

The sequences of the present invention can be used to provide polynucleotide reagents, e.g., PCR primers, targeted to specific loci in the human genome, that can enhance the reliability of DNA-based forensic identifications by, for example, providing another "identification marker" (i.e. another DNA sequence that is unique to a particular individual). As mentioned above, actual base sequence information can be used for identification as an accurate alternative to patterns formed by restriction enzyme generated fragments. Sequences targeted to noncoding regions of SECX gene are particularly appropriate for this use, as greater numbers of polymorphisms occur in the noncoding regions, making it easier to differentiate individuals using this technique. Examples of polynucleotide reagents include the SECX sequences or portions thereof, e.g., fragments derived from the noncoding regions of a SECX gene described herein, having a length of at least 20 bases, preferably at least 30 bases.

The SECX sequences described herein can further be used to provide polynucleotide reagents, e.g., labeled or labelable probes that can be used, for example, in an in situ hybridization technique, to identify a specific tissue, e.g., brain tissue, etc. This can be very useful in cases where a forensic pathologist is presented with a tissue of unknown origin. Panels of such SECX probes can be used to identify tissue by species and/or by organ type.

In a similar fashion, these reagents, e.g., SECX primers or probes can be used to screen tissue culture for contamination (i.e. screen for the presence of a mixture of different types of cells in a culture).

Determination of the Biological Effect of the Therapeutic

In various embodiments of the present invention, suitable in vitro or in vivo assays are utilized to determine the effect of a specific Therapeutic and whether its administration is indicated for treatment of the affected tissue.

In various specific embodiments, in vitro assays may be performed with representative cells of the type(s) involved in the patient's disorder, to determine if a given Therapeutic exerts the desired effect upon the cell type(s). Compounds for use in therapy may be tested in suitable animal model systems including, but not limited to rats, mice, chicken, cows, monkeys, rabbits, and the like, prior to testing in human subjects. Similarly, for in vivo testing, any of the animal model system known in the art may be used prior to administration to human subjects.

Malignancies

SECX proteins are located at the cellular membrane and are thought to be involved in the regulation of cell proliferation and differentiation. Accordingly, Therapeutics of the present invention may be useful in the therapeutic or prophylactic treatment of diseases or disorders that are associated with cell hyperproliferation and/or loss of control of cell proliferation (e.g., cancers, malignancies and tumors). For a review of such hyperproliferation disorders, see e.g., Fishman, et al., 1985. Medicine, 2nd ed., J. B. Lippincott Co., Philadelphia, Pa.

Therapeutics of the present invention may be assayed by any method known within the art for efficacy in treating or preventing malignancies and related disorders. Such assays include, but are not limited to, in vitro assays utilizing transformed cells or cells derived from the patient's tumor, as well as in vivo assays using animal models of cancer or malignancies. Potentially effective Therapeutics are those that, for example, inhibit the proliferation of tumor-derived or transformed cells in culture or cause a regression of tumors in animal models, in comparison to the controls.

In the practice of the present invention, once a malignancy or cancer has been shown to be amenable to treatment by modulating (i.e., inhibiting, antagonizing or agonizing) activity, that cancer or malignancy may subsequently be treated or prevented by the administration of a Therapeutic that serves to modulate protein function.

Premalignant conditions

The Therapeutics of the present invention that are effective in the therapeutic or prophylactic treatment of cancer or malignancies may also be administered for the treatment of pre-malignant conditions and/or to prevent the progression of a pre-malignancy to a neoplastic or malignant state. Such prophylactic or therapeutic use is indicated in conditions known or suspected of preceding progression to neoplasia or cancer, in particular, where non-neoplastic cell growth consisting of hyperplasia, metaplasia or, most particularly, dysplasia has occurred. For a review of such abnormal cell growth see e.g., Robbins & Angell, 1976. Basic Pathology, 2nd ed., W. B. Saunders Co., Philadelphia, Pa.

Hyperplasia is a form of controlled cell proliferation involving an increase in cell number in a tissue or organ, without significant alteration in its structure or function. For example, it has been demonstrated that endometrial hyperplasia often precedes endometrial cancer. Metaplasia is a form of controlled cell growth in which one type of mature or fully differentiated cell substitutes for another type of mature cell. Metaplasia may occur in epithelial or connective tissue cells. Dysplasia is generally considered a precursor of cancer, and is found mainly in the epithelia. Dysplasia is the most disorderly form of non-neoplastic cell growth, and involves a loss in individual cell uniformity and in the architectural orientation of cells. Dysplasia characteristically occurs where there exists chronic irritation or inflammation, and is often found in the cervix, respiratory passages, oral cavity, and gall bladder.

Alternatively, or in addition to the presence of abnormal cell growth characterized as hyperplasia, metaplasia, or dysplasia, the presence of one or more characteristics of a transformed or malignant phenotype displayed either in vivo or in vitro within a cell sample derived from a patient, is indicative of the desirability of prophylactic/therapeutic administration of a Therapeutic that possesses the ability to modulate activity of An aforementioned protein. Characteristics of a transformed phenotype include, but are not limited to: (i) morphological changes; (ii) looser substratum attachment; (iii) loss of cell-to-cell contact inhibition; (iv) loss of anchorage dependence; (v) protease release; (vi) increased sugar transport; (vii) decreased serum requirement; (viii) expression of fetal antigens, (ix) disappearance of the 250 kDal cell-surface protein, and the like. See e.g., Richards, et al., 1986. Molecular Pathology, W. B. Saunders Co., Philadelphia, Pa.

In a specific embodiment of the present invention, a patient that exhibits one or more of the following predisposing factors for malignancy is treated by administration of an effective amount of a Therapeutic: (i) a chromosomal translocation associated with a malignancy (e.g., the Philadelphia chromosome (bcr/abl) for chronic myelogenous leukemia and t(14;18) for follicular lymphoma, etc.); (ii) familial polyposis or Gardner's syndrome (possible forerunners of colon cancer); (iii) monoclonal gammopathy of undetermined significance (a possible precursor of multiple myeloma) and (iv) a first degree kinship with persons having a cancer or pre-cancerous disease showing a Mendelian (genetic) inheritance pattern (e.g., familial polyposis of the colon, Gardner's syndrome, hereditary exostosis, polyendocrine adenomatosis, Peutz-Jeghers syndrome, neurofibromatosis of Von Recklinghausen, medullary thyroid carcinoma with amyloid production and pheochromocytoma, retinoblastoma, carotid body tumor, cutaneous melanocarcinoma, intraocular melanocarcinoma, xeroderma pigmentosum, ataxia telangiectasia, Chediak-Higashi syndrome, albinism, Fanconi's aplastic anemia and Bloom's syndrome).

In another embodiment, a Therapeutic of the present invention is administered to a human patient to prevent the progression to breast, colon, lung, pancreatic, or uterine cancer, or melanoma or sarcoma.

Hyperproliferative and dysproliferative disorders

In one embodiment of the present invention, a Therapeutic is administered in the therapeutic or prophylactic treatment of hyperproliferative or benign dysproliferative disorders. The efficacy in treating or preventing hyperproliferative diseases or disorders of a Therapeutic of the present invention may be assayed by any method known within the art. Such assays include in vitro cell proliferation assays, in vitro or in vivo assays using animal models of hyperproliferative diseases or disorders, or the like. Potentially effective Therapeutics may, for example, promote cell proliferation in culture or cause growth or cell proliferation in animal models in comparison to controls.

Specific embodiments of the present invention are directed to the treatment or prevention of cirrhosis of the liver (a condition in which scarring has overtaken normal liver regeneration processes); treatment of keloid (hypertrophic scar) formation causing disfiguring of the skin in which the scarring process interferes with normal renewal; psoriasis (a common skin condition characterized by excessive proliferation of the skin and delay in proper cell fate determination); benign tumors; fibrocystic conditions and tissue hypertrophy (e.g., benign prostatic hypertrophy).

Neurodegenerative disorders

SECX protein have been implicated in the deregulation of cellular maturation and apoptosis, which are both characteristic of neurodegenerative disease. Accordingly, Therapeutics of the invention, particularly but not limited to those that modulate (or supply) activity of an aforementioned protein, may be effective in treating or preventing neurodegenerative disease. Therapeutics of the present invention that modulate the activity of an aforementioned protein involved in neurodegenerative disorders can be assayed by any method known in the art for efficacy in treating or preventing such neurodegenerative diseases and disorders. Such assays include in vitro assays for regulated cell maturation or inhibition of apoptosis or in vivo assays using animal models of neurodegenerative diseases or disorders, or any of the assays described below. Potentially effective Therapeutics, for example but not by way of limitation, promote regulated cell maturation and prevent cell apoptosis in culture, or reduce neurodegeneration in animal models in comparison to controls.

Once a neurodegenerative disease or disorder has been shown to be amenable to treatment by modulation activity, that neurodegenerative disease or disorder can be treated or prevented by administration of a Therapeutic that modulates activity. Such diseases include all degenerative disorders involved with aging, especially osteoarthritis and neurodegenerative disorders.

Disorders related to organ transplantation

SECX has been implicated in disorders related to organ transplantation, in particular but not limited to organ rejection. Therapeutics of the invention, particularly those that modulate (or supply) activity, may be effective in treating or preventing diseases or disorders related to organ transplantation. Therapeutics of the invention (particularly Therapeutics that modulate the levels or activity of an aforementioned protein) can be assayed by any method known in the art for efficacy in treating or preventing such diseases and disorders related to organ transplantation. Such assays include in vitro assays for using cell culture models as described below; or in vivo assays using animal models of diseases and disorders related to organ transplantation, see e.g., below. Potentially effective Therapeutics, for example but not by way of limitation, reduce immune rejection responses in animal models in comparison to controls.

Accordingly, once diseases and disorders related to organ transplantation are shown to be amenable to treatment by modulation of activity, such diseases or disorders can be treated or prevented by administration of a Therapeutic that modulates activity.

Cardiovascular Disease

SECX has been implicated in cardiovascular disorders, including in atherosclerotic plaque formation. Diseases such as cardiovascular disease, including cerebral thrombosis or hemorrhage, ischemic heart or renal disease, peripheral vascular disease, or thrombosis of other major vessel, and other diseases, including diabetes mellitus, hypertension, hypothyroidism, cholesterol ester storage disease, systemic lupus erythematosus, homocysteinemia, and familial protein or lipid processing diseases, and the like, are either directly or indirectly associated with atherosclerosis. Accordingly, Therapeutics of the invention, particularly those that modulate (or supply) activity or formation may be effective in treating or preventing atherosclerosis-associated diseases or disorders. Therapeutics of the invention (particularly Therapeutics that modulate the levels or activity) can be assayed by any method known in the art, including those described below, for efficacy in treating or preventing such diseases and disorders.

A vast array of animal and cell culture models exist for processes involved in atherosclerosis. A limited and non-exclusive list of animal models includes knockout mice for premature atherosclerosis (Kurabayashi and Yazaki, 1996, Int. Angiol. 15: 187–194), transgenic mouse models of atherosclerosis (Kappel et al., 1994, FASEB J. 8: 583–592), antisense oligonucleotide treatment of animal models (Callow, 1995, Curr. Opin. Cardiol. 10: 569–576), transgenic rabbit models for atherosclerosis (Taylor, 1997, Ann. N.Y. Acad. Sci 811: 146–152), hypercholesterolemic animal models (Rosenfeld, 1996, Diabetes Res. Clin. Pract. 30 Suppl.: 1–11), hyperlipidemic mice (Paigen et al., 1994, Curr. Opin. Lipidol. 5: 258–264), and inhibition of lipoxygenase in animals (Sigal et al., 1994, Ann. N.Y. Acad. Sci. 714: 211–224). In addition, in vitro cell models include but are not limited to monocytes exposed to low density lipoprotein (Frostegard et al., 1996, Atherosclerosis 121: 93–103), cloned vascular smooth muscle cells (Suttles et al., 1995, Exp. Cell Res. 218: 331–338), endothelial cell-derived chemoattractant exposed T cells (Katz et al., 1994, J. Leukoc. Biol. 55: 567–573), cultured human aortic endothelial cells (Farber et al., 1992, Am. J. Physiol. 262: H1088–1085), and foam cell cultures (Libby et al., 1996, Curr Opin Lipidol 7: 330–335). Potentially effective Therapeutics, for example but not by way of limitation, reduce foam cell formation in cell culture models, or reduce atherosclerotic plaque formation in hypercholesterolemic mouse models of atherosclerosis in comparison to controls.

Accordingly, once an atherosclerosis-associated disease or disorder has been shown to be amenable to treatment by modulation of activity or formation, that disease or disorder can be treated or prevented by administration of a Therapeutic that modulates activity.

Cytokine and Cell Proliferation/Differentiation Activity

A SECX protein of the present invention may exhibit cytokine, cell proliferation (either inducing or inhibiting) or cell differentiation (either inducing or inhibiting) activity or may induce production of other cytokines in certain cell populations. Many protein factors discovered to date, including all known cytokines, have exhibited activity in one or more factor dependent cell proliferation assays, and hence the assays serve as a convenient confirmation of cytokine activity. The activity of a protein of the present invention is evidenced by any one of a number of routine factor dependent cell proliferation assays for cell lines including, without limitation, 32D, DA2, DA1G, T10, B9, B9/11, BaF3, MC9/G, M+ (preB M+), 2E8, RB5, DA1, 123, T1165, HT2, CTLL2, TF-1, Mo7e and CMK.

The activity of a protein of the invention may, among other means, be measured by the following methods: Assays for T-cell or thymocyte proliferation include without limitation those described in: Current Protocols in Immunology, Ed by Coligan et al., Greene Publishing Associates and Wiley-Interscience (Chapter 3 and Chapter 7); Takai et al., *J Immunol* 137:3494–3500, 1986; Bertagnoili et al., *J Immunol* 145:1706–1712, 1990; Bertagnolli et al., *Cell Immunol* 133:327–341, 1991; Bertagnolli, et al., *J Immunol* 149:3778–3783, 1992; Bowman et al., *J Immunol* 152:1756–1761, 1994.

Assays for cytokine production and/or proliferation of spleen cells, lymph node cells or thymocytes include, without limitation, those described by Kruisbeek and Shevach, In: Current Protocols in Immunology. Coligan et al., eds. Vol 1, pp. 3.12.1–14, John Wiley and Sons, Toronto 1994; and by Schreiber, In: Current Protocols in Immunology. Coligan eds. Vol 1 pp. 6.8.1–8, John Wiley and Sons, Toronto 1994.

Assays for proliferation and differentiation of hematopoietic and lymphopoietic cells include, without limitation, those described by Bottomly et al., In: Current Protocols in Immunology. Coligan et al., eds. Vol 1 pp. 6.3.1–6.3.12, John Wiley and Sons, Toronto 1991; deVries et al., *J Exp Med* 173:1205–1211, 1991; Moreau et al., *Nature* 336:690–692, 1988; Greenberger et al., *Proc Natl Acad Sci U.S.A.* 80:2931–2938, 1983; Nordan, In: Current Protocols in Immunology. Coligan et al., eds. Vol 1 pp. 6.6.1–5, John Wiley and Sons, Toronto 1991; Smith et al., *Proc Natl Acad Sci U.S.A.* 83:1857–1861, 1986; Measurement of human Interleukin II-Bennett, et al. In: Current Protocols in Immunology. Coligan et al., eds. Vol 1 pp. 6.15.1 John Wiley and Sons, Toronto 1991; Ciarletta, et al., In: Current Protocols in Immunology. Coligan et al., eds. Vol 1 pp. 6.13.1, John Wiley and Sons, Toronto 1991.

Assays for T-cell clone responses to antigens (which will identify, among others, proteins that affect APC-T cell interactions as well as direct T-cell effects by measuring proliferation and cytokine production) include, without limitation, those described In: Current Protocols in Immunology. Coligan et al., eds., Greene Publishing Associates and Wiley-Interscience (Chapter 3Chapter 6, Chapter 7); Weinberger et al., *Proc Natl Acad Sci USA* 77:6091–6095, 1980; Weinberger et al., *Eur J Immun* 11:405–411, 1981; Takai et al., *J Immunol* 137:3494–3500, 1986; Takai et al., *J Immunol* 140:508–512, 1988.

Immune Stimulating or Suppressing Activity

A SECX protein of the present invention may also exhibit immune stimulating or immune suppressing activity, including without limitation the activities for which assays are described herein. A protein may be useful in the treatment of various immune deficiencies and disorders (including severe combined immunodeficiency (SCID)), e.g., in regulating (up or down) growth and proliferation of T and/or B lymphocytes, as well as effecting the cytolytic activity of NK cells and other cell populations. These immune deficiencies may be genetic or be caused by vital (e.g., HIV) as well as bacterial or fungal infections, or may result from autoimmune disorders. More specifically, infectious diseases causes by vital, bacterial, fungal or other infection may be treatable using a protein of the present invention, including infections by HIV, hepatitis viruses, herpesviruses, mycobacteria, Leishmania species, malaria species, and various fungal infections such as candidiasis. Of course, in this regard, a protein of the present invention may also be useful where a boost to the immune system generally may be desirable, i.e., in the treatment of cancer.

Autoimmune disorders which may be treated using a protein of the present invention include, for example, connective tissue disease, multiple sclerosis, systemic lupus erythematosus, rheumatoid arthritis, autoimmune pulmonary inflammation, Guillain-Barre syndrome, autoimmune thyroiditis, insulin dependent diabetes mellitus, myasthenia gravis, graft-versus-host disease and autoimmune inflammatory eye disease. Such a protein of the present invention may also to be useful in the treatment of allergic reactions and conditions, such as asthma (particularly allergic asthma) or other respiratory problems. Other conditions, in which immune suppression is desired (including, for example, organ transplantation), may also be treatable using a protein of the present invention.

Using the proteins of the invention it may also be possible to immune responses, in a number of ways. Down regulation may be in the form of inhibiting or blocking an immune response already in progress or may involve preventing the induction of an immune response. The functions of activated T cells may be inhibited by suppressing T cell responses or by inducing specific tolerance in T cells, or both. Immunosuppression of T cell responses is generally an active, non-antigen-specific, process which requires continuous exposure of the T cells to the suppressive agent. Tolerance, which involves inducing non-responsiveness or energy in T cells, is distinguishable from immunosuppression in that it is generally antigen-specific and persists after exposure to the tolerizing agent has ceased. Operationally, tolerance can be demonstrated by the lack of a T cell response upon re-exposure to specific antigen in the absence of the tolerizing agent.

Down regulating or preventing one or more antigen functions (including without limitation B lymphocyte antigen functions (such as, for example, B7), e.g., preventing high level lymphokine synthesis by activated T cells, will be useful in situations of tissue, skin and organ transplantation and in graft-versus-host disease (GVHD). For example, blockage of T cell function should result in reduced tissue destruction in tissue transplantation. Typically, in tissue transplants, rejection of the transplant is initiated through its recognition as foreign by T cells, followed by an immune reaction that destroys the transplant. The administration of a molecule which inhibits or blocks interaction of a B7 lymphocyte antigen with its natural ligand(s) on immune cells (such as a soluble, monomeric form of a peptide having B7-2 activity alone or in conjunction with a monomeric form of a peptide having an activity of another B lymphocyte antigen (e.g., B7-1, B7-3) or blocking antibody), prior to transplantation can lead to the binding of the molecule to the natural ligand(s) on the immune cells without transmitting the corresponding costimulatory signal. Blocking B lymphocyte antigen function in this matter prevents cytokine synthesis by immune cells, such as T cells, and thus acts as an immunosuppressant. Moreover, the lack of costimulation may also be sufficient to energize the T cells, thereby inducing tolerance in a subject. Induction of long-term tolerance by B lymphocyte antigen-blocking reagents may avoid the necessity of repeated administration of these blocking reagents. To achieve sufficient immunosuppression or tolerance in a subject, it may also be necessary to block the function of B lymphocyte antigens.

The efficacy of particular blocking reagents in preventing organ transplant rejection or GVHD can be assessed using animal models that are predictive of efficacy in humans. Examples of appropriate systems which can be used include allogeneic cardiac grafts in rats and xenogeneic pancreatic islet cell grafts in mice, both of which have been used to examine the immunosuppressive effects of CTLA4Ig fusion proteins in vivo as described in Lenschow et al., Science 257:789–792 (1992) and Turka et al., *Proc Natl Acad Sci USA*, 89:11102–11105 (1992). In addition, murine models of GVHD (see Paul ed., Fundamental Immunology, Raven Press, New York, 1989, pp. 846–847) can be used to determine the effect of blocking B lymphocyte antigen function in vivo on the development of that disease.

Blocking antigen function may also be therapeutically useful for treating autoimmune diseases. Many autoimmune disorders are the result of inappropriate activation of T cells that are reactive against self tissue and which promote the production of cytokines and auto-antibodies involved in the pathology of the diseases. Preventing the activation of autoreactive T cells may reduce or eliminate disease symptoms. Administration of reagents which block costimulation of T cells by disrupting receptor:ligand interactions of B lymphocyte antigens can be used to inhibit T cell activation and prevent production of auto-antibodies or T cell-derived cytokines which may be involved in the disease process. Additionally, blocking reagents may induce antigen-specific tolerance of autoreactive T cells which could lead to long-term relief from the disease. The efficacy of blocking reagents in preventing or alleviating autoimmune disorders can be determined using a number of well-characterized animal models of human autoimmune diseases. Examples include murine experimental autoimmune encephalitis, systemic lupus erythematosis in MRL/lpr/lpr mice or NZB hybrid mice, murine autoimmune collagen arthritis, diabetes mellitus in NOD mice and BB rats, and murine experimental myasthenia gravis (see Paul ed., Fundamental Immunology, Raven Press, New York, 1989, pp. 840–856).

Upregulation of an antigen function (preferably a B lymphocyte antigen function), as a means of up regulating immune responses, may also be useful in therapy. Upregulation of immune responses may be in the form of enhancing an existing immune response or eliciting an initial immune response. For example, enhancing an immune response through stimulating B lymphocyte antigen function may be useful in cases of viral infection. In addition, systemic vital diseases such as influenza, the common cold, and encephalitis might be alleviated by the administration of stimulatory forms of B lymphocyte antigens systemically.

Alternatively, anti-viral immune responses may be enhanced in an infected patient by removing T cells from the patient, costimulating the T cells in vitro with viral antigen-pulsed APCs either expressing a peptide of the present invention or together with a stimulatory form of a soluble peptide of the present invention and reintroducing the in vitro activated T cells into the patient. Another method of enhancing anti-vital immune responses would be to isolate infected cells from a patient, transfect them with a nucleic acid encoding a protein of the present invention as described herein such that the cells express all or a portion of the protein on their surface, and reintroduce the transfected cells into the patient. The infected cells would now be capable of delivering a costimulatory signal to, and thereby activate, T cells in vivo.

In another application, up regulation or enhancement of antigen function (preferably B lymphocyte antigen function) may be useful in the induction of tumor immunity. Tumor cells (e.g., sarcoma, melanoma, lymphoma, leukemia, neuroblastoma, carcinoma) transfected with a nucleic acid encoding at least one peptide of the present invention can be administered to a subject to overcome tumor-specific tolerance in the subject. If desired, the tumor cell can be transfected to express a combination of peptides. For example, tumor cells obtained from a patient can be transfected ex vivo with an expression vector directing the expression of a peptide having B7-2-like activity alone, or in conjunction with a peptide having B7-1-like activity and/or B7-3-like activity. The transfected tumor cells are returned to the patient to result in expression of the peptides on the surface of the transfected cell. Alternatively, gene therapy techniques can be used to target a tumor cell for transfection in vivo.

The presence of the peptide of the present invention having the activity of a B lymphocyte antigen(s) on the surface of the tumor cell provides the necessary costimulation signal to T cells to induce a T cell mediated immune response against the transfected tumor cells. In addition, tumor cells which lack MHC class I or MHC class II molecules, or which fail to reexpress sufficient amounts of MHC class I or MHC class II molecules, can be transfected with nucleic acid encoding all or a portion of (e.g., a cytoplasmic-domain truncated portion) of an MHC class I $\alpha$ chain protein and $\beta_2$ microglobulin protein or an MHC class II a chain protein and an MHC class II $\beta$ chain protein to thereby express MHC class I or MHC class II proteins on the cell surface. Expression of the appropriate class I or class II MHC in conjunction with a peptide having the activity of a B lymphocyte antigen (e.g., B7-1, B7-2, B7-3) induces a T cell mediated immune response against the transfected tumor cell. Optionally, a gene encoding an antisense construct which blocks expression of an MHC class II associated protein, such as the invariant chain, can also be cotransfected with a DNA encoding a peptide having the activity of a B lymphocyte antigen to promote presentation of tumor associated antigens and induce tumor specific immunity. Thus, the induction of a T cell mediated immune response in a human subject may be sufficient to overcome tumor-specific tolerance in the subject.

The activity of a protein of the invention may, among other means, be measured by the following methods: Suitable assays for thymocyte or splenocyte cytotoxicity include, without limitation, those described In: Current Protocols in Immunology. Coligan et al., eds. Greene Publishing Associates and Wiley-Interscience (Chapter 3, Chapter 7); Herrmann et al., *Proc Natl Acad Sci USA* 78:2488–2492, 1981; Herrmann et al., *J Immunol* 128:1968–1974, 1982; Handa et al., *J Immunol* 135:1564–1572, 1985; Takai et al., *J Immunol* 137:3494–3500, 1986; Takai et al., *J Immunol* 140:508–512, 1988; Herrmann et al., *Proc Natl Acad Sci USA* 78:2488–2492, 1981; Herrmann et al., *J Immunol* 128:1968–1974, 1982; Handa et al., *J Inmunol* 135:1564–1572, 1985; Takai et al., *J Immunol* 137:3494–3500, 1986; Bowman et al., *J Virology* 61:1992–1998; Takai et al., *J Immunol* 140:508–512, 1988; Bertagnolli et al., *Cell Immunol* 133:327–341, 1991; Brown et al., *J Immunol* 153:3079–3092, 1994.

Assays for T-cell-dependent immunoglobulin responses and isotype switching (which will identify, among others, proteins that modulate T-cell dependent antibody responses and that affect Th1/Th2 profiles) include, without limitation, those described in: Maliszewski, *J Immunol* 144:3028–3033, 1990; and Mond and Brunswick In: Current Protocols in Immunology. Coligan et al., (eds.) Vol 1 pp. 3.8.1–3.8.16, John Wiley and Sons, Toronto 1994.

Mixed lymphocyte reaction (MLR) assays (which will identify, among others, proteins that generate predominantly Th1 and CTL responses) include, without limitation, those described In: Current Protocols in Immunology. Coligan et al., eds. Greene Publishing Associates and Wiley-Interscience (Chapter 3, Chapter 7); Takai et al., *J Immunol* 137:3494–3500, 1986; Takai et al., *J Immunol* 140:508–512, 1988; Bertagnolli et al., *J Immunol* 149:3778–3783, 1992.

Dendritic cell-dependent assays (which will identify, among others, proteins expressed by dendritic cells that activate naive T-cells) include, without limitation, those described in: Guery et al., *J Immunol* 134:536–544, 1995; Inaba et al., *J Exp Med* 173:549–559, 1991; Macatoniaet al., *J Immunol* 154:5071–5079, 1995; Porgador et al., *J Exp Med* 182:255–260, 1995; Nair et al., *J Virol* 67:4062–4069, 1993; Huang et al., *Science* 264:961–965, 1994; Macatonia et al., *J Exp Med* 169:1255–1264, 1989; Bhardwaj et al., *J Clin Investig* 94:797–807, 1994; and Inaba et al., *J Exp Med* 172:631–640, 1990.

Assays for lymphocyte survival/apoptosis (which will identify, among others, proteins that prevent apoptosis after superantigen induction and proteins that regulate lymphocyte homeostasis) include, without limitation, those described in: Darzynkiewicz et al., *Cytometry* 13:795–808, 1992; Gorczyca et al., *Leukemia* 7:659–670, 1993; Gorczyca et al., *Cancer Res* 53:1945–1951, 1993; Itoh et al., *Cell* 66:233–243, 1991; Zacharchuk, *J Immunol* 145:4037–4045, 1990; Zamai et al., *Cytometry* 14:891–897, 1993; Gorczyca et al., *Internat J Oncol* 1:639–648, 1992.

Assays for proteins that influence early steps of T-cell commitment and development include, without limitation, those described in: Antica et al., *Blood* 84:111–117, 1994; Fine et al., *Cell Immunol* 155: 111–122, 1994; Galy et al., *Blood* 85:2770–2778, 1995; Toki et al., *Proc Nat Acad Sci USA* 88:7548–7551, 1991.

Hematopoiesis Regulating Activity

A SECX protein of the present invention may be useful in regulation of hematopoiesis and, consequently, in the treatment of myeloid or lymphoid cell deficiencies. Even marginal biological activity in support of colony forming cells or of factor-dependent cell lines indicates involvement in regulating hematopoiesis, e.g. in supporting the growth and proliferation of erythroid progenitor cells alone or in combination with other cytokines, thereby indicating utility, for example, in treating various anemias or for use in conjunction with irradiation/chemotherapy to stimulate the production of erythroid precursors and/or erythroid cells; in supporting the growth and proliferation of myeloid cells such as granulocytes and monocytes/macrophages (i.e., traditional CSF activity) useful, for example, in conjunction with chemotherapy to prevent or treat consequent myelosuppression; in supporting the growth and proliferation of megakaryocytes and consequently of platelets thereby allowing prevention or treatment of various platelet disorders such as thrombocytopenia, and generally for use in place of or complimentary to platelet transfusions; and/or in supporting the growth and proliferation of hematopoietic stem cells which are capable of maturing to any and all of the above-mentioned hematopoietic cells and therefore find therapeutic utility in various stem cell disorders (such as those usually treated with transplantation, including, without limitation, aplastic anemia and paroxysmal nocturnal hemoglobinuria), as well as in repopulating the stem cell compartment post irradiation/chemotherapy, either in-vivo or ex-vivo (i.e., in conjunction with bone marrow transplantation or with peripheral progenitor cell transplantation (homologous or heterologous)) as normal cells or genetically manipulated for gene therapy.

The activity of a protein of the invention may, among other means, be measured by the following methods:

Suitable assays for proliferation and differentiation of various hematopoietic lines are cited above.

Assays for embryonic stem cell differentiation (which will identify, among others, proteins that influence embryonic differentiation hematopoiesis) include, without limitation, those described in: Johansson et al. *Cellular Biology* 15:141–151, 1995; Kelleret al., *Mol. Cell. Biol.* 13:473–486, 1993; McClanahan et al., *Blood* 81:2903–2915, 1993.

Assays for stem cell survival and differentiation (which will identify, among others, proteins that regulate lymphohematopoiesis) include, without limitation, those described in: Methylcellulose colony forming assays, Freshney, In: Culture of Hematapoietic Cells. Freshney, et al. (eds.) Vol pp. 265–268, Wiley-Liss, Inc., New York, N.Y 1994; Hirayama et al., *Proc Natl Acad Sci USA* 89:5907–5911, 1992; McNiece and Briddeli, In: Culture of Hematopoietic Cells. Freshney, et al. (eds.) Vol pp. 23–39, Wiley-Liss, Inc., New York, N.Y. 1994; Neben et al., *Exp Hematol* 22:353–359, 1994; Ploemacher, In: Culture of Hematopoietic Cells. Freshney, et al. eds. Vol pp. 1–21, Wiley-Liss, Inc., New York, N.Y. 1994; Spooncer et al., In: Culture of Hematopoietic Cells. Freshhey, et al., (eds.) Vol pp. 163–179, Wiley-Liss, Inc., New York, N.Y. 1994; Sutherland, In: Culture of Hematopoietic Cells. Freshney, et al., (eds.) Vol pp. $_{139}$-$_1$62, Wiley-Liss, Inc., New York, N.Y. 1994.

Tissue Growth Activity

A SECX protein of the present invention also may have utility in compositions used for bone, cartilage, tendon, ligament and/or nerve tissue growth or regeneration, as well as for wound healing and tissue repair and replacement, and in the treatment of burns, incisions and ulcers.

A protein of the present invention, which induces cartilage and/or bone growth in circumstances where bone is not normally formed, has application in the healing of bone fractures and cartilage damage or defects in humans and other animals. Such a preparation employing a protein of the invention may have prophylactic use in closed as well as open fracture reduction and also in the improved fixation of artificial joints. De novo bone formation induced by an osteogenic agent contributes to the repair of congenital, trauma induced, or oncologic resection induced craniofacial defects, and also is useful in cosmetic plastic surgery.

A protein of this invention may also be used in the treatment of periodontal disease, and in other tooth repair processes. Such agents may provide an environment to attract bone-forming cells, stimulate growth of bone-forming cells or induce differentiation of progenitors of bone-forming cells. A protein of the invention may also be useful in the treatment of osteoporosis or osteoarthritis, such as through stimulation of bone and/or cartilage repair or by blocking inflammation or processes of tissue destruction (collagenase activity, osteoclast activity, etc.) mediated by inflammatory processes.

Another category of tissue regeneration activity that may be attributable to the protein of the present invention is tendon/ligament formation. A protein of the present invention, which induces tendon/ligament-like tissue or other tissue formation in circumstances where such tissue is not normally formed, has application in the healing of tendon or ligament tears, deformities and other tendon or ligament defects in humans and other animals. Such a preparation employing a tendon/ligament-like tissue inducing protein may have prophylactic use in preventing damage to tendon or ligament tissue, as well as use in the improved fixation of tendon or ligament to bone or other tissues, and in repairing defects to tendon or ligament tissue. De novo tendon/ligament-like tissue formation induced by a composition of the present invention contributes to the repair of congenital, trauma induced, or other tendon or ligament defects of other origin, and is also useful in cosmetic plastic surgery for attachment or repair of tendons or ligaments. The compositions of the present invention may provide an environment to attract tendon- or ligament-forming cells, stimulate growth of tendon- or ligament-forming cells, induce differentiation of progenitors of tendon- or ligament-forming cells, or induce growth of tendon/ligament cells or progenitors ex vivo for return in vivo to effect tissue repair. The compositions of the invention may also be useful in the treatment of tendonitis, carpal tunnel syndrome and other tendon or ligament defects. The compositions may also include an appropriate matrix and/or sequestering agent as a career as is well known in the art.

The protein of the present invention may also be useful for proliferation of neural cells and for regeneration of nerve and brain tissue, i.e. for the treatment of central and peripheral nervous system diseases and neuropathies, as well as mechanical and traumatic disorders, which involve degeneration, death or trauma to neural cells or nerve tissue. More specifically, a protein may be used in the treatment of diseases of the peripheral nervous system, such as peripheral nerve injuries, peripheral neuropathy and localized neuropathies, and central nervous system diseases, such as Alzheimer's, Parkinson's disease, Huntington's disease, amyotrophic lateral sclerosis, and Shy-Drager syndrome. Further conditions which may be treated in accordance with the present invention include mechanical and traumatic disorders, such as spinal cord disorders, head trauma and cerebrovascular diseases such as stroke. Peripheral neuropathies resulting from chemotherapy or other medical therapies may also be treatable using a protein of the invention.

Proteins of the invention may also be useful to promote better or faster closure of non-healing wounds, including without limitation pressure ulcers, ulcers associated with vascular insufficiency, surgical and traumatic wounds, and the like.

It is expected that a protein of the present invention may also exhibit activity for generation or regeneration of other tissues, such as organs (including, for example, pancreas, liver, intestine, kidney, skin, endothelium), muscle (smooth, skeletal or cardiac) and vascular (including vascular endothelium) tissue, or for promoting the growth of cells comprising such tissues. Part of the desired effects may be by inhibition or modulation of fibrotic scarring to allow normal tissue to regenerate. A protein of the invention may also exhibit angiogenic activity.

A protein of the present invention may also be useful for gut protection or regeneration and treatment of lung or liver fibrosis, reperfusion injury in various tissues, and conditions resulting from systemic cytokine damage.

A protein of the present invention may also be useful for promoting or inhibiting differentiation of tissues described above from precursor tissues or cells; or for inhibiting the growth of tissues described above.

The activity of a protein of the invention may, among other means, be measured by the following methods:

Assays for tissue generation activity include, without limitation, those described in: International Patent Publication No. WO95/16035 (bone, cartilage, tendon); International Patent Publication No. WO95/05846 (nerve, neuronal); International Patent Publication No. WO91/07491 (skin, endothelium).

Assays for wound healing activity include, without limitation, those described in: Winter, Epidermal Wound Healing, pp. 71–112 (Maibach and Rovee, eds.), Year Book Medical Publishers, Inc., Chicago, as modified by Eaglstein and Menz, *J. Invest. Dermatol* 71:382–84 (1978).

Activin/Inhibin Activity

A SECX protein of the present invention may also exhibit activin- or inhibin-related activities. Inhibins are characterized by their ability to inhibit the release of follicle stimulating hormone (FSH), while activins and are characterized by their ability to stimulate the release of follicle stimulating hormone (FSH). Thus, a protein of the present invention, alone or in heterodimers with a member of the inhibin a family, may be useful as a contraceptive based on the ability of inhibins to decrease fertility in female mammals and decrease spermatogenesis in male mammals. Administration of sufficient amounts of other inhibins can induce infertility in these mammals. Alternatively, the protein of the invention, as a homodimer or as a heterodimer with other protein subunits of the inhibin-b group, may be useful as a fertility inducing therapeutic, based upon the ability of activin molecules in stimulating FSH release from cells of the anterior pituitary. See, for example, U.S. Pat. No. 4,798,885. A protein of the invention may also be useful for advancement of the onset of fertility in sexually immature mammals, so as to increase the lifetime reproductive performance of domestic animals such as cows, sheep and pigs.

The activity of a protein of the invention may, among other means, be measured by the following methods:

Assays for activin/inhibin activity include, without limitation, those described in: Vale et al., *Endocrinology* 91:562–572, 1972; Ling et al., *Nature* 321:779–782, 1986; Vale et al., *Nature* 321:776–779, 1986; Mason et al., *Nature* 318:659–663, 1985; Forage et al., *Proc Natl Acad Sci USA* 83:3091–3095, 1986.

Chemotactic/Chemokinetic Activity

A protein of the present invention may have chemotactic or chemokinetic activity (e.g., act as a chemokine) for mammalian cells, including, for example, monocytes, fibroblasts, neutrophils, T-cells, mast cells, eosinophils, epithelial and/or endothelial cells. Chemotactic and chemokinetic proteins can be used to mobilize or attract a desired cell population to a desired site of action. Chemotactic or chemokinetic proteins provide particular advantages in treatment of wounds and other trauma to tissues, as well as in treatment of localized infections. For example, attraction of lymphocytes, monocytes or neutrophils to tumors or sites of infection may result in improved immune responses against the tumor or infecting agent.

A protein or peptide has chemotactic activity for a particular cell population if it can stimulate, directly or indirectly, the directed orientation or movement of such cell population. Preferably, the protein or peptide has the ability to directly stimulate directed movement of cells. Whether a particular protein has chemotactic activity for a population of cells can be readily determined by employing such protein or peptide in any known assay for cell chemotaxis.

The activity of a protein of the invention may, among other means, be measured by following methods. Assays for chemotactic activity (which will identify proteins that induce or prevent chemotaxis) consist of assays that measure the ability of a protein to induce the migration of cells across a membrane as well as the ability of a protein to induce the adhesion of one cell population to another cell population. Suitable assays for movement and adhesion include, without limitation, those described in: Current Protocols in Immunology, Coligan et al., eds. (Chapter 6.12, Measurement of Alpha and Beta Chemokines 6.12.1–6.12.28); Taub et al. *J Clin Invest* 95:1370–1376, 1995; Lind et al. *APMIS* 103:140–146, 1995; Muller et al., *Eur J Immunol* 25: 1744–1748; Gruber et al. *J Immunol* 152:5860–5867, 1994; Johnston et al., *J Immunol* 153: 1762–1768, 1994.

Hemostatic and Thrombolytic Activity

A protein of the invention may also exhibit hemostatic or thrombolytic activity. As a result, such a protein is expected to be useful in treatment of various coagulation disorders (including hereditary disorders, such as hemophilias) or to enhance coagulation and other hemostatic events in treating wounds resulting from trauma, surgery or other causes. A protein of the invention may also be useful for dissolving or inhibiting formation of thromboses and for treatment and prevention of conditions resulting therefrom (such as, for example, infarction of cardiac and central nervous system vessels (e.g., stroke).

The activity of a protein of the invention may, among other means, be measured by the following methods:

Assay for hemostatic and thrombolytic activity include, without limitation, those described in: Linet et al., *J. Clin. Pharmacol.* 26:131–140, 1986; Burdick et al., *Thrombosis Res.* 45:413–419, 1987; Humphrey et al., *Fibrinolysis* 5:71–79 (1991); Schaub, *Prostaglandins* 35:467–474, 1988.

Receptor/Ligand Activity

A protein of the present invention may also demonstrate activity as receptors, receptor ligands or inhibitors or agonists of receptor/ligand interactions. Examples of such receptors and ligands include, without limitation, cytokine receptors and their ligands, receptor kinases and their ligands, receptor phosphatases and their ligands, receptors involved in cell—cell interactions and their ligands (including without limitation, cellular adhesion molecules (such as selectins, integrins and their ligands) and receptor/ligand pairs involved in antigen presentation, antigen recognition and development of cellular and humoral immune responses). Receptors and ligands are also useful for screening of potential peptide or small molecule inhibitors of the relevant receptor/ligand interaction. A protein of the present invention (including, without limitation, fragments of receptors and ligands) may themselves be useful as inhibitors of receptor/ligand interactions.

The activity of a protein of the invention may, among other means, be measured by the following methods:

Suitable assays for receptor-ligand activity include without limitation those described in: Current Protocols in Immunology, Ed by Coligan, et al., Greene Publishing Associates and Wiley-Interscience (Chapter 7.28, Measurement of Cellular Adhesion under static conditions 7.28.1–7.28.22), Takai et al., *Proc Natl Acad Sci USA* 84:6864–6868, 1987; Bierer et al., *J. Exp. Med.* 168:1145–1156, 1988; Rosenstein et al., *J. Exp. Med.* 169:149–160 1989; Stoltenborg et al., *J Immunol Methods* 175:59–68, 1994; Stitt et al., *Cell* 80:661–670, 1995.

Anti-Inflammatory Activity

Proteins of the present invention may also exhibit anti-inflammatory activity. The anti-inflammatory activity may be achieved by providing a stimulus to cells involved in the inflammatory response, by inhibiting or promoting cell—cell interactions (such as, for example, cell adhesion), by inhibiting or promoting chemotaxis of cells involved in the inflammatory process, inhibiting or promoting cell extravasation, or by stimulating or suppressing production of other factors which more directly inhibit or promote an inflammatory response. Proteins exhibiting such activities can be used to treat inflammatory conditions including chronic or acute conditions), including without limitation inflammation associated with infection (such as septic shock, sepsis or systemic inflammatory response syndrome (SIRS)), ischemia-reperfusion injury, endotoxin lethality, arthritis, complement-mediated hyperacute rejection, nephritis, cytokine or chemokine-induced lung injury, inflammatory bowel disease, Crohn's disease or resulting from over production of cytokines such as TNF or IL-1. Proteins of the invention may also be useful to treat anaphylaxis and hypersensitivity to an antigenic substance or material.

Tumor Inhibition Activity

In addition to the activities described above for immunological treatment or prevention of tumors, a protein of the invention may exhibit other anti-tumor activities. A protein may inhibit tumor growth directly or indirectly (such as, for example, via ADCC). A protein may exhibit its tumor inhibitory activity by acting on tumor tissue or tumor precursor tissue, by inhibiting formation of tissues necessary to support tumor growth (such as, for example, by inhibiting angiogenesis), by causing production of other factors, agents or cell types which inhibit tumor growth, or by suppressing, eliminating or inhibiting factors, agents or cell types which promote tumor growth.

Other Activities

A protein of the invention may also exhibit one or more of the following additional activities or effects: inhibiting the growth, infection or function of, or killing, infectious agents, including, without limitation, bacteria, viruses, fungi and other parasites; effecting (suppressing or enhancing) bodily characteristics, including, without limitation, height, weight, hair color, eye color, skin, fat to lean ratio or other tissue pigmentation, or organ or body part size or shape (such as, for example, breast augmentation or diminution, change in bone form or shape); effecting biorhythms or circadian cycles or rhythms; effecting the fertility of male or female subjects; effecting the metabolism, catabolism, anabolism, processing, utilization, storage or elimination of dietary fat, lipid, protein, carbohydrate, vitamins, minerals, cofactors or other nutritional factors or component(s); effecting behavioral characteristics, including, without limitation, appetite, libido, stress, cognition (including cognitive disorders), depression (including depressive disorders) and violent behaviors; providing analgesic effects or other pain reducing effects; promoting differentiation and growth of embryonic stem cells in lineages other than hematopoietic lineages; hormonal or endocrine activity; in the case of enzymes, correcting deficiencies of the enzyme and treating deficiency-related diseases; treatment of hyperproliferative disorders (such as, for example, psoriasis); immunoglobulin-like activity (such as, for example, the ability to bind antigens or complement); and the ability to act as an antigen in a vaccine composition to raise an immune response against such protein or another material or entity which is cross-reactive with such protein.

Predictive Medicine

The present invention also pertains to the field of predictive medicine in which diagnostic assays, prognostic assays, pharmacogenomics, and monitoring clinical trials are used for prognostic (predictive) purposes to thereby treat an individual prophylactically. Accordingly, one aspect of the present invention relates to diagnostic assays for determining SECX protein and/or nucleic acid expression as well as SECX activity, in the context of a biological sample (e.g., blood, serum, cells, tissue) to thereby determine whether an individual is afflicted with a disease or disorder, or is at risk of developing a disorder, associated with aberrant SECX expression or activity. The invention also provides for prognostic (or predictive) assays for determining whether an individual is at risk of developing a disorder associated with SECX protein, nucleic acid expression or activity. For example, mutations in a SECX gene can be assayed in a biological sample. Such assays can be used for prognostic or predictive purpose to thereby prophylactically treat an individual prior to the onset of a disorder characterized by or associated with SECX protein, nucleic acid expression or activity.

Another aspect of the invention provides methods for determining SECX protein, nucleic acid expression or SECX activity in an individual to thereby select appropriate therapeutic or prophylactic agents for that individual (referred to herein as "pharmacogenomics"). Pharmacogenomics allows for the selection of agents (e.g., drugs) for therapeutic or prophylactic treatment of an individual based on the genotype of the individual (e.g., the genotype of the individual examined to determine the ability of the individual to respond to a particular agent.)

Yet another aspect of the invention pertains to monitoring the influence of agents (e.g., drugs, compounds) on the expression or activity of SECX in clinical trials.

These and other agents are described in further detail in the following sections.

Diagnostic Assays

An exemplary method for detecting the presence or absence of SECX in a biological sample involves obtaining a biological sample from a test subject and contacting the biological sample with a compound or an agent capable of detecting SECX protein or nucleic acid (e.g., mRNA, genomic DNA) that encodes SECX protein such that the presence of SECX is detected in the biological sample. An agent for detecting SECX mRNA or genomic DNA is a labeled nucleic acid probe capable of hybridizing to SECX mRNA or genomic DNA. The nucleic acid probe can be, for example, a full-length SECX nucleic acid, or a portion thereof, such as an oligonucleotide of at least 15, 30, 50, 100, 250 or 500 nucleotides in length and sufficient to specifically hybridize under stringent conditions to SECX mRNA or genomic DNA. Other suitable probes for use in the diagnostic assays of the invention are described herein.

An agent for detecting SECX protein is an antibody capable of binding to SECX protein, preferably an antibody with a detectable label. Antibodies can be polyclonal, or more preferably, monoclonal. An intact antibody, or a fragment thereof (e.g., Fab or $F(ab')_2$) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin. The term "biological sample" is intended to include tissues, cells and biological fluids isolated from a subject, as well as tissues, cells and fluids present within a subject. That is, the detection method of the invention can be used to detect SECX mRNA, protein, or genomic DNA in a biological sample in vitro as well as in vivo. For example, in vitro techniques for detection of SECX mRNA include Northern hybridizations and in situ hybridizations. In vitro techniques for detection of SECX protein include enzyme linked immunosorbent assays (ELISAs), Western blots, immunoprecipitations and immunofluorescence. In vitro techniques for detection of SECX genomic DNA include Southern hybridizations. Furthermore, in vivo techniques for detection of SECX protein include introducing into a subject a labeled anti-SECX antibody. For example, the antibody can be labeled with a radioactive marker whose presence and location in a subject can be detected by standard imaging techniques.

In one embodiment, the biological sample contains protein molecules from the test subject. Alternatively, the biological sample can contain mRNA molecules from the test subject or genomic DNA molecules from the test subject. A preferred biological sample is a peripheral blood leukocyte sample isolated by conventional means from a subject.

In another embodiment, the methods further involve obtaining a control biological sample from a control subject, contacting the control sample with a compound or agent capable of detecting SECX protein, mRNA, or genomic DNA, such that the presence of SECX protein, mRNA or genomic DNA is detected in the biological sample, and comparing the presence of SECX protein, mRNA or genomic DNA in the control sample with the presence of SECX protein, mRNA or genomic DNA in the test sample.

The invention also encompasses kits for detecting the presence of SECX in a biological sample. For example, the kit can comprise: a labeled compound or agent capable of detecting SECX protein or mRNA in a biological sample; means for determining the amount of SECX in the sample; and means for comparing the amount of SECX in the sample with a standard. The compound or agent can be packaged in a suitable container. The kit can further comprise instructions for using the kit to detect SECX protein or nucleic acid.

Prognostic Assays

The diagnostic methods described herein can furthermore be utilized to identify subjects having or at risk of developing a disease or disorder associated with aberrant SECX expression or activity. For example, the assays described herein, such as the preceding diagnostic assays or the following assays, can be utilized to identify a subject having or at risk of developing a disorder associated with SECX protein, nucleic acid expression or activity such as cancer or fibrotic disorders, or a SECX-specific disease as described in the individual sections 1–14, above. Alternatively, the prognostic assays can be utilized to identify a subject having or at risk for developing a disease or disorder. Thus, the present invention provides a method for identifying a disease or disorder associated with aberrant SECX expression or activity in which a test sample is obtained from a subject and SECX protein or nucleic acid (e.g., mRNA, genomic DNA) is detected, wherein the presence of SECX protein or nucleic acid is diagnostic for a subject having or at risk of developing a disease or disorder associated with aberrant SECX expression or activity. As used herein, a "test sample" refers to a biological sample obtained from a subject of interest. For example, a test sample can be a biological fluid (e.g., serum), cell sample, or tissue.

Furthermore, the prognostic assays described herein can be used to determine whether a subject can be administered an agent (e.g., an agonist, antagonist, peptidomimetic, protein, peptide, nucleic acid, small molecule, or other drug candidate) to treat a disease or disorder associated with aberrant SECX expression or activity. For example, such methods can be used to determine whether a subject can be effectively treated with an agent for a disorder, such as cancer or preclampsia or a SECX-specific disease as described in the individual sections 1–14, above. Thus, the present invention provides methods for determining whether a subject can be effectively treated with an agent for a disorder associated with aberrant SECX expression or activity in which a test sample is obtained and SECX protein or nucleic acid is detected (e.g., wherein the presence of SECX protein or nucleic acid is diagnostic for a subject that can be administered the agent to treat a disorder associated with aberrant SECX expression or activity.)

The methods of the invention can also be used to detect genetic lesions in a SECX gene, thereby determining if a subject with the lesioned gene is at risk for a disorder characterized by aberrant cell proliferation and/or differentiation. In various embodiments, the methods include detecting, in a sample of cells from the subject, the presence or absence of a genetic lesion characterized by at least one of an alteration affecting the integrity of a gene encoding a SECX-protein, or the mis-expression of the SECX gene. For example, such genetic lesions can be detected by ascertaining the existence of at least one of (1) a deletion of one or more nucleotides from a SECX gene; (2) an addition of one or more nucleotides to a SECX gene; (3) a substitution of one or more nucleotides of a SECX gene, (4) a chromosomal rearrangement of a SECX gene; (5) an alteration in the level of a messenger RNA transcript of a SECX gene, (6) aberrant modification of a SECX gene, such as of the methylation pattern of the genomic DNA, (7) the presence of a non-wild type splicing pattern of a messenger RNA transcript of a SECX gene, (8) a non-wild type level of a SECX-protein, (9) allelic loss of a SECX gene, and (10) inappropriate post-translational modification of a SECX-protein. As described herein, there are a large number of assay techniques known in the art which can be used for detecting lesions in a SECX gene. A preferred biological sample is a peripheral blood leukocyte sample isolated by conventional means from a subject. However, any biological sample containing nucleated cells may be used, including, for example, buccal mucosal cells.

In certain embodiments, detection of the lesion involves the use of a probe/primer in a polymerase chain reaction (PCR) (see, e.g., U.S. Pat. Nos. 4,683,195 and 4,683,202), such as anchor PCR or RACE PCR, or, alternatively, in a ligation chain reaction (LCR) (see, e.g., Landegran et al. (1988) *Science* 241:1077–1080; and Nakazawa et al. (1994) *PNAS* 91:360–364), the latter of which can be particularly useful for detecting point mutations in the SECX-gene (see Abravaya et al. (1995) *Nucl Acids Res* 23:675–682). This method can include the steps of collecting a sample of cells from a patient, isolating nucleic acid (e.g., genomic, mRNA or both) from the cells of the sample, contacting the nucleic acid sample with one or more primers that specifically hybridize to a SECX gene under conditions such that hybridization and amplification of the SECX gene (if present) occurs, and detecting the presence or absence of an amplification product, or detecting the size of the amplification product and comparing the length to a control sample. It is anticipated that PCR and/or LCR may be desirable to use as a preliminary amplification step in conjunction with any of the techniques used for detecting mutations described herein.

Alternative amplification methods include: self sustained sequence replication (Guatelli et al., 1990, *Proc Natl Acad Sci USA* 87:1874–1878), transcriptional amplification system (Kwoh, et al., 1989, *Proc Natl Acad Sci USA* 86:1173–1177), Q-Beta Replicase (Lizardi et al, 1988, *Bio-Technology* 6:1197), or any other nucleic acid amplification method, followed by the detection of the amplified molecules using techniques well known to those of skill in the art. These detection schemes are especially useful for the detection of nucleic acid molecules if such molecules are present in very low numbers.

In an alternative embodiment, mutations in a SECX gene from a sample cell can be identified by alterations in restriction enzyme cleavage patterns. For example, sample and control DNA is isolated, amplified (optionally), digested with one or more restriction endonucleases, and fragment length sizes are determined by gel electrophoresis and compared. Differences in fragment length sizes between sample and control DNA indicates mutations in the sample DNA. Moreover, the use of sequence specific ribozymes (see, for example, U.S. Pat. No. 5,493,531) can be used to score for the presence of specific mutations by development or loss of a ribozyme cleavage site.

In other embodiments, genetic mutations in SECX can be identified by hybridizing a sample and control nucleic acids, e.g., DNA or RNA, to high density arrays containing hundreds or thousands of oligonucleotides probes (Cronin et al. (1996) *Human Mutation* 7: 244–255; Kozal et al. (1996) *Nature Medicine* 2: 753–759). For example, genetic mutations in SECX can be identified in two dimensional arrays containing light-generated DNA probes as described in Cronin et al. above. Briefly, a first hybridization array of probes can be used to scan through long stretches of DNA in a sample and control to identify base changes between the sequences by making linear arrays of sequential overlapping probes. This step allows the identification of point mutations. This step is followed by a second hybridization array that allows the characterization of specific mutations by using smaller, specialized probe arrays complementary to all variants or mutations detected. Each mutation array is composed of parallel probe sets, one complementary to the wild-type gene and the other complementary to the mutant gene.

In yet another embodiment, any of a variety of sequencing reactions known in the art can be used to directly sequence the SECX gene and detect mutations by comparing the sequence of the sample SECX with the corresponding wild-type (control) sequence. Examples of sequencing reactions include those based on techniques developed by Maxim and Gilbert (1977) *PNAS* 74:560 or Sanger (1977) *PNAS* 74:5463. It is also contemplated that any of a variety of automated sequencing procedures can be utilized when performing the diagnostic assays (Naeve et al., 1995) *BioTechniques* 19:448), including sequencing by mass spectrometry (see, e.g., PCT International Publ. No. WO 94/16101; Cohen et al. (1996) *Adv Chromatogr* 36:127–162; and Griffin et al. (1993) *Appl Biochem Biotechnol* 38:147–159).

Other methods for detecting mutations in the SECX gene include methods in which protection from cleavage agents is used to detect mismatched bases in RNA/RNA or RNA/DNA heteroduplexes (Myers et al. (1985) *Science* 230:1242). In general, the art technique of "mismatch cleavage" starts by providing heteroduplexes of formed by hybridizing (labeled) RNA or DNA containing the wild-type SECX sequence with potentially mutant RNA or DNA obtained from a tissue sample. The double-stranded duplexes are treated with an agent that cleaves single-stranded regions of the duplex such as which will exist due to basepair mismatches between the control and sample strands. For instance, RNA/DNA duplexes can be treated with RNase and DNA/DNA hybrids treated with S1 nuclease to enzymatically digesting the mismatched regions. In other embodiments, either DNA/DNA or RNA/DNA duplexes can be treated with hydroxylamine or osmium tetroxide and with piperidine in order to digest mismatched regions. After digestion of the mismatched regions, the resulting material is then separated by size on denaturing polyacrylamide gels to determine the site of mutation. See, for example, Cotton et al (1988) *Proc Natl Acad Sci USA* 85:4397; Saleeba et at (1992) *Methods Enzymol* 217:286–295. In an embodiment, the control DNA or RNA can be labeled for detection.

In still another embodiment, the mismatch cleavage reaction employs one or more proteins that recognize mismatched base pairs in double-stranded DNA (so called "DNA mismatch repair" enzymes) in defined systems for detecting and mapping point mutations in SECX cDNAs obtained from samples of cells. For example, the mutY enzyme of *E. coli* cleaves A at G/A mismatches and the thymidine DNA glycosylase from HeLa cells cleaves T at G/T mismatches (Hsu et al. (1994) *Carcinogenesis* 15:1657–1662). According to an exemplary embodiment, a probe based on a SECX sequence, e.g., a wild-type SECX sequence, is hybridized to a cDNA or other DNA product from a test cell(s). The duplex is treated with a DNA mismatch repair enzyme, and the cleavage products, if any, can be detected from electrophoresis protocols or the like. See, for example, U.S. Pat. No. 5,459,039.

In other embodiments, alterations in electrophoretic mobility will be used to identify mutations in SECX genes. For example, single strand conformation polymorphism (SSCP) may be used to detect differences in electrophoretic mobility between mutant and wild type nucleic acids (Orita et al. (1989) *Proc Natl Acad Sci USA:* 86:2766, see also Cotton (1993) *Mutat Res* 285:125–144; Hayashi (1992) *Genet Anal Tech Appl* 9:73–79). Single-stranded DNA fragments of sample and control SECX nucleic acids will be denatured and allowed to renature. The secondary structure of single-stranded nucleic acids varies according to sequence, the resulting alteration in electrophoretic mobility enables the detection of even a single base change. The DNA fragments may be labeled or detected with labeled probes. The sensitivity of the assay may be enhanced by using RNA (rather than DNA), in which the secondary structure is more sensitive to a change in sequence. In one embodiment, the subject method utilizes heteroduplex analysis to separate double stranded heteroduplex molecules on the basis of changes in electrophoretic mobility (Keen et al. (1991) *Trends Genet* 7:5).

In yet another embodiment the movement of mutant or wild-type fragments in polyacrylamide gels containing a gradient of denaturant is assayed using denaturing gradient gel electrophoresis (DGGE) (Myers et al (1985) *Nature* 313:495). When DGGE is used as the method of analysis, DNA will be modified to insure that it does not completely denature, for example by adding a GC clamp of approximately 40 bp of high-melting GC-rich DNA by PCR. In a further embodiment, a temperature gradient is used in place of a denaturing gradient to identify differences in the mobility of control and sample DNA (Rosenbaum and Reissner (1987) *Biophys Chem* 265:12753).

Examples of other techniques for detecting point mutations include, but are not limited to, selective oligonucleotide hybridization, selective amplification, or selective primer extension. For example, oligonucleotide primers may be prepared in which the known mutation is placed centrally and then hybridized to target DNA under conditions that permit hybridization only if a perfect match is found (Saiki et al. (1986) *Nature* 324:163); Saiki et al. (1989) *Proc Natl Acad. Sci USA* 86:6230). Such allele specific oligonucleotides are hybridized to PCR amplified target DNA or a number of different mutations when the oligonucleotides are attached to the hybridizing membrane and hybridized with labeled target DNA.

Alternatively, allele specific amplification technology that depends on selective PCR amplification may be used in conjunction with the instant invention. Oligonucleotides used as primers for specific amplification may carry the mutation of interest in the center of the molecule (so that amplification depends on differential hybridization) (Gibbs et al. (1989) *Nucleic Acids Res* 17:2437–2448) or at the extreme 3' end of one primer where, under appropriate conditions, mismatch can prevent, or reduce polymerase extension (Prossner (1993) *Tibtech* 11:238). In addition it may be desirable to introduce a novel restriction site in the region of the mutation to create cleavage-based detection (Gasparini et al (1992) *Mol Cell Probes* 6:1). It is anticipated that in certain embodiments amplification may also be performed using Taq ligase for amplification (Barany (1991) *Proc Natl Acad Sci USA* 88:189). In such cases, ligation will occur only if there is a perfect match at the 3' end of the 5' sequence, making it possible to detect the presence of a known mutation at a specific site by looking for the presence or absence of amplification.

The methods described herein may be performed, for example, by utilizing pre-packaged diagnostic kits comprising at least one probe nucleic acid or antibody reagent described herein, which may be conveniently used, e.g., in clinical settings to diagnose patients exhibiting symptoms or family history of a disease or illness involving a SECX gene.

Furthermore, any cell type or tissue, preferably peripheral blood leukocytes, in which SECX is expressed may be utilized in the prognostic assays described herein. However, any biological sample containing nucleated cells may be used, including, for example, buccal mucosal cells.

Pharmacogenomics

Agents, or modulators that have a stimulatory or inhibitory effect on SECX activity (e.g., SECX gene expression), as identified by a screening assay described herein can be administered to individuals to treat (prophylactically or therapeutically) disorders (e.g., cancer or gestational disorders or a SECX-specific disease as described in the individual sections 1–14, above) associated with aberrant SECX activity. In conjunction with such treatment, the pharmacogenomics (i.e., the study of the relationship between an individual's genotype and that individual's response to a foreign compound or drug) of the individual may be considered. Differences in metabolism of therapeutics can lead to severe toxicity or therapeutic failure by altering the relation between dose and blood concentration of the pharmacologically active drug. Thus, the pharmacogenomics of the individual permits the selection of effective agents (e.g., drugs) for prophylactic or therapeutic treatments based on a consideration of the individual's genotype. Such pharmacogenomics can further be used to determine appropriate dosages and therapeutic regimens. Accordingly, the activity of SECX protein, expression of SECX nucleic acid, or mutation content of SECX genes in an individual can be determined to thereby select appropriate agent(s) for therapeutic or prophylactic treatment of the individual.

Pharmacogenomics deals with clinically significant hereditary variations in the response to drugs due to altered drug disposition and abnormal action in affected persons. See e.g., Eichelbaum, *Clin Exp Pharmacol Physiol*, 1996, 23:983–985 and Linder, *Clin Chem*, 1997, 43:254–266. In general, two types of pharmacogenetic conditions can be differentiated. Genetic conditions transmitted as a single factor altering the way drugs act on the body (altered drug action) or genetic conditions transmitted as single factors altering the way the body acts on drugs (altered drug metabolism). These pharmacogenetic conditions can occur either as rare defects or as polymorphisms. For example, glucose-6-phosphate dehydrogenase (G6PD) deficiency is a common inherited enzymopathy in which the main clinical complication is haemolysis after ingestion of oxidant drugs (anti-malarials, sulfonamides, analgesics, nitrofurans) and consumption of fava beans.

As an illustrative embodiment, the activity of drug metabolizing enzymes is a major determinant of both the intensity and duration of drug action. The discovery of genetic polymorphisms of drug metabolizing enzymes (e.g., N-acetyltransferase 2 (NAT 2) and cytochrome P450 enzymes CYP2D6 and CYP2C19) has provided an explanation as to why some patients do not obtain the expected drug effects or show exaggerated drug response and serious toxicity after taking the standard and safe dose of a drug. These polymorphisms are expressed in two phenotypes in the population, the extensive metabolizer (EM) and poor metabolizer (PM). The prevalence of PM is different among different populations. For example, the gene coding for CYP2D6 is highly polymorphic and several mutations have been identified in PM, which all lead to the absence of functional CYP2D6. Poor metabolizers of CYP2D6 and CYP2C19 quite frequently experience exaggerated drug response and side effects when they receive standard doses. If a metabolite is the active therapeutic moiety, PM show no therapeutic response, as demonstrated for the analgesic effect of codeine mediated by its CYP2D6-formed metabolite morphine. The other extreme are the so called ultra-rapid metabolizers who do not respond to standard doses. Recently, the molecular basis of ultra-rapid metabolism has been identified to be due to CYP2D6 gene amplification.

Thus, the activity of SECX protein, expression of SECX nucleic acid, or mutation content of SECX genes in an individual can be determined to thereby select appropriate agent(s) for therapeutic or prophylactic treatment of the individual. In addition, pharmacogenetic studies can be used to apply genotyping of polymorphic alleles encoding drug-metabolizing enzymes to the identification of an individual's drug responsiveness phenotype. This knowledge, when applied to dosing or drug selection, can avoid adverse reactions or therapeutic failure and thus enhance therapeutic or prophylactic efficiency when treating a subject with a SECX modulator, such as a modulator identified by one of the exemplary screening assays described herein.

Monitoring of Effects During Clinical Trials

Monitoring the influence of agents (e.g., drugs, compounds) on the expression or activity of SECX (e.g., the ability to modulate aberrant cell proliferation and/or differentiation) can be applied not only in basic drug screening, but also in clinical trials. For example, the effectiveness of an agent determined by a screening assay as described herein to increase SECX gene expression, protein levels, or upregulate SECX activity, can be monitored in clinical trails of subjects exhibiting decreased SECX gene expression, protein levels, or downregulated SECX activity. Alternatively, the effectiveness of an agent determined by a screening assay to decrease SECX gene expression, protein levels, or downregulate SECX activity, can be monitored in clinical trails of subjects exhibiting increased SECX gene expression, protein levels, or upregulated SECX activity. In such clinical trials, the expression or activity of SECX and, preferably, other genes that have been implicated in, for example, a cellular proliferation disorder or a SECX-specific disease as described in the individual sections 1–14, above, can be used as a "read out" or markers of the immune responsiveness of a particular cell.

For example, and not by way of limitation, genes, including SECX, that are modulated in cells by treatment with an agent (e.g., compound, drug or small molecule) that modulates SECX activity (e.g., identified in a screening assay as described herein) can be identified. Thus, to study the effect of agents on cellular proliferation disorders, for example, in a clinical trial, cells can be isolated and RNA prepared and analyzed for the levels of expression of SECX and other genes implicated in the disorder. The levels of gene expression (i.e., a gene expression pattern) can be quantified by Northern blot analysis or RT-PCR, as described herein, or alternatively by measuring the amount of protein produced, by one of the methods as described herein, or by measuring the levels of activity of SECX or other genes. In this way, the gene expression pattern can serve as a marker, indicative of the physiological response of the cells to the agent. Accordingly, this response state may be determined before, and at various points during, treatment of the individual with the agent.

In one embodiment, the present invention provides a method for monitoring the effectiveness of treatment of a subject with an agent (e.g., an agonist, antagonist, protein, peptide, peptidomimetic, nucleic acid, small molecule, or other drug candidate identified by the screening assays described herein) comprising the steps of (i) obtaining a pre-administration sample from a subject prior to administration of the agent; (ii) detecting the level of expression of a SECX protein, mRNA, or genomic DNA in the preadministration sample; (iii) obtaining one or more post-administration samples from the subject; (iv) detecting the level of expression or activity of the SECX protein, mRNA, or genomic DNA in the post-administration samples; (v) comparing the level of expression or activity of the SECX protein, mRNA, or genomic DNA in the pre-administration sample with the SECX protein, mRNA, or genomic DNA in the post administration sample or samples; and (vi) altering the administration of the agent to the subject accordingly. For example, increased administration of the agent may be desirable to increase the expression or activity of SECX to higher levels than detected, i.e., to increase the effectiveness of the agent. Alternatively, decreased administration of the agent may be desirable to decrease expression or activity of SECX to lower levels than detected, i.e., to decrease the effectiveness of the agent.

Methods of Treatment

The present invention provides for both prophylactic and therapeutic methods of treating a subject at risk of (or susceptible to) a disorder or having a disorder associated with aberrant SECX expression or activity.

Disorders

Diseases and disorders that are characterized by increased (relative to a subject not suffering from the disease or disorder) levels or biological activity may be treated with Therapeutics that antagonize (i.e., reduce or inhibit) activity. Therapeutics that antagonize activity may be administered in a therapeutic or prophylactic manner. Therapeutics that may be utilized include, but are not limited to, (i) an aforementioned peptide, or analogs, derivatives, fragments or homologs thereof; (ii) antibodies to an aforementioned peptide; (iii) nucleic acids encoding an aforementioned peptide; (iv) administration of antisense nucleic acid and nucleic acids that are "dysfunctional" (i.e., due to a heterologous insertion within the coding sequences of coding sequences to an aforementioned peptide) that are utilized to "knockout" endogenous function of an aforementioned peptide by homologous recombination (see, e.g., Capecchi, 1989, *Science* 244: 1288–1292); or (v) modulators (i.e., inhibitors, agonists and antagonists, including additional peptide mimetic of the invention or antibodies specific to a peptide of the invention) that alter the interaction between an aforementioned peptide and its binding partner.

Diseases and disorders that are characterized by decreased (relative to a subject not suffering from the disease or disorder) levels or biological activity may be treated with Therapeutics that increase (i.e., are agonists to) activity. Therapeutics that upregulate activity may be administered in a therapeutic or prophylactic manner. Therapeutics that may be utilized include, but are not limited to, an aforementioned peptide, or analogs, derivatives, fragments or homologs thereof; or an agonist that increases bioavailability.

Increased or decreased levels can be readily detected by quantifying peptide and/or RNA, by obtaining a patient tissue sample (e.g., from biopsy tissue) and assaying it in vitro for RNA or peptide levels, structure and/or activity of the expressed peptides (or mRNAs of an aforementioned peptide). Methods that are well-known within the art include, but are not limited to, immunoassays (e.g., by Western blot analysis, immunoprecipitation followed by sodium dodecyl sulfate (SDS) polyacrylamide gel electrophoresis, immunocytochemistry, etc.) and/or hybridization assays to detect expression of mRNAs (e.g., Northern assays, dot blots, in situ hybridization, etc.).

Prophylactic Methods

In one aspect, the invention provides a method for preventing, in a subject, a disease or condition associated with an aberrant SECX expression or activity, by administering to the subject an agent that modulates SECX expression or at least one SECX activity. Subjects at risk for a disease that is caused or contributed to by aberrant SECX expression or activity can be identified by, for example, any or a combination of diagnostic or prognostic assays as described herein. Administration of a prophylactic agent can occur prior to the manifestation of symptoms characteristic of the SECX aberrancy, such that a disease or disorder is prevented or, alternatively, delayed in its progression. Depending on the type of SECX aberrancy, for example, a SECX agonist or SECX antagonist agent can be used for treating the subject. The appropriate agent can be determined based on screening assays described herein. The prophylactic methods of the present invention are further discussed in the following subsections.

Therapeutic Methods

Another aspect of the invention pertains to methods of modulating SECX expression or activity for therapeutic purposes. The modulatory method of the invention involves contacting a cell with an agent that modulates one or more of the activities of SECX protein activity associated with the cell. An agent that modulates SECX protein activity can be an agent as described herein, such as a nucleic acid or a protein, a naturally-occurring cognate ligand of a SECX protein, a peptide, a SECX peptidomimetic, or other small molecule. In one embodiment, the agent stimulates one or more SECX protein activity. Examples of such stimulatory agents include active SECX protein and a nucleic acid molecule encoding SECX that has been introduced into the cell. In another embodiment, the agent inhibits one or more SECX protein activity. Examples of such inhibitory agents include antisense SECX nucleic acid molecules and anti-SECX antibodies. These modulatory methods can be performed in vitro (e.g., by culturing the cell with the agent) or, alternatively, in vivo (e.g., by administering the agent to a subject). As such, the present invention provides methods of treating an individual afflicted with a disease or disorder characterized by aberrant expression or activity of a SECX protein or nucleic acid molecule. In one embodiment, the method involves administering an agent (e.g., an agent identified by a screening assay described herein), or combination of agents that modulates (e.g., upregulates or downregulates) SECX expression or activity. In another embodiment, the method involves administering a SECX protein or nucleic acid molecule as therapy to compensate for reduced or aberrant SECX expression or activity.

Stimulation of SECX activity is desirable in situations in which SECX is abnormally downregulated and/or in which increased SECX activity is likely to have a beneficial effect. One example of such a situation is where a subject has a disorder characterized by aberrant cell proliferation and/or differentiation (e.g., cancer). Another example of such a situation is where the subject has a gestational disease (e.g., preclampsia). Other diseases of the invention include the SECX-specific diseases as described in the individual sections 1–14, above.

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the appended claims.

This invention is further illustrated by the following examples, which should not be construed as limiting. The contents of all references, patents and published patent applications cited throughout this application are hereby incorporated by reference.

EXAMPLES

Example 1

Radiation Hybrid Mapping Identifies the Chromosomal Location of the Clones of the Invention

Radiation hybrid mapping using human chromosome markers was carried out for many of the clones described in the present invention. The procedure used to obtain these results is analogous to methods known in the art, for example, Steen, et al. 1999 *Genome Research* 9: AP1–AP8. A panel of 93 cell clones containing randomized radiation-induced human chromosomal fragments was screened in 96 well plates using PCR primers designed to identify the given clones in a unique fashion. The results are presented in Table 2, which provides the clone number, the chromosome on which the clone is found, the distance in cR from a marker gene to the sought clone, and the identity of the marker gene.

TABLE 2

Radiation Hybrid Mapping Results for Clones of the Invention

| Clone No. | Chromosome No. | Distance, cR | Marker Gene |
|---|---|---|---|
| 2777610 | 3 | 564.40 | AFM320WD1 |
| 2864933-1 and 2864933-2 | 5 | 316.40 | WI-9907 |
| 2982339 | 3 | 355.00 | AFM320WD1 |
| 3911675 | 10 | 391.30 | IB3079 |
| 4004731-1 | 12 | 404.60 | WI-5272 |
| 4035508 | 11 | 230.10 | WI-4920 |
| 4339264 | 19 | 311.50 | IB1264 |

Example 2

Molecular Cloning of 2864933-1

The predicted open reading frame for the 2864933-1 protein codes for a 939 amino acid long Type I transmembrane protein with an overall 95% identity to the mouse semaphorin Via protein. The predicted signal peptide sequence is between residues 1–18, and the predicted transmembrane domain is between residues 645–661. A fragment of the cDNA for the 2864933-1 protein, coding for the extracellular domain of predicted mature protein (i.e., after removal of the signal peptide) from residue 19 to 644, has been cloned from human fetal brain cDNA.

The following oligonucleotide primers were designed to amplify the sought mature form of 2864933-1 4 by PCR:

2864933 MatF

GGATCC GGT TTC CCA GAA GAT TCT
GAG CCA ATC                                    (SEQ ID NO:33)

2864933 F-TOPO-Reverse

CTC GAG CTG GTC GTG GCC TTT GAG
GTA ACT TTC                                    (SEQ ID NO:34)

For cloning purposes, the forward primer includes an in frame BamHI restriction site and the reverse primer contains an in frame XhoI restriction site.

PCR reactions were set up using 5 ng human fetal brain cDNA. The reaction mixture contained 1 microM of each of the 2864933 MatF and 2864933 F-TOPO-Reverse primers, 5 micromoles dNTP (Clontech Laboratories, Palo Alto Calif.) and 1 microliter of 50×Advantage-HF 2 polymerase (Clontech Laboratories, Palo Alto Calif.) in 50 microliter volume. The following reaction conditions were used:

a) 96° C. 3 minutes
b) 96° C. 30 seconds denaturation
c) 60° C. 30 seconds, primer annealing.
d) 72° C. 3 minutes extension.
Repeat steps (b)–(d) 45 times
e) 72° C. 10 minutes final extension The expected amplified product of approximately 1.9 kbp was detected by agarose gel electrophoresis. The fragment was isolated from the gel and ligated to the vector pCR2.1 (Invitrogen, Carlsbad, Calif.) using M13 Forward, M13 Reverse primers. The cloned insert was sequenced as PCR amplicons using the following gene-specific primers:

| | |
|---|---|
| 2864933-Seq-0CACAAGCCAGGACGGAACA | (SEQ ID NO:35) |
| 2864933-Seq-1 TGG AAC TAA TGC CTT CAA C | (SEQ ID NO:36) |
| 2864933-Seq-2 GAG TCCTGGAGAAACA GTGGA | (SEQ ID NO:37) |
| 2864933-Seq-3 ATGAGGCAGTGCCCTCCATC | (SEQ ID NO:38) |
| 2864933-Seq-4 CCATATTGTGGATGGATAA | (SEQ ID NO:39) |
| 2864933-Seq-5 GACACTCAATCCAAAGACC | (SEQ ID NO:40) |
| 2864933-Seq-6 CCATCACGCAGCAGGGCTA | (SEQ ID NO:41) |

The cloned cDNA (SEQ ID NO:29) was verified to have an open reading frame coding for the predicted mature extracellular domain of 2864933 between residues 19 and 644 (SEQ ID NO:30)(FIG. 15). In FIG. 15, the BamHI and XhoI cloning sites, and the amino acids encoded by them (which are therefore not part of the cloned sequence), are in bold font. The construct is called pCR2.1–2864933.

Example 3

Expression of h2864933 in Human Embryonic Kidney 293 Cells

Oligonucleotide primers pSec-V5-His Forward and pSec-V5-His Reverse were designed to amplify a fragment from the pcDNA3.1-V5His (Invitrogen, Carlsbad, Calif.) expression vector. The PCR product was digested with XhoI and ApaI and ligated into the XhoI/ApaI digested pSecTag2 B vector harboring an Ig kappa leader sequence (Invitrogen, Carlsbad Calif.). The correct structure of the resulting vector, pSecV5His, was verified by DNA sequence analysis. The vector pSecV5His was digested with PmeI and NheI, and the PmeI-NheI fragment was ligated into the BamHI/Klenow and NheI treated vector pCEP4 (Invitrogen, Carlsbad, Calif.). The resulting vector was named pCEP4/Sec.

pSec-V5-His Forward

CTCGTCCTCGAGGGTAAGCCTATCCCTAAC (SEQ ID NO:42)

pSec-V5-His Reverse

CTCGTCGGGCCCCTGATCAGCGGGTTT
AAAC                                           (SEQ ID NO:43),

The 2 kb BamHI-XhoI fragment containing the h2864933 sequence was isolated from pCR2.1-2864933 (Example 2) and subcloned into BamHI-XhoI digested pCEP4/Sec to generate expression vector pCEP4/Sec-2864933. The pCEP4/Sec-2864933 vector was transfected into 293 cells using the LipofectaminePlus reagent following the manufacturer's instructions (Gibco/BRL, Life Technologies, Inc., Rockville, Md.). The cell pellet and supernatant were harvested 72 hours after transfection and examined for h2864933 expression by Western blotting (reducing conditions) with an anti-V5 antibody. FIG. 16 shows that h2864933 secreted by 293 cells is detected in two bands carrying the V5 epitope at about 70 kDa and about 100-kDa. The 70 kDa band is presumed to represent the unglycosylated protein, and corresponds to the $M_r$ expected for the 626 residue clone with the addition of the V5 epitope. The program PROSITE predicts six N-glycosylation sites in the extracellular h286493 domain. It is thought that the 100 kDa band originates from glycosylated form(s) of the protein.

Example 4

Molecular Cloning of 3352358-1

The predicted open reading frame of clone 3352358-1 codes for a 653 amino acid residue Type I transmembrane protein with the transmembrane domain predicted to lie between residues 522 and 551. The cDNA coding for the extracellular segment of the predicted mature protein (i.e., after cleavage of the signal peptide), has been cloned.

The secretory signal prediction method, GCG:SPSCAN—Eukaryote, predicts a signal peptidase cleavage site for 3352358-1 between residues 41 and 42. Accordingly, the following oligonucleotide primers were designed to PCR amplify the predicted mature extracellular domain of 3352358 from residue 42 to 486:

3352358CForward

CTCGTCGGATCCAACTGCCCCTCCGTCT GCTCGTGCAG (SEQ ID NO:44), and

3352358CReverse

CTCGTCGTCGACCGTGGTAGAGGTGGTAT ATGCCGGCTG (SEQ ID NO:45).

For cloning purposes, the forward primer includes an in frame BamHI restriction site and the reverse primer contains an in frame SalI restriction site.

Two separate PCR reactions were set up using 5 ng human testis and fetal brain cDNA templates, respectively. The reaction mixtures contained 1 microM of each of the 3352358CForward and 3352358CReverse primers, 5 micromoles dNTP (Clontech Laboratories, Palo Alto Calif.) and 1 microliter of 50×Advantage-HF 2 polymerase (Clontech Laboratories, Palo Alto Calif.) in 50 microliter volume. The following reaction conditions were used:

a) 96° C. 3 minutes b) 96° C. 30 seconds denaturation c) 70° C. 30 seconds, primer annealing. This temperature was gradually decreased by 1° C./cycle d) 72° C. 3 minutes extension.

Repeat steps (b)–(d) 10 times e) 96° C. 30 seconds denaturation f) 60° C. 30 seconds annealing g) 72° C. 3 minutes extension Repeat steps (e)–(g) 25 times h) 72° C. 10 minutes final extension The expected amplified product of 1335 bp was detected by agarose gel electrophoresis in both samples. The fragments were purified from agarose gel and ligated to pCR2.1 vector (Invitrogen, Carlsbad, Calif.). Using M13 Forward and M13 Reverse vector primers and the following gene specific primers:

3352358 Seq-1 GTGCAGTAACCAGTT CAGCA (SEQ ID NO:46),

3352358 Seq-2 ACCTGTCCAAGCTGC GGGAG (SEQ ID NO:47),

3352358 Seq-3 TTGACGGGCTGGCTTCACTT (SEQ ID NO:48),

3352358 Seq-4 GACAGTGCTCAGCCAC GCCT (SEQ ID NO:49), the cloned insert was sequenced as PCR amplicons and verified as an open reading frame designated as 3352358-S153A. The nucleotide sequence (SEQ ID NO:31) obtained for this clone is shown in FIG. 17 Panel A. The cloning sites are in underlined italic font. The sequence obtained for clone 3352358-S153A differs from the sequence expected for clone 3352358-1 at six positions. These are indicated in FIG. 17A by underlined bold font. The translated protein sequence (SEQ ID NO:32) for clone 3352358-S153A is given in FIG. 17 Panel B. Five of the sequence differences found at the nucleotide level are translated into amino acid differences, compared to the sequence expected for clone 3352358-1; these are likewise indicated in FIG. 17B by underlined bold font. (In FIG. 17B, the two amino acid residues encoded by the cloning sites at each end are not shown. The first amino acid residue of FIG. 17B is encoded by nucleotides 7–9 of FIG. 17A.)

Example 5

Expression of h3352358 in Human Embryonic Kidney 293 Cells

Figure 18:
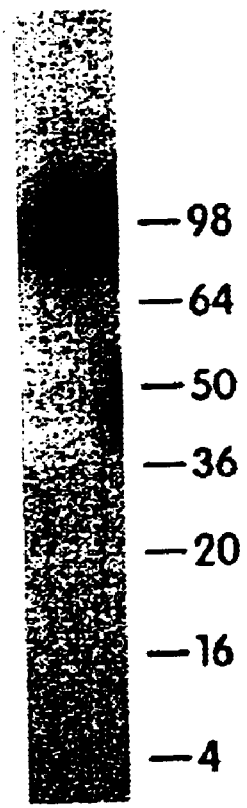
FIG. 18 depicts expression of the pCEP4/Sec-3352358 vector in 293 cells analyzed in a Western blot of 293 cell extracts after reducing SDS-PAGE.

The vector pCEP4/Sec was prepared as described in Example 3. A 1.3 kb fragment containing the h3352358 sequence was isolated from pCR2.1-3352358 (prepared in Example 4) by BamHI-SalI digestion and subcloned into BamHI-XhoI digested pCEP4/Sec to generate the expression vector pCEP4/Sec-3352358. The pCEP4/Sec-3352358 vector was transfected into 293 cells using the LipofectaminePlus™ reagent following the manufacturer's instructions (Gibco/BRL). The cell pellet and supernatant were harvested 72 hours after transfection and examined for h3352358 expression by Western blotting (reducing conditions) with an anti-V5 antibody. FIG. 18 shows that h3352358 secreted by 293 cells is detected in a band carrying the V5 epitope at about 98 kDa. This band is presumed to represent the glycosylated form of the protein, since the program PROSITE predicts eight N-glycosylation sites in the extracellular h3352358 domain polypeptide.

Example 6

Expression of 2777610 in Tissues Determined by TaqMan™ Analysis

The expression of 2777610 was evaluated by real time quantitative PCR in tissues indicated in Table 3, below. The numbering in column 1 of Table 3 corresponds to the lane order of the histograms in FIGS. 19A–C through FIG. 23.

TABLE 3

| Panel of cell types used in TaqMan ™ Analysis | |
|---|---|
| 1 | Endothelial cells |
| 2 | Endothelial cells (treated) |
| 3 | Pancreas |
| 4 | Pancreatic ca. CAPAN 2 |
| 5 | Adipose |
| 6 | Adrenal gland |
| 7 | Thyroid |
| 8 | Salivary gland |
| 9 | Pituitary gland |
| 10 | Brain (fetal) |
| 11 | Brain (whole) |

TABLE 3-continued

Panel of cell types used in TaqMan ™ Analysis

| | |
|---|---|
| 12 | Brain (amygdala) |
| 13 | Brain (cerebellum) |
| 14 | Brain (hippocampus) |
| 15 | Brain (hypothalamus) |
| 16 | Brain (substantia nigra) |
| 17 | Brain (thalamus) |
| 18 | Spinal cord |
| 19 | CNS ca. (glio/astro) U87-MG |
| 20 | CNS ca. (glio/astro) U-118-MG |
| 21 | CNS ca. (astro) SW1783 |
| 22 | CNS ca.* (neuro; met) SK-N-AS |
| 23 | CNS ca. (astro) SF-539 |
| 24 | CNS ca. (astro) SNB-75 |
| 25 | CNS ca. (glio) SNB-19 |
| 26 | CNS ca. (glio) U251 |
| 27 | CNS ca. (glio) SF-295 |
| 28 | Heart |
| 29 | Skeletal muscle |
| 30 | Bone marrow |
| 31 | Thymus |
| 32 | Spleen |
| 33 | Lymph node |
| 34 | Colon (ascending) |
| 35 | Stomach |
| 36 | Small intestine |
| 37 | Colon ca. SW480 |
| 38 | Colon ca.* (SW480 met)SW620 |
| 39 | Colon ca. HT29 |
| 40 | Colon ca. HCT-116 |
| 41 | Colon ca. CaCo-2 |
| 42 | Colon ca. HCT-15 |
| 43 | Colon ca. HCC-2998 |
| 44 | Gastric ca.* (liver met) NCI-N87 |
| 45 | Bladder |
| 46 | Trachea |
| 47 | Kidney |
| 48 | Kidney (fetal) |
| 49 | Renal ca. 786-0 |
| 50 | Renal ca. A498 |
| 51 | Renal ca. RXF 393 |
| 52 | Renal ca. ACHN |
| 53 | Renal ca. UO-31 |
| 54 | Renal ca. TK-10 |
| 55 | Liver |
| 56 | Liver (fetal) |
| 57 | Liver ca. (hepatoblast) HepG2 |
| 58 | Lung |
| 59 | Lung (fetal) |
| 60 | Lung ca. (small cell) LX-1 |
| 61 | Lung ca. (small cell) NCI-H69 |
| 62 | Lung ca. (s.cell var.) SHP-77 |
| 63 | Lung ca. (large cell)NCI-H460 |
| 64 | Lung ca. (non-sm. cell) A549 |
| 65 | Lung ca. (non-s.cell) NCI-H23 |
| 66 | Lung ca (non-s.cell) HOP-62 |
| 67 | Lung ca. (non-s.cl) NCI-H522 |
| 68 | Lung ca. (squam.) SW 900 |
| 69 | Lung ca. (squam.) NCI-H596 |
| 70 | Mammary gland |
| 71 | Breast ca.* (pl. effusion) MCF-7 |
| 72 | Breast ca.* (pl.ef) MDA-MB-231 |
| 73 | Breast ca.* (pl. effusion) T47D |
| 74 | Breast ca. BT-549 |
| 75 | Breast ca. MDA-N |
| 76 | Ovary |
| 77 | Ovarian ca. OVCAR-3 |
| 78 | Ovarian ca. OVCAR-4 |
| 79 | Ovarian ca. OVCAR-5 |
| 80 | Ovarian ca. OVCAR-8 |
| 81 | Ovarian ca. IGROV-1 |
| 82 | Ovarian ca.* (ascites) SK-OV-3 |
| 83 | Myometrium |
| 84 | Uterus |
| 85 | Placenta |
| 86 | Prostate |
| 87 | Prostate ca.* (bone met)PC-3 |
| 88 | Testis |
| 89 | Melanoma Hs688(A).T |
| 90 | Melanoma* (met) Hs688(B).T |
| 91 | Melanoma UACC-62 |
| 92 | Melanoma M14 |
| 93 | Melanoma LOX IMVI |
| 94 | Melanoma* (met) SK-MEL-5 |
| 95 | Melanoma SK-MEL-28 |
| 96 | Melanoma UACC-257 |

In the PCR assay used, a fluorogenic probe, consisting of an oligonucleotide with both a reporter and a quencher dye attached, is annealed specifically to the target sequence between the forward and reverse primers. When the probe is cleaved by the 5' nuclease activity of the DNA polymerase, the reporter dye is separated from the quencher dye and a sequence-specific signal is generated. With each cycle, additional reporter dye molecules are cleaved from their respective probes, and the increase in fluorescence intensity is monitored during the PCR.

Probes and primers were designed according to Perkin Elmer Biosystem's *Primer Express* Software package (version I for Apple Computer's Macintosh Power PC) using the sequence of 2777610 as input. Default settings were used for reaction conditions and the following parameters were set before selecting primers: primer concentration=250 nM, primer melting temperature ($T_m$) range=58°–60° C., primer optimal Tm=59° C., maximum primer difference=2° C., probe does not have 5' G, probe $T_m$ must be 10° C. greater than primer $T_m$, amplicon size 75 bp to 100 bp. The probes and primers selected (see below) were synthesized, double HPLC purified to remove uncoupled dye and evaluated by mass spectroscopy for efficient coupling of reporter and quencher dyes to the 5' and 3' ends of the probe, respectively.

PCR conditions: Sample RNA was provided from a broad range of normal and tumor tissues. The RNA from each tissue (poly A+ RNA, 2.8 pg) and from the cell lines (total RNA, 70 ng) was spotted in each well of a 96 well PCR plate. PCR cocktails including the forward primer, reverse primer and a 2777610-specific probe (see below; and another set of primers and a probe for another gene to serve as a reference) were set up using 1×TaqMan™ PCR Master Mix for the PE Biosystems 7700, with 5 mM MgCl2, dNTPs (dA, dG, dC, dU at 1:1:1:2 ratios), 0.25 U/ml AmpliTaq Gold™ (PE Biosystems), and 0.4 U/µl RNase inhibitor, and 0.25 U/µl reverse transcriptase. Reverse transcription was performed at 48° C. for 30 minutes followed by amplification/PCR cycles as follows: 95° C. 10 min, then 40 cycles of 95° C. for 15 seconds, 60° C. for 1 minute.

TaqMan Probes and Primers Used in Analysis:

Ag 111 (F): 5'-CCTTTCAAAATCCTCTCTGA
    CTCAC-3' (SEQ ID NO:50)

Ag 111 (R): 5'-TCACCGAAGAAAAACGACA
    CAC-3' (SEQ ID NO:51)

Ag 111 (P): TET-5'-CCTGGCACCCTGGCAGCTCAGA-3'-
    TAMRA (SEQ ID NO:52)

Example 7

Expression of 2864933 in Tissues Determined by TaqMan™ Analysis

TaqMan™ analysis of the expression of 2864933 was carried out as described in Example 6. Reverse transcription was performed at 48° C. for 30 minutes followed by amplification/PCR cycles as follows: 95° C. 10 min, then 40 cycles of 95° C for 15 seconds, 60° C. for 1 minute. Primer-probe sets are as described below. The results are shown in FIG. 19, Panels A, B, and C, respectively. Cell types for each panel in FIG. 19 are as provided in Table 3, above.

Two sets of primers and a probe targeted regions of the nucleic acids that are common to 2864933-1 and 2864933-2. Primer-probe set 88 includes Ag 88 (SEQ ID NOs:53–55) and primer-probe set 291 includes Ag 291(SEQ ID NOs:56–58).

Ag 88 (F): 5'-CATCTTCAACAGGCCAT
GGTT-3' (SEQ ID NO:53)

Ag 88 (R): 5'-AGCAGCTGTGTCCACT
GCAA-3' (SEQ ID NO:54)

Ag 88 (P): TET-5'-TGAGAACAATGGTCAGATACCGCCTTAC-
CAA-3'-TAMRA (SEQ ID NO:55)

Ag 291 (F): 5'-CGCAGTCATTTACCGGA
GTCTT-3' (SEQ ID NO:56)

Ag 291 (R): 5'-TTCTTTCAACCATTTT
GAATCGTG-3' (SEQ ID NO:57)

Ag 291 (P): TET-5'-AGCCCTACCCTGCGGACCGTCA-3'-
TAMRA (SEQ ID NO:58)

A third set of primers and a probe targeted the segment that is specifically present only in the longer splice variant, 2864933-1. Primer-probe set 341 includes Ag 341 (SEQ ID NOs:59–61).

Ag 341 (F): 5'-TCCTTTGTGGCACTGAATGG-3'(SEQ ID NO:59)

Ag 341 (R): 5'-CCCTCTTGAGCCGTCGAA-3' (SEQ ID NO:60)

Ag 341 (P): FAM-5'-TCCCTCTTGCCCAGCACAACCAC-3'-
TAMRA (SEQ ID NO:61)

Example 8

Expression of 3352358 in Tissues Determined by TaqMan™ Analysis

TaqMan™ analysis of the expression of 3352358 was carried out as described in Example 6, using the tissue panel as described in Table 3. Reverse transcription was performed at 48° C. for 30 minutes followed by amplification/PCR cycles as follows: 95° C. 10 min, then 40 cycles of 95° C. for 15 seconds, 60° C. for one (1) minute.

TaqMan™ probes and primers used in Analysis of 3352358 are shown below (primer and probe annealing positions to sequence input shown in color and underline respectively). Primer-probe set 42 includes Ag 42 (SEQ ID NOs:62–64). The results are shown in FIG. 20.

Ag 42 (F): 5'-CGCGAAAGTACAAGCCT
GTTC-3' (SEQ ID NO:62)

Ag 42 (R): 5'-GAATGAGCACCGTGGTA
GAGG-3' (SEQ ID NO:63)

Ag 42 (P): TET-5'-CGTCCACTGGTTACCAGCCGGCATATA-3'-
TAMRA (SEQ ID NO:64)

Example 9

Expression of 3911675 in Tissues Determined by TaqMan™ Analysis

Figure 21:
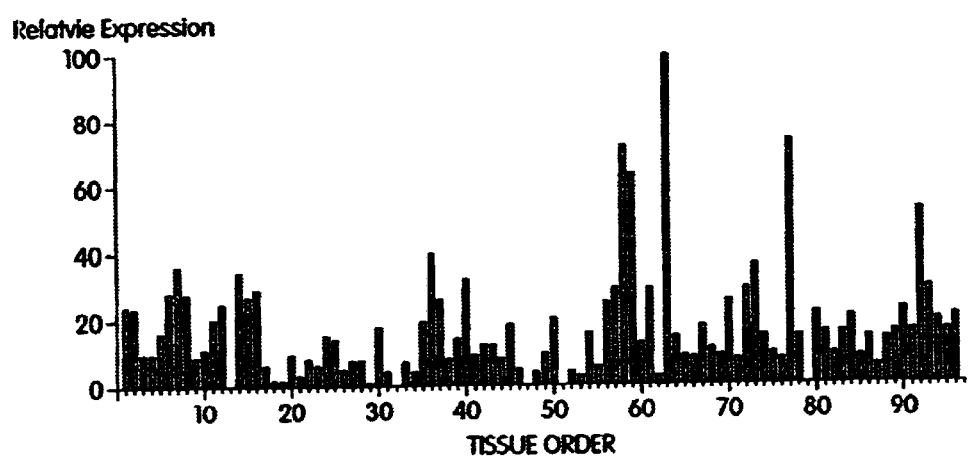
FIG. 21 depicts real time quantitative PCR (TaqMan™) analysis of the expression of 3911675.

TaqMan™ analysis of the expression of 3911675 was carried out as described in Example 6, using the tissue panel as described in Table 3. Reverse transcription was performed at 48° C. for 30 minutes followed by amplification/PCR cycles as follows: 95° C. 10 min, then 40 cycles of 95° C for 15 seconds, 60° C. for 1 minute. TaqMan Probes and Primers Used in the expression Analysis of 3911675 are the primer-probe set 115, which includes Ag 115 (SEQ ID NOs:65–67). The results are shown in FIG. 21.

Ag 115 (F): 5'-TGGACTCATCCCACTT
GCTCT-3' (SEQ ID NO:65)

Ag 115 (R): 5'-CCTGCGCAAAAAGTT
GTGAA-3' (SEQ ID NO:66)

Ag 115 (P): TET-5'-CAGCTGAATCCTGACATCATATCCA-
CACTGTGT-3'-TAMRA (SEQ ID NO:67)

Example 10

Expression of 4035508 in Tissues Determined by TaqMan™ Analysis

Figure 22:
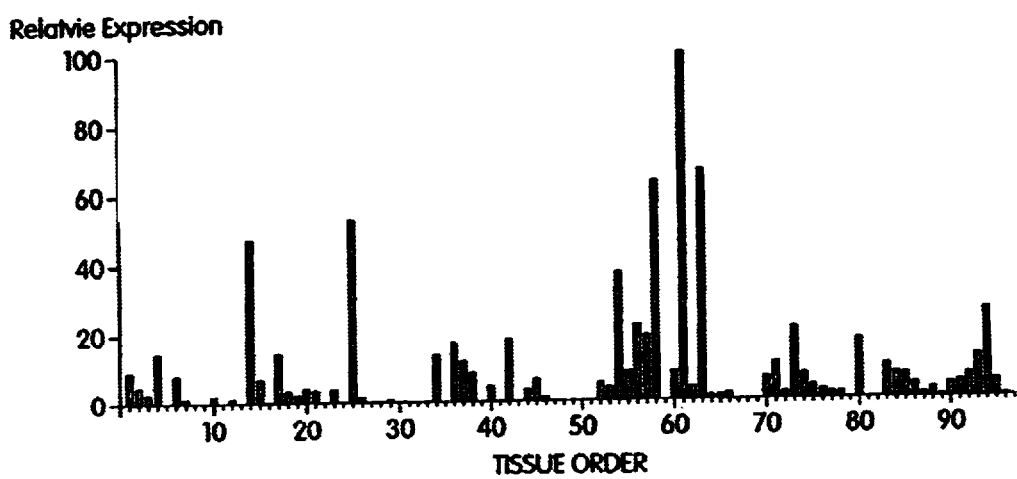
FIG. 22 depicts real time quantitative PCR (TaqMan™) analysis of the expression of 4035508.

TaqMan™ analysis of the expression of 4035508 was carried out as described in Example 6, using the tissue panel as described in Table 3. Reverse transcription was performed at 48° C. for 30 minutes followed by amplification/PCR cycles as follows: 95° C. 10 min, then 40 cycles of 95° C. for 15 seconds, 60° C. for 1 minute. TaqMan probes and primers used in the expression analysis for clone 4035508 include the primer-probe set 118, termed Ag 118 (SEQ ID NOs:68–70). The results are shown in FIG. 22.

Ag 118 (F): 5'-TCTCTGTCTGCAGTACCT
GGCAT-3' (SEQ ID NO:68)

Ag 118 (R): 5'-GGCAGTGGGTATGG
GATGTG-3' (SEQ ID NO:69)

Ag 118 (P): FAM-5'-ACTTTCCTCCTGATGCCCCGGG-3'-
TAMRA (SEQ ID NO:70)

Example 11

Expression of 4339264 in Tissues Determined by TaqMan™ Analysis

Figure 23:
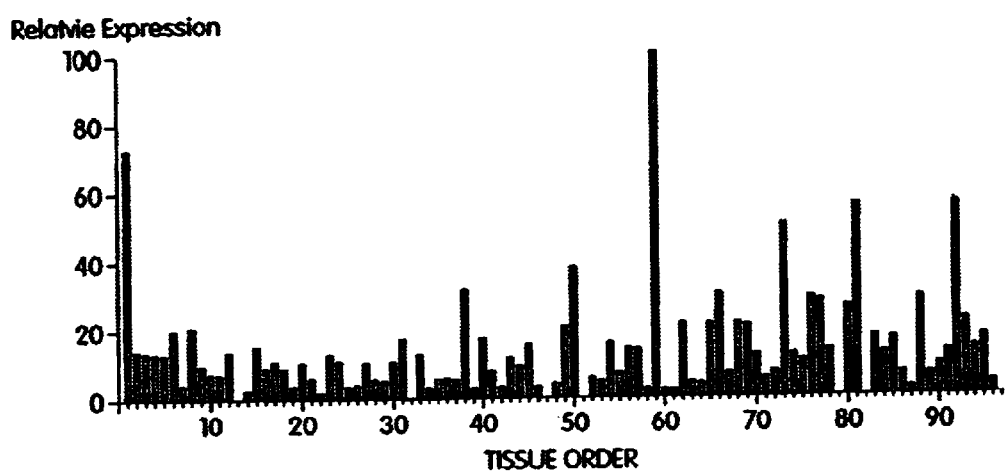
FIG. 23 depicts real time quantitative PCR (TaqMan™) analysis of the expression of 4339264.

TaqMan™ analysis of the expression of 4339264 was carried out as described in Example 6, using the tissue panel as described in Table 3. Reverse transcription was performed at 48° C. for 30 minutes followed by amplification/PCR cycles as follows: 95° C. 10 min, then 40 cycles of 95° C. for 15 seconds, 60° C. for 1 minute. TaqMan probes and primers used in the expression analysis for clone 4339264 include the primer-probe set 120, termed Ag 120 (SEQ ID NOs:71–73). The results are shown in FIG. 23.

Ag 120 (F): 5'-AAAGGCGGAGGAAAGAA
GTACTC-3' (SEQ ID NO:71)

Ag 120 (R): 5'-GCTCCCGTTCCCTCTCCA-3' (SEQ ID NO: 72)

Ag 120 (P): FAM-5'-CCTCTTTGTTCTTCTTGC-
CCGAGTTTTCTTT-3'-TAMRA (SEQ ID NO: 73)

EQUIVALENTS

From the foregoing detailed description of the specific embodiments of the invention, it should be apparent that unique nucleotides, polypeptides, and methods of use thereof for the SECX genes have been described. Although particular embodiments have been disclosed herein in detail, this has been done by way of example for purposes of illustration only, and is not intended to be limiting with respect to the scope of the appended claims which follow. In particular, it is contemplated by the inventor that various substitutions, alterations, and modifications may be made to the invention without departing from the spirit and scope of the invention as defined by the claims. For instance, the choice of which SECX nucleotide or polypeptide or method of use thereof is believed to be a matter of routine for a person of ordinary skill in the art with knowledge of the embodiments described herein.

SEQUENCE LISTING

<160> NUMBER OF SEQ ID NOS: 81

<210> SEQ ID NO 1
<211> LENGTH: 1812
<212> TYPE: DNA
<213> ORGANISM: Homo sapiens
<220> FEATURE:
<221> NAME/KEY: CDS
<222> LOCATION: (537)..(1535)

<400> SEQUENCE: 1

```
atgactgccg ccataagaag acagagagaa ctgagtatcc tcccaaaggt gaatttcaat      60
ttttgttatt atgagtgtgc ttgcttatat aaaagaatat gcttaaggga aaaaaggtgc     120
tttaaagtta atattctaca aaccatagtt tatgagcata agaaattaca taatttacag     180
caatctgatg tattagtaat aataatgtat tattatctct aaacagtgt tttgttttat     240 ggctaacagt agcacctgtg aatgaggcag aacctgttat ttggatttca caaggatgtg     300
aaagtaatgg tactgttaaa agtaccaaaa atgtattata tgctttaaaa attctagcca     360
gaaaacagta ttttccttt caacacatct attgaaagtg ttggataaat gcaggatgtt     420
aatatgctat aaacataaag tctgttttta aaaaatagca tttgaaaatc atgaagggct     480
ttttgttttc ttttgtttgt atatatgttt attggtaaaa ggtgacactg aagca atg     539
                                                                  Met
                                                                   1 aac aca aca gtg atg caa ggc ttc aac aga tct gag cgg tgc ccc aga     587
Asn Thr Thr Val Met Gln Gly Phe Asn Arg Ser Glu Arg Cys Pro Arg
            5                  10                  15 gac act cgg ata gta cag ctg gta ttc cca gcc ctc tac aca gtg gtt     635
Asp Thr Arg Ile Val Gln Leu Val Phe Pro Ala Leu Tyr Thr Val Val
         20                  25                  30 ttc ttg acc ggc atc ctg ctg aat act ttg gct ctg tgg gtg ttt gtt     683
Phe Leu Thr Gly Ile Leu Leu Asn Thr Leu Ala Leu Trp Val Phe Val
     35                  40                  45 cac atc ccc agc tcc tcc acc ttc atc atc tac ctc aaa aac act ttg     731
His Ile Pro Ser Ser Ser Thr Phe Ile Ile Tyr Leu Lys Asn Thr Leu
 50                  55                  60                  65 gtg gcc gac ttg ata atg aca ctc atg ctt cct ttc aaa atc ctc tct     779
Val Ala Asp Leu Ile Met Thr Leu Met Leu Pro Phe Lys Ile Leu Ser
                 70                  75                  80 gac tca cac ctg gca ccc tgg cag ctc aga gct ttt gtg tgt cgt ttt     827
Asp Ser His Leu Ala Pro Trp Gln Leu Arg Ala Phe Val Cys Arg Phe
             85                  90                  95 tct tcg gtg ata ttt tat gag acc atg tat gtg ggc atc gtg ctg tta     875
Ser Ser Val Ile Phe Tyr Glu Thr Met Tyr Val Gly Ile Val Leu Leu
        100                 105                 110 ggg ctc ata gcc ttt gac aga ttc ctc aag atc atc aga cct ttg aga     923
Gly Leu Ile Ala Phe Asp Arg Phe Leu Lys Ile Ile Arg Pro Leu Arg
    115                 120                 125 aat att ttt cta aaa aaa cct gtt ttt gca aaa acg gtc tca atc ttc     971
Asn Ile Phe Leu Lys Lys Pro Val Phe Ala Lys Thr Val Ser Ile Phe
130                 135                 140                 145 atc tgg ttc ttt ttg ttc ttc atc tcc ctg cca aat atg atc ttg agc    1019
Ile Trp Phe Phe Leu Phe Phe Ile Ser Leu Pro Asn Met Ile Leu Ser
                150                 155                 160 aac aag gaa gca aca cca tcg tct gtg aaa aag tgt gct tcc tta aag    1067
Asn Lys Glu Ala Thr Pro Ser Ser Val Lys Lys Cys Ala Ser Leu Lys
            165                 170                 175
```

-continued

| | | |
|---|---|---|
| ggg cct ctg ggg ctg aaa tgg cat caa atg gta aat aac ata tgc cag<br>Gly Pro Leu Gly Leu Lys Trp His Gln Met Val Asn Asn Ile Cys Gln<br>    180                            185                      190 | | 1115 |
| ttt att ttc tgg act gtt ttt atc cta atg ctt gtg ttt tat gtg gtt<br>Phe Ile Phe Trp Thr Val Phe Ile Leu Met Leu Val Phe Tyr Val Val<br>    195                            200                      205 | | 1163 |
| att gca aaa aaa gta tat gat tct tat aga aag tcc aaa agt aag gac<br>Ile Ala Lys Lys Val Tyr Asp Ser Tyr Arg Lys Ser Lys Ser Lys Asp<br>210                        215                      220                      225 | | 1211 |
| aga aaa aac aac aaa aag ctg gaa ggc aaa gta ttt gtt gtc gtg gct<br>Arg Lys Asn Asn Lys Lys Leu Glu Gly Lys Val Phe Val Val Val Ala<br>                      230                      235                      240 | | 1259 |
| gtc ttc ttt gtg tgt ttt gct cca ttt cat ttt gcc aga gtt cca tat<br>Val Phe Phe Val Cys Phe Ala Pro Phe His Phe Ala Arg Val Pro Tyr<br>    245                            250                      255 | | 1307 |
| act cac agt caa acc aac aat aag act gac tgt aga ctg caa aat caa<br>Thr His Ser Gln Thr Asn Asn Lys Thr Asp Cys Arg Leu Gln Asn Gln<br>                      260                      265                      270 | | 1355 |
| ctg ttt att gct aaa gaa aca act ctc ttt ttg gca gca act aac att<br>Leu Phe Ile Ala Lys Glu Thr Thr Leu Phe Leu Ala Ala Thr Asn Ile<br>    275                            280                      285 | | 1403 |
| tgt atg gat ccc tta ata tac ata ttc tta tgt aaa aaa ttc aca gaa<br>Cys Met Asp Pro Leu Ile Tyr Ile Phe Leu Cys Lys Lys Phe Thr Glu<br>290                        295                      300                      305 | | 1451 |
| aag cta cca tgt atg caa ggg aga aag acc aca gca tca agc caa gaa<br>Lys Leu Pro Cys Met Gln Gly Arg Lys Thr Thr Ala Ser Ser Gln Glu<br>                      310                      315                      320 | | 1499 |
| aat cat agc agt cag aca gac aac ata acc tta ggc tgacaactgt<br>Asn His Ser Ser Gln Thr Asp Asn Ile Thr Leu Gly<br>                      325                      330 | | 1545 |
| acatagggtt aacttctatt tattgatgag acttccgtag ataatgtgga aatcaaattt | | 1605 |
| aaccaagaaa aaaagattgg aacaaatgct ctcttacatt ttattatcct cgtgtacaga | | 1665 |
| aaagattata taaaatttaa atccacatag atctattcat aagctgaatg aaccattact | | 1725 |
| aagagaatgc aacaggatac aaatggccac tagaggtcat tatttctttc tttctttatt | | 1785 |
| cagcggccgc tttttttttt tttttttt | | 1812 |

<210> SEQ ID NO 2
<211> LENGTH: 333
<212> TYPE: PRT
<213> ORGANISM: Homo sapiens

<400> SEQUENCE: 2

Met Asn Thr Thr Val Met Gln Gly Phe Asn Arg Ser Glu Arg Cys Pro
1                     5                            10                          15

Arg Asp Thr Arg Ile Val Gln Leu Val Phe Pro Ala Leu Tyr Thr Val
                    20                          25                          30

Val Phe Leu Thr Gly Ile Leu Leu Asn Thr Leu Ala Leu Trp Val Phe
            35                        40                          45

Val His Ile Pro Ser Ser Thr Phe Ile Ile Tyr Leu Lys Asn Thr
        50                          55                          60

Leu Val Ala Asp Leu Ile Met Thr Leu Met Leu Pro Phe Lys Ile Leu
65                    70                          75                        80

Ser Asp Ser His Leu Ala Pro Trp Gln Leu Arg Ala Phe Val Cys Arg
                    85                          90                          95

Phe Ser Ser Val Ile Phe Tyr Glu Thr Met Tyr Val Gly Ile Val Leu
                  100                        105                      110

```
Leu Gly Leu Ile Ala Phe Asp Arg Phe Leu Lys Ile Ile Arg Pro Leu
        115                 120                 125

Arg Asn Ile Phe Leu Lys Lys Pro Val Phe Ala Lys Thr Val Ser Ile
        130                 135                 140

Phe Ile Trp Phe Phe Leu Phe Phe Ile Ser Leu Pro Asn Met Ile Leu
145                 150                 155                 160

Ser Asn Lys Glu Ala Thr Pro Ser Ser Val Lys Cys Ala Ser Leu
                165                 170                 175

Lys Gly Pro Leu Gly Leu Lys Trp His Gln Met Val Asn Asn Ile Cys
            180                 185                 190

Gln Phe Ile Phe Trp Thr Val Phe Ile Leu Met Leu Val Phe Tyr Val
        195                 200                 205

Val Ile Ala Lys Lys Val Tyr Asp Ser Tyr Arg Lys Ser Lys Ser Lys
        210                 215                 220

Asp Arg Lys Asn Asn Lys Lys Leu Glu Gly Lys Val Phe Val Val Val
225                 230                 235                 240

Ala Val Phe Phe Val Cys Phe Ala Pro Phe His Phe Ala Arg Val Pro
                245                 250                 255

Tyr Thr His Ser Gln Thr Asn Asn Lys Thr Asp Cys Arg Leu Gln Asn
            260                 265                 270

Gln Leu Phe Ile Ala Lys Glu Thr Thr Leu Phe Leu Ala Ala Thr Asn
        275                 280                 285

Ile Cys Met Asp Pro Leu Ile Tyr Ile Phe Leu Cys Lys Lys Phe Thr
290                 295                 300

Glu Lys Leu Pro Cys Met Gln Gly Arg Lys Thr Thr Ala Ser Ser Gln
305                 310                 315                 320

Glu Asn His Ser Ser Gln Thr Asp Asn Ile Thr Leu Gly
                325                 330

<210> SEQ ID NO 3
<211> LENGTH: 3498
<212> TYPE: DNA
<213> ORGANISM: Homo sapiens
<220> FEATURE:
<221> NAME/KEY: CDS
<222> LOCATION: (214)..(3030)
<221> NAME/KEY: misc_feature
<222> LOCATION: (3047)
<223> OTHER INFORMATION: an n may be any one of a or t or g or c

<400> SEQUENCE: 3
gcgactattt ccccaaaga  gacaagcaca catgtaggaa tgacaaaggc ttgcgaagga      60
gagagcgcag cccgcggccc ggagagatcc cctcgataat ggattactaa atgggataca    120
cgctgtacca gttcgctccg agccccggcc gcctgtccgt cgatgcaccg aaaagggtga    180
agtagagaaa taaagtctcc ccgctgaact act atg agg tca gaa gcc ttg ctg     234
                                    Met Arg Ser Glu Ala Leu Leu
                                     1               5 cta tat ttc aca ctg cta cac ttt gct ggg gct ggt ttc cca gaa gat      282
Leu Tyr Phe Thr Leu Leu His Phe Ala Gly Ala Gly Phe Pro Glu Asp
        10                  15                  20 tct gag cca atc agt att tcg cat ggc aac tat aca aaa cag tat ccg      330
Ser Glu Pro Ile Ser Ile Ser His Gly Asn Tyr Thr Lys Gln Tyr Pro
    25                  30                  35 gtg ttt gtg ggc cac aag cca gga cgg aac acc aca cag agg cac agg      378
Val Phe Val Gly His Lys Pro Gly Arg Asn Thr Thr Gln Arg His Arg
40                  45                  50                  55 ctg gac atc cag atg att atg atc atg aac gga acc ctc tac att gct      426
```

```
                Leu Asp Ile Gln Met Ile Met Ile Met Asn Gly Thr Leu Tyr Ile Ala
                                60                  65                  70 gct agg gac cat att tat act gtt gat ata gac aca tca cac acg gaa            474
Ala Arg Asp His Ile Tyr Thr Val Asp Ile Asp Thr Ser His Thr Glu
            75                  80                  85 gaa att tat tgt agc aaa aaa ctg aca tgg aaa tct aga cag gcc gat            522
Glu Ile Tyr Cys Ser Lys Lys Leu Thr Trp Lys Ser Arg Gln Ala Asp
        90                  95                 100 gta gac aca tgc aga atg aag gga aaa cat aag gat gag tgc cac aac            570
Val Asp Thr Cys Arg Met Lys Gly Lys His Lys Asp Glu Cys His Asn
    105                 110                 115 ttt att aaa gtt ctt cta aag aaa aac gat gat gca ttg ttt gtc tgt            618
Phe Ile Lys Val Leu Leu Lys Lys Asn Asp Asp Ala Leu Phe Val Cys
120                 125                 130                 135 gga act aat gcc ttc aac cct tcc tgc aga aac tat aag atg gat aca            666
Gly Thr Asn Ala Phe Asn Pro Ser Cys Arg Asn Tyr Lys Met Asp Thr
            140                 145                 150 ttg gaa cca ttc ggg gat gaa ttc agc gga atg gcc aga tgc cca tat            714
Leu Glu Pro Phe Gly Asp Glu Phe Ser Gly Met Ala Arg Cys Pro Tyr
        155                 160                 165 gat gcc aaa cat gcc aac gtt gca ctg ttt gca gat gga aaa cta tac            762
Asp Ala Lys His Ala Asn Val Ala Leu Phe Ala Asp Gly Lys Leu Tyr
    170                 175                 180 tca gcc aca gtg act gac ttc ctt gcc att gac gca gtc att tac cgg            810
Ser Ala Thr Val Thr Asp Phe Leu Ala Ile Asp Ala Val Ile Tyr Arg
185                 190                 195 agt ctt gga gaa agc cct acc ctg cgg acc gtc aag cac gat tca aaa            858
Ser Leu Gly Glu Ser Pro Thr Leu Arg Thr Val Lys His Asp Ser Lys
200                 205                 210                 215 tgg ttg aaa gaa cca tac ttt gtt caa gcc gtg gat tac gga gat tat            906
Trp Leu Lys Glu Pro Tyr Phe Val Gln Ala Val Asp Tyr Gly Asp Tyr
            220                 225                 230 atc tac ttc ttc ttc agg gaa ata gca gtg gag tat aac acc atg gga            954
Ile Tyr Phe Phe Phe Arg Glu Ile Ala Val Glu Tyr Asn Thr Met Gly
        235                 240                 245 aag gta gtt ttc cca aga gtg gct cag gtt tgt aag aat gat atg gga           1002
Lys Val Val Phe Pro Arg Val Ala Gln Val Cys Lys Asn Asp Met Gly
    250                 255                 260 gga tct caa aga gtc ctg gag aaa cag tgg acg tcg ttc ctg aag gcg           1050
Gly Ser Gln Arg Val Leu Glu Lys Gln Trp Thr Ser Phe Leu Lys Ala
265                 270                 275 cgc ttg aac tgc tca gtt cct gga gac tct cat ttt tat ttc aac att           1098
Arg Leu Asn Cys Ser Val Pro Gly Asp Ser His Phe Tyr Phe Asn Ile
280                 285                 290                 295 ctc cag gca gtt aca gat gtg att cgt atc aac ggg cgt gat gtt gtc           1146
Leu Gln Ala Val Thr Asp Val Ile Arg Ile Asn Gly Arg Asp Val Val
            300                 305                 310 ctg gca acg ttt tct aca cct tat aac agc atc cct ggg tct gca gtc           1194
Leu Ala Thr Phe Ser Thr Pro Tyr Asn Ser Ile Pro Gly Ser Ala Val
        315                 320                 325 tgt gcc tat gac atg ctt gac att gcc agt gtt ttt act ggg aga ttc           1242
Cys Ala Tyr Asp Met Leu Asp Ile Ala Ser Val Phe Thr Gly Arg Phe
    330                 335                 340 aag gaa cag aag tct cct gat tcc acc tgg aca cca gtt cct gat gaa           1290
Lys Glu Gln Lys Ser Pro Asp Ser Thr Trp Thr Pro Val Pro Asp Glu
345                 350                 355 cga gtt cct aag ccc agg cca ggt tgc tgt gct ggc tca tcc tcc tta           1338
Arg Val Pro Lys Pro Arg Pro Gly Cys Cys Ala Gly Ser Ser Ser Leu
360                 365                 370                 375
```

-continued

| | | |
|---|---|---|
| gaa aga tat gca acc tcc aat gag ttc cct gat gat acc ctg aac ttc<br>Glu Arg Tyr Ala Thr Ser Asn Glu Phe Pro Asp Asp Thr Leu Asn Phe<br>380                        385                      390 | 1386 |
| atc aag acg cac ccg ctc atg gat gag gca gtg ccc tcc atc ttc aac<br>Ile Lys Thr His Pro Leu Met Asp Glu Ala Val Pro Ser Ile Phe Asn<br>           395                      400                      405 | 1434 |
| agg cca tgg ttc ctg aga aca atg gtc aga tac cgc ctt acc aaa att<br>Arg Pro Trp Phe Leu Arg Thr Met Val Arg Tyr Arg Leu Thr Lys Ile<br>        410                      415                      420 | 1482 |
| gca gtg gac aca gct gct ggg cca tat cag aat cac act gtg gtt ttt<br>Ala Val Asp Thr Ala Ala Gly Pro Tyr Gln Asn His Thr Val Val Phe<br>425                        430                      435 | 1530 |
| ctg gga tca gag aag gga atc atc ttg aag ttt ttg gcc aga ata gga<br>Leu Gly Ser Glu Lys Gly Ile Ile Leu Lys Phe Leu Ala Arg Ile Gly<br>440                        445                      450                      455 | 1578 |
| aat agt ggt ttt cta aat gac agc ctt ttc ctg gag gag atg agt gtt<br>Asn Ser Gly Phe Leu Asn Asp Ser Leu Phe Leu Glu Glu Met Ser Val<br>                  460                      465                      470 | 1626 |
| tac aac tct gaa aaa tgc agc tat gat gga gtc gaa gac aaa agg atc<br>Tyr Asn Ser Glu Lys Cys Ser Tyr Asp Gly Val Glu Asp Lys Arg Ile<br>            475                      480                      485 | 1674 |
| atg ggc atg cag ctg gac aga gca agc agc tct ctg tat gtt gcg ttc<br>Met Gly Met Gln Leu Asp Arg Ala Ser Ser Ser Leu Tyr Val Ala Phe<br>490                        495                      500 | 1722 |
| tct acc tgt gtg ata aag gtt ccc ctt ggc cgg tgt gaa cga cat ggg<br>Ser Thr Cys Val Ile Lys Val Pro Leu Gly Arg Cys Glu Arg His Gly<br>505                        510                      515 | 1770 |
| aag tgt aaa aaa acc tgt att gcc tcc aga gac cca tat tgt gga tgg<br>Lys Cys Lys Lys Thr Cys Ile Ala Ser Arg Asp Pro Tyr Cys Gly Trp<br>520                        525                      530                      535 | 1818 |
| ata aag gaa ggt ggt gcc tgc agc cat tta tca ccc aac agc aga ctg<br>Ile Lys Glu Gly Gly Ala Cys Ser His Leu Ser Pro Asn Ser Arg Leu<br>                  540                      545                      550 | 1866 |
| act ttt gag cag gac ata gag cgt ggc aat aca gat ggt ctg ggg gac<br>Thr Phe Glu Gln Asp Ile Glu Arg Gly Asn Thr Asp Gly Leu Gly Asp<br>            555                      560                      565 | 1914 |
| tgt cac aat tcc ttt gtg gca ctg aat ggg cat tcc agt tcc ctc ttg<br>Cys His Asn Ser Phe Val Ala Leu Asn Gly His Ser Ser Ser Leu Leu<br>                  570                      575                      580 | 1962 |
| ccc agc aca acc aca tca gat tcg acg gct caa gag ggg tat gag tct<br>Pro Ser Thr Thr Thr Ser Asp Ser Thr Ala Gln Glu Gly Tyr Glu Ser<br>585                        590                      595 | 2010 |
| agg gga gga atg ctg gac tgg aag cat ctg ctt gac tca cct gac agc<br>Arg Gly Gly Met Leu Asp Trp Lys His Leu Leu Asp Ser Pro Asp Ser<br>600                        605                      610                      615 | 2058 |
| aca gac cct ttg ggg gca gtg tct tcc cat aat cac caa gac aag aag<br>Thr Asp Pro Leu Gly Ala Val Ser Ser His Asn His Gln Asp Lys Lys<br>                  620                      625                      630 | 2106 |
| gga gtg att cgg gaa agt tac ctc aaa ggc cac gac cag ctg gtt ccc<br>Gly Val Ile Arg Glu Ser Tyr Leu Lys Gly His Asp Gln Leu Val Pro<br>                635                      640                      645 | 2154 |
| gtc acc ctc ttg gcc att gca gtc atc ctg gct ttc gtc atg ggg gcc<br>Val Thr Leu Leu Ala Ile Ala Val Ile Leu Ala Phe Val Met Gly Ala<br>650                        655                      660 | 2202 |
| gtc ttc tcg ggc atc acc gtc tac tgc gtc tgt gat cat cgg cgc aaa<br>Val Phe Ser Gly Ile Thr Val Tyr Cys Val Cys Asp His Arg Arg Lys<br>665                        670                      675 | 2250 |
| gac gtg gct gtg gtg cag cgc aag gag aag gag ctc acc cac tcg cgc<br>Asp Val Ala Val Val Gln Arg Lys Glu Lys Glu Leu Thr His Ser Arg<br>680                        685                      690                      695 | 2298 |

```
cgg ggc tcc atg agc agc gtc acc aag ctc agc ggc ctc ttt ggg gac            2346
Arg Gly Ser Met Ser Ser Val Thr Lys Leu Ser Gly Leu Phe Gly Asp
                    700             705             710 act caa tcc aaa gac cca aag ccg gag gcc atc ctc acg cca ctc atg            2394
Thr Gln Ser Lys Asp Pro Lys Pro Glu Ala Ile Leu Thr Pro Leu Met
                715             720             725 cac aac ggc aag ctc gcc act ccc ggc aac acg gcc aag atg ctc att            2442
His Asn Gly Lys Leu Ala Thr Pro Gly Asn Thr Ala Lys Met Leu Ile
            730             735             740 aaa gca gac cag cac cac ctg gac ctg acg gcc ctc ccc acc cca gag            2490
Lys Ala Asp Gln His His Leu Asp Leu Thr Ala Leu Pro Thr Pro Glu
        745             750             755 tca acc cca acg ctg cag cag aag cgg gaa ccc agc cgc ggc acc cgc            2538
Ser Thr Pro Thr Leu Gln Gln Lys Arg Glu Pro Ser Arg Gly Thr Arg
    760             765             770             775 gag tgg gag agg aac cag aac ctc atc aat gcc tgc aca aag gac atg            2586
Glu Trp Glu Arg Asn Gln Asn Leu Ile Asn Ala Cys Thr Lys Asp Met
                    780             785             790 ccc ccc atg ggc tcc cct gtg att ccc acg gac ctg ccc ctg cgg gcc            2634
Pro Pro Met Gly Ser Pro Val Ile Pro Thr Asp Leu Pro Leu Arg Ala
                795             800             805 tcc ccc agc cac atc ccc agc gtg gtg gtc ctg ccc atc acg cag cag            2682
Ser Pro Ser His Ile Pro Ser Val Val Val Leu Pro Ile Thr Gln Gln
            810             815             820 ggc tac cag cat gag tac gtg gac cag ccc aaa atg agc gag gtg gcc            2730
Gly Tyr Gln His Glu Tyr Val Asp Gln Pro Lys Met Ser Glu Val Ala
        825             830             835 cag atg gcg ctg gag gac cag gcc gcc aca ctg gag tat aag acc atc            2778
Gln Met Ala Leu Glu Asp Gln Ala Ala Thr Leu Glu Tyr Lys Thr Ile
840             845             850             855 aag gaa cat ctc agc agc aag agt ccc aac cat ggg gtg aac ctt gtg            2826
Lys Glu His Leu Ser Ser Lys Ser Pro Asn His Gly Val Asn Leu Val
                    860             865             870 gag aac ctg gac agc ctg ccc ccc aaa gtt cca cag cgg gag gcc tcc            2874
Glu Asn Leu Asp Ser Leu Pro Pro Lys Val Pro Gln Arg Glu Ala Ser
                875             880             885 ctg ggt ccc ccg gga gcc tcc ctg tct cag acc ggt cta agc aag cgg            2922
Leu Gly Pro Pro Gly Ala Ser Leu Ser Gln Thr Gly Leu Ser Lys Arg
            890             895             900 ctg gaa atg cac cac tcc tct tcc tac ggg gtt gac tat aag agg agc            2970
Leu Glu Met His His Ser Ser Ser Tyr Gly Val Asp Tyr Lys Arg Ser
        905             910             915 tac ccc acg aac tcg ctc acg aga agc cac ctg acc acc tac tct cat            3018
Tyr Pro Thr Asn Ser Leu Thr Arg Ser His Leu Thr Thr Tyr Ser His
920             925             930             935 cag aag caa cac taaccccgac aattcanctc tgacttcaaa gggaccagag               3070
Gln Lys Gln His ctttggcagg ggagacaacc cgccgcccgc cccgcagagg gtggactcca tccaggtgca          3130
cagctcccag ccatctggcc aggccgtgac tgtctcgagg cagcccagcc tcaacgccta          3190
caactcactg acaaggtcgg ggctgaagcg tacgccctcg ctaaagccgg acgtaccccc          3250
caaaccatcc tttgctcccc tttccacatc catgaagccc aatgatgcgt gtacataatc          3310 ccaggggag ggggtcaggt gtcgaaccag caggcaaggc gaggtgtccg ctcagctcag           3370
caaggttctc aactgcctcg agtacccacc aaaccaaaaa ggcctgcggc agaaccgagg          3430
gacgctgggt cctcctctct gggacacagg ggtactcacg aaaactgggc cgcgtggttt         3490
ggtgaaag                                                                   3498
```

```
<210> SEQ ID NO 4
<211> LENGTH: 939
<212> TYPE: PRT
<213> ORGANISM: Homo sapiens

<400> SEQUENCE: 4
```

| Met | Arg | Ser | Glu | Ala | Leu | Leu | Tyr | Phe | Thr | Leu | His | Phe | Ala |
|-----|-----|-----|-----|-----|-----|-----|-----|-----|-----|-----|-----|-----|-----|
| 1   |     |     |     | 5   |     |     |     |     | 10  |     |     |     | 15  |

Gly Ala Gly Phe Pro Glu Asp Ser Glu Pro Ile Ser Ile Ser His Gly
              20                  25                  30

Asn Tyr Thr Lys Gln Tyr Pro Val Phe Val Gly His Lys Pro Gly Arg
             35                  40                  45

Asn Thr Thr Gln Arg His Arg Leu Asp Ile Gln Met Ile Met Ile Met
         50                  55                  60

Asn Gly Thr Leu Tyr Ile Ala Ala Arg Asp His Ile Tyr Thr Val Asp
 65                  70                  75                  80

Ile Asp Thr Ser His Thr Glu Glu Ile Tyr Cys Ser Lys Lys Leu Thr
                 85                  90                  95

Trp Lys Ser Arg Gln Ala Asp Val Asp Thr Cys Arg Met Lys Gly Lys
             100                 105                 110

His Lys Asp Glu Cys His Asn Phe Ile Lys Val Leu Leu Lys Lys Asn
         115                 120                 125

Asp Asp Ala Leu Phe Val Cys Gly Thr Asn Ala Phe Asn Pro Ser Cys
130                 135                 140

Arg Asn Tyr Lys Met Asp Thr Leu Glu Pro Phe Gly Asp Glu Phe Ser
145                 150                 155                 160

Gly Met Ala Arg Cys Pro Tyr Asp Ala Lys His Ala Asn Val Ala Leu
                 165                 170                 175

Phe Ala Asp Gly Lys Leu Tyr Ser Ala Thr Val Thr Asp Phe Leu Ala
             180                 185                 190

Ile Asp Ala Val Ile Tyr Arg Ser Leu Gly Glu Ser Pro Thr Leu Arg
         195                 200                 205

Thr Val Lys His Asp Ser Lys Trp Leu Lys Glu Pro Tyr Phe Val Gln
    210                 215                 220

Ala Val Asp Tyr Gly Asp Tyr Ile Tyr Phe Phe Phe Arg Glu Ile Ala
225                 230                 235                 240

Val Glu Tyr Asn Thr Met Gly Lys Val Val Phe Pro Arg Val Ala Gln
                 245                 250                 255

Val Cys Lys Asn Asp Met Gly Gly Ser Gln Arg Val Leu Glu Lys Gln
             260                 265                 270

Trp Thr Ser Phe Leu Lys Ala Arg Leu Asn Cys Ser Val Pro Gly Asp
         275                 280                 285

Ser His Phe Tyr Phe Asn Ile Leu Gln Ala Val Thr Asp Val Ile Arg
    290                 295                 300

Ile Asn Gly Arg Asp Val Val Leu Ala Thr Phe Ser Thr Pro Tyr Asn
305                 310                 315                 320

Ser Ile Pro Gly Ser Ala Val Cys Ala Tyr Asp Met Leu Asp Ile Ala
                 325                 330                 335

Ser Val Phe Thr Gly Arg Phe Lys Glu Gln Lys Ser Pro Asp Ser Thr
             340                 345                 350

Trp Thr Pro Val Pro Asp Glu Arg Val Pro Lys Pro Arg Pro Gly Cys
         355                 360                 365

Cys Ala Gly Ser Ser Ser Leu Glu Arg Tyr Ala Thr Ser Asn Glu Phe

```
            370             375             380
Pro Asp Asp Thr Leu Asn Phe Ile Lys Thr His Pro Leu Met Asp Glu
385             390             395             400

Ala Val Pro Ser Ile Phe Asn Arg Pro Trp Phe Leu Arg Thr Met Val
                405             410             415

Arg Tyr Arg Leu Thr Lys Ile Ala Val Asp Thr Ala Ala Gly Pro Tyr
            420             425             430

Gln Asn His Thr Val Val Phe Leu Gly Ser Glu Lys Gly Ile Ile Leu
            435             440             445

Lys Phe Leu Ala Arg Ile Gly Asn Ser Gly Phe Leu Asn Asp Ser Leu
450             455             460

Phe Leu Glu Glu Met Ser Val Tyr Asn Ser Glu Lys Cys Ser Tyr Asp
465             470             475             480

Gly Val Glu Asp Lys Arg Ile Met Gly Met Gln Leu Asp Arg Ala Ser
                485             490             495

Ser Ser Leu Tyr Val Ala Phe Ser Thr Cys Val Ile Lys Val Pro Leu
            500             505             510

Gly Arg Cys Glu Arg His Gly Lys Cys Lys Lys Thr Cys Ile Ala Ser
            515             520             525

Arg Asp Pro Tyr Cys Gly Trp Ile Lys Glu Gly Gly Ala Cys Ser His
530             535             540

Leu Ser Pro Asn Ser Arg Leu Thr Phe Glu Gln Asp Ile Glu Arg Gly
545             550             555             560

Asn Thr Asp Gly Leu Gly Asp Cys His Asn Ser Phe Val Ala Leu Asn
                565             570             575

Gly His Ser Ser Ser Leu Leu Pro Ser Thr Thr Thr Ser Asp Ser Thr
            580             585             590

Ala Gln Glu Gly Tyr Glu Ser Arg Gly Gly Met Leu Asp Trp Lys His
            595             600             605

Leu Leu Asp Ser Pro Asp Ser Thr Asp Pro Leu Gly Ala Val Ser Ser
610             615             620

His Asn His Gln Asp Lys Lys Gly Val Ile Arg Glu Ser Tyr Leu Lys
625             630             635             640

Gly His Asp Gln Leu Val Pro Val Thr Leu Leu Ala Ile Ala Val Ile
            645             650             655

Leu Ala Phe Val Met Gly Ala Val Phe Ser Gly Ile Thr Val Tyr Cys
            660             665             670

Val Cys Asp His Arg Arg Lys Asp Val Ala Val Val Gln Arg Lys Glu
            675             680             685

Lys Glu Leu Thr His Ser Arg Arg Gly Ser Met Ser Ser Val Thr Lys
            690             695             700

Leu Ser Gly Leu Phe Gly Asp Thr Gln Ser Lys Asp Pro Lys Pro Glu
705             710             715             720

Ala Ile Leu Thr Pro Leu Met His Asn Gly Lys Leu Ala Thr Pro Gly
                725             730             735

Asn Thr Ala Lys Met Leu Ile Lys Ala Asp Gln His His Leu Asp Leu
            740             745             750

Thr Ala Leu Pro Thr Pro Glu Ser Thr Pro Thr Leu Gln Gln Lys Arg
            755             760             765

Glu Pro Ser Arg Gly Thr Arg Glu Trp Glu Arg Asn Gln Asn Leu Ile
            770             775             780

Asn Ala Cys Thr Lys Asp Met Pro Pro Met Gly Ser Pro Val Ile Pro
785             790             795             800
```

```
Thr Asp Leu Pro Leu Arg Ala Ser Pro Ser His Ile Pro Ser Val Val
            805                 810                 815
Val Leu Pro Ile Thr Gln Gln Gly Tyr Gln His Glu Tyr Val Asp Gln
        820                 825                 830
Pro Lys Met Ser Glu Val Ala Gln Met Ala Leu Glu Asp Gln Ala Ala
        835                 840                 845
Thr Leu Glu Tyr Lys Thr Ile Lys Glu His Leu Ser Ser Lys Ser Pro
    850                 855                 860
Asn His Gly Val Asn Leu Val Glu Asn Leu Asp Ser Leu Pro Pro Lys
865                 870                 875                 880
Val Pro Gln Arg Glu Ala Ser Leu Gly Pro Pro Gly Ala Ser Leu Ser
            885                 890                 895
Gln Thr Gly Leu Ser Lys Arg Leu Glu Met His His Ser Ser Ser Tyr
        900                 905                 910
Gly Val Asp Tyr Lys Arg Ser Tyr Pro Thr Asn Ser Leu Thr Arg Ser
    915                 920                 925
His Leu Thr Thr Tyr Ser His Gln Lys Gln His
    930                 935
```

<210> SEQ ID NO 5
<211> LENGTH: 3333
<212> TYPE: DNA
<213> ORGANISM: Homo sapiens
<220> FEATURE:
<221> NAME/KEY: CDS
<222> LOCATION: (214)..(2865)
<221> NAME/KEY: misc_feature
<222> LOCATION: (2882)
<223> OTHER INFORMATION: an n may be any one of a or t or g or c

<400> SEQUENCE: 5

```
gcgactattt cccccaaaga dacaagcaca catgtaggaa tgacaaaggc ttgcgaagga         60
gagagcgcag cccgcggccc ggagagatcc cctcgataat ggattactaa atgggataca        120
cgctgtacca gttcgctccg agccccggcc gcctgtccgt cgatgcaccg aaaagggtga        180
agtagagaaa taaagtctcc ccgctgaact act atg agg tca gaa gcc ttg ctg        234
                                    Met Arg Ser Glu Ala Leu Leu
                                      1               5 cta tat ttc aca ctg cta cac ttt gct ggg gct ggt ttc cca gaa gat        282
Leu Tyr Phe Thr Leu Leu His Phe Ala Gly Ala Gly Phe Pro Glu Asp
        10                  15                  20 tct gag cca atc agt att tcg cat ggc aac tat aca aaa cag tat ccg        330
Ser Glu Pro Ile Ser Ile Ser His Gly Asn Tyr Thr Lys Gln Tyr Pro
    25                  30                  35 gtg ttt gtg ggc cac aag cca gga cgg aac acc aca cag agg cac agg        378
Val Phe Val Gly His Lys Pro Gly Arg Asn Thr Thr Gln Arg His Arg
 40                  45                  50                  55 ctg gac atc cag atg att atg atc atg aac gga acc ctc tac att gct        426
Leu Asp Ile Gln Met Ile Met Ile Met Asn Gly Thr Leu Tyr Ile Ala
                60                  65                  70 gct agg gac cat att tat act gtt gat ata gac aca tca cac acg gaa        474
Ala Arg Asp His Ile Tyr Thr Val Asp Ile Asp Thr Ser His Thr Glu
            75                  80                  85 gaa att tat tgt agc aaa aaa ctg aca tgg aaa tct aga cag gcc gat        522
Glu Ile Tyr Cys Ser Lys Lys Leu Thr Trp Lys Ser Arg Gln Ala Asp
        90                  95                 100 gta gac aca tgc aga atg aag gga aaa cat aag gat gag tgc cac aac        570
Val Asp Thr Cys Arg Met Lys Gly Lys His Lys Asp Glu Cys His Asn
    105                 110                 115
```

-continued

| | |
|---|---|
| ttt att aaa gtt ctt cta aag aaa aac gat gat gca ttg ttt gtc tgt<br>Phe Ile Lys Val Leu Leu Lys Lys Asn Asp Asp Ala Leu Phe Val Cys<br>120                        125                      130                    135 | 618 |
| gga act aat gcc ttc aac cct tcc tgc aga aac tat aag atg gat aca<br>Gly Thr Asn Ala Phe Asn Pro Ser Cys Arg Asn Tyr Lys Met Asp Thr<br>                      140                      145                      150 | 666 |
| ttg gaa cca ttc ggg gat gaa ttc agc gga atg gcc aga tgc cca tat<br>Leu Glu Pro Phe Gly Asp Glu Phe Ser Gly Met Ala Arg Cys Pro Tyr<br>                155                      160                      165 | 714 |
| gat gcc aaa cat gcc aac gtt gca ctg ttt gca gat gga aaa cta tac<br>Asp Ala Lys His Ala Asn Val Ala Leu Phe Ala Asp Gly Lys Leu Tyr<br>            170                      175                      180 | 762 |
| tca gcc aca gtg act gac ttc ctt gcc att gac gca gtc att tac cgg<br>Ser Ala Thr Val Thr Asp Phe Leu Ala Ile Asp Ala Val Ile Tyr Arg<br>185                        190                      195 | 810 |
| agt ctt gga gaa agc cct acc ctg cgg acc gtc aag cac gat tca aaa<br>Ser Leu Gly Glu Ser Pro Thr Leu Arg Thr Val Lys His Asp Ser Lys<br>200                        205                      210                    215 | 858 |
| tgg ttg aaa gaa cca tac ttt gtt caa gcc gtg gat tac gga gat tat<br>Trp Leu Lys Glu Pro Tyr Phe Val Gln Ala Val Asp Tyr Gly Asp Tyr<br>                      220                      225                      230 | 906 |
| atc tac ttc ttc ttc agg gaa ata gca gtg gag tat aac acc atg gga<br>Ile Tyr Phe Phe Phe Arg Glu Ile Ala Val Glu Tyr Asn Thr Met Gly<br>                235                      240                      245 | 954 |
| aag gta gtt ttc cca aga gtg gct cag gtt tgt aag aat gat atg gga<br>Lys Val Val Phe Pro Arg Val Ala Gln Val Cys Lys Asn Asp Met Gly<br>            250                      255                      260 | 1002 |
| gga tct caa aga gtc ctg gag aaa cag tgg acg tcg ttc ctg aag gcg<br>Gly Ser Gln Arg Val Leu Glu Lys Gln Trp Thr Ser Phe Leu Lys Ala<br>265                        270                      275 | 1050 |
| cgc ttg aac tgc tca gtt cct gga gac tct cat ttt tat ttc aac att<br>Arg Leu Asn Cys Ser Val Pro Gly Asp Ser His Phe Tyr Phe Asn Ile<br>280                        285                      290                    295 | 1098 |
| ctc cag gca gtt aca gat gtg att cgt atc aac ggg cgt gat gtt gtc<br>Leu Gln Ala Val Thr Asp Val Ile Arg Ile Asn Gly Arg Asp Val Val<br>                      300                      305                      310 | 1146 |
| ctg gca acg ttt tct aca cct tat aac agc atc cct ggg tct gca gtc<br>Leu Ala Thr Phe Ser Thr Pro Tyr Asn Ser Ile Pro Gly Ser Ala Val<br>                315                      320                      325 | 1194 |
| tgt gcc tat gac atg ctt gac att gcc agt gtt ttt act ggg aga ttc<br>Cys Ala Tyr Asp Met Leu Asp Ile Ala Ser Val Phe Thr Gly Arg Phe<br>            330                      335                      340 | 1242 |
| aag gaa cag aag tct cct gat tcc acc tgg aca cca gtt cct gat gaa<br>Lys Glu Gln Lys Ser Pro Asp Ser Thr Trp Thr Pro Val Pro Asp Glu<br>345                        350                      355 | 1290 |
| cga gtt cct aag ccc agg cca ggt tgc tgt gct ggc tca tcc tcc tta<br>Arg Val Pro Lys Pro Arg Pro Gly Cys Cys Ala Gly Ser Ser Ser Leu<br>360                        365                      370                    375 | 1338 |
| gaa aga tat gca acc tcc aat gag ttc cct gat gat acc ctg aac ttc<br>Glu Arg Tyr Ala Thr Ser Asn Glu Phe Pro Asp Asp Thr Leu Asn Phe<br>                      380                      385                      390 | 1386 |
| atc aag acg cac ccg ctc atg gat gag gca gtg ccc tcc atc ttc aac<br>Ile Lys Thr His Pro Leu Met Asp Glu Ala Val Pro Ser Ile Phe Asn<br>                395                      400                    405 | 1434 |
| agg cca tgg ttc ctg aga aca atg gtc aga tac cgc ctt acc aaa att<br>Arg Pro Trp Phe Leu Arg Thr Met Val Arg Tyr Arg Leu Thr Lys Ile<br>            410                      415                    420 | 1482 |
| gca gtg gac aca gct gct ggg cca tat cag aat cac act gtg gtt ttt<br>Ala Val Asp Thr Ala Ala Gly Pro Tyr Gln Asn His Thr Val Val Phe | 1530 |

```
                425                 430                 435
ctg gga tca gag aag gga atc atc ttg aag ttt ttg gcc aga ata gga      1578
Leu Gly Ser Glu Lys Gly Ile Ile Leu Lys Phe Leu Ala Arg Ile Gly
440                 445                 450                 455 aat agt ggt ttt cta aat gac agc ctt ttc ctg gag gag atg agt gtt      1626
Asn Ser Gly Phe Leu Asn Asp Ser Leu Phe Leu Glu Glu Met Ser Val
                    460                 465                 470 tac aac tct gaa aaa tgc agc tat gat gga gtc gaa gac aaa agg atc      1674
Tyr Asn Ser Glu Lys Cys Ser Tyr Asp Gly Val Glu Asp Lys Arg Ile
                475                 480                 485 atg ggc atg cag ctg gac aga gca agc agc tct ctg tat gtt gcg ttc      1722
Met Gly Met Gln Leu Asp Arg Ala Ser Ser Ser Leu Tyr Val Ala Phe
            490                 495                 500 tct acc tgt gtg ata aag gtt ccc ctt ggc cgg tgt gaa cga cat ggg      1770
Ser Thr Cys Val Ile Lys Val Pro Leu Gly Arg Cys Glu Arg His Gly
        505                 510                 515 aag tgt aaa aaa acc tgt att gcc tcc aga gac cca tat tgt gga tgg      1818
Lys Cys Lys Lys Thr Cys Ile Ala Ser Arg Asp Pro Tyr Cys Gly Trp
520                 525                 530                 535 ata aag gaa ggt ggt gcc tgc agc cat tta tca ccc aac agc aga ctg      1866
Ile Lys Glu Gly Gly Ala Cys Ser His Leu Ser Pro Asn Ser Arg Leu
                    540                 545                 550 act ttt gag cag gac ata gag cgt ggc aat aca gat ggt ctg ggg gac      1914
Thr Phe Glu Gln Asp Ile Glu Arg Gly Asn Thr Asp Gly Leu Gly Asp
                555                 560                 565 tgt cac aat tcc ttt gtg gca ctg aat gga gtg att cgg gaa agt tac      1962
Cys His Asn Ser Phe Val Ala Leu Asn Gly Val Ile Arg Glu Ser Tyr
            570                 575                 580 ctc aaa ggc cac gac cag ctg gtt ccc gtc acc ctc ttg gcc att gca      2010
Leu Lys Gly His Asp Gln Leu Val Pro Val Thr Leu Leu Ala Ile Ala
        585                 590                 595 gtc atc ctg gct ttc gtc atg ggg gcc gtc ttc tcg ggc atc acc gtc      2058
Val Ile Leu Ala Phe Val Met Gly Ala Val Phe Ser Gly Ile Thr Val
600                 605                 610                 615 tac tgc gtc tgt gat cat cgg cgc aaa gac gtg gct gtg gtg cag cgc      2106
Tyr Cys Val Cys Asp His Arg Arg Lys Asp Val Ala Val Val Gln Arg
                    620                 625                 630 aag gag aag gag ctc acc cac tcg cgc cgg ggc tcc atg agc agc gtc      2154
Lys Glu Lys Glu Leu Thr His Ser Arg Arg Gly Ser Met Ser Ser Val
                635                 640                 645 acc aag ctc agc ggc ctc ttt ggg gac act caa tcc aaa gac cca aag      2202
Thr Lys Leu Ser Gly Leu Phe Gly Asp Thr Gln Ser Lys Asp Pro Lys
            650                 655                 660 ccg gag gcc atc ctc acg cca ctc atg cac aac ggc aag ctc gcc act      2250
Pro Glu Ala Ile Leu Thr Pro Leu Met His Asn Gly Lys Leu Ala Thr
        665                 670                 675 ccc ggc aac acg gcc aag atg ctc att aaa gca gac cag cac cac ctg      2298
Pro Gly Asn Thr Ala Lys Met Leu Ile Lys Ala Asp Gln His His Leu
680                 685                 690                 695 gac ctg acg gcc ctc ccc acc cca gag tca acc cca acg ctg cag cag      2346
Asp Leu Thr Ala Leu Pro Thr Pro Glu Ser Thr Pro Thr Leu Gln Gln
                    700                 705                 710 aag cgg gaa ccc agc cgc ggc acc cgc gag tgg gag agg aac cag aac      2394
Lys Arg Glu Pro Ser Arg Gly Thr Arg Glu Trp Glu Arg Asn Gln Asn
                715                 720                 725 ctc atc aat gcc tgc aca aag gac atg ccc ccc atg ggc tcc cct gtg      2442
Leu Ile Asn Ala Cys Thr Lys Asp Met Pro Pro Met Gly Ser Pro Val
            730                 735                 740 att ccc acg gac ctg ccc ctg cgg gcc tcc ccc agc cac atc ccc agc      2490
```

-continued

```
Ile Pro Thr Asp Leu Pro Leu Arg Ala Ser Pro Ser His Ile Pro Ser
        745                 750                 755 gtg gtc gtc ctg ccc atc acg cag cag ggc tac cag cat gag tac gtg      2538
Val Val Val Leu Pro Ile Thr Gln Gln Gly Tyr Gln His Glu Tyr Val
760                 765                 770                 775 gac cag ccc aaa atg agc gag gtg gcc cag atg gcg ctg gag gac cag      2586
Asp Gln Pro Lys Met Ser Glu Val Ala Gln Met Ala Leu Glu Asp Gln
                780                 785                 790 gcc gcc aca ctg gag tat aag acc atc aag gaa cat ctc agc agc aag      2634
Ala Ala Thr Leu Glu Tyr Lys Thr Ile Lys Glu His Leu Ser Ser Lys
            795                 800                 805 agt ccc aac cat ggg gtg aac ctt gtg gag aac ctg gac agc ctg ccc      2682
Ser Pro Asn His Gly Val Asn Leu Val Glu Asn Leu Asp Ser Leu Pro
        810                 815                 820 ccc aaa gtt cca cag cgg gag gcc tcc ctg ggt ccc ccg gga gcc tcc      2730
Pro Lys Val Pro Gln Arg Glu Ala Ser Leu Gly Pro Pro Gly Ala Ser
825                 830                 835 ctg tct cag acc ggt cta agc aag cgg ctg gaa atg cac cac tcc tct      2778
Leu Ser Gln Thr Gly Leu Ser Lys Arg Leu Glu Met His His Ser Ser
840                 845                 850                 855 tcc tac ggg gtt gac tat aag agg agc tac ccc acg aac tcg ctc acg      2826
Ser Tyr Gly Val Asp Tyr Lys Arg Ser Tyr Pro Thr Asn Ser Leu Thr
                860                 865                 870 aga agc cac ctg acc acc tac tct cat cag aag caa cac taaccccgac      2875
Arg Ser His Leu Thr Thr Tyr Ser His Gln Lys Gln His
            875                 880 aattcanctc tgacttcaaa gggaccagag ctttggcagg ggagacaacc cgccgcccgc    2935
cccgcagagg gtggactcca tccaggtgca cagctcccag ccatctggcc aggccgtgac    2995
tgtctcgagg cagcccagcc tcaacgccta caactcactg acaaggtcgg ggctgaagcg    3055
tacgccctcg ctaaagccgg acgtacccccc caaaccatcc tttgctcccc tttccacatc   3115
catgaagccc aatgatgcgt gtacataatc ccaggggag ggggtcaggt gtcgaaccag     3175
caggcaaggc gaggtgtccg ctcagctcag caaggttctc aactgcctcg agtacccacc    3235
aaaccaaaaa ggcctgcggc agaaccgagg gacgctgggt cctcctctct gggacacagg    3295
ggtactcacg aaaactgggc cgcgtggttt ggtgaaag                            3333
```

<210> SEQ ID NO 6
<211> LENGTH: 884
<212> TYPE: PRT
<213> ORGANISM: Homo sapiens

<400> SEQUENCE: 6

```
Met Arg Ser Glu Ala Leu Leu Leu Tyr Phe Thr Leu Leu His Phe Ala
 1               5                  10                  15

Gly Ala Gly Phe Pro Glu Asp Ser Glu Pro Ile Ser Ile Ser His Gly
            20                  25                  30

Asn Tyr Thr Lys Gln Tyr Pro Val Phe Val Gly His Lys Pro Gly Arg
        35                  40                  45

Asn Thr Thr Gln Arg His Arg Leu Asp Ile Gln Met Ile Met Ile Met
    50                  55                  60

Asn Gly Thr Leu Tyr Ile Ala Ala Arg Asp His Ile Tyr Thr Val Asp
65                  70                  75                  80

Ile Asp Thr Ser His Thr Glu Glu Ile Tyr Cys Ser Lys Lys Leu Thr
                85                  90                  95

Trp Lys Ser Arg Gln Ala Asp Val Asp Thr Cys Arg Met Lys Gly Lys
            100                 105                 110
```

-continued

```
His Lys Asp Glu Cys His Asn Phe Ile Lys Val Leu Lys Lys Asn
        115                 120                 125
Asp Asp Ala Leu Phe Val Cys Gly Thr Asn Ala Phe Asn Pro Ser Cys
130                 135                 140
Arg Asn Tyr Lys Met Asp Thr Leu Glu Pro Phe Gly Asp Glu Phe Ser
145                 150                 155                 160
Gly Met Ala Arg Cys Pro Tyr Asp Ala Lys His Ala Asn Val Ala Leu
                165                 170                 175
Phe Ala Asp Gly Lys Leu Tyr Ser Ala Thr Val Thr Asp Phe Leu Ala
            180                 185                 190
Ile Asp Ala Val Ile Tyr Arg Ser Leu Gly Glu Ser Pro Thr Leu Arg
        195                 200                 205
Thr Val Lys His Asp Ser Lys Trp Leu Lys Glu Pro Tyr Phe Val Gln
    210                 215                 220
Ala Val Asp Tyr Gly Asp Tyr Ile Tyr Phe Phe Arg Glu Ile Ala
225                 230                 235                 240
Val Glu Tyr Asn Thr Met Gly Lys Val Val Phe Pro Arg Val Ala Gln
                245                 250                 255
Val Cys Lys Asn Asp Met Gly Gly Ser Gln Arg Val Leu Glu Lys Gln
            260                 265                 270
Trp Thr Ser Phe Leu Lys Ala Arg Leu Asn Cys Ser Val Pro Gly Asp
        275                 280                 285
Ser His Phe Tyr Phe Asn Ile Leu Gln Ala Val Thr Asp Val Ile Arg
    290                 295                 300
Ile Asn Gly Arg Asp Val Val Leu Ala Thr Phe Ser Thr Pro Tyr Asn
305                 310                 315                 320
Ser Ile Pro Gly Ser Ala Val Cys Ala Tyr Asp Met Leu Asp Ile Ala
                325                 330                 335
Ser Val Phe Thr Gly Arg Phe Lys Glu Gln Lys Ser Pro Asp Ser Thr
            340                 345                 350
Trp Thr Pro Val Pro Asp Glu Arg Val Pro Lys Pro Arg Pro Gly Cys
        355                 360                 365
Cys Ala Gly Ser Ser Leu Glu Arg Tyr Ala Thr Ser Asn Glu Phe
370                 375                 380
Pro Asp Asp Thr Leu Asn Phe Ile Lys Thr His Pro Leu Met Asp Glu
385                 390                 395                 400
Ala Val Pro Ser Ile Phe Asn Arg Pro Trp Phe Leu Arg Thr Met Val
                405                 410                 415
Arg Tyr Arg Leu Thr Lys Ile Ala Val Asp Thr Ala Ala Gly Pro Tyr
            420                 425                 430
Gln Asn His Thr Val Val Phe Leu Gly Ser Glu Lys Gly Ile Ile Leu
        435                 440                 445
Lys Phe Leu Ala Arg Ile Gly Asn Ser Gly Phe Leu Asn Asp Ser Leu
    450                 455                 460
Phe Leu Glu Glu Met Ser Val Tyr Asn Ser Glu Lys Cys Ser Tyr Asp
465                 470                 475                 480
Gly Val Glu Asp Lys Arg Ile Met Gly Met Gln Leu Asp Arg Ala Ser
                485                 490                 495
Ser Ser Leu Tyr Val Ala Phe Ser Thr Cys Val Ile Lys Val Pro Leu
            500                 505                 510
Gly Arg Cys Glu Arg His Gly Lys Cys Lys Lys Thr Cys Ile Ala Ser
        515                 520                 525
```

Arg Asp Pro Tyr Cys Gly Trp Ile Lys Glu Gly Gly Ala Cys Ser His
    530                 535                 540

Leu Ser Pro Asn Ser Arg Leu Thr Phe Glu Gln Asp Ile Glu Arg Gly
545                 550                 555                 560

Asn Thr Asp Gly Leu Gly Asp Cys His Asn Ser Phe Val Ala Leu Asn
                565                 570                 575

Gly Val Ile Arg Glu Ser Tyr Leu Lys Gly His Asp Gln Leu Val Pro
            580                 585                 590

Val Thr Leu Leu Ala Ile Ala Val Ile Leu Ala Phe Val Met Gly Ala
        595                 600                 605

Val Phe Ser Gly Ile Thr Val Tyr Cys Val Cys Asp His Arg Arg Lys
    610                 615                 620

Asp Val Ala Val Val Gln Arg Lys Glu Lys Glu Leu Thr His Ser Arg
625                 630                 635                 640

Arg Gly Ser Met Ser Ser Val Thr Lys Leu Ser Gly Leu Phe Gly Asp
                645                 650                 655

Thr Gln Ser Lys Asp Pro Lys Pro Glu Ala Ile Leu Thr Pro Leu Met
            660                 665                 670

His Asn Gly Lys Leu Ala Thr Pro Gly Asn Thr Ala Lys Met Leu Ile
        675                 680                 685

Lys Ala Asp Gln His His Leu Asp Leu Thr Ala Leu Pro Thr Pro Glu
690                 695                 700

Ser Thr Pro Thr Leu Gln Gln Lys Arg Glu Pro Ser Arg Gly Thr Arg
705                 710                 715                 720

Glu Trp Glu Arg Asn Gln Asn Leu Ile Asn Ala Cys Thr Lys Asp Met
                725                 730                 735

Pro Pro Met Gly Ser Pro Val Ile Pro Thr Asp Leu Pro Leu Arg Ala
            740                 745                 750

Ser Pro Ser His Ile Pro Ser Val Val Leu Pro Ile Thr Gln Gln
        755                 760                 765

Gly Tyr Gln His Glu Tyr Val Asp Gln Pro Lys Met Ser Glu Val Ala
    770                 775                 780

Gln Met Ala Leu Glu Asp Gln Ala Ala Thr Leu Glu Tyr Lys Thr Ile
785                 790                 795                 800

Lys Glu His Leu Ser Ser Lys Ser Pro Asn His Gly Val Asn Leu Val
                805                 810                 815

Glu Asn Leu Asp Ser Leu Pro Pro Lys Val Pro Gln Arg Glu Ala Ser
            820                 825                 830

Leu Gly Pro Pro Gly Ala Ser Leu Ser Gln Thr Gly Leu Ser Lys Arg
        835                 840                 845

Leu Glu Met His His Ser Ser Ser Tyr Gly Val Asp Tyr Lys Arg Ser
850                 855                 860

Tyr Pro Thr Asn Ser Leu Thr Arg Ser His Leu Thr Thr Tyr Ser His
865                 870                 875                 880

Gln Lys Gln His

<210> SEQ ID NO 7
<211> LENGTH: 856
<212> TYPE: DNA
<213> ORGANISM: Homo sapiens
<220> FEATURE:
<221> NAME/KEY: CDS
<222> LOCATION: (138)..(725)

<400> SEQUENCE: 7

```
tctcccctttt ccagctgaaa ggctattgtt catgagatta gaattccagt caacactggt      60
attggaaact attttgcagt agtagacaag ggagttcgca atcattcata tcattacatt     120
tctgtgtttt ctctgtg atg atc atg aac att gct cag agc aat gct gtg       170
                   Met Ile Met Asn Ile Ala Gln Ser Asn Ala Val
                    1               5                  10 ata tca cag tgg cta ttt atg att aga tca ttt cat tgc atg ctt aca      218
Ile Ser Gln Trp Leu Phe Met Ile Arg Ser Phe His Cys Met Leu Thr
             15                  20                  25 ctt ttc atg gaa aaa tgt aac aaa tgt caa aat ata aat cag aaa ttc      266
Leu Phe Met Glu Lys Cys Asn Lys Cys Gln Asn Ile Asn Gln Lys Phe
         30                  35                  40 ttg ctc caa ata att gca aag aac ttg ttt tca acc cca ctt ttg gaa      314
Leu Leu Gln Ile Ile Ala Lys Asn Leu Phe Ser Thr Pro Leu Leu Glu
 45                  50                  55 tat tca aaa aag ttt agg gta att acc agg ttt ggt gtg tgt cac ttc      362
Tyr Ser Lys Lys Phe Arg Val Ile Thr Arg Phe Gly Val Cys His Phe
 60                  65                  70                  75 tgg gct gag agg gat ttt agg ttt cag aga aat aaa ttg tgt ttt acc      410
Trp Ala Glu Arg Asp Phe Arg Phe Gln Arg Asn Lys Leu Cys Phe Thr
                 80                  85                  90 ggg agc cgg tgt tgt cca tgt agg ttc agg gct ttt aga aat ttt agg      458
Gly Ser Arg Cys Cys Pro Cys Arg Phe Arg Ala Phe Arg Asn Phe Arg
             95                 100                 105 tgt aat tgt tcc ggc act tgt ggt tct ttc agg ttt ggt tct tgg cgg      506
Cys Asn Cys Ser Gly Thr Cys Gly Ser Phe Arg Phe Gly Ser Trp Arg
        110                 115                 120 ttt ggg ccg ggg gcg tcg ttt agg tgt aga agg gat aga tgt agt ttg      554
Phe Gly Pro Gly Ala Ser Phe Arg Cys Arg Arg Asp Arg Cys Ser Leu
125                 130                 135 ctg ggg agc agg tgt cgt agg ctg cat ttc tgg act ggt aaa gat ttc      602
Leu Gly Ser Arg Cys Arg Arg Leu His Phe Trp Thr Gly Lys Asp Phe
140                 145                 150                 155 cag ttt ttg agg aac aaa tgg tgt ttc act tgg agc cag tgt tgc cct      650
Gln Phe Leu Arg Asn Lys Trp Cys Phe Thr Trp Ser Gln Cys Cys Pro
                160                 165                 170 tgg ctg ttc aag agt tct aga agt ttt agg tgg gat aga atc cag aat      698
Trp Leu Phe Lys Ser Ser Arg Ser Phe Arg Trp Asp Arg Ile Gln Asn
            175                 180                 185 acg atc act tgt tgc tgg gta gga atc tgatatctca ggctcatcta            745
Thr Ile Thr Cys Cys Trp Val Gly Ile
        190                 195 atgttgtagg gcttgagaaa acatcataag ttgcagtttg aggctgcaga actttggaat    805
ctttccagaa tttcctgagg caaaacacc cttcccttt gaaaaaccta g               856

<210> SEQ ID NO 8
<211> LENGTH: 196
<212> TYPE: PRT
<213> ORGANISM: Homo sapiens

<400> SEQUENCE: 8

Met Ile Met Asn Ile Ala Gln Ser Asn Ala Val Ile Ser Gln Trp Leu
 1               5                  10                  15

Phe Met Ile Arg Ser Phe His Cys Met Leu Thr Leu Phe Met Glu Lys
            20                  25                  30

Cys Asn Lys Cys Gln Asn Ile Asn Gln Lys Phe Leu Leu Gln Ile Ile
        35                  40                  45

Ala Lys Asn Leu Phe Ser Thr Pro Leu Leu Glu Tyr Ser Lys Lys Phe
    50                  55                  60
```

```
Arg Val Ile Thr Arg Phe Gly Val Cys His Phe Trp Ala Glu Arg Asp
 65                  70                  75                  80

Phe Arg Phe Gln Arg Asn Lys Leu Cys Phe Thr Gly Ser Arg Cys Cys
                 85                  90                  95

Pro Cys Arg Phe Arg Ala Phe Arg Asn Phe Arg Cys Asn Cys Ser Gly
            100                 105                 110

Thr Cys Gly Ser Phe Arg Phe Gly Ser Trp Arg Phe Gly Pro Gly Ala
        115                 120                 125

Ser Phe Arg Cys Arg Arg Asp Arg Cys Ser Leu Leu Gly Ser Arg Cys
    130                 135                 140

Arg Arg Leu His Phe Trp Thr Gly Lys Asp Phe Gln Phe Leu Arg Asn
145                 150                 155                 160

Lys Trp Cys Phe Thr Trp Ser Gln Cys Cys Pro Trp Leu Phe Lys Ser
                165                 170                 175

Ser Arg Ser Phe Arg Trp Asp Arg Ile Gln Asn Thr Ile Thr Cys Cys
            180                 185                 190

Trp Val Gly Ile
        195

<210> SEQ ID NO 9
<211> LENGTH: 2341
<212> TYPE: DNA
<213> ORGANISM: Homo sapiens
<220> FEATURE:
<221> NAME/KEY: CDS
<222> LOCATION: (215)..(2173)

<400> SEQUENCE: 9
cacttccccc ttttgttaat taaaactaag aagtcggaat gggaacgagg tgcccagctc      60
ccgtggagaa agcttaagga caccacgcca gtgctttcct gccttccttc cgagatggaa     120
agaggagctc ctagctcact taagccgggg tagggctggt tctcctttcc gagccaaaat     180
cccaggcgat ggtgaattat gaacgtgcca cacc atg aag ctc ttg tgg cag gta    235
                                    Met Lys Leu Leu Trp Gln Val
                                     1               5 act gtg cac cac cac acc tgg aat gcc atc ctg ctc ccg ttc gtc tac      283
Thr Val His His His Thr Trp Asn Ala Ile Leu Leu Pro Phe Val Tyr
        10                  15                  20 ctc acg gcg caa gtg tgg att ctg tgt gca gcc atc gct gct gcc gcc      331
Leu Thr Ala Gln Val Trp Ile Leu Cys Ala Ala Ile Ala Ala Ala Ala
    25                  30                  35 tca gcc ggg ccc cag aac tgc ccc tcc gtc tgc tcg tgc agt aac cag      379
Ser Ala Gly Pro Gln Asn Cys Pro Ser Val Cys Ser Cys Ser Asn Gln
40                  45                  50                  55 ttc agc aag gtg gtg tgc acg cgc cgg ggc ctc tcc gag gtc ccg cag      427
Phe Ser Lys Val Val Cys Thr Arg Arg Gly Leu Ser Glu Val Pro Gln
                60                  65                  70 ggt att ccc tcg aac acc cgg tac ctc aac ctc atg gag aac aac atc      475
Gly Ile Pro Ser Asn Thr Arg Tyr Leu Asn Leu Met Glu Asn Asn Ile
            75                  80                  85 cag atg atc cag gcc gac acc ttc cgc cac ctc cac cac ctg gag gtc      523
Gln Met Ile Gln Ala Asp Thr Phe Arg His Leu His His Leu Glu Val
        90                  95                  100 ctg cag ttg ggc agg aac tcc atc cgg cag att gag gtg ggg gcc ttc      571
Leu Gln Leu Gly Arg Asn Ser Ile Arg Gln Ile Glu Val Gly Ala Phe
    105                 110                 115 aac ggc ctg gcc agc ctc agc acc ctg gag ctg ttc gac aac tgg ctg      619
Asn Gly Leu Ala Ser Leu Ser Thr Leu Glu Leu Phe Asp Asn Trp Leu
```

```
                120                 125                 130                 135
aca gtc atc cct agc ggg gcc ttt gaa tac ctg tcc aag ctg cgg gag      667
Thr Val Ile Pro Ser Gly Ala Phe Glu Tyr Leu Ser Lys Leu Arg Glu
                140                 145                 150 ctc tgg ctt cgc aac aac ccc atc gaa agc atc ccc tct tac gcc ttc      715
Leu Trp Leu Arg Asn Asn Pro Ile Glu Ser Ile Pro Ser Tyr Ala Phe
            155                 160                 165 aac cgg gtg ccc tcc ctc atg cgc ctg gac ttg ggg gag ctc aag aag      763
Asn Arg Val Pro Ser Leu Met Arg Leu Asp Leu Gly Glu Leu Lys Lys
        170                 175                 180 ctg gag tat atc tct gag gga gct ttt gag ggg ctg ttc aac ctc aag      811
Leu Glu Tyr Ile Ser Glu Gly Ala Phe Glu Gly Leu Phe Asn Leu Lys
    185                 190                 195 tat ctg aac ttg ggc atg tgc aac att aaa gac atg ccc aat ctc acc      859
Tyr Leu Asn Leu Gly Met Cys Asn Ile Lys Asp Met Pro Asn Leu Thr
200                 205                 210                 215 ccc ctg gtg ggg ctg gag gag ctg gag atg tca ggg aac cac ttc cct      907
Pro Leu Val Gly Leu Glu Glu Leu Glu Met Ser Gly Asn His Phe Pro
                220                 225                 230 gag atc agg cct ggc tcc ttc cat ggc ctg agc tcc ctc aag aag ctc      955
Glu Ile Arg Pro Gly Ser Phe His Gly Leu Ser Ser Leu Lys Lys Leu
            235                 240                 245 tgg gtc atg aac tca cag gtc agc ctg att gag cgg aat gct ttt gac     1003
Trp Val Met Asn Ser Gln Val Ser Leu Ile Glu Arg Asn Ala Phe Asp
        250                 255                 260 ggg ctg gct tca ctt gtg gaa ctc aac ttg gcc cac aat aac ctc tct     1051
Gly Leu Ala Ser Leu Val Glu Leu Asn Leu Ala His Asn Asn Leu Ser
    265                 270                 275 tct ttg ccc cat gac ctc ttt acc ccg ctg agg tac ctg gtg gag ttg     1099
Ser Leu Pro His Asp Leu Phe Thr Pro Leu Arg Tyr Leu Val Glu Leu
280                 285                 290                 295 cat cta cac cac aac cct tgg aac tgt gat tgt gac att ctg tgg cta     1147
His Leu His His Asn Pro Trp Asn Cys Asp Cys Asp Ile Leu Trp Leu
                300                 305                 310 gcc tgg tgg ctt cga gag tat ata ccc acc aat tcc acc tgc tgt ggc     1195
Ala Trp Trp Leu Arg Glu Tyr Ile Pro Thr Asn Ser Thr Cys Cys Gly
            315                 320                 325 cgc tgt cat gct ccc atg cac atg cga ggc cgc tac ctc gtg gag gtg     1243
Arg Cys His Ala Pro Met His Met Arg Gly Arg Tyr Leu Val Glu Val
        330                 335                 340 gac cag gcc tcc ttc cag tgc tct gcc ccc ttc atc atg gac gca cct     1291
Asp Gln Ala Ser Phe Gln Cys Ser Ala Pro Phe Ile Met Asp Ala Pro
    345                 350                 355 cga gac ctc aac att tct gag ggt cgg atg gca gaa ctt aag tgt cgg     1339
Arg Asp Leu Asn Ile Ser Glu Gly Arg Met Ala Glu Leu Lys Cys Arg
360                 365                 370                 375 act ccc cct atg tcc tcc gtg aag tgg ttg ctg ccc aat ggg aca gtg     1387
Thr Pro Pro Met Ser Ser Val Lys Trp Leu Leu Pro Asn Gly Thr Val
                380                 385                 390 ctc agc cac gcc tcc cgc cac cca agg atc tct gtc ctc aac gac ggc     1435
Leu Ser His Ala Ser Arg His Pro Arg Ile Ser Val Leu Asn Asp Gly
            395                 400                 405 acc ttg aac ttt tcc cac gtg ctg ctt tca gac act ggg gtg tac aca     1483
Thr Leu Asn Phe Ser His Val Leu Leu Ser Asp Thr Gly Val Tyr Thr
        410                 415                 420 tgc atg ggg acc aat gtt gca ggc aac tcc aac gcc tcg gcc tac ctc     1531
Cys Met Gly Thr Asn Val Ala Gly Asn Ser Asn Ala Ser Ala Tyr Leu
    425                 430                 435 aat ggg agc acg gct gag ctt aac acc tcc aac tac agc ttc ttc acc     1579
```

-continued

```
Asn Gly Ser Thr Ala Glu Leu Asn Thr Ser Asn Tyr Ser Phe Phe Thr
440                 445                 450                 455 aca gga aca ggg gag acc acg gag atc tcg cct gag gac aca acg cga       1627
Thr Gly Thr Gly Glu Thr Thr Glu Ile Ser Pro Glu Asp Thr Thr Arg
                460                 465                 470 aag tac aag cct gtt cct acc acg tcc act ggt tac cag ccg gca tat       1675
Lys Tyr Lys Pro Val Pro Thr Thr Ser Thr Gly Tyr Gln Pro Ala Tyr
        475                 480                 485 acc acc tct acc acg gtg ctc att cag act acc cgt gtg ccc aag cag       1723
Thr Thr Ser Thr Thr Val Leu Ile Gln Thr Thr Arg Val Pro Lys Gln
            490                 495                 500 gtg gca gta ccc gcg aca gac acc act gac aag atg cag acc agc ctg       1771
Val Ala Val Pro Ala Thr Asp Thr Thr Asp Lys Met Gln Thr Ser Leu
        505                 510                 515 gat gaa gtc atg aag acc acc aag atc atc att ggc tgc ttt gtg gca       1819
Asp Glu Val Met Lys Thr Thr Lys Ile Ile Ile Gly Cys Phe Val Ala
520                 525                 530                 535 gtg act ctg cta gct gcc gcc atg ttg att gtc ttc tat aaa ctt cgt       1867
Val Thr Leu Leu Ala Ala Ala Met Leu Ile Val Phe Tyr Lys Leu Arg
                540                 545                 550 aag cgg cac cag cag cgg agt aca gtc aca gcc gcc cgg act gtt gag       1915
Lys Arg His Gln Gln Arg Ser Thr Val Thr Ala Ala Arg Thr Val Glu
        555                 560                 565 ata atc cag gtg gac gaa gac atc cca gca gca aca tcc gca gca gca       1963
Ile Ile Gln Val Asp Glu Asp Ile Pro Ala Ala Thr Ser Ala Ala Ala
            570                 575                 580 aca gca gct ccg tcc ggt gta tca ggt gaa ggg gca gta gtg ctg ccc       2011
Thr Ala Ala Pro Ser Gly Val Ser Gly Glu Gly Ala Val Val Leu Pro
585                 590                 595 aca att cat gac cat att aac tac aac acc tac aaa cca gca cat ggg       2059
Thr Ile His Asp His Ile Asn Tyr Asn Thr Tyr Lys Pro Ala His Gly
                600                 605                 610                 615 gcc cac tgg aca gaa aac agc ctg ggg aac tct ctg cac ccc aca gtc       2107
Ala His Trp Thr Glu Asn Ser Leu Gly Asn Ser Leu His Pro Thr Val
        620                 625                 630 acc act atc tct gaa cct tat ata att cag acc cat acc aag gac aag       2155
Thr Thr Ile Ser Glu Pro Tyr Ile Ile Gln Thr His Thr Lys Asp Lys
            635                 640                 645 gta cag gaa act caa ata tgactcccct cccccaaaaa acttataaaa              2203
Val Gln Glu Thr Gln Ile
650 tgcaatagaa tgcacacaaa gacagcaact tttgtacaga gtggggagag acttttctt      2263 gtatatgctt atatattaag tctatgggct ggttaaaaaa aacagattat attaaaattt     2323 aaagacaaaa agtcaaaa                                                    2341

<210> SEQ ID NO 10
<211> LENGTH: 653
<212> TYPE: PRT
<213> ORGANISM: Homo sapiens

<400> SEQUENCE: 10

Met Lys Leu Leu Trp Gln Val Thr Val His His Thr Trp Asn Ala
 1               5                  10                  15

Ile Leu Leu Pro Phe Val Tyr Leu Thr Ala Gln Val Trp Ile Leu Cys
                20                  25                  30

Ala Ala Ile Ala Ala Ala Ala Ser Ala Gly Pro Gln Asn Cys Pro Ser
            35                  40                  45

Val Cys Ser Cys Ser Asn Gln Phe Ser Lys Val Val Cys Thr Arg Arg
```

-continued

```
                50                  55                  60
Gly Leu Ser Glu Val Pro Gln Gly Ile Pro Ser Asn Thr Arg Tyr Leu
 65                  70                  75                  80
Asn Leu Met Glu Asn Asn Ile Gln Met Ile Gln Ala Asp Thr Phe Arg
                 85                  90                  95
His Leu His His Leu Glu Val Leu Gln Leu Gly Arg Asn Ser Ile Arg
                100                 105                 110
Gln Ile Glu Val Gly Ala Phe Asn Gly Leu Ala Ser Leu Ser Thr Leu
                115                 120                 125
Glu Leu Phe Asp Asn Trp Leu Thr Val Ile Pro Ser Gly Ala Phe Glu
            130                 135                 140
Tyr Leu Ser Lys Leu Arg Glu Leu Trp Leu Arg Asn Asn Pro Ile Glu
145                 150                 155                 160
Ser Ile Pro Ser Tyr Ala Phe Asn Arg Val Pro Ser Leu Met Arg Leu
                165                 170                 175
Asp Leu Gly Glu Leu Lys Lys Leu Glu Tyr Ile Ser Glu Gly Ala Phe
                180                 185                 190
Glu Gly Leu Phe Asn Leu Lys Tyr Leu Asn Leu Gly Met Cys Asn Ile
            195                 200                 205
Lys Asp Met Pro Asn Leu Thr Pro Leu Val Gly Leu Glu Glu Leu Glu
210                 215                 220
Met Ser Gly Asn His Phe Pro Glu Ile Arg Pro Gly Ser Phe His Gly
225                 230                 235                 240
Leu Ser Ser Leu Lys Lys Leu Trp Val Met Asn Ser Gln Val Ser Leu
                245                 250                 255
Ile Glu Arg Asn Ala Phe Asp Gly Leu Ala Ser Leu Val Glu Leu Asn
                260                 265                 270
Leu Ala His Asn Asn Leu Ser Ser Leu Pro His Asp Leu Phe Thr Pro
            275                 280                 285
Leu Arg Tyr Leu Val Glu Leu His Leu His His Asn Pro Trp Asn Cys
290                 295                 300
Asp Cys Asp Ile Leu Trp Leu Ala Trp Trp Leu Arg Glu Tyr Ile Pro
305                 310                 315                 320
Thr Asn Ser Thr Cys Cys Gly Arg Cys His Ala Pro Met His Met Arg
                325                 330                 335
Gly Arg Tyr Leu Val Glu Val Asp Gln Ala Ser Phe Gln Cys Ser Ala
                340                 345                 350
Pro Phe Ile Met Asp Ala Pro Arg Asp Leu Asn Ile Ser Glu Gly Arg
            355                 360                 365
Met Ala Glu Leu Lys Cys Arg Thr Pro Pro Met Ser Ser Val Lys Trp
370                 375                 380
Leu Leu Pro Asn Gly Thr Val Leu Ser His Ala Ser Arg His Pro Arg
385                 390                 395                 400
Ile Ser Val Leu Asn Asp Gly Thr Leu Asn Phe Ser His Val Leu Leu
                405                 410                 415
Ser Asp Thr Gly Val Tyr Thr Cys Met Gly Thr Asn Val Ala Gly Asn
                420                 425                 430
Ser Asn Ala Ser Ala Tyr Leu Asn Gly Ser Thr Ala Glu Leu Asn Thr
            435                 440                 445
Ser Asn Tyr Ser Phe Phe Thr Thr Gly Thr Gly Glu Thr Thr Glu Ile
            450                 455                 460
Ser Pro Glu Asp Thr Thr Arg Lys Tyr Lys Pro Val Pro Thr Thr Ser
465                 470                 475                 480
```

-continued

```
Thr Gly Tyr Gln Pro Ala Tyr Thr Thr Ser Thr Val Leu Ile Gln
            485                 490                 495

Thr Thr Arg Val Pro Lys Gln Val Ala Val Pro Ala Thr Asp Thr Thr
        500                 505                 510

Asp Lys Met Gln Thr Ser Leu Asp Glu Val Met Lys Thr Thr Lys Ile
    515                 520                 525

Ile Ile Gly Cys Phe Val Ala Val Thr Leu Leu Ala Ala Ala Met Leu
    530                 535                 540

Ile Val Phe Tyr Lys Leu Arg Lys Arg His Gln Gln Arg Ser Thr Val
545                 550                 555                 560

Thr Ala Ala Arg Thr Val Glu Ile Ile Gln Val Asp Glu Asp Ile Pro
                565                 570                 575

Ala Ala Thr Ser Ala Ala Ala Thr Ala Ala Pro Ser Gly Val Ser Gly
            580                 585                 590

Glu Gly Ala Val Val Leu Pro Thr Ile His Asp His Ile Asn Tyr Asn
        595                 600                 605

Thr Tyr Lys Pro Ala His Gly Ala His Trp Thr Glu Asn Ser Leu Gly
    610                 615                 620

Asn Ser Leu His Pro Thr Val Thr Ile Ser Glu Pro Tyr Ile Ile
625                 630                 635                 640

Gln Thr His Thr Lys Asp Lys Val Gln Glu Thr Gln Ile
            645                 650
```

<210> SEQ ID NO 11
<211> LENGTH: 2607
<212> TYPE: DNA
<213> ORGANISM: Homo sapiens
<220> FEATURE:
<221> NAME/KEY: CDS
<222> LOCATION: (215)..(1984)

<400> SEQUENCE: 11

```
cacttccccc ttttgttaat taaaactaag aagtcggaat gggaacgagg tgcccagctc      60
ccgtggagaa agcttaagga caccacgcca gtgctttcct gccttccttc cgagatggaa     120
agaggagctc ctagctcact taagccgggg tagggctggt tctcctttcc gagccaaaat     180
cccaggcgat ggtgaattat gaacgtgcca cacc atg aag ctc ttg tgg cag gta    235
                                    Met Lys Leu Leu Trp Gln Val
                                      1               5 act gtg cac cac cac acc tgg aat gcc atc ctg ctc ccg ttc gtc tac      283
Thr Val His His His Thr Trp Asn Ala Ile Leu Leu Pro Phe Val Tyr
            10                  15                  20 ctc acg gcg caa gtg tgg att ctg tgt gca gcc atc gct gct gcc gcc      331
Leu Thr Ala Gln Val Trp Ile Leu Cys Ala Ala Ile Ala Ala Ala Ala
        25                  30                  35 tca gcc ggg ccc cag aac tgc ccc tcc gtc tgc tcg tgc agt aac cag      379
Ser Ala Gly Pro Gln Asn Cys Pro Ser Val Cys Ser Cys Ser Asn Gln
    40                  45                  50                  55 ttc agc aag gtg gtg tgc acg cgc cgg ggc ctc tcc gag gtc ccg cag      427
Phe Ser Lys Val Val Cys Thr Arg Arg Gly Leu Ser Glu Val Pro Gln
                60                  65                  70 ggt att ccc tcg aac acc cgg tac ctc aac ctc atg gag aac aac atc      475
Gly Ile Pro Ser Asn Thr Arg Tyr Leu Asn Leu Met Glu Asn Asn Ile
            75                  80                  85 cag atg atc cag gcc gac acc ttc cgc cac ctc cac cac ctg gag gtc      523
Gln Met Ile Gln Ala Asp Thr Phe Arg His Leu His His Leu Glu Val
        90                  95                 100
```

| | | |
|---|---|---|
| ctg cag ttg ggc agg aac tcc atc cgg cag att gag gtg ggg gcc ttc<br>Leu Gln Leu Gly Arg Asn Ser Ile Arg Gln Ile Glu Val Gly Ala Phe<br>105                         110                     115 | 571 |
| aac ggc ctg gcc agc ctc agc acc ctg gag ctg ttc gac aac tgg ctg<br>Asn Gly Leu Ala Ser Leu Ser Thr Leu Glu Leu Phe Asp Asn Trp Leu<br>120                       125                     130                 135 | 619 |
| aca gtc atc cct agc ggg gcc ttt gaa tac ctg tcc aag ctg cgg gag<br>Thr Val Ile Pro Ser Gly Ala Phe Glu Tyr Leu Ser Lys Leu Arg Glu<br>               140                     145                     150 | 667 |
| ctc tgg ctt cgc aac aac ccc atc gaa agc atc ccc tct tac gcc ttc<br>Leu Trp Leu Arg Asn Asn Pro Ile Glu Ser Ile Pro Ser Tyr Ala Phe<br>        155                     160                     165 | 715 |
| aac cgg gtg ccc tcc ctc atg cgc ctg gac ttg ggg gag ctc aag aag<br>Asn Arg Val Pro Ser Leu Met Arg Leu Asp Leu Gly Glu Leu Lys Lys<br>             170                     175                     180 | 763 |
| ctg gag tat atc tct gag gga gct ttt gag ggg ctg ttc aac ctc aag<br>Leu Glu Tyr Ile Ser Glu Gly Ala Phe Glu Gly Leu Phe Asn Leu Lys<br>185                         190                     195 | 811 |
| tat ctg aac ttg ggc atg tgc aac att aaa gac atg ccc aat ctc acc<br>Tyr Leu Asn Leu Gly Met Cys Asn Ile Lys Asp Met Pro Asn Leu Thr<br>200                         205                     210                 215 | 859 |
| ccc ctg gtg ggg ctg gag gag ctg gag atg tca ggg aac cac ttc cct<br>Pro Leu Val Gly Leu Glu Glu Leu Glu Met Ser Gly Asn His Phe Pro<br>               220                     225                     230 | 907 |
| gag atc agg cct ggc tcc ttc cat ggc ctg agc tcc ctc aag aag ctc<br>Glu Ile Arg Pro Gly Ser Phe His Gly Leu Ser Ser Leu Lys Lys Leu<br>        235                     240                     245 | 955 |
| tgg gtc atg aac tca cag gtc agc ctg att gag cgg aat gct ttt gac<br>Trp Val Met Asn Ser Gln Val Ser Leu Ile Glu Arg Asn Ala Phe Asp<br>             250                     255                     260 | 1003 |
| ggg ctg gct tca ctt gtg gaa ctc aac ttg gcc cac aat aac ctc tct<br>Gly Leu Ala Ser Leu Val Glu Leu Asn Leu Ala His Asn Asn Leu Ser<br>265                         270                     275 | 1051 |
| tct ttg ccc cat gac ctc ttt acc ccg ctg agg tac ctg gtg gag ttg<br>Ser Leu Pro His Asp Leu Phe Thr Pro Leu Arg Tyr Leu Val Glu Leu<br>280                         285                     290                 295 | 1099 |
| cat cta cac cac aac cct tgg aac tgt gat tgt gac att ctg tgg cta<br>His Leu His His Asn Pro Trp Asn Cys Asp Cys Asp Ile Leu Trp Leu<br>               300                     305                     310 | 1147 |
| gcc tgg tgg ctt cga gag tat ata ccc acc aat tcc acc tgc tgt ggc<br>Ala Trp Trp Leu Arg Glu Tyr Ile Pro Thr Asn Ser Thr Cys Cys Gly<br>        315                     320                     325 | 1195 |
| cgc tgt cat gct ccc atg cac atg cga ggc cgc tac ctc gtg gag gtg<br>Arg Cys His Ala Pro Met His Met Arg Gly Arg Tyr Leu Val Glu Val<br>             330                     335                     340 | 1243 |
| gac cag gcc tcc ttc cag tgc tct gcc ccc ttc atc atg gac gca cct<br>Asp Gln Ala Ser Phe Gln Cys Ser Ala Pro Phe Ile Met Asp Ala Pro<br>345                         350                     355 | 1291 |
| cga gac ctc aac att tct gag ggt cgg atg gca gaa ctt aag tgt cgg<br>Arg Asp Leu Asn Ile Ser Glu Gly Arg Met Ala Glu Leu Lys Cys Arg<br>360                         365                     370                 375 | 1339 |
| act ccc cct atg tcc tcc gtg aag tgg ttg ctg ccc aat ggg aca gtg<br>Thr Pro Pro Met Ser Ser Val Lys Trp Leu Leu Pro Asn Gly Thr Val<br>             380                     385                     390 | 1387 |
| ctc agc cac gcc tcc cgc cac cca agg atc tct gtc ctc aac gac ggc<br>Leu Ser His Ala Ser Arg His Pro Arg Ile Ser Val Leu Asn Asp Gly<br>        395                     400                     405 | 1435 |
| acc ttg aac ttt tcc cac gtg ctg ctt tca gac act ggg gtg tac aca<br>Thr Leu Asn Phe Ser His Val Leu Leu Ser Asp Thr Gly Val Tyr Thr<br>410                         415                     420 | 1483 |

```
tgc atg ggg acc aat gtt gca ggc aac tcc aac gcc tcg gcc tac ctc      1531
Cys Met Gly Thr Asn Val Ala Gly Asn Ser Asn Ala Ser Ala Tyr Leu
    425                 430                 435 aat ggg agc acg gct gag ctt aac acc tcc aac tac agc ttc ttc acc      1579
Asn Gly Ser Thr Ala Glu Leu Asn Thr Ser Asn Tyr Ser Phe Phe Thr
440                 445                 450                 455 aca gga aca ggg gag acc acg gag atc tcg cct gag gac aca acg cga      1627
Thr Gly Thr Gly Glu Thr Thr Glu Ile Ser Pro Glu Asp Thr Thr Arg
                460                 465                 470 aag tac aag cct gtt cct acc acg tcc act ggt tac cag ccg gca tat      1675
Lys Tyr Lys Pro Val Pro Thr Thr Ser Thr Gly Tyr Gln Pro Ala Tyr
            475                 480                 485 acc acc tct acc acg gtg ctc att cag act acc cgt gtg ccc aag cag      1723
Thr Thr Ser Thr Thr Val Leu Ile Gln Thr Thr Arg Val Pro Lys Gln
        490                 495                 500 gtg gca gta ccc gcg aca gac acc act gac aag atg cag acc agc ctg      1771
Val Ala Val Pro Ala Thr Asp Thr Thr Asp Lys Met Gln Thr Ser Leu
    505                 510                 515 gat gaa gtc atg aag acc acc aag atc atc att ggc tgc ttt gtg gca      1819
Asp Glu Val Met Lys Thr Thr Lys Ile Ile Ile Gly Cys Phe Val Ala
520                 525                 530                 535 gtg act ctg cta gct gcc gcc atg ttg att gtc ttc tat aaa ctt cgt      1867
Val Thr Leu Leu Ala Ala Ala Met Leu Ile Val Phe Tyr Lys Leu Arg
                540                 545                 550 aag cgg cac cag cag cgg agt aca gtc aca gcc gcc ccc aca ctg gag      1915
Lys Arg His Gln Gln Arg Ser Thr Val Thr Ala Ala Pro Thr Leu Glu
            555                 560                 565 aga aaa cac agg gac aaa aac aca cca caa caa aaa cac cca caa caa      1963
Arg Lys His Arg Asp Lys Asn Thr Pro Gln Gln Lys His Pro Gln Gln
        570                 575                 580 aaa caa cag ccc ccc ccg gta taacaggaaa gggcacaata gcgccccaca         2014
Lys Gln Gln Pro Pro Pro Val
    585                 590 aaacacaaca acataaaaaa caaaacacac acaaaccagc acatggggcc cactggacag    2074
aaaacagcct ggggaactct gtgcaccccca cagtcaccac tatctctgaa ccttatataa   2134
ttcagaccca taccaaggac aaggtacagg aaactcaaat atgactcccc tcccccaaaa    2194
aacttataaa atgcaataga atgcacacaa agacagcaac ttttgtacag agtggggaga    2254 gacttttct tgtatatgct tatatattaa gtctatgggc tggttaaaaa aaacagatta     2314
tattaaaatt taaagacaaa aagtcaaaac aaaaatattt tctaacttgt aagttctatt    2374 taaaggggt gggggggaat cttgggaacg ttgtgggta caagccacaa gttaacttgc      2434
tatgctgcca gaagggattt ctggtataag gttgaaattg ctgagataaa ataaactaaa    2494
acaacaaaca tccttaaaga ggtagggtgt gggctgctga aggggcaaga gggatagact    2554
gaatctgtca tttttagaag atgcttcata ggacacagga ctatccattt cta           2607

<210> SEQ ID NO 12
<211> LENGTH: 590
<212> TYPE: PRT
<213> ORGANISM: Homo sapiens

<400> SEQUENCE: 12

Met Lys Leu Leu Trp Gln Val Thr Val His His His Thr Trp Asn Ala
 1               5                  10                  15

Ile Leu Leu Pro Phe Val Tyr Leu Thr Ala Gln Val Trp Ile Leu Cys
            20                  25                  30
```

-continued

```
Ala Ala Ile Ala Ala Ala Ala Ser Ala Gly Pro Gln Asn Cys Pro Ser
         35                  40                  45
Val Cys Ser Cys Ser Asn Gln Phe Ser Lys Val Val Cys Thr Arg Arg
 50                  55                  60
Gly Leu Ser Glu Val Pro Gln Gly Ile Pro Ser Asn Thr Arg Tyr Leu
 65                  70                  75                  80
Asn Leu Met Glu Asn Asn Ile Gln Met Ile Gln Ala Asp Thr Phe Arg
                 85                  90                  95
His Leu His His Leu Glu Val Leu Gln Leu Gly Arg Asn Ser Ile Arg
                100                 105                 110
Gln Ile Glu Val Gly Ala Phe Asn Gly Leu Ala Ser Leu Ser Thr Leu
            115                 120                 125
Glu Leu Phe Asp Asn Trp Leu Thr Val Ile Pro Ser Gly Ala Phe Glu
        130                 135                 140
Tyr Leu Ser Lys Leu Arg Glu Leu Trp Leu Arg Asn Asn Pro Ile Glu
145                 150                 155                 160
Ser Ile Pro Ser Tyr Ala Phe Asn Arg Val Pro Ser Leu Met Arg Leu
                165                 170                 175
Asp Leu Gly Glu Leu Lys Lys Leu Glu Tyr Ile Ser Glu Gly Ala Phe
            180                 185                 190
Glu Gly Leu Phe Asn Leu Lys Tyr Leu Asn Leu Gly Met Cys Asn Ile
        195                 200                 205
Lys Asp Met Pro Asn Leu Thr Pro Leu Val Gly Leu Glu Glu Leu Glu
210                 215                 220
Met Ser Gly Asn His Phe Pro Glu Ile Arg Pro Gly Ser Phe His Gly
225                 230                 235                 240
Leu Ser Ser Leu Lys Lys Leu Trp Val Met Asn Ser Gln Val Ser Leu
                245                 250                 255
Ile Glu Arg Asn Ala Phe Asp Gly Leu Ala Ser Leu Val Glu Leu Asn
            260                 265                 270
Leu Ala His Asn Asn Leu Ser Ser Leu Pro His Asp Leu Phe Thr Pro
        275                 280                 285
Leu Arg Tyr Leu Val Glu Leu His Leu His His Asn Pro Trp Asn Cys
290                 295                 300
Asp Cys Asp Ile Leu Trp Leu Ala Trp Trp Leu Arg Glu Tyr Ile Pro
305                 310                 315                 320
Thr Asn Ser Thr Cys Cys Gly Arg Cys His Ala Pro Met His Met Arg
                325                 330                 335
Gly Arg Tyr Leu Val Glu Val Asp Gln Ala Ser Phe Gln Cys Ser Ala
            340                 345                 350
Pro Phe Ile Met Asp Ala Pro Arg Asp Leu Asn Ile Ser Glu Gly Arg
        355                 360                 365
Met Ala Glu Leu Lys Cys Arg Thr Pro Pro Met Ser Ser Val Lys Trp
370                 375                 380
Leu Leu Pro Asn Gly Thr Val Leu Ser His Ala Ser Arg His Pro Arg
385                 390                 395                 400
Ile Ser Val Leu Asn Asp Gly Thr Leu Asn Phe Ser His Val Leu Leu
                405                 410                 415
Ser Asp Thr Gly Val Tyr Thr Cys Met Gly Thr Asn Val Ala Gly Asn
            420                 425                 430
Ser Asn Ala Ser Ala Tyr Leu Asn Gly Ser Thr Ala Glu Leu Asn Thr
        435                 440                 445
Ser Asn Tyr Ser Phe Phe Thr Thr Gly Thr Gly Glu Thr Thr Glu Ile
```

```
                   450                 455                 460
Ser Pro Glu Asp Thr Thr Arg Lys Tyr Lys Pro Val Pro Thr Thr Ser
465                 470                 475                 480

Thr Gly Tyr Gln Pro Ala Tyr Thr Thr Ser Thr Thr Val Leu Ile Gln
                485                 490                 495

Thr Thr Arg Val Pro Lys Gln Val Ala Val Pro Ala Thr Asp Thr Thr
            500                 505                 510

Asp Lys Met Gln Thr Ser Leu Asp Glu Val Met Lys Thr Thr Lys Ile
        515                 520                 525

Ile Ile Gly Cys Phe Val Ala Val Thr Leu Leu Ala Ala Ala Met Leu
    530                 535                 540

Ile Val Phe Tyr Lys Leu Arg Lys Arg His Gln Gln Arg Ser Thr Val
545                 550                 555                 560

Thr Ala Ala Pro Thr Leu Glu Arg Lys His Arg Asp Lys Asn Thr Pro
                565                 570                 575

Gln Gln Lys His Pro Gln Gln Lys Gln Gln Pro Pro Val
                580                 585                 590

<210> SEQ ID NO 13
<211> LENGTH: 1340
<212> TYPE: DNA
<213> ORGANISM: Homo sapiens
<220> FEATURE:
<221> NAME/KEY: CDS
<222> LOCATION: (421)..(1287)
<221> NAME/KEY: misc_feature
<222> LOCATION: (22)
<223> OTHER INFORMATION: an n may be any one of a or t or g or c

<400> SEQUENCE: 13
ggcgtttgtg gccgtccggc tnccctgaca tgcagatttc cacccagaag acagagaagg     60
agccagtggt catggaatgg gctggggtca aagactgggt gcctgggagc tgaggcagcc    120
accgtttcag cctggccagc cctctggacc ccgaggttgg accctactgt gacacaccta    180
ccatgcggac actcttcaac ctcctctggc ttgccctggc ctgcagccct gttcacacta    240
ccctgtcaaa gtcagatgcc aaaaaagccg cctcaaagac gctgctggag aagagtcagt    300
tttcagataa gccggtgcaa gaccggggtt tggtggtgac ggacctcaaa gctgagagtg    360
tggttcttga gcatcgcagc tactgctcgg caaaggcccg ggacagacac tttgctgggg    420 atg tac tgg gct atg tca ctc cac cag tgg aac agc cat ggc tac gat    468
Met Tyr Trp Ala Met Ser Leu His Gln Trp Asn Ser His Gly Tyr Asp
  1               5                  10                  15 gtc acc aag gtc ttt ggg agc aag ttc aca cag atc tca ccc gtc tgg    516
Val Thr Lys Val Phe Gly Ser Lys Phe Thr Gln Ile Ser Pro Val Trp
             20                  25                  30 ctg cag ctg aag aga cgt ggc cgt gag atg ttt gag gtc acg ggc ctc    564
Leu Gln Leu Lys Arg Arg Gly Arg Glu Met Phe Glu Val Thr Gly Leu
         35                  40                  45 cac gac gtg gac caa ggg tgg atg cga gct gtc agg aag cat gcc aag    612
His Asp Val Asp Gln Gly Trp Met Arg Ala Val Arg Lys His Ala Lys
     50                  55                  60 ggc ctg cac ata gtg cct cgg ctc ctg ttt gag gac tgg act tac gat    660
Gly Leu His Ile Val Pro Arg Leu Leu Phe Glu Asp Trp Thr Tyr Asp
 65                  70                  75                  80 gat ttc cgg aac gtc tta gac agt gag gat gag ata gag gag ctg agc    708
Asp Phe Arg Asn Val Leu Asp Ser Glu Asp Glu Ile Glu Glu Leu Ser
                 85                  90                  95 aag acc gtg gtc cag gtg gca aag aac cag cat ttc gat ggc ttc gtg    756
```

-continued

```
                                                                            804
gtg gag gtc tgg aac cag ctg cta agc cag aag cgc gtg ggc ctc atc
Val Glu Val Trp Asn Gln Leu Leu Ser Gln Lys Arg Val Gly Leu Ile
        115                 120                 125

852
cac atg ctc acc cac ttg gcc gag gct ctg cac cag gcc cgg ctg ctg
His Met Leu Thr His Leu Ala Glu Ala Leu His Gln Ala Arg Leu Leu
    130                 135                 140

900
gcc ctc ctg gtc atc ccg cct gcc atc acc ccc ggg acc gac cag ctg
Ala Leu Leu Val Ile Pro Pro Ala Ile Thr Pro Gly Thr Asp Gln Leu
145                 150                 155                 160

948
ggc atg ttc acg cac aag gag ttt gag cag ctg gcc ccc gtg ctg gat
Gly Met Phe Thr His Lys Glu Phe Glu Gln Leu Ala Pro Val Leu Asp
                165                 170                 175

996
ggt ttc agc ctc atg acc tac gac tac tct aca gcg cat cag cct ggc
Gly Phe Ser Leu Met Thr Tyr Asp Tyr Ser Thr Ala His Gln Pro Gly
            180                 185                 190

1044
cct aat gca ccc ctg tcc tgg gtt cga gcc tgc gtc cag gtc ctg gac
Pro Asn Ala Pro Leu Ser Trp Val Arg Ala Cys Val Gln Val Leu Asp
        195                 200                 205

1092
ccg aag tcc aag tgg cga agc aaa atc ctc ctg ggg ctc aac ttc tat
Pro Lys Ser Lys Trp Arg Ser Lys Ile Leu Leu Gly Leu Asn Phe Tyr
    210                 215                 220

1140
ggt atg gac tac gcg acc tcc aag gat gcc cgt gag cct gtt gtc ggg
Gly Met Asp Tyr Ala Thr Ser Lys Asp Ala Arg Glu Pro Val Val Gly
225                 230                 235                 240

1188
gcc agg tac atg cag aca ctg aag tct gca ttc gta ctc tta gca aac
Ala Arg Tyr Met Gln Thr Leu Lys Ser Ala Phe Val Leu Leu Ala Asn
                245                 250                 255

1236
ttg gaa aat ttg agg cga aat tct tca aat aaa aaa aaa aaa aaa
Leu Glu Asn Leu Arg Arg Asn Ser Ser Asn Lys Lys Lys Lys Lys
            260                 265                 270

1284
aat ttt ttc tgt ttc ttc tct tct gtc ttc tcg ttt gga gac cac aaa
Asn Phe Phe Cys Phe Phe Ser Ser Val Phe Ser Phe Gly Asp His Lys
        275                 280                 285

1340
cac tagatccatt gaatttgtcc cacagctcac gaatacacct tttacctttt gga
His
```

```
<210> SEQ ID NO 14
<211> LENGTH: 289
<212> TYPE: PRT
<213> ORGANISM: Homo sapiens

<400> SEQUENCE: 14

Met Tyr Trp Ala Met Ser Leu His Gln Trp Asn Ser His Gly Tyr Asp
 1               5                  10                  15

Val Thr Lys Val Phe Gly Ser Lys Phe Thr Gln Ile Ser Pro Val Trp
            20                  25                  30

Leu Gln Leu Lys Arg Arg Gly Arg Glu Met Phe Glu Val Thr Gly Leu
        35                  40                  45

His Asp Val Asp Gln Gly Trp Met Arg Ala Val Arg Lys His Ala Lys
    50                  55                  60

Gly Leu His Ile Val Pro Arg Leu Leu Phe Glu Asp Trp Thr Tyr Asp
65                  70                  75                  80

Asp Phe Arg Asn Val Leu Asp Ser Glu Asp Glu Ile Glu Glu Leu Ser
                85                  90                  95

Lys Thr Val Val Gln Val Ala Lys Asn Gln His Phe Asp Gly Phe Val
            100                 105                 110
```

```
Val Glu Val Trp Asn Gln Leu Leu Ser Gln Lys Arg Val Gly Leu Ile
        115                 120                 125

His Met Leu Thr His Leu Ala Glu Ala Leu His Gln Ala Arg Leu Leu
130                 135                 140

Ala Leu Leu Val Ile Pro Pro Ala Ile Thr Pro Gly Thr Asp Gln Leu
145                 150                 155                 160

Gly Met Phe Thr His Lys Glu Phe Glu Gln Leu Ala Pro Val Leu Asp
                165                 170                 175

Gly Phe Ser Leu Met Thr Tyr Asp Tyr Ser Thr Ala His Gln Pro Gly
                180                 185                 190

Pro Asn Ala Pro Leu Ser Trp Val Arg Ala Cys Val Gln Val Leu Asp
                195                 200                 205

Pro Lys Ser Lys Trp Arg Ser Lys Ile Leu Leu Gly Leu Asn Phe Tyr
        210                 215                 220

Gly Met Asp Tyr Ala Thr Ser Lys Asp Ala Arg Glu Pro Val Val Gly
225                 230                 235                 240

Ala Arg Tyr Met Gln Thr Leu Lys Ser Ala Phe Val Leu Leu Ala Asn
                245                 250                 255

Leu Glu Asn Leu Arg Arg Asn Ser Ser Asn Lys Lys Lys Lys Lys Lys
                260                 265                 270

Asn Phe Phe Cys Phe Phe Ser Ser Val Phe Ser Phe Gly Asp His Lys
        275                 280                 285

His

<210> SEQ ID NO 15
<211> LENGTH: 1428
<212> TYPE: DNA
<213> ORGANISM: Homo sapiens
<220> FEATURE:
<221> NAME/KEY: CDS
<222> LOCATION: (96)..(905)

<400> SEQUENCE: 15
acgcgtgcag gtggcggaac ttgctctaac ttcctcggcc gagccgggcc gcgccgccgc      60
tgccgccgcc gcgcgcggat tctgcttctc agaag atg cac tat tat aga tac        113
                                        Met His Tyr Tyr Arg Tyr
                                        1               5 tct aac gcc aag gtc agc tgc tgg tac aag tac ctc ctt ttc agc tac       161
Ser Asn Ala Lys Val Ser Cys Trp Tyr Lys Tyr Leu Leu Phe Ser Tyr
                10                  15                  20 aac atc atc ttc tgg ttg gct gga gtt gtc ttc ctt gga gtc ggg ttg       209
Asn Ile Ile Phe Trp Leu Ala Gly Val Val Phe Leu Gly Val Gly Leu
            25                  30                  35 tgg gca tgg agc gaa aag ggt gtg ctg tcc gac ctc acc aaa gtg acc       257
Trp Ala Trp Ser Glu Lys Gly Val Leu Ser Asp Leu Thr Lys Val Thr
        40                  45                  50 cgg atg cat gga atc gac cct gcg gtg ctg gtc ctg atg gtg ggc gcg       305
Arg Met His Gly Ile Asp Pro Ala Val Leu Val Leu Met Val Gly Ala
55                  60                  65                  70 gtg atg ttc acc ctg ggg ttc gcc ggc cgc gtg ggg gcg cgc agg gag       353
Val Met Phe Thr Leu Gly Phe Ala Gly Arg Val Gly Ala Arg Arg Glu
                75                  80                  85 aat atc tgc ttg ctc aac ttt ttc tgt ggc acc atc gtg ctc atc ttc       401
Asn Ile Cys Leu Leu Asn Phe Phe Cys Gly Thr Ile Val Leu Ile Phe
            90                  95                  100 ttc ctg gag ctg gct gtg gcc gtg ctg gcc ttc ctg ttc cag gac tgg       449
Phe Leu Glu Leu Ala Val Ala Val Leu Ala Phe Leu Phe Gln Asp Trp
        105                 110                 115
```

```
gtg agg gac cgg ttc cgg gag ttc ttc gag agc aac atc aag tcc tac      497
Val Arg Asp Arg Phe Arg Glu Phe Phe Glu Ser Asn Ile Lys Ser Tyr
    120                 125                 130 cgg gac gat atc gat ctg caa aac ctc atc gac tcc ctt cag aaa gct      545
Arg Asp Asp Ile Asp Leu Gln Asn Leu Ile Asp Ser Leu Gln Lys Ala
135                 140                 145                 150 aac cag tgc tgt ggc gca tat ggc cct gaa gac tgg gac ctc aac gtc      593
Asn Gln Cys Cys Gly Ala Tyr Gly Pro Glu Asp Trp Asp Leu Asn Val
                155                 160                 165 tac ttc aat tgc agc ggt gcc agc tac agc cga gag aag tgc ggg gtc      641
Tyr Phe Asn Cys Ser Gly Ala Ser Tyr Ser Arg Glu Lys Cys Gly Val
            170                 175                 180 ccc ttc tcc tgc tgc gtg cca gat cct gcg caa aaa gtt gtg aac aca      689
Pro Phe Ser Cys Cys Val Pro Asp Pro Ala Gln Lys Val Val Asn Thr
        185                 190                 195 cag tgt gga tat gat gtc agg att cag ctg aag agc aag tgg gat gag      737
Gln Cys Gly Tyr Asp Val Arg Ile Gln Leu Lys Ser Lys Trp Asp Glu
    200                 205                 210 tcc atc ttc acg aaa ggc tgc atc cag gcg ctg gaa agc tgg ctc ccg      785
Ser Ile Phe Thr Lys Gly Cys Ile Gln Ala Leu Glu Ser Trp Leu Pro
215                 220                 225                 230 cgg aac att tac att gtg gct ggc gtc ttc atc gcc atc tcg ctg ttg      833
Arg Asn Ile Tyr Ile Val Ala Gly Val Phe Ile Ala Ile Ser Leu Leu
                235                 240                 245 cag ata ttt ggc atc ttc ctg gca agg acg ctg atc tca gac atc gag      881
Gln Ile Phe Gly Ile Phe Leu Ala Arg Thr Leu Ile Ser Asp Ile Glu
            250                 255                 260 gca gtg aag acc ggc cat cac ttc tgaggagcag agttgaggga gccgagctga    935
Ala Val Lys Thr Gly His His Phe
        265                 270 gccacgctgg gaggccagag cctttctctg ccatcagccc tacgtccaga gggagaggag    995
ccgacacccc cagagccagt gccccatctt aagcatcagc gtgacgtgac ctctctgttt   1055
ctgcttgctg gtgctgaaga ccaagggtcc cccttgatac ctgcccaaac ttgtgactgc   1115
atccctctgg agtctaccca gagacagaga atgtgtcttt atgtgggagt ggtgactctg   1175
aaagacagag agggctcctg tggctgccag gagggcttga ctcagacccc ctgcagctca   1235
agcatgtctg caggacaccc tggtcccctc tccactggca tccagacatc tgctttgggt   1295
catccacatc tgtgggtggg ccgtgggtag agggacccac aggcgtggac agggcatctc   1355
tctccatcaa gcaaagcagc atgggggcct gcccgtaacg ggaggcggac gtggccccgc   1415
tgggcctctc cga                                                     1428
```

<210> SEQ ID NO 16
<211> LENGTH: 270
<212> TYPE: PRT
<213> ORGANISM: Homo sapiens

<400> SEQUENCE: 16

```
Met His Tyr Tyr Arg Tyr Ser Asn Ala Lys Val Ser Cys Trp Tyr Lys
1               5                   10                  15

Tyr Leu Leu Phe Ser Tyr Asn Ile Ile Phe Trp Leu Ala Gly Val Val
            20                  25                  30

Phe Leu Gly Val Gly Leu Trp Ala Trp Ser Glu Lys Gly Val Leu Ser
        35                  40                  45

Asp Leu Thr Lys Val Thr Arg Met His Gly Ile Asp Pro Ala Val Leu
    50                  55                  60
```

```
Val Leu Met Val Gly Ala Val Met Phe Thr Leu Gly Phe Ala Gly Arg
 65                  70                  75                  80

Val Gly Ala Arg Arg Glu Asn Ile Cys Leu Leu Asn Phe Phe Cys Gly
             85                  90                  95

Thr Ile Val Leu Ile Phe Phe Leu Glu Leu Ala Val Ala Val Leu Ala
            100                 105                 110

Phe Leu Phe Gln Asp Trp Val Arg Asp Arg Phe Arg Glu Phe Phe Glu
        115                 120                 125

Ser Asn Ile Lys Ser Tyr Arg Asp Asp Ile Asp Leu Gln Asn Leu Ile
    130                 135                 140

Asp Ser Leu Gln Lys Ala Asn Gln Cys Cys Gly Ala Tyr Gly Pro Glu
145                 150                 155                 160

Asp Trp Asp Leu Asn Val Tyr Phe Asn Cys Ser Gly Ala Ser Tyr Ser
                165                 170                 175

Arg Glu Lys Cys Gly Val Pro Phe Ser Cys Cys Val Pro Asp Pro Ala
            180                 185                 190

Gln Lys Val Val Asn Thr Gln Cys Gly Tyr Asp Val Arg Ile Gln Leu
        195                 200                 205

Lys Ser Lys Trp Asp Glu Ser Ile Phe Thr Lys Gly Cys Ile Gln Ala
    210                 215                 220

Leu Glu Ser Trp Leu Pro Arg Asn Ile Tyr Ile Val Ala Gly Val Phe
225                 230                 235                 240

Ile Ala Ile Ser Leu Leu Gln Ile Phe Gly Ile Phe Leu Ala Arg Thr
                245                 250                 255

Leu Ile Ser Asp Ile Glu Ala Val Lys Thr Gly His His Phe
                260                 265                 270

<210> SEQ ID NO 17
<211> LENGTH: 1767
<212> TYPE: DNA
<213> ORGANISM: Homo sapiens
<220> FEATURE:
<221> NAME/KEY: CDS
<222> LOCATION: (51)..(983)

<400> SEQUENCE: 17
aacggcgcag gtcccagcag ctggggttcc ccctcagccc gtgagcagcc atg tcc      56
                                                      Met Ser
                                                        1 aac ccc agc gcc cca cca cca tat gaa gac cgc aac ccc ctg tac cca   104
Asn Pro Ser Ala Pro Pro Pro Tyr Glu Asp Arg Asn Pro Leu Tyr Pro
        5                   10                  15 ggc cct ctg ccc cct ggg ggc tat ggc cag cca tct gtc ctg cca gga   152
Gly Pro Leu Pro Pro Gly Gly Tyr Gly Gln Pro Ser Val Leu Pro Gly
 20                  25                  30 ggg tat cct gcc tac cct ggc tac ccg cag cct ggc tac ggt cac cct   200
Gly Tyr Pro Ala Tyr Pro Gly Tyr Pro Gln Pro Gly Tyr Gly His Pro
 35                  40                  45                  50 gct ggc tac cca cag ccc atg ccc ccc acc cac ccg atg ccc atg aac   248
Ala Gly Tyr Pro Gln Pro Met Pro Pro Thr His Pro Met Pro Met Asn
                 55                  60                  65 tac ggc cca ggc cat ggc tat gat ggg gag gag aga gcg gtg agt gat   296
Tyr Gly Pro Gly His Gly Tyr Asp Gly Glu Glu Arg Ala Val Ser Asp
                 70                  75                  80 agc ttc ggg cct gga gaa tgg gat gac cgg aaa gtg cga cac act ttt   344
Ser Phe Gly Pro Gly Glu Trp Asp Asp Arg Lys Val Arg His Thr Phe
     85                  90                  95 atc cga aag gtt tac tcc atc atc tcc ggg cag ctg ctc atc act ggg   392
```

```
Ile Arg Lys Val Tyr Ser Ile Ile Ser Gly Gln Leu Leu Ile Thr Gly
    100                 105                 110 gcc atc att gct atc ttc acc ttt ggg gaa cct gtc agc gcc ttt ggc     440
Ala Ile Ile Ala Ile Phe Thr Phe Gly Glu Pro Val Ser Ala Phe Gly
115                 120                 125                 130 agg aga aat gtg gct gtc tac tac gtg tcc tat gct gtc ttc agt gtc     488
Arg Arg Asn Val Ala Val Tyr Tyr Val Ser Tyr Ala Val Phe Ser Val
                135                 140                 145 acc tac ctg atc ctt gcc tgc tgc cag gga ccc aga cgc cgt ttc cca     536
Thr Tyr Leu Ile Leu Ala Cys Cys Gln Gly Pro Arg Arg Arg Phe Pro
            150                 155                 160 tgg aac atc att ctg ctg acc ctt ttt act ttt gcc atg ggc ttc atg     584
Trp Asn Ile Ile Leu Leu Thr Leu Phe Thr Phe Ala Met Gly Phe Met
        165                 170                 175 acg ggc acc att tcc agt atg tac caa acc aaa gcc gtc atc att gca     632
Thr Gly Thr Ile Ser Ser Met Tyr Gln Thr Lys Ala Val Ile Ile Ala
    180                 185                 190 atg atc atc act gcg gtg gta tcc att tca gtc acc atc ttc tgc ttt     680
Met Ile Ile Thr Ala Val Val Ser Ile Ser Val Thr Ile Phe Cys Phe
195                 200                 205                 210 cag acc aag gtg gac ttc acc tcg tgc aca ggc ctc ttc tgt gtc ctg     728
Gln Thr Lys Val Asp Phe Thr Ser Cys Thr Gly Leu Phe Cys Val Leu
                215                 220                 225 gga att gtg ctc ctg gtg act ggg att gtc act agc att gtg ctc tac     776
Gly Ile Val Leu Leu Val Thr Gly Ile Val Thr Ser Ile Val Leu Tyr
            230                 235                 240 ttc caa tac gtt tac tgg ctc cac atg ctc tat gct gct ctg ggg gcc     824
Phe Gln Tyr Val Tyr Trp Leu His Met Leu Tyr Ala Ala Leu Gly Ala
        245                 250                 255 att tgt ttc acc ctg ttc ctg gct tac gac aca cag ctg gtc ctg ggg     872
Ile Cys Phe Thr Leu Phe Leu Ala Tyr Asp Thr Gln Leu Val Leu Gly
    260                 265                 270 aac cgg aag cac acc atc agc ccc gag gac tac atc act ggc gcc ctg     920
Asn Arg Lys His Thr Ile Ser Pro Glu Asp Tyr Ile Thr Gly Ala Leu
275                 280                 285                 290 cag att tac aca gac atc atc tac atc ttc acc ttt gtg ctg cag ctg     968
Gln Ile Tyr Thr Asp Ile Ile Tyr Ile Phe Thr Phe Val Leu Gln Leu
                295                 300                 305 atg ggg gat cgc aat taaggagcaa gccccatttt tcacccgatc ctgggctctc    1023
Met Gly Asp Arg Asn
            310 ccttccaagc tagagggctg ggccctatga ctgtggtctg ggctttaggc cccttccctt    1083 cccccttgagt aacatgccca gtttcctttc tgtcctggag acaggtggcc tctctggcta   1143 tggatgtgtg ggtacttggt ggggacggag gagctaggga ctaactgttg ctcttggtgg    1203 gcttggcagg gactaggctg aagatgtgtc ttctccccgc cacctactgt atgacaccac    1263 attcttccta acagctgggg ttgtgaggaa tatgaaaaga gccattcgga tagctagaag    1323 ggaatatgaa aggtagaagt gacttcaagg tcacgaggtt ccctcccac ctctgtcaca    1383 ggcttcttga ctacgtagtt ggagctattt cttcccccag caaagccaga gagctttgtc    1443 cccggcctcc tggacacata ggccattatc ctgtattcct ttggcttggc atctttttagc   1503 tcaggaaggt agaagagatc tgtgcccatg gtctccttg cttcaatccc ttcttgtttc    1563 agtgacatat gtattgttta ctgggttag ggatggggga cagataatag aacgagcaaa    1623 gtaacctata caggccagca tggaacagca tctcccctgg gcttgctcct ggcttgtgac    1683 gctataagac agagcaggcc acatgtggcc atctgctccc cattcttgaa agctgctggg    1743
```

-continued

```
gcctccttgc aggcttctgg atcc                                              1767
```

<210> SEQ ID NO 18
<211> LENGTH: 311
<212> TYPE: PRT
<213> ORGANISM: Homo sapiens

<400> SEQUENCE: 18

```
Met Ser Asn Pro Ser Ala Pro Pro Tyr Glu Asp Arg Asn Pro Leu
 1               5                  10                  15

Tyr Pro Gly Pro Leu Pro Pro Gly Gly Tyr Gly Gln Pro Ser Val Leu
            20                  25                  30

Pro Gly Gly Tyr Pro Ala Tyr Pro Gly Tyr Pro Gln Pro Gly Tyr Gly
        35                  40                  45

His Pro Ala Gly Tyr Pro Gln Pro Met Pro Pro Thr His Pro Met Pro
 50                  55                  60

Met Asn Tyr Gly Pro Gly His Gly Tyr Asp Gly Glu Arg Ala Val
 65                  70                  75                  80

Ser Asp Ser Phe Gly Pro Gly Glu Trp Asp Asp Arg Lys Val Arg His
                85                  90                  95

Thr Phe Ile Arg Lys Val Tyr Ser Ile Ile Ser Gly Gln Leu Leu Ile
               100                 105                 110

Thr Gly Ala Ile Ile Ala Ile Phe Thr Phe Gly Glu Pro Val Ser Ala
           115                 120                 125

Phe Gly Arg Arg Asn Val Ala Val Tyr Tyr Val Ser Tyr Ala Val Phe
        130                 135                 140

Ser Val Thr Tyr Leu Ile Leu Ala Cys Cys Gln Gly Pro Arg Arg Arg
145                 150                 155                 160

Phe Pro Trp Asn Ile Ile Leu Leu Thr Leu Phe Thr Phe Ala Met Gly
                165                 170                 175

Phe Met Thr Gly Thr Ile Ser Ser Met Tyr Gln Thr Lys Ala Val Ile
            180                 185                 190

Ile Ala Met Ile Ile Thr Ala Val Val Ser Ile Ser Val Thr Ile Phe
        195                 200                 205

Cys Phe Gln Thr Lys Val Asp Phe Thr Ser Cys Thr Gly Leu Phe Cys
    210                 215                 220

Val Leu Gly Ile Val Leu Leu Val Thr Gly Ile Val Thr Ser Ile Val
225                 230                 235                 240

Leu Tyr Phe Gln Tyr Val Tyr Trp Leu His Met Leu Tyr Ala Ala Leu
                245                 250                 255

Gly Ala Ile Cys Phe Thr Leu Phe Leu Ala Tyr Asp Thr Gln Leu Val
            260                 265                 270

Leu Gly Asn Arg Lys His Thr Ile Ser Pro Glu Asp Tyr Ile Thr Gly
        275                 280                 285

Ala Leu Gln Ile Tyr Thr Asp Ile Ile Tyr Ile Phe Thr Phe Val Leu
    290                 295                 300

Gln Leu Met Gly Asp Arg Asn
305                 310
```

<210> SEQ ID NO 19
<211> LENGTH: 1686
<212> TYPE: DNA
<213> ORGANISM: Homo sapiens
<220> FEATURE:
<221> NAME/KEY: CDS
<222> LOCATION: (372)..(1277)
<221> NAME/KEY: misc_feature -continued

```
<222> LOCATION: (1490)..(1630)
<223> OTHER INFORMATION: an n may be any one of a or t or g or c

<400> SEQUENCE: 19
ttcataacaa aaatccaggc caggcacggt ggctcatttt taaaagtcaa aagaaaaaat      60
agtacttaaa aaatagaaaa ataaaatact gtacaccaaa ataagctaga aaatggaac      120 taagaaataa tatttgaaat taatataaaa tgaagctaca gaaggcataa gtaagtccaa     180
atgttggctc tttgaaagac tattaaataa ttacacagaa agtctaataa agagaaaaga    240
gagaaaaaaa ctgtcagaat gctaccgaac tgtactgctt ctacagtgag aacacggatc    300
tgacttgtcg gcagcccaag tgtgacaagt gcaatgctgc ctatcctcac ctggctcacc    360
tgccatctgc c atg gca gac tca tcc ttc cgg ttt cct cgc aca tgg tgg    410
            Met Ala Asp Ser Ser Phe Arg Phe Pro Arg Thr Trp Trp
            1               5                   10 cag tct gcg gag gat gtg cac aga gaa aag atc cag tta gac ctg gaa    458
Gln Ser Ala Glu Asp Val His Arg Glu Lys Ile Gln Leu Asp Leu Glu
 15                  20                  25 gct gaa ttc tac ttc act cac cta att gtg atg ttc aag tcc ccc agg    506
Ala Glu Phe Tyr Phe Thr His Leu Ile Val Met Phe Lys Ser Pro Arg
 30              35                  40                  45 ccg gct gcc atg gtg ctg gac cgc tcc cag gac ttt ggg aaa aca tgg    554
Pro Ala Ala Met Val Leu Asp Arg Ser Gln Asp Phe Gly Lys Thr Trp
             50                  55                  60 aag cct tat aag tac ttt gcg act aac tgc tcc gct aca ttt ggc ctg    602
Lys Pro Tyr Lys Tyr Phe Ala Thr Asn Cys Ser Ala Thr Phe Gly Leu
         65                  70                  75 gaa gat gat gtt gtc aag aag ggc gct att tgt act tct aaa tac tcc    650
Glu Asp Asp Val Val Lys Lys Gly Ala Ile Cys Thr Ser Lys Tyr Ser
     80                  85                  90 agt cct ttt cca tgc act gga gga gag gtt att ttc aaa gct ttg tca    698
Ser Pro Phe Pro Cys Thr Gly Gly Glu Val Ile Phe Lys Ala Leu Ser
 95                 100                 105 cca cca tac gat aca gag aac cct tac agt gcc aaa gtt cag gag cag    746
Pro Pro Tyr Asp Thr Glu Asn Pro Tyr Ser Ala Lys Val Gln Glu Gln
110                 115                 120                 125 ctg aag atc acc aac ctt cgc gtg cag ctg ctg aaa cga cag tct tgt    794
Leu Lys Ile Thr Asn Leu Arg Val Gln Leu Leu Lys Arg Gln Ser Cys
                130                 135                 140 ccc tgt cag aga aat gac ctg aac gaa gag cct caa cat ttt aca cac    842
Pro Cys Gln Arg Asn Asp Leu Asn Glu Glu Pro Gln His Phe Thr His
            145                 150                 155 tat gca atc tat gat ttc att gtc aag ggc agc tgc ttc tgc aat ggc    890
Tyr Ala Ile Tyr Asp Phe Ile Val Lys Gly Ser Cys Phe Cys Asn Gly
        160                 165                 170 cac gct gat caa tgc ata cct gtt cat ggc ttc aga cct gtc aag gcc    938
His Ala Asp Gln Cys Ile Pro Val His Gly Phe Arg Pro Val Lys Ala
175                 180                 185 cca gga aca ttc cac atg gtc cat ggg aag tgt atg tgt aag cac aac    986
Pro Gly Thr Phe His Met Val His Gly Lys Cys Met Cys Lys His Asn
190                 195                 200                 205 aca gca ggc agc cac tgc cag cac tgt gcc ccg tta tac aat gac cgg   1034
Thr Ala Gly Ser His Cys Gln His Cys Ala Pro Leu Tyr Asn Asp Arg
                210                 215                 220 cca tgg gag gca gct gat ggc aaa acg ggg gct ccc aac gag tgc aga   1082
Pro Trp Glu Ala Ala Asp Gly Lys Thr Gly Ala Pro Asn Glu Cys Arg
            225                 230                 235 acc tgc aag tgt aat ggg cat gct gat acc tgt cac ttc gac gtt aat   1130
Thr Cys Lys Cys Asn Gly His Ala Asp Thr Cys His Phe Asp Val Asn
```

```
              240                 245                 250
gtg tgg gag gca tca ggg aat cgt agt ggt ggt gtc tgt gat gac tgt     1178
Val Trp Glu Ala Ser Gly Asn Arg Ser Gly Gly Val Cys Asp Asp Cys
    255                 260                 265 cag cac aac aca gaa gga cag tat tgc cag agg tgc aag cca ggc ttc     1226
Gln His Asn Thr Glu Gly Gln Tyr Cys Gln Arg Cys Lys Pro Gly Phe
270                 275                 280                 285 tat cgt gac ctg cgg aga ccc ttc tca gct cca gat gct tgc aaa cgt     1274
Tyr Arg Asp Leu Arg Arg Pro Phe Ser Ala Pro Asp Ala Cys Lys Arg
                    290                 295                 300 aag taacctgtgg tttccagaaa ataggctgat tgtacaaga gatgaatctc            1327
Lys tttatccctc attctgctaa cccaagagaa ggaggtcatt gaggttctga gataacacac    1387
ttacagatat cggttaattt cttcattgat aagaagcaag aattttcaac cattgggtga    1447
aaacagtata atattcatca aaagtaattt cctttctcat tctncataaa gtaaaaatta    1507
ttccctatac gctgcatttt ggtaaacagg atgactaata gaaaaaaaaa tgatgaanaa    1567
ggagactatt taagaactta agactacttg ggagtagaag gtagacaata atggactcan    1627
ctgatgaaat aaaggtaagt actggacttg gaatatcttt accttacagg gaacttaac    1686

<210> SEQ ID NO 20
<211> LENGTH: 302
<212> TYPE: PRT
<213> ORGANISM: Homo sapiens

<400> SEQUENCE: 20

Met Ala Asp Ser Ser Phe Arg Phe Pro Arg Thr Trp Trp Gln Ser Ala
1               5                   10                  15

Glu Asp Val His Arg Glu Lys Ile Gln Leu Asp Leu Glu Ala Glu Phe
                20                  25                  30

Tyr Phe Thr His Leu Ile Val Met Phe Lys Ser Pro Arg Pro Ala Ala
            35                  40                  45

Met Val Leu Asp Arg Ser Gln Asp Phe Gly Lys Thr Trp Lys Pro Tyr
        50                  55                  60

Lys Tyr Phe Ala Thr Asn Cys Ser Ala Thr Phe Gly Leu Glu Asp Asp
65                  70                  75                  80

Val Val Lys Lys Gly Ala Ile Cys Thr Ser Lys Tyr Ser Ser Pro Phe
                85                  90                  95

Pro Cys Thr Gly Gly Glu Val Ile Phe Lys Ala Leu Ser Pro Pro Tyr
            100                 105                 110

Asp Thr Glu Asn Pro Tyr Ser Ala Lys Val Gln Glu Gln Leu Lys Ile
        115                 120                 125

Thr Asn Leu Arg Val Gln Leu Leu Lys Arg Gln Ser Cys Pro Cys Gln
130                 135                 140

Arg Asn Asp Leu Asn Glu Glu Pro Gln His Phe Thr His Tyr Ala Ile
145                 150                 155                 160

Tyr Asp Phe Ile Val Lys Gly Ser Cys Phe Cys Asn Gly His Ala Asp
                165                 170                 175

Gln Cys Ile Pro Val His Gly Phe Arg Pro Val Lys Ala Pro Gly Thr
            180                 185                 190

Phe His Met Val His Gly Lys Cys Met Cys Lys His Asn Thr Ala Gly
        195                 200                 205

Ser His Cys Gln His Cys Ala Pro Leu Tyr Asn Asp Arg Pro Trp Glu
210                 215                 220
```

```
Ala Ala Asp Gly Lys Thr Gly Ala Pro Asn Glu Cys Arg Thr Cys Lys
225                 230                 235                 240

Cys Asn Gly His Ala Asp Thr Cys His Phe Asp Val Asn Val Trp Glu
                245                 250                 255

Ala Ser Gly Asn Arg Ser Gly Gly Val Cys Asp Asp Cys Gln His Asn
                260                 265                 270

Thr Glu Gly Gln Tyr Cys Gln Arg Cys Lys Pro Gly Phe Tyr Arg Asp
            275                 280                 285

Leu Arg Arg Pro Phe Ser Ala Pro Asp Ala Cys Lys Arg Lys
        290                 295                 300

<210> SEQ ID NO 21
<211> LENGTH: 2010
<212> TYPE: DNA
<213> ORGANISM: Homo sapiens
<220> FEATURE:
<221> NAME/KEY: CDS
<222> LOCATION: (243)..(1658)

<400> SEQUENCE: 21
gctccgcgac tcggcctctc cacccctcc ccagcctttc tctcgccctc ttctcccaca      60
ctcccggccg gcgcctcggc tttgtgcgag gagatggtgt agcccctgg ccgccgaaga    120 ggagccggac acttgtctcc cgtctccgag ctgctcccca ccctggagg agagaccccc    180 ccctcggctc ggcgccttct gcgtctcccg gctggtgggg aagcctctgc ccgccggca   240 cc atg agt gaa cag agt atc tgt cag gca aga gct gct gtg atg gtt      287
   Met Ser Glu Gln Ser Ile Cys Gln Ala Arg Ala Ala Val Met Val
   1               5                   10                  15 tat gat gat gcc aat aag aag tgg gtg cca gct ggt ggc tca act gga    335
Tyr Asp Asp Ala Asn Lys Lys Trp Val Pro Ala Gly Gly Ser Thr Gly
                20                  25                  30 ttc agc aga gtt cat atc tat cac cat aca ggc aac aac aca ttc aga    383
Phe Ser Arg Val His Ile Tyr His His Thr Gly Asn Asn Thr Phe Arg
            35                  40                  45 gtg gtg ggc agg aag att cag gac cat cag gtc gtg ata aac tgt gcc    431
Val Val Gly Arg Lys Ile Gln Asp His Gln Val Val Ile Asn Cys Ala
        50                  55                  60 att cct aaa ggg ttg aag tac aat caa gct aca cag acc ttc cac cag    479
Ile Pro Lys Gly Leu Lys Tyr Asn Gln Ala Thr Gln Thr Phe His Gln
65                  70                  75 tgg cga gat gct aga cag gtg tat ggt ctc aac ttt ggc agc aaa gag    527
Trp Arg Asp Ala Arg Gln Val Tyr Gly Leu Asn Phe Gly Ser Lys Glu
    80                  85                  90                  95 gat gcc aat gtc ttc gca agt gcc atg atg cat gcc tta gaa gtg tta    575
Asp Ala Asn Val Phe Ala Ser Ala Met Met His Ala Leu Glu Val Leu
                100                 105                 110 aat tca cag gaa aca ggg cca aca ttg cct aga caa aac tca caa cta    623
Asn Ser Gln Glu Thr Gly Pro Thr Leu Pro Arg Gln Asn Ser Gln Leu
            115                 120                 125 cct gct caa gtt caa aat ggc cca tcc caa gaa gaa ttg gaa att caa    671
Pro Ala Gln Val Gln Asn Gly Pro Ser Gln Glu Glu Leu Glu Ile Gln
        130                 135                 140 aga aga caa cta caa gaa cag caa cgg caa aag gag ctg gag cgg gaa    719
Arg Arg Gln Leu Gln Glu Gln Gln Arg Gln Lys Glu Leu Glu Arg Glu
145                 150                 155 agg ctg aag cga gaa aga atg gaa aga gaa agg aag aag aga gag agg    767
Arg Leu Lys Arg Glu Arg Met Glu Arg Glu Arg Lys Lys Arg Glu Arg
    160                 165                 170                 175 tta gaa agg gaa agg ctg gag agg gag cga ctg gaa caa gaa cag ctg    815
```

```
                                                          -continued

Leu Glu Arg Glu Arg Leu Glu Arg Glu Arg Leu Glu Gln Glu Gln Leu
                180                 185                 190 gag aga gag aga caa gaa cgg gaa cgg cag gaa cgc ctg gag cgg cag          863
Glu Arg Glu Arg Gln Glu Arg Glu Arg Gln Glu Arg Leu Glu Arg Gln
            195                 200                 205 gaa cgc ctg gag cgg cag gaa cgc ctg gag cgg cag gaa cgc ctg gat          911
Glu Arg Leu Glu Arg Gln Glu Arg Leu Glu Arg Gln Glu Arg Leu Asp
        210                 215                 220 cgg gag agg caa gaa aga caa gaa cga gag agg ctg gag aga ctg gaa          959
Arg Glu Arg Gln Glu Arg Gln Glu Arg Glu Arg Leu Glu Arg Leu Glu
    225                 230                 235 cgg gag agg caa gaa agg gag cga caa gag cag tta gaa agg gaa cag         1007
Arg Glu Arg Gln Glu Arg Glu Arg Gln Glu Gln Leu Glu Arg Glu Gln
240                 245                 250                 255 ctg gaa tgg gag aga gag cgc aga ata tca agt gct gct gcc cct gcc         1055
Leu Glu Trp Glu Arg Glu Arg Arg Ile Ser Ser Ala Ala Ala Pro Ala
                260                 265                 270 tct gtt gag act cct cta aac tct gtg ctg gga gac tct tct gct tct         1103
Ser Val Glu Thr Pro Leu Asn Ser Val Leu Gly Asp Ser Ser Ala Ser
            275                 280                 285 gag cca ggc ttg cag gca gcc tct cag ccg gcc gag act cca tcc caa         1151
Glu Pro Gly Leu Gln Ala Ala Ser Gln Pro Ala Glu Thr Pro Ser Gln
        290                 295                 300 cag gaa gac aat cgc cct tta act gga ctt gca gct gca att gcc gga         1199
Gln Glu Asp Asn Arg Pro Leu Thr Gly Leu Ala Ala Ala Ile Ala Gly
    305                 310                 315 gca aaa ctt agg aaa gtg tca cgg atg gag gat acc tct ttc cca agt         1247
Ala Lys Leu Arg Lys Val Ser Arg Met Glu Asp Thr Ser Phe Pro Ser
320                 325                 330                 335 gga ggg aat gct att ggt gtg aac tcc gcc tca tct aaa aca gat aca         1295
Gly Gly Asn Ala Ile Gly Val Asn Ser Ala Ser Ser Lys Thr Asp Thr
                340                 345                 350 ggc cgt gga aat gga ccc ctt cct tta ggg ggt agt ggt tta atg gaa         1343
Gly Arg Gly Asn Gly Pro Leu Pro Leu Gly Gly Ser Gly Leu Met Glu
            355                 360                 365 gaa atg agt gcc ctg ctg gcc acg agg aga aga att gct gaa aag gga         1391
Glu Met Ser Ala Leu Leu Ala Thr Arg Arg Arg Ile Ala Glu Lys Gly
        370                 375                 380 tca aca ata gaa aca gaa caa aaa gag gac aaa ggt gaa gat tca gag         1439
Ser Thr Ile Glu Thr Glu Gln Lys Glu Asp Lys Gly Glu Asp Ser Glu
    385                 390                 395 cct gta act tct aag gcc tct tca aca agt aca cct gaa cca aca aga         1487
Pro Val Thr Ser Lys Ala Ser Ser Thr Ser Thr Pro Glu Pro Thr Arg
400                 405                 410                 415 aaa cct tgg gaa aga aca aat aca atg aat ggc agc aag tca cct gtt         1535
Lys Pro Trp Glu Arg Thr Asn Thr Met Asn Gly Ser Lys Ser Pro Val
                420                 425                 430 atc tcc aga cct cca agg aaa aat cag att gtt ttt gac aac agg tcc         1583
Ile Ser Arg Pro Pro Arg Lys Asn Gln Ile Val Phe Asp Asn Arg Ser
            435                 440                 445 tat gat tca tta cac aga cca aaa tcc aca ccc gtt atc aca gcc cag         1631
Tyr Asp Ser Leu His Arg Pro Lys Ser Thr Pro Val Ile Thr Ala Gln
        450                 455                 460 tgc caa tgg agt cca gac gga agg act tgactatgac aggctgaagc               1678
Cys Gln Trp Ser Pro Asp Gly Arg Thr
    465                 470 aggacatttt agatgaaatg agaaaagaat taacaaagct aaaagaagag ctcattgatg       1738
caatcaggca ggaactgagc aagtcaaata ctgcatagag gaacagacta aggagagata       1798
```

```
ggactttaat ctggaggaaa aatatcctac aaacaacaac tgttcacaac agcaaacccc    1858
tacatttatg agctgtaaga agaaaatgga gacaaacaga aggagggaaa aaccaaccta    1918
ctctgaaagc cttcagacat tatgactctg gtgataagct ctttccctct ccgtttgctg    1978
cttttttctg gccaacatca gaatggtaac ac                                  2010
```

<210> SEQ ID NO 22
<211> LENGTH: 472
<212> TYPE: PRT
<213> ORGANISM: Homo sapiens

<400> SEQUENCE: 22

```
Met Ser Glu Gln Ser Ile Cys Gln Ala Arg Ala Ala Val Met Val Tyr
  1               5                  10                  15

Asp Asp Ala Asn Lys Lys Trp Val Pro Ala Gly Gly Ser Thr Gly Phe
             20                  25                  30

Ser Arg Val His Ile Tyr His His Thr Gly Asn Asn Thr Phe Arg Val
         35                  40                  45

Val Gly Arg Lys Ile Gln Asp His Gln Val Val Ile Asn Cys Ala Ile
     50                  55                  60

Pro Lys Gly Leu Lys Tyr Asn Gln Ala Thr Gln Thr Phe His Gln Trp
 65                  70                  75                  80

Arg Asp Ala Arg Gln Val Tyr Gly Leu Asn Phe Gly Ser Lys Glu Asp
                 85                  90                  95

Ala Asn Val Phe Ala Ser Ala Met Met His Ala Leu Glu Val Leu Asn
            100                 105                 110

Ser Gln Glu Thr Gly Pro Thr Leu Pro Arg Gln Asn Ser Gln Leu Pro
        115                 120                 125

Ala Gln Val Gln Asn Gly Pro Ser Gln Glu Glu Leu Glu Ile Gln Arg
    130                 135                 140

Arg Gln Leu Gln Glu Gln Gln Arg Gln Lys Glu Leu Glu Arg Glu Arg
145                 150                 155                 160

Leu Lys Arg Glu Arg Met Glu Arg Glu Arg Lys Lys Arg Glu Arg Leu
                165                 170                 175

Glu Arg Glu Arg Leu Glu Arg Glu Arg Leu Glu Gln Glu Gln Leu Glu
            180                 185                 190

Arg Glu Arg Gln Glu Arg Glu Arg Gln Glu Arg Leu Glu Arg Gln Glu
        195                 200                 205

Arg Leu Glu Arg Gln Glu Arg Leu Glu Arg Gln Glu Arg Leu Asp Arg
    210                 215                 220

Glu Arg Gln Glu Arg Gln Glu Arg Glu Arg Leu Glu Arg Leu Glu Arg
225                 230                 235                 240

Glu Arg Gln Glu Arg Glu Arg Gln Glu Gln Leu Glu Arg Glu Gln Leu
                245                 250                 255

Glu Trp Glu Arg Glu Arg Arg Ile Ser Ser Ala Ala Pro Ala Ser
            260                 265                 270

Val Glu Thr Pro Leu Asn Ser Val Leu Gly Asp Ser Ser Ala Ser Glu
        275                 280                 285

Pro Gly Leu Gln Ala Ala Ser Gln Pro Ala Glu Thr Pro Ser Gln Gln
    290                 295                 300

Glu Asp Asn Arg Pro Leu Thr Gly Leu Ala Ala Ala Ile Ala Gly Ala
305                 310                 315                 320

Lys Leu Arg Lys Val Ser Arg Met Glu Asp Thr Ser Phe Pro Ser Gly
                325                 330                 335
```

```
Gly Asn Ala Ile Gly Val Asn Ser Ala Ser Ser Lys Thr Asp Thr Gly
            340                 345                 350

Arg Gly Asn Gly Pro Leu Pro Leu Gly Gly Ser Gly Leu Met Glu Glu
        355                 360                 365

Met Ser Ala Leu Leu Ala Thr Arg Arg Ile Ala Glu Lys Gly Ser
    370                 375                 380

Thr Ile Glu Thr Glu Gln Lys Glu Asp Lys Gly Glu Asp Ser Glu Pro
385                 390                 395                 400

Val Thr Ser Lys Ala Ser Ser Thr Ser Thr Pro Glu Pro Thr Arg Lys
                405                 410                 415

Pro Trp Glu Arg Thr Asn Thr Met Asn Gly Ser Lys Ser Pro Val Ile
            420                 425                 430

Ser Arg Pro Pro Arg Lys Asn Gln Ile Val Phe Asp Asn Arg Ser Tyr
        435                 440                 445

Asp Ser Leu His Arg Pro Lys Ser Thr Pro Val Ile Thr Ala Gln Cys
    450                 455                 460

Gln Trp Ser Pro Asp Gly Arg Thr
465                 470

<210> SEQ ID NO 23
<211> LENGTH: 1952
<212> TYPE: DNA
<213> ORGANISM: Homo sapiens
<220> FEATURE:
<221> NAME/KEY: CDS
<222> LOCATION: (243)..(1715)

<400> SEQUENCE: 23
gctccgcgac tcggcctctc caccccctcc ccagcctttc tctcgccctc ttctcccaca        60
ctcccggccg gcgcctcggc tttgtgcgag gagatggtgt agcccccctgg ccgccgaaga      120 ggagccggac acttgtctcc cgtctccgag ctgctcccca ccctggagg agagaccccc       180 ccctcggctc ggcgccttct gcgtctcccg gctggtgggg aagcctctgc ccgccggca       240 cc atg agt gaa cag agt atc tgt cag gca aga gct gct gtg atg gtt        287
   Met Ser Glu Gln Ser Ile Cys Gln Ala Arg Ala Ala Val Met Val
       1               5                  10                  15 tat gat gat gcc aat aag aag tgg gtg cca gct ggt ggc tca act gga      335
Tyr Asp Asp Ala Asn Lys Lys Trp Val Pro Ala Gly Gly Ser Thr Gly
                20                  25                  30 ttc agc aga gtt cat atc tat cac cat aca ggc aac aac aca ttc aga      383
Phe Ser Arg Val His Ile Tyr His His Thr Gly Asn Asn Thr Phe Arg
            35                  40                  45 gtg gtg ggc agg aag att cag gac cat cag gtc gtg ata aac tgt gcc      431
Val Val Gly Arg Lys Ile Gln Asp His Gln Val Val Ile Asn Cys Ala
        50                  55                  60 att cct aaa ggg ttg aag tac aat caa gct aca cag acc ttc cac cag      479
Ile Pro Lys Gly Leu Lys Tyr Asn Gln Ala Thr Gln Thr Phe His Gln
65                  70                  75 tgg cga gat gct aga cag gtg tat ggt ctc aac ttt ggc agc aaa gag      527
Trp Arg Asp Ala Arg Gln Val Tyr Gly Leu Asn Phe Gly Ser Lys Glu
80                  85                  90                  95 gat gcc aat gtc ttc gca agt gcc atg atg cat gcc tta gaa gtg tta      575
Asp Ala Asn Val Phe Ala Ser Ala Met Met His Ala Leu Glu Val Leu
                100                 105                 110 aat tca cag gaa aca ggg cca aca ttg cct aga caa aac tca caa cta      623
Asn Ser Gln Glu Thr Gly Pro Thr Leu Pro Arg Gln Asn Ser Gln Leu
            115                 120                 125 cct gct caa gtt caa aat ggc cca tcc caa gaa gaa ttg gaa att caa      671
```

```
Pro Ala Gln Val Gln Asn Gly Pro Ser Gln Glu Glu Leu Glu Ile Gln
        130                 135                 140 aga aga caa cta caa gaa cag caa cgg caa aag gag ctg gag cgg gaa       719
Arg Arg Gln Leu Gln Glu Gln Gln Arg Gln Lys Glu Leu Glu Arg Glu
145                 150                 155 agg ctg aag cga gaa aga atg gaa aga gaa agg aag aag aga gag agg       767
Arg Leu Lys Arg Glu Arg Met Glu Arg Glu Arg Lys Lys Arg Glu Arg
160                 165                 170                 175 tta gaa agg gaa agg ctg gag agg gag cga ctg gaa caa gaa cag ctg       815
Leu Glu Arg Glu Arg Leu Glu Arg Glu Arg Leu Glu Gln Glu Gln Leu
                180                 185                 190 gag aga gag aga caa gaa cgg gaa cgg cag gaa cgc ctg gag cgg cag       863
Glu Arg Glu Arg Gln Glu Arg Glu Arg Gln Glu Arg Leu Glu Arg Gln
                195                 200                 205 gaa cgc ctg gag cgg cag gaa cgc ctg gag cgg cag gaa cgc ctg gat       911
Glu Arg Leu Glu Arg Gln Glu Arg Leu Glu Arg Gln Glu Arg Leu Asp
                210                 215                 220 cgg gag agg caa gaa aga caa gaa cga gag agg ctg gag aga ctg gaa       959
Arg Glu Arg Gln Glu Arg Gln Glu Arg Glu Arg Leu Glu Arg Leu Glu
225                 230                 235 cgg gag agg caa gaa agg gag cga caa gag cag tta gaa agg gaa cag      1007
Arg Glu Arg Gln Glu Arg Glu Arg Gln Glu Gln Leu Glu Arg Glu Gln
240                 245                 250                 255 ctg gaa tgg gag aga gag cgc aga ata tca agt gct gct gcc cct gcc      1055
Leu Glu Trp Glu Arg Glu Arg Arg Ile Ser Ser Ala Ala Ala Pro Ala
                260                 265                 270 tct gtt gag act cct cta aac tct gtg ctg gga gac tct tct gct tct      1103
Ser Val Glu Thr Pro Leu Asn Ser Val Leu Gly Asp Ser Ser Ala Ser
                275                 280                 285 gag cca ggc ttg cag gca gcc tct cag ccg gcc gag act cca tcc caa      1151
Glu Pro Gly Leu Gln Ala Ala Ser Gln Pro Ala Glu Thr Pro Ser Gln
        290                 295                 300 cag gaa gac aat cgc cct tta act gga ctt gca gct gca att gcc gga      1199
Gln Glu Asp Asn Arg Pro Leu Thr Gly Leu Ala Ala Ala Ile Ala Gly
        305                 310                 315 gca aaa ctt agg aaa gtg tca cgg atg gag gat acc tct ttc cca agt      1247
Ala Lys Leu Arg Lys Val Ser Arg Met Glu Asp Thr Ser Phe Pro Ser
320                 325                 330                 335 gga ggg aat gct att ggt gtg aac tcc gcc tca tct aaa aca gat aca      1295
Gly Gly Asn Ala Ile Gly Val Asn Ser Ala Ser Ser Lys Thr Asp Thr
                340                 345                 350 ggc cgt gga aat gga ccc ctt cct tta ggg ggt agt ggt tta atg gaa      1343
Gly Arg Gly Asn Gly Pro Leu Pro Leu Gly Gly Ser Gly Leu Met Glu
                355                 360                 365 gaa atg agt gcc ctg ctg gcc acg agg aga aga att gct gaa aag gga      1391
Glu Met Ser Ala Leu Leu Ala Thr Arg Arg Arg Ile Ala Glu Lys Gly
        370                 375                 380 tca aca ata gaa aca gaa caa aaa gag gac aaa ggt gaa gat tca gag      1439
Ser Thr Ile Glu Thr Glu Gln Lys Glu Asp Lys Gly Glu Asp Ser Glu
385                 390                 395 cct gta act tct aag gcc tct tca aca agt aca cct gaa cca aca aga      1487
Pro Val Thr Ser Lys Ala Ser Ser Thr Ser Thr Pro Glu Pro Thr Arg
400                 405                 410                 415 aaa cct tgg gaa aga aca aat aca atg aat ggc agc aag tca cct gtt      1535
Lys Pro Trp Glu Arg Thr Asn Thr Met Asn Gly Ser Lys Ser Pro Val
                420                 425                 430 atc tcc aga cca aaa tcc aca ccc tta tca cag ccc agt gcc aat gga      1583
Ile Ser Arg Pro Lys Ser Thr Pro Leu Ser Gln Pro Ser Ala Asn Gly
                435                 440                 445
```

-continued

```
gtc cag acg gaa gga ctt gac tat gac agg ctg aag cag gac att tta    1631
Val Gln Thr Glu Gly Leu Asp Tyr Asp Arg Leu Lys Gln Asp Ile Leu
            450                 455                 460 gat gaa atg aga aaa gaa tta aca aag cta aaa gaa gag ctc att gat    1679
Asp Glu Met Arg Lys Glu Leu Thr Lys Leu Lys Glu Glu Leu Ile Asp
        465                 470                 475 gca atc agg cag gaa ctg agc aag tca aat act gca tagaggaaca         1725
Ala Ile Arg Gln Glu Leu Ser Lys Ser Asn Thr Ala
480                 485                 490 gactaaggag agataggact ttaatctgga ggaaaaatat cctacaaaca acaactgttc  1785
acaacagcaa acccctacat ttatgagctg taagaagaaa atggagacaa acagaaggag  1845
ggaaaaacca acctactctg aaagccttca gacattatga ctctggtgat aagctctttc  1905
cctctccgtt tgctgctttt ttctggccaa catcagaatg gtaacac                1952
```

<210> SEQ ID NO 24
<211> LENGTH: 491
<212> TYPE: PRT
<213> ORGANISM: Homo sapiens

<400> SEQUENCE: 24

```
Met Ser Glu Gln Ser Ile Cys Gln Ala Arg Ala Val Met Val Tyr
 1               5                  10                  15

Asp Asp Ala Asn Lys Lys Trp Val Pro Ala Gly Gly Ser Thr Gly Phe
                20                  25                  30

Ser Arg Val His Ile Tyr His His Thr Gly Asn Asn Thr Phe Arg Val
            35                  40                  45

Val Gly Arg Lys Ile Gln Asp His Gln Val Val Ile Asn Cys Ala Ile
        50                  55                  60

Pro Lys Gly Leu Lys Tyr Asn Gln Ala Thr Gln Thr Phe His Gln Trp
    65                  70                  75                  80

Arg Asp Ala Arg Gln Val Tyr Gly Leu Asn Phe Gly Ser Lys Glu Asp
                    85                  90                  95

Ala Asn Val Phe Ala Ser Ala Met Met His Ala Leu Glu Val Leu Asn
                100                 105                 110

Ser Gln Glu Thr Gly Pro Thr Leu Pro Arg Gln Asn Ser Gln Leu Pro
            115                 120                 125

Ala Gln Val Gln Asn Gly Pro Ser Gln Glu Glu Leu Glu Ile Gln Arg
        130                 135                 140

Arg Gln Leu Gln Glu Gln Gln Arg Gln Lys Glu Leu Glu Arg Glu Arg
    145                 150                 155                 160

Leu Lys Arg Glu Arg Met Glu Arg Glu Arg Lys Lys Arg Glu Arg Leu
                    165                 170                 175

Glu Arg Glu Arg Leu Glu Arg Glu Arg Leu Glu Gln Glu Gln Leu Glu
                180                 185                 190

Arg Glu Arg Gln Glu Arg Glu Arg Gln Glu Arg Leu Glu Arg Gln Glu
            195                 200                 205

Arg Leu Glu Arg Gln Glu Arg Leu Glu Arg Gln Glu Arg Leu Asp Arg
        210                 215                 220

Glu Arg Gln Glu Arg Gln Glu Arg Glu Arg Leu Glu Arg Leu Glu Arg
    225                 230                 235                 240

Glu Arg Gln Glu Arg Glu Arg Gln Glu Gln Leu Glu Arg Glu Gln Leu
                    245                 250                 255

Glu Trp Glu Arg Glu Arg Arg Ile Ser Ser Ala Ala Pro Ala Ser
                260                 265                 270
```

```
Val Glu Thr Pro Leu Asn Ser Val Leu Gly Asp Ser Ala Ser Glu
            275                 280                 285

Pro Gly Leu Gln Ala Ala Ser Gln Pro Ala Glu Thr Pro Ser Gln Gln
        290                 295                 300

Glu Asp Asn Arg Pro Leu Thr Gly Leu Ala Ala Ile Ala Gly Ala
305                 310                 315                 320

Lys Leu Arg Lys Val Ser Arg Met Glu Asp Thr Ser Phe Pro Ser Gly
                325                 330                 335

Gly Asn Ala Ile Gly Val Asn Ser Ala Ser Ser Lys Thr Asp Thr Gly
                340                 345                 350

Arg Gly Asn Gly Pro Leu Pro Leu Gly Gly Ser Gly Leu Met Glu Glu
            355                 360                 365

Met Ser Ala Leu Leu Ala Thr Arg Arg Ile Ala Glu Lys Gly Ser
        370                 375                 380

Thr Ile Glu Thr Glu Gln Lys Glu Asp Lys Gly Glu Asp Ser Glu Pro
385                 390                 395                 400

Val Thr Ser Lys Ala Ser Ser Thr Ser Thr Pro Glu Pro Thr Arg Lys
                405                 410                 415

Pro Trp Glu Arg Thr Asn Thr Met Asn Gly Ser Lys Ser Pro Val Ile
                420                 425                 430

Ser Arg Pro Lys Ser Thr Pro Leu Ser Gln Pro Ser Ala Asn Gly Val
            435                 440                 445

Gln Thr Glu Gly Leu Asp Tyr Asp Arg Leu Lys Gln Asp Ile Leu Asp
        450                 455                 460

Glu Met Arg Lys Glu Leu Thr Lys Leu Lys Glu Glu Leu Ile Asp Ala
465                 470                 475                 480

Ile Arg Gln Glu Leu Ser Lys Ser Asn Thr Ala
                485                 490
```

<210> SEQ ID NO 25
<211> LENGTH: 827
<212> TYPE: DNA
<213> ORGANISM: Homo sapiens
<220> FEATURE:
<221> NAME/KEY: CDS
<222> LOCATION: (233)..(601)

<400> SEQUENCE: 25

```
gaattcgagc gcaggagctc cgcttctcca cctgctcccg gggagctagt gggatccaga      60
gaatcacccg ctgatggttt tgcccaggc ctgaaacaac cagagagcta cgggaaagga     120
agggcttggc ttgccagagg aattttccaa gtgctcaaac gccaggctta cggcgcctgt     180
gatccgtcca ggaggacaaa gtgggatttg aggatccact ccacttctgc tc atg gcg    238
                                                            Met Ala
                                                             1 cgc cag ggc ctg ccc ctg cac gtg gcc aca ctg ctg act ggg ctg ctg      286
Arg Gln Gly Leu Pro Leu His Val Ala Thr Leu Leu Thr Gly Leu Leu
        5                  10                  15 gaa tgc ctg ggc ttt gct ggc gtc ctc ttt ggc tgg cct tca cta gtg      334
Glu Cys Leu Gly Phe Ala Gly Val Leu Phe Gly Trp Pro Ser Leu Val
    20                  25                  30 ttt gtc ttc aag aat gaa gat tac ttt aag gat ctg tgt gga cca gat      382
Phe Val Phe Lys Asn Glu Asp Tyr Phe Lys Asp Leu Cys Gly Pro Asp
 35                  40                  45                  50 gct ggg ccg att ggc aat gcc aca ggg cag gct gac tgc aaa gcc cag      430
Ala Gly Pro Ile Gly Asn Ala Thr Gly Gln Ala Asp Cys Lys Ala Gln
                55                  60                  65
```

```
gat gag agg ttc tca ctc atc ttc acc ctg ggg tcc ttc atg aac aac    478
Asp Glu Arg Phe Ser Leu Ile Phe Thr Leu Gly Ser Phe Met Asn Asn
         70                  75                  80 ttc atg aca ttc ccc act ggc tac atc ttt gac cgg ttc aag acc acc    526
Phe Met Thr Phe Pro Thr Gly Tyr Ile Phe Asp Arg Phe Lys Thr Thr
     85                  90                  95 gtg gca cgc ctc ata gcc ata ttt ttc tac acc acc gcc aca ctc atc    574
Val Ala Arg Leu Ile Ala Ile Phe Phe Tyr Thr Thr Ala Thr Leu Ile
100                 105                 110 ata gcc ttc acc tct gca gct tct tta tgaaaaaggc atcagcctca          621
Ile Ala Phe Thr Ser Ala Ala Ser Leu
115                 120 gggcctcctt catcttcatc tctgtctgca agtacctggc atgtagcacg cactttcctc   681
ctgatgcccc gggggcacat cccatacccca ctgcccccca actacagcta tggcctgtgc  741
cctgggaatg gcaccacaaa ggaagagaag gaaacagctg agcatgaaaa cagggagcta   801
cagtcaaagg agttcctttc agcgaa                                        827

<210> SEQ ID NO 26
<211> LENGTH: 123
<212> TYPE: PRT
<213> ORGANISM: Homo sapiens

<400> SEQUENCE: 26

Met Ala Arg Gln Gly Leu Pro Leu His Val Ala Thr Leu Leu Thr Gly
1               5                   10                  15

Leu Leu Glu Cys Leu Gly Phe Ala Gly Val Leu Phe Gly Trp Pro Ser
            20                  25                  30

Leu Val Phe Val Phe Lys Asn Glu Asp Tyr Phe Lys Asp Leu Cys Gly
        35                  40                  45

Pro Asp Ala Gly Pro Ile Gly Asn Ala Thr Gly Gln Ala Asp Cys Lys
    50                  55                  60

Ala Gln Asp Glu Arg Phe Ser Leu Ile Phe Thr Leu Gly Ser Phe Met
65                  70                  75                  80

Asn Asn Phe Met Thr Phe Pro Thr Gly Tyr Ile Phe Asp Arg Phe Lys
                85                  90                  95

Thr Thr Val Ala Arg Leu Ile Ala Ile Phe Phe Tyr Thr Thr Ala Thr
            100                 105                 110

Leu Ile Ile Ala Phe Thr Ser Ala Ala Ser Leu
        115                 120

<210> SEQ ID NO 27
<211> LENGTH: 1063
<212> TYPE: DNA
<213> ORGANISM: Homo sapiens
<220> FEATURE:
<221> NAME/KEY: CDS
<222> LOCATION: (48)..(944)

<400> SEQUENCE: 27
cttttttcag ataacatctt ctgagtcata accagcctgg gtccccc atg atc gtg     56
                                                    Met Ile Val
                                                    1 ggg tcc cct cgg gcc ctg aca cag ccc ctg ggt ctc ctt cgc ctg ctg    104
Gly Ser Pro Arg Ala Leu Thr Gln Pro Leu Gly Leu Leu Arg Leu Leu
    5                   10                  15 cag ctg gtg tct acc tgc gtg gcc ttc tcg ctg gtg gct agc gtg ggc    152
Gln Leu Val Ser Thr Cys Val Ala Phe Ser Leu Val Ala Ser Val Gly
20                  25                  30                  35
```

-continued

```
gcc tgg acg ggg tcc atg ggc aac tgg tcc atg ttc acc tgg tgc ttc        200
Ala Trp Thr Gly Ser Met Gly Asn Trp Ser Met Phe Thr Trp Cys Phe
            40                  45                  50 tgc ttc tcc gtg acc ctg atc atc ctc atc gtg gag ctg tgc ggg ctc        248
Cys Phe Ser Val Thr Leu Ile Ile Leu Ile Val Glu Leu Cys Gly Leu
    55                  60                  65 cag gcc cgc ttc ccc ctg tct tgg cgc aac ttc ccc atc acc ttc gcc        296
Gln Ala Arg Phe Pro Leu Ser Trp Arg Asn Phe Pro Ile Thr Phe Ala
        70                  75                  80 tgc tat gcg gcc ctc ttc tgc ctc tcg gcc tcc atc atc tac ccc acc        344
Cys Tyr Ala Ala Leu Phe Cys Leu Ser Ala Ser Ile Ile Tyr Pro Thr
            85                  90                  95 acc tat gtc cag ttc ctg tcc cac ggc gtc cgg gac cac gcc atc            392
Thr Tyr Val Gln Phe Leu Ser His Gly Arg Ser Arg Asp His Ala Ile
100                 105                 110                 115 gcc gcc acc ttc ttc tcc tgc atc gcg tgt gtg gct tac gcc acc gaa        440
Ala Ala Thr Phe Phe Ser Cys Ile Ala Cys Val Ala Tyr Ala Thr Glu
                120                 125                 130 gtg gcc tgg acc cgg gcc cgg ccc ggc gag atc act ggc tat atg gcc        488
Val Ala Trp Thr Arg Ala Arg Pro Gly Glu Ile Thr Gly Tyr Met Ala
            135                 140                 145 acc gta ccc ggg ctg ctg aag gtg ctg gag acc ttc gtt gcc tgc atc        536
Thr Val Pro Gly Leu Leu Lys Val Leu Glu Thr Phe Val Ala Cys Ile
        150                 155                 160 atc ttc gcg ttc atc agc gac ccc aac ctg tac cag cac cag ccg gcc        584
Ile Phe Ala Phe Ile Ser Asp Pro Asn Leu Tyr Gln His Gln Pro Ala
165                 170                 175 ctg gag tgg tgc gtg gcg gtg tac gcc atc tgc ttc atc cta gcg gcc        632
Leu Glu Trp Cys Val Ala Val Tyr Ala Ile Cys Phe Ile Leu Ala Ala
180                 185                 190                 195 atc gcc atc ctg ctg aac ctg ggg gag tgc acc aac gtg cta ccc atc        680
Ile Ala Ile Leu Leu Asn Leu Gly Glu Cys Thr Asn Val Leu Pro Ile
                200                 205                 210 ccc ttc ccc agc ttc ctg tcg ggg ctg gcc ttg ctg tct gtc ctc ctc        728
Pro Phe Pro Ser Phe Leu Ser Gly Leu Ala Leu Leu Ser Val Leu Leu
            215                 220                 225 tat gcc acc gcc ctt gtt ctc tgg ccc ctc tac cag ttc gat gag aag        776
Tyr Ala Thr Ala Leu Val Leu Trp Pro Leu Tyr Gln Phe Asp Glu Lys
        230                 235                 240 tat ggc ggc cag cct cgg cgc tcg aga gat gta agc tgc agc cgc agc        824
Tyr Gly Gly Gln Pro Arg Arg Ser Arg Asp Val Ser Cys Ser Arg Ser
245                 250                 255 cat gcc tac tac gtg tgt gcc tgg gac cgc cga ctg gct gtg gcc atc        872
His Ala Tyr Tyr Val Cys Ala Trp Asp Arg Arg Leu Ala Val Ala Ile
260                 265                 270                 275 ctg acg gcc atc aac cta ctg gcg tat gtg gct gac ctg gtg cac tct        920
Leu Thr Ala Ile Asn Leu Leu Ala Tyr Val Ala Asp Leu Val His Ser
                280                 285                 290 gcc cac ctg gtt ttt gtc aag gtc taagactctc ccaagaggct cccgttccct      974
Ala His Leu Val Phe Val Lys Val
                295 ctccaacctc tttgttcttc ttgcccgagt tttctttatg gagtacttct ttcctccgcc     1034 tttcctctgt tttcctcttc ctgtctccc                                       1063
```

<210> SEQ ID NO 28
<211> LENGTH: 299
<212> TYPE: PRT
<213> ORGANISM: Homo sapiens

<400> SEQUENCE: 28

```
Met Ile Val Gly Ser Pro Arg Ala Leu Thr Gln Pro Leu Gly Leu Leu
  1               5                  10                  15

Arg Leu Leu Gln Leu Val Ser Thr Cys Val Ala Phe Ser Leu Val Ala
             20                  25                  30

Ser Val Gly Ala Trp Thr Gly Ser Met Gly Asn Trp Ser Met Phe Thr
         35                  40                  45

Trp Cys Phe Cys Phe Ser Val Thr Leu Ile Ile Leu Ile Val Glu Leu
     50                  55                  60

Cys Gly Leu Gln Ala Arg Phe Pro Leu Ser Trp Arg Asn Phe Pro Ile
 65                  70                  75                  80

Thr Phe Ala Cys Tyr Ala Ala Leu Phe Cys Leu Ser Ala Ser Ile Ile
                 85                  90                  95

Tyr Pro Thr Thr Tyr Val Gln Phe Leu Ser His Gly Arg Ser Arg Asp
            100                 105                 110

His Ala Ile Ala Ala Thr Phe Phe Ser Cys Ile Ala Cys Val Ala Tyr
            115                 120                 125

Ala Thr Glu Val Ala Trp Thr Arg Ala Arg Pro Gly Glu Ile Thr Gly
        130                 135                 140

Tyr Met Ala Thr Val Pro Gly Leu Leu Lys Val Leu Glu Thr Phe Val
145                 150                 155                 160

Ala Cys Ile Ile Phe Ala Phe Ile Ser Asp Pro Asn Leu Tyr Gln His
                165                 170                 175

Gln Pro Ala Leu Glu Trp Cys Val Ala Val Tyr Ala Ile Cys Phe Ile
            180                 185                 190

Leu Ala Ala Ile Ala Ile Leu Leu Asn Leu Gly Glu Cys Thr Asn Val
        195                 200                 205

Leu Pro Ile Pro Phe Pro Ser Phe Leu Ser Gly Leu Ala Leu Leu Ser
210                 215                 220

Val Leu Leu Tyr Ala Thr Ala Leu Val Leu Trp Pro Leu Tyr Gln Phe
225                 230                 235                 240

Asp Glu Lys Tyr Gly Gly Gln Pro Arg Arg Ser Arg Asp Val Ser Cys
                245                 250                 255

Ser Arg Ser His Ala Tyr Tyr Val Cys Ala Trp Asp Arg Arg Leu Ala
            260                 265                 270

Val Ala Ile Leu Thr Ala Ile Asn Leu Leu Ala Tyr Val Ala Asp Leu
        275                 280                 285

Val His Ser Ala His Leu Val Phe Val Lys Val
            290                 295

<210> SEQ ID NO 29
<211> LENGTH: 1890
<212> TYPE: DNA
<213> ORGANISM: Homo sapiens
<220> FEATURE:
<221> NAME/KEY: CDS
<222> LOCATION: (1)..(1890)

<400> SEQUENCE: 29 gga tcc ggt ttc cca gaa gat tct gag cca atc agt att tcg cat ggc    48
Gly Ser Gly Phe Pro Glu Asp Ser Glu Pro Ile Ser Ile Ser His Gly
  1               5                  10                  15 aac tat aca aaa cag tat ccg gtg ttt gtg ggc cac aag cca gga cgg    96
Asn Tyr Thr Lys Gln Tyr Pro Val Phe Val Gly His Lys Pro Gly Arg
             20                  25                  30 aac acc aca cag agg cac agg ctg gac atc cag atg att atg atc atg   144
Asn Thr Thr Gln Arg His Arg Leu Asp Ile Gln Met Ile Met Ile Met
```

-continued

|     |     |     |     |     | 35  |     |     |     |     | 40  |     |     |     |     | 45  |      |
|-----|-----|-----|-----|-----|-----|-----|-----|-----|-----|-----|-----|-----|-----|-----|-----|------|
| aac | gga | acc | ctc | tac | att | gct | gct | agg | gac | cat | att | tat | act | gtt | gat | 192  |
| Asn | Gly | Thr | Leu | Tyr | Ile | Ala | Ala | Arg | Asp | His | Ile | Tyr | Thr | Val | Asp |      |
|     | 50  |     |     |     |     | 55  |     |     |     |     | 60  |     |     |     |     |      |

| ata | gac | aca | tca | cac | acg | gaa | gaa | att | tat | tgt | agc | aaa | aaa | ctg | aca | 240 |
|-----|-----|-----|-----|-----|-----|-----|-----|-----|-----|-----|-----|-----|-----|-----|-----|-----|
| Ile | Asp | Thr | Ser | His | Thr | Glu | Glu | Ile | Tyr | Cys | Ser | Lys | Lys | Leu | Thr |     |
| 65  |     |     |     |     | 70  |     |     |     |     | 75  |     |     |     |     | 80  |     |

| tgg | aaa | tct | aga | cag | gcc | gat | gta | gac | aca | tgc | aga | atg | aag | gga | aaa | 288 |
|-----|-----|-----|-----|-----|-----|-----|-----|-----|-----|-----|-----|-----|-----|-----|-----|-----|
| Trp | Lys | Ser | Arg | Gln | Ala | Asp | Val | Asp | Thr | Cys | Arg | Met | Lys | Gly | Lys |     |
|     |     |     |     | 85  |     |     |     |     | 90  |     |     |     |     | 95  |     |     |

| cat | aag | gat | gag | tgc | cac | aac | ttt | att | aaa | gtt | ctt | cta | aag | aaa | aac | 336 |
|-----|-----|-----|-----|-----|-----|-----|-----|-----|-----|-----|-----|-----|-----|-----|-----|-----|
| His | Lys | Asp | Glu | Cys | His | Asn | Phe | Ile | Lys | Val | Leu | Leu | Lys | Lys | Asn |     |
|     |     |     |     | 100 |     |     |     |     | 105 |     |     |     |     | 110 |     |     |

| gat | gat | gca | ttg | ttt | gtc | tgt | gga | act | aat | gcc | ttc | aac | cct | tcc | tgc | 384 |
|-----|-----|-----|-----|-----|-----|-----|-----|-----|-----|-----|-----|-----|-----|-----|-----|-----|
| Asp | Asp | Ala | Leu | Phe | Val | Cys | Gly | Thr | Asn | Ala | Phe | Asn | Pro | Ser | Cys |     |
|     |     |     | 115 |     |     |     |     | 120 |     |     |     |     | 125 |     |     |     |

| aga | aac | tat | aag | atg | gat | aca | ttg | gaa | cca | ttc | ggg | gat | gaa | ttc | agc | 432 |
|-----|-----|-----|-----|-----|-----|-----|-----|-----|-----|-----|-----|-----|-----|-----|-----|-----|
| Arg | Asn | Tyr | Lys | Met | Asp | Thr | Leu | Glu | Pro | Phe | Gly | Asp | Glu | Phe | Ser |     |
|     | 130 |     |     |     |     | 135 |     |     |     |     | 140 |     |     |     |     |     |

| gga | atg | gcc | aga | tgc | cca | tat | gat | gcc | aaa | cat | gcc | aac | gtt | gca | ctg | 480 |
|-----|-----|-----|-----|-----|-----|-----|-----|-----|-----|-----|-----|-----|-----|-----|-----|-----|
| Gly | Met | Ala | Arg | Cys | Pro | Tyr | Asp | Ala | Lys | His | Ala | Asn | Val | Ala | Leu |     |
| 145 |     |     |     |     | 150 |     |     |     |     | 155 |     |     |     |     | 160 |     |

| ttt | gca | gat | gga | aaa | cta | tac | tca | gcc | aca | gtg | act | gac | ttc | ctt | gcc | 528 |
|-----|-----|-----|-----|-----|-----|-----|-----|-----|-----|-----|-----|-----|-----|-----|-----|-----|
| Phe | Ala | Asp | Gly | Lys | Leu | Tyr | Ser | Ala | Thr | Val | Thr | Asp | Phe | Leu | Ala |     |
|     |     |     |     | 165 |     |     |     |     | 170 |     |     |     |     | 175 |     |     |

| att | gac | gca | gtc | att | tac | cgg | agt | ctt | gga | gaa | agc | cct | acc | ctg | cgg | 576 |
|-----|-----|-----|-----|-----|-----|-----|-----|-----|-----|-----|-----|-----|-----|-----|-----|-----|
| Ile | Asp | Ala | Val | Ile | Tyr | Arg | Ser | Leu | Gly | Glu | Ser | Pro | Thr | Leu | Arg |     |
|     |     |     | 180 |     |     |     |     | 185 |     |     |     |     | 190 |     |     |     |

| acc | gtc | aag | cac | gat | tca | aaa | tgg | ttg | aaa | gaa | cca | tac | ttt | gtt | caa | 624 |
|-----|-----|-----|-----|-----|-----|-----|-----|-----|-----|-----|-----|-----|-----|-----|-----|-----|
| Thr | Val | Lys | His | Asp | Ser | Lys | Trp | Leu | Lys | Glu | Pro | Tyr | Phe | Val | Gln |     |
|     | 195 |     |     |     |     | 200 |     |     |     |     | 205 |     |     |     |     |     |

| gcc | gtg | gat | tac | gga | gat | tat | atc | tac | ttc | ttc | ttc | agg | gaa | ata | gca | 672 |
|-----|-----|-----|-----|-----|-----|-----|-----|-----|-----|-----|-----|-----|-----|-----|-----|-----|
| Ala | Val | Asp | Tyr | Gly | Asp | Tyr | Ile | Tyr | Phe | Phe | Phe | Arg | Glu | Ile | Ala |     |
|     | 210 |     |     |     |     | 215 |     |     |     |     | 220 |     |     |     |     |     |

| gtg | gag | tat | aac | acc | atg | gga | aag | gta | gtt | ttc | cca | aga | gtg | gct | cag | 720 |
|-----|-----|-----|-----|-----|-----|-----|-----|-----|-----|-----|-----|-----|-----|-----|-----|-----|
| Val | Glu | Tyr | Asn | Thr | Met | Gly | Lys | Val | Val | Phe | Pro | Arg | Val | Ala | Gln |     |
| 225 |     |     |     |     | 230 |     |     |     |     | 235 |     |     |     |     | 240 |     |

| gtt | tgt | aag | aat | gat | atg | gga | gga | tct | caa | aga | gtc | ctg | gag | aaa | cag | 768 |
|-----|-----|-----|-----|-----|-----|-----|-----|-----|-----|-----|-----|-----|-----|-----|-----|-----|
| Val | Cys | Lys | Asn | Asp | Met | Gly | Gly | Ser | Gln | Arg | Val | Leu | Glu | Lys | Gln |     |
|     |     |     |     | 245 |     |     |     |     | 250 |     |     |     |     | 255 |     |     |

| tgg | acg | tcg | ttc | ctg | aag | gcg | cgc | ttg | aac | tgc | tca | gtt | cct | gga | gac | 816 |
|-----|-----|-----|-----|-----|-----|-----|-----|-----|-----|-----|-----|-----|-----|-----|-----|-----|
| Trp | Thr | Ser | Phe | Leu | Lys | Ala | Arg | Leu | Asn | Cys | Ser | Val | Pro | Gly | Asp |     |
|     |     |     | 260 |     |     |     |     | 265 |     |     |     |     | 270 |     |     |     |

| tct | cat | ttt | tat | ttc | aac | att | ctc | cag | gca | gtt | aca | gat | gtg | att | cgt | 864 |
|-----|-----|-----|-----|-----|-----|-----|-----|-----|-----|-----|-----|-----|-----|-----|-----|-----|
| Ser | His | Phe | Tyr | Phe | Asn | Ile | Leu | Gln | Ala | Val | Thr | Asp | Val | Ile | Arg |     |
|     |     | 275 |     |     |     |     | 280 |     |     |     |     | 285 |     |     |     |     |

| atc | aac | ggg | cgt | gat | gtt | gtc | ctg | gca | acg | ttt | tct | aca | cct | tat | aac | 912 |
|-----|-----|-----|-----|-----|-----|-----|-----|-----|-----|-----|-----|-----|-----|-----|-----|-----|
| Ile | Asn | Gly | Arg | Asp | Val | Val | Leu | Ala | Thr | Phe | Ser | Thr | Pro | Tyr | Asn |     |
|     | 290 |     |     |     |     | 295 |     |     |     |     | 300 |     |     |     |     |     |

| agc | atc | cct | ggg | tct | gca | gtc | tgt | gcc | tat | gac | atg | ctt | gac | att | gcc | 960 |
|-----|-----|-----|-----|-----|-----|-----|-----|-----|-----|-----|-----|-----|-----|-----|-----|-----|
| Ser | Ile | Pro | Gly | Ser | Ala | Val | Cys | Ala | Tyr | Asp | Met | Leu | Asp | Ile | Ala |     |
| 305 |     |     |     |     | 310 |     |     |     |     | 315 |     |     |     |     | 320 |     |

| agt | gtt | ttt | act | ggg | aga | ttc | aag | gaa | cag | aag | tct | cct | gat | tcc | acc | 1008 |
|-----|-----|-----|-----|-----|-----|-----|-----|-----|-----|-----|-----|-----|-----|-----|-----|------|
| Ser | Val | Phe | Thr | Gly | Arg | Phe | Lys | Glu | Gln | Lys | Ser | Pro | Asp | Ser | Thr |      |
|     |     |     |     | 325 |     |     |     |     | 330 |     |     |     |     | 335 |     |      |

| tgg | aca | cca | gtt | cct | gat | gaa | cga | gtt | cct | aag | ccc | agg | cca | ggt | tgc | 1056 |
|-----|-----|-----|-----|-----|-----|-----|-----|-----|-----|-----|-----|-----|-----|-----|-----|------|
| Trp | Thr | Pro | Val | Pro | Asp | Glu | Arg | Val | Pro | Lys | Pro | Arg | Pro | Gly | Cys |      |
|     |     |     | 340 |     |     |     |     | 345 |     |     |     |     | 350 |     |     |      |

| tgt | gct | ggc | tca | tcc | tcc | tta | gaa | aga | tat | gca | acc | tcc | aat | gag | ttc | 1104 |

```
                Cys Ala Gly Ser Ser Ser Leu Glu Arg Tyr Ala Thr Ser Asn Glu Phe
                    355                 360                 365 cct gat gat acc ctg aac ttc atc aag acg cac ccg ctc atg gat gag      1152
Pro Asp Asp Thr Leu Asn Phe Ile Lys Thr His Pro Leu Met Asp Glu
370                 375                 380 gca gtg ccc tcc atc ttc aac agg cca tgg ttc ctg aga aca atg gtc      1200
Ala Val Pro Ser Ile Phe Asn Arg Pro Trp Phe Leu Arg Thr Met Val
385                 390                 395                 400 aga tac cgc ctt acc aaa att gca gtg gac aca gct gct ggg cca tat      1248
Arg Tyr Arg Leu Thr Lys Ile Ala Val Asp Thr Ala Ala Gly Pro Tyr
                405                 410                 415 cag aat cac act gtg gtt ttt ctg gga tca gag aag gga atc atc ttg      1296
Gln Asn His Thr Val Val Phe Leu Gly Ser Glu Lys Gly Ile Ile Leu
            420                 425                 430 aag ttt ttg gcc aga ata gga aat agt ggt ttt cta aat gac agc ctt      1344
Lys Phe Leu Ala Arg Ile Gly Asn Ser Gly Phe Leu Asn Asp Ser Leu
        435                 440                 445 ttc ctg gag gag atg agt gtt tac aac tct gaa aaa tgc agc tat gat      1392
Phe Leu Glu Glu Met Ser Val Tyr Asn Ser Glu Lys Cys Ser Tyr Asp
450                 455                 460 gga gtc gaa gac aaa agg atc atg ggc atg cag ctg gac aga gca agc      1440
Gly Val Glu Asp Lys Arg Ile Met Gly Met Gln Leu Asp Arg Ala Ser
465                 470                 475                 480 agc tct ctg tat gtt gcg ttc tct acc tgt gtg ata aag gtt ccc ctt      1488
Ser Ser Leu Tyr Val Ala Phe Ser Thr Cys Val Ile Lys Val Pro Leu
                485                 490                 495 ggc cgg tgt gaa cga cat ggg aag tgt aaa aaa acc tgt att gcc tcc      1536
Gly Arg Cys Glu Arg His Gly Lys Cys Lys Lys Thr Cys Ile Ala Ser
            500                 505                 510 aga gac cca tat tgt gga tgg ata aag gaa ggt ggt gcc tgc agc cat      1584
Arg Asp Pro Tyr Cys Gly Trp Ile Lys Glu Gly Gly Ala Cys Ser His
        515                 520                 525 tta tca ccc aac agc aga ctg act ttt gag cag gac ata gag cgt ggc      1632
Leu Ser Pro Asn Ser Arg Leu Thr Phe Glu Gln Asp Ile Glu Arg Gly
530                 535                 540 aat aca gat ggt ctg ggg gac tgt cac aat tcc ttt gtg gca ctg aat      1680
Asn Thr Asp Gly Leu Gly Asp Cys His Asn Ser Phe Val Ala Leu Asn
545                 550                 555                 560 ggg cat tcc agt tcc ctc ttg ccc agc aca acc aca tca gat tcg acg      1728
Gly His Ser Ser Ser Leu Leu Pro Ser Thr Thr Thr Ser Asp Ser Thr
                565                 570                 575 gct caa gag ggg tat gag tct agg gga gga atg ctg gac tgg aag cat      1776
Ala Gln Glu Gly Tyr Glu Ser Arg Gly Gly Met Leu Asp Trp Lys His
            580                 585                 590 ctg ctt gac tca cct gac agc aca gac cct ttg ggg gca gtg tct tcc      1824
Leu Leu Asp Ser Pro Asp Ser Thr Asp Pro Leu Gly Ala Val Ser Ser
        595                 600                 605 cat aat cac caa gac aag aag gga gtg att cgg gaa agt tac ctc aaa      1872
His Asn His Gln Asp Lys Lys Gly Val Ile Arg Glu Ser Tyr Leu Lys
    610                 615                 620 ggc cac gac cag ctc gag                                              1890
Gly His Asp Gln Leu Glu
625                 630

<210> SEQ ID NO 30
<211> LENGTH: 630
<212> TYPE: PRT
<213> ORGANISM: Homo sapiens

<400> SEQUENCE: 30
```

-continued

```
Gly Ser Gly Phe Pro Glu Asp Ser Glu Pro Ile Ser Ile Ser His Gly
 1               5                  10                  15

Asn Tyr Thr Lys Gln Tyr Pro Val Phe Val Gly His Lys Pro Gly Arg
             20                  25                  30

Asn Thr Thr Gln Arg His Arg Leu Asp Ile Gln Met Ile Met Ile Met
         35                  40                  45

Asn Gly Thr Leu Tyr Ile Ala Ala Arg Asp His Ile Tyr Thr Val Asp
     50                  55                  60

Ile Asp Thr Ser His Thr Glu Glu Ile Tyr Cys Ser Lys Lys Leu Thr
 65                  70                  75                  80

Trp Lys Ser Arg Gln Ala Asp Val Asp Thr Cys Arg Met Lys Gly Lys
                 85                  90                  95

His Lys Asp Glu Cys His Asn Phe Ile Lys Val Leu Leu Lys Lys Asn
            100                 105                 110

Asp Asp Ala Leu Phe Val Cys Gly Thr Asn Ala Phe Asn Pro Ser Cys
        115                 120                 125

Arg Asn Tyr Lys Met Asp Thr Leu Glu Pro Phe Gly Asp Glu Phe Ser
    130                 135                 140

Gly Met Ala Arg Cys Pro Tyr Asp Ala Lys His Ala Asn Val Ala Leu
145                 150                 155                 160

Phe Ala Asp Gly Lys Leu Tyr Ser Ala Thr Val Thr Asp Phe Leu Ala
                165                 170                 175

Ile Asp Ala Val Ile Tyr Arg Ser Leu Gly Glu Ser Pro Thr Leu Arg
            180                 185                 190

Thr Val Lys His Asp Ser Lys Trp Leu Lys Glu Pro Tyr Phe Val Gln
        195                 200                 205

Ala Val Asp Tyr Gly Asp Tyr Ile Tyr Phe Phe Arg Glu Ile Ala
    210                 215                 220

Val Glu Tyr Asn Thr Met Gly Lys Val Val Phe Pro Arg Val Ala Gln
225                 230                 235                 240

Val Cys Lys Asn Asp Met Gly Gly Ser Gln Arg Val Leu Glu Lys Gln
                245                 250                 255

Trp Thr Ser Phe Leu Lys Ala Arg Leu Asn Cys Ser Val Pro Gly Asp
            260                 265                 270

Ser His Phe Tyr Phe Asn Ile Leu Gln Ala Val Thr Asp Val Ile Arg
        275                 280                 285

Ile Asn Gly Arg Asp Val Val Leu Ala Thr Phe Ser Thr Pro Tyr Asn
    290                 295                 300

Ser Ile Pro Gly Ser Ala Val Cys Ala Tyr Asp Met Leu Asp Ile Ala
305                 310                 315                 320

Ser Val Phe Thr Gly Arg Phe Lys Glu Gln Lys Ser Pro Asp Ser Thr
                325                 330                 335

Trp Thr Pro Val Pro Asp Glu Arg Val Pro Lys Pro Arg Pro Gly Cys
            340                 345                 350

Cys Ala Gly Ser Ser Ser Leu Glu Arg Tyr Ala Thr Ser Asn Glu Phe
        355                 360                 365

Pro Asp Asp Thr Leu Asn Phe Ile Lys Thr His Pro Leu Met Asp Glu
    370                 375                 380

Ala Val Pro Ser Ile Phe Asn Arg Pro Trp Phe Leu Arg Thr Met Val
385                 390                 395                 400

Arg Tyr Arg Leu Thr Lys Ile Ala Val Asp Thr Ala Ala Gly Pro Tyr
                405                 410                 415

Gln Asn His Thr Val Val Phe Leu Gly Ser Glu Lys Gly Ile Ile Leu
```

-continued

```
                420               425               430
Lys Phe Leu Ala Arg Ile Gly Asn Ser Gly Phe Leu Asn Asp Ser Leu
            435               440               445
Phe Leu Glu Glu Met Ser Val Tyr Asn Ser Glu Lys Cys Ser Tyr Asp
        450               455               460
Gly Val Glu Asp Lys Arg Ile Met Gly Met Gln Leu Asp Arg Ala Ser
465               470               475               480
Ser Ser Leu Tyr Val Ala Phe Ser Thr Cys Val Ile Lys Val Pro Leu
                485               490               495
Gly Arg Cys Glu Arg His Gly Lys Cys Lys Lys Thr Cys Ile Ala Ser
            500               505               510
Arg Asp Pro Tyr Cys Gly Trp Ile Lys Glu Gly Ala Cys Ser His
        515               520               525
Leu Ser Pro Asn Ser Arg Leu Thr Phe Glu Gln Asp Ile Glu Arg Gly
        530               535               540
Asn Thr Asp Gly Leu Gly Asp Cys His Asn Ser Phe Val Ala Leu Asn
545               550               555               560
Gly His Ser Ser Ser Leu Leu Pro Ser Thr Thr Thr Ser Asp Ser Thr
                565               570               575
Ala Gln Glu Gly Tyr Glu Ser Arg Gly Gly Met Leu Asp Trp Lys His
            580               585               590
Leu Leu Asp Ser Pro Asp Ser Thr Asp Pro Leu Gly Ala Val Ser Ser
            595               600               605
His Asn His Gln Asp Lys Lys Gly Val Ile Arg Glu Ser Tyr Leu Lys
        610               615               620
Gly His Asp Gln Leu Glu
625               630

<210> SEQ ID NO 31
<211> LENGTH: 1356
<212> TYPE: DNA
<213> ORGANISM: Homo sapiens

<400> SEQUENCE: 31
ggatccaact gccctccgt ctgctcgtgc agtaaccagt tcagcaaggt ggtgtgcacg    60
cgccggggcc tctccgagt cccgcagggt attccctcga cacccggta cctcaacctc   120 atggagaaca catccagat gatccaggcc gacaccttcc gccacctcca ccacctggag   180
gtcctgcagt tgggcaggaa ctccatccgg cagattgagg tgggggcctt caacggcctg   240
gccagcctca cacctggga gctgttcgac aactggctga cagtcatccc tagcggggcc   300
tttgaatacc tgtccaagct gcgggagctc tggcttcgca caacccccat cgaaagcatc   360
ccctcttacg tcttcaaccg ggtgccctcc ctcatgcgcc tggacttggg ggagctcaag   420
aagctggagt atatctctga gggagctttt gagggggctgt tcaacctcaa gtatctgaac   480
ttgggcatgt gcaacattaa agacatgccc aatctcaccc cctggtggg gctggaggag   540 ctggagatgt cagggaacca cttccctgag atcaggcctg gctccttcca tggcctgagc   600
tccctcaaga agctctgggt catgaactca caggtcagcc tgattgagcg gaatgctttt   660
gacgggctgg cttcacttgt ggaactcaac ttggcccaca ataacctctc ttctttgccc   720
catgacctct ttacccgct gaggtacctg gtggagttgc atctacacca caaccttgg   780 aactgtgatt gtgacattct gtggctagcc tggtggcttc gagagtatat acccaccaat   840
tccacctgct gtggccgctg tcatgctccc atgcacatgc gaggccgcta cctcgtggag   900
```

-continued

```
gtggaccagg cctccttcca gtgctctgcc cccttcatca tggacgcacc tcgagacctc    960
aacatttctg agggtcggat ggcagaactt aagtgtcgga ctcccctat  gtcctccgtg   1020 aagtggttgc tgcccaatgg gacagtgctc agccatgcct cccgccaccc aaggatctct   1080
gtcctcaacg acggcacctt gaactttttcc cacgtgctgc tttcagacac cggggtgtac  1140
acatgcatgg tgaccaatgt tgcaggcaac tccaacgcct cggcctacct caatgtgagc   1200
acggctgagc ttaacacctc caactacagc ttcttcacca cagtaacagt ggagaccacg   1260
gagatctcgc ctgaggacac aacgcgaaag tacaagcctg ttcctaccac gtccactggt   1320
taccagccgg catataccac ctctaccacg gtcgag                             1356
```

<210> SEQ ID NO 32
<211> LENGTH: 448
<212> TYPE: PRT
<213> ORGANISM: Homo sapiens

<400> SEQUENCE: 32

```
Asn Cys Pro Ser Val Cys Ser Cys Ser Asn Gln Phe Ser Lys Val Val
 1               5                  10                  15

Cys Thr Arg Arg Gly Leu Ser Glu Val Pro Gln Gly Ile Pro Ser Asn
            20                  25                  30

Thr Arg Tyr Leu Asn Leu Met Glu Asn Asn Ile Gln Met Ile Gln Ala
        35                  40                  45

Asp Thr Phe Arg His Leu His His Leu Glu Val Leu Gln Leu Gly Arg
    50                  55                  60

Asn Ser Ile Arg Gln Ile Glu Val Gly Ala Phe Asn Gly Leu Ala Ser
65                  70                  75                  80

Leu Asn Thr Leu Glu Leu Phe Asp Asn Trp Leu Thr Val Ile Pro Ser
                85                  90                  95

Gly Ala Phe Glu Tyr Leu Ser Lys Leu Arg Glu Leu Trp Leu Arg Asn
           100                 105                 110

Asn Pro Ile Glu Ser Ile Pro Ser Tyr Ala Phe Asn Arg Val Pro Ser
       115                 120                 125

Leu Met Arg Leu Asp Leu Gly Glu Leu Lys Lys Leu Glu Tyr Ile Ser
   130                 135                 140

Glu Gly Ala Phe Glu Gly Leu Phe Asn Leu Lys Tyr Leu Asn Leu Gly
145                 150                 155                 160

Met Cys Asn Ile Lys Asp Met Pro Asn Leu Thr Pro Leu Val Gly Leu
                165                 170                 175

Glu Glu Leu Glu Met Ser Gly Asn His Phe Pro Glu Ile Arg Pro Gly
           180                 185                 190

Ser Phe His Gly Leu Ser Ser Leu Lys Lys Leu Trp Val Met Asn Ser
       195                 200                 205

Gln Val Ser Leu Ile Glu Arg Asn Ala Phe Asp Gly Leu Ala Ser Leu
   210                 215                 220

Val Glu Leu Asn Leu Ala His Asn Asn Leu Ser Ser Leu Pro His Asp
225                 230                 235                 240

Leu Phe Thr Pro Leu Arg Tyr Leu Val Glu Leu His Leu His Asn
                245                 250                 255

Pro Trp Asn Cys Asp Cys Asp Ile Leu Trp Leu Ala Trp Trp Leu Arg
           260                 265                 270

Glu Tyr Ile Pro Thr Asn Ser Thr Cys Cys Gly Arg Cys His Ala Pro
       275                 280                 285

Met His Met Arg Gly Arg Tyr Leu Val Glu Val Asp Gln Ala Ser Phe
```

```
                    290                 295                 300
Gln Cys Ser Ala Pro Phe Ile Met Asp Ala Pro Arg Asp Leu Asn Ile
305                 310                 315                 320

Ser Glu Gly Arg Met Ala Glu Leu Lys Cys Arg Thr Pro Pro Met Ser
                325                 330                 335

Ser Val Lys Trp Leu Leu Pro Asn Gly Thr Val Leu Ser His Ala Ser
                340                 345                 350

Arg His Pro Arg Ile Ser Val Leu Asn Asp Gly Thr Leu Asn Phe Ser
                355                 360                 365

His Val Leu Leu Ser Asp Thr Gly Val Tyr Thr Cys Met Val Thr Asn
                370                 375                 380

Val Ala Gly Asn Ser Asn Ala Ser Ala Tyr Leu Asn Val Ser Thr Ala
385                 390                 395                 400

Glu Leu Asn Thr Ser Asn Tyr Ser Phe Phe Thr Thr Val Thr Val Glu
                405                 410                 415

Thr Thr Glu Ile Ser Pro Glu Asp Thr Thr Arg Lys Tyr Lys Pro Val
                420                 425                 430

Pro Thr Thr Ser Thr Gly Tyr Gln Pro Ala Tyr Thr Thr Ser Thr Thr
                435                 440                 445

<210> SEQ ID NO 33
<211> LENGTH: 33
<212> TYPE: DNA
<213> ORGANISM: Artificial Sequence
<220> FEATURE:
<223> OTHER INFORMATION: Description of Artificial Sequence: Primer

<400> SEQUENCE: 33
ggatccggtt tcccagaaga ttctgagcca atc                         33

<210> SEQ ID NO 34
<211> LENGTH: 33
<212> TYPE: DNA
<213> ORGANISM: Artificial Sequence
<220> FEATURE:
<223> OTHER INFORMATION: Description of Artificial Sequence: Primer

<400> SEQUENCE: 34
ctcgagctgg tcgtggcctt tgaggtaact ttc                         33

<210> SEQ ID NO 35
<211> LENGTH: 19
<212> TYPE: DNA
<213> ORGANISM: Artificial Sequence
<220> FEATURE:
<223> OTHER INFORMATION: Description of Artificial Sequence: Primer

<400> SEQUENCE: 35
cacaagccag gacggaaca                                         19

<210> SEQ ID NO 36
<211> LENGTH: 19
<212> TYPE: DNA
<213> ORGANISM: Artificial Sequence
<220> FEATURE:
<223> OTHER INFORMATION: Description of Artificial Sequence: Primer

<400> SEQUENCE: 36
tggaactaat gccttcaac                                         19

<210> SEQ ID NO 37
```

```
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 37
gagtcctgga gaaacagtgg a                                            21

<210> SEQ ID NO 38
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 38
atgaggcagt gccctccatc                                              20

<210> SEQ ID NO 39
<211> LENGTH: 19
<212> TYPE: DNA
<213> ORGANISM: Artificial Sequence
<220> FEATURE:
<223> OTHER INFORMATION: Description of Artificial Sequence: Primer

<400> SEQUENCE: 39
ccatattgtg gatggataa                                               19

<210> SEQ ID NO 40
<211> LENGTH: 19
<212> TYPE: DNA
<213> ORGANISM: Artificial Sequence
<220> FEATURE:
<223> OTHER INFORMATION: Description of Artificial Sequence: Primer

<400> SEQUENCE: 40
gacactcaat ccaaagacc                                               19

<210> SEQ ID NO 41
<211> LENGTH: 19
<212> TYPE: DNA
<213> ORGANISM: Artificial Sequence
<220> FEATURE:
<223> OTHER INFORMATION: Description of Artificial Sequence: Primer

<400> SEQUENCE: 41
ccatcacgca gcagggcta                                               19

<210> SEQ ID NO 42
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 42
ctcgtcctcg agggtaagcc tatccctaac                                   30

<210> SEQ ID NO 43
<211> LENGTH: 31
<212> TYPE: DNA
<213> ORGANISM: Artificial Sequence
<220> FEATURE:
<223> OTHER INFORMATION: Description of Artificial Sequence: Primer

<400> SEQUENCE: 43
```

```
ctcgtcgggc ccctgatcag cgggtttaaa c                            31

<210> SEQ ID NO 44
<211> LENGTH: 38
<212> TYPE: DNA
<213> ORGANISM: Artificial Sequence
<220> FEATURE:
<223> OTHER INFORMATION: Description of Artificial Sequence: Primer

<400> SEQUENCE: 44
ctcgtcggat ccaactgccc ctccgtctgc tcgtgcag                     38

<210> SEQ ID NO 45
<211> LENGTH: 39
<212> TYPE: DNA
<213> ORGANISM: Artificial Sequence
<220> FEATURE:
<223> OTHER INFORMATION: Description of Artificial Sequence: Primer

<400> SEQUENCE: 45
ctcgtcgtcg accgtggtag aggtggtata tgccggctg                    39

<210> SEQ ID NO 46
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 46
gtgcagtaac cagttcagca                                         20

<210> SEQ ID NO 47
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 47
acctgtccaa gctgcgggag                                         20

<210> SEQ ID NO 48
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 48
ttgacgggct ggcttcactt                                         20

<210> SEQ ID NO 49
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 49
gacagtgctc agccacgcct                                         20

<210> SEQ ID NO 50
<211> LENGTH: 25
<212> TYPE: DNA
```

```
<213> ORGANISM: Artificial Sequence
<220> FEATURE:
<223> OTHER INFORMATION: Description of Artificial Sequence: Primer

<400> SEQUENCE: 50
cctttcaaaa tcctctctga ctcac                                         25

<210> SEQ ID NO 51
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 51
tcaccgaaga aaacgacac ac                                             22

<210> SEQ ID NO 52
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 52
cctggcaccc tggcagctca ga                                            22

<210> SEQ ID NO 53
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 53
catcttcaac aggccatggt t                                             21

<210> SEQ ID NO 54
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 54
agcagctgtg tccactgcaa                                               20

<210> SEQ ID NO 55
<211> LENGTH: 31
<212> TYPE: DNA
<213> ORGANISM: Artificial Sequence
<220> FEATURE:
<223> OTHER INFORMATION: Description of Artificial Sequence: Primer

<400> SEQUENCE: 55
tgagaacaat ggtcagatac cgccttacca a                                  31

<210> SEQ ID NO 56
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 56
cgcagtcatt taccggagtc tt                                            22
```

<210> SEQ ID NO 57
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 57
ttctttcaac cattttgaat cgtg                                          24

<210> SEQ ID NO 58
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 58
agccctaccc tgcggaccgt ca                                            22

<210> SEQ ID NO 59
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 59
tcctttgtgg cactgaatgg                                               20

<210> SEQ ID NO 60
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 60
ccctcttgag ccgtcgaa                                                 18

<210> SEQ ID NO 61
<211> LENGTH: 23
<212> TYPE: DNA
<213> ORGANISM: Artificial Sequence
<220> FEATURE:
<223> OTHER INFORMATION: Description of Artificial Sequence: Primer

<400> SEQUENCE: 61
tccctcttgc ccagcacaac cac                                           23

<210> SEQ ID NO 62
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 62
cgcgaaagta caagcctgtt c                                             21

<210> SEQ ID NO 63
<211> LENGTH: 21
<212> TYPE: DNA
<213> ORGANISM: Artificial Sequence
<220> FEATURE:

<223> OTHER INFORMATION: Description of Artificial Sequence: Primer

<400> SEQUENCE: 63
gaatgagcac cgtggtagag g                                             21

<210> SEQ ID NO 64
<211> LENGTH: 27
<212> TYPE: DNA
<213> ORGANISM: Artificial Sequence
<220> FEATURE:
<223> OTHER INFORMATION: Description of Artificial Sequence: Primer

<400> SEQUENCE: 64
cgtccactgg ttaccagccg gcatata                                       27

<210> SEQ ID NO 65
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 65
tggactcatc ccacttgctc t                                             21

<210> SEQ ID NO 66
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 66
cctgcgcaaa aagttgtgaa                                               20

<210> SEQ ID NO 67
<211> LENGTH: 33
<212> TYPE: DNA
<213> ORGANISM: Artificial Sequence
<220> FEATURE:
<223> OTHER INFORMATION: Description of Artificial Sequence: Primer

<400> SEQUENCE: 67
cagctgaatc ctgacatcat atccacactg tgt                                33

<210> SEQ ID NO 68
<211> LENGTH: 23
<212> TYPE: DNA
<213> ORGANISM: Artificial Sequence
<220> FEATURE:
<223> OTHER INFORMATION: Description of Artificial Sequence: Primer

<400> SEQUENCE: 68
tctctgtctg cagtacctgg cat                                           23

<210> SEQ ID NO 69
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 69
ggcagtgggt atgggatgtg                                               20

```
<210> SEQ ID NO 70
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 70
actttcctcc tgatgccccg gg                                              22

<210> SEQ ID NO 71
<211> LENGTH: 23
<212> TYPE: DNA
<213> ORGANISM: Artificial Sequence
<220> FEATURE:
<223> OTHER INFORMATION: Description of Artificial Sequence: Primer

<400> SEQUENCE: 71
aaaggcggag gaaagaagta ctc                                             23

<210> SEQ ID NO 72
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 72
gctcccgttc cctctcca                                                   18

<210> SEQ ID NO 73
<211> LENGTH: 31
<212> TYPE: DNA
<213> ORGANISM: Artificial Sequence
<220> FEATURE:
<223> OTHER INFORMATION: Description of Artificial Sequence: Primer

<400> SEQUENCE: 73
cctctttgtt cttcttgccc gagttttctt t                                    31

<210> SEQ ID NO 74
<211> LENGTH: 1287
<212> TYPE: DNA
<213> ORGANISM: Homo sapiens
<220> FEATURE:
<221> NAME/KEY: CDS
<222> LOCATION: (1)..(978)
<221> NAME/KEY: misc_feature
<222> LOCATION: (1139)..(1172)
<223> OTHER INFORMATION: an n may be any one of a or t or g or c

<400> SEQUENCE: 74 gcc tcc ctg aca tgc agc cct ctg gac ccc gag gtt gga ccc tac tgt        48
Ala Ser Leu Thr Cys Ser Pro Leu Asp Pro Glu Val Gly Pro Tyr Cys
 1               5                  10                  15 gac aca cct acc atg cgg aca ctc ttc aac ctc ctc tgg ctt gcc ctg        96
Asp Thr Pro Thr Met Arg Thr Leu Phe Asn Leu Leu Trp Leu Ala Leu
                20                  25                  30 gcc tgc agc cct gtt cac act acc ctg tca aag tca gat gcc aaa aaa       144
Ala Cys Ser Pro Val His Thr Thr Leu Ser Lys Ser Asp Ala Lys Lys
            35                  40                  45 gcc gcc tca aag acg ctg ctg gag aag agt cag ttt tca gat aag ccg       192
Ala Ala Ser Lys Thr Leu Leu Glu Lys Ser Gln Phe Ser Asp Lys Pro
        50                  55                  60 gtg caa gac cgg ggt ttg gtg gtg acg gac ctc aaa gct gag agt gtg       240
Val Gln Asp Arg Gly Leu Val Val Thr Asp Leu Lys Ala Glu Ser Val
```

```
                    65                    70                         75                         80
gtt ctt gag cat cgc agc tac tgc tcg gca aag gcc cgg gac aga cac              288
Val Leu Glu His Arg Ser Tyr Cys Ser Ala Lys Ala Arg Asp Arg His
                85                    90                         95 ttt gct ggg gat gta ctg ggc tat gtc act cca tgg aac agc cat ggc              336
Phe Ala Gly Asp Val Leu Gly Tyr Val Thr Pro Trp Asn Ser His Gly
            100                       105                        110 tac gat gtc acc aag gtc ttt ggg agc aag ttc aca cag atc tca ccc              384
Tyr Asp Val Thr Lys Val Phe Gly Ser Lys Phe Thr Gln Ile Ser Pro
            115                       120                        125 gtc tgg ctg cag ctg aag aga cgt ggc cgt gag atg ttt gag gtc acg              432
Val Trp Leu Gln Leu Lys Arg Arg Gly Arg Glu Met Phe Glu Val Thr
        130                       135                        140 ggc ctc cac gac gtg gac caa ggg tgg atg cga gct gtc agg aag cat              480
Gly Leu His Asp Val Asp Gln Gly Trp Met Arg Ala Val Arg Lys His
145                       150                       155                        160 gcc aag ggc ctg cac ata gtg cct cgg ctc ctg ttt gag gac tgg act              528
Ala Lys Gly Leu His Ile Val Pro Arg Leu Leu Phe Glu Asp Trp Thr
                    165                       170                        175 tac gat gat ttc cgg aac gtc tta gac agt gag gat gag ata gag gag              576
Tyr Asp Asp Phe Arg Asn Val Leu Asp Ser Glu Asp Glu Ile Glu Glu
                180                       185                        190 ctg agc aag acc gtg gtc cag gtg gca aag aac cag cat ttc gat ggc              624
Leu Ser Lys Thr Val Val Gln Val Ala Lys Asn Gln His Phe Asp Gly
            195                       200                        205 ttc gtg gtg gag gtc tgg aac cag ctg cta agc cag aag cgc gtg ggc              672
Phe Val Val Glu Val Trp Asn Gln Leu Leu Ser Gln Lys Arg Val Gly
        210                       215                        220 ctc atc cac atg ctc acc cac ttg gcc gag gct ctg cac cag gcc cgg              720
Leu Ile His Met Leu Thr His Leu Ala Glu Ala Leu His Gln Ala Arg
225                       230                       235                        240 ctg ctg gcc ctc ctg gtc atc ccg cct gcc atc acc ccc ggg acc gac              768
Leu Leu Ala Leu Leu Val Ile Pro Pro Ala Ile Thr Pro Gly Thr Asp
                    245                       250                        255 cag ctg ggc atg ttc acg cac aag gag ttt gag cag ctg gcc ccc gtg              816
Gln Leu Gly Met Phe Thr His Lys Glu Phe Glu Gln Leu Ala Pro Val
                260                       265                        270 ctg gat ggt ttc agc ctc atg acc tac gac tac gca aca ctg tcc tgg              864
Leu Asp Gly Phe Ser Leu Met Thr Tyr Asp Tyr Ala Thr Leu Ser Trp
            275                       280                        285 gtt cga gcc tgc gtc cag gtc ctg gat ccc tgg ggc tca act tct atg              912
Val Arg Ala Cys Val Gln Val Leu Asp Pro Trp Gly Ser Thr Ser Met
        290                       295                       300 gta tgg act acg cga cct cca agg atg ccc gtg agc ctg ttg tcg ggg              960
Val Trp Thr Thr Arg Pro Pro Arg Met Pro Val Ser Leu Leu Ser Gly
305                       310                       315                        320 cca ggt aca tcc aga cac tgaaggacca caggccccgg atggtgtggg                     1008
Pro Gly Thr Ser Arg His
                    325 acggccaggc tcagagcac ttcttcgagt acaagaagag ccgcagtggg aggcacgtcg             1068 tcttctaccc aaccctgaag tccctgcagg tgcggctgga gctggcccgg gagctgggcg            1128 ttggggtctc natntgggag ctgggccagg gcctggacta cttntacgac ctgctctagg            1188 tgggcattgc ggcctccgcg gtggacgtgt tcttttctaa gccatggagt gagtgagcag            1248 gtgtgaaata caggcctcca ctccgtttac aaaaaaaaa                                   1287

<210> SEQ ID NO 75
<211> LENGTH: 326
```

```
<212> TYPE: PRT
<213> ORGANISM: Homo sapiens

<400> SEQUENCE: 75

Ala Ser Leu Thr Cys Ser Pro Leu Asp Pro Glu Val Gly Pro Tyr Cys
 1               5                  10                  15

Asp Thr Pro Thr Met Arg Thr Leu Phe Asn Leu Leu Trp Leu Ala Leu
            20                  25                  30

Ala Cys Ser Pro Val His Thr Thr Leu Ser Lys Ser Asp Ala Lys Lys
        35                  40                  45

Ala Ala Ser Lys Thr Leu Leu Glu Lys Ser Gln Phe Ser Asp Lys Pro
    50                  55                  60

Val Gln Asp Arg Gly Leu Val Val Thr Asp Leu Lys Ala Glu Ser Val
 65                  70                  75                  80

Val Leu Glu His Arg Ser Tyr Cys Ser Ala Lys Ala Arg Asp Arg His
                85                  90                  95

Phe Ala Gly Asp Val Leu Gly Tyr Val Thr Pro Trp Asn Ser His Gly
            100                 105                 110

Tyr Asp Val Thr Lys Val Phe Gly Ser Lys Phe Thr Gln Ile Ser Pro
        115                 120                 125

Val Trp Leu Gln Leu Lys Arg Arg Gly Arg Glu Met Phe Glu Val Thr
    130                 135                 140

Gly Leu His Asp Val Asp Gln Gly Trp Met Arg Ala Val Arg Lys His
145                 150                 155                 160

Ala Lys Gly Leu His Ile Val Pro Arg Leu Leu Phe Glu Asp Trp Thr
                165                 170                 175

Tyr Asp Asp Phe Arg Asn Val Leu Asp Ser Glu Asp Glu Ile Glu Glu
            180                 185                 190

Leu Ser Lys Thr Val Val Gln Val Ala Lys Asn Gln His Phe Asp Gly
        195                 200                 205

Phe Val Val Glu Val Trp Asn Gln Leu Leu Ser Gln Lys Arg Val Gly
    210                 215                 220

Leu Ile His Met Leu Thr His Leu Ala Glu Ala Leu His Gln Ala Arg
225                 230                 235                 240

Leu Leu Ala Leu Leu Val Ile Pro Pro Ala Ile Thr Pro Gly Thr Asp
                245                 250                 255

Gln Leu Gly Met Phe Thr His Lys Glu Phe Glu Gln Leu Ala Pro Val
            260                 265                 270

Leu Asp Gly Phe Ser Leu Met Thr Tyr Asp Tyr Ala Thr Leu Ser Trp
        275                 280                 285

Val Arg Ala Cys Val Gln Val Leu Asp Pro Trp Gly Ser Thr Ser Met
    290                 295                 300

Val Trp Thr Thr Arg Pro Pro Arg Met Pro Val Ser Leu Leu Ser Gly
305                 310                 315                 320

Pro Gly Thr Ser Arg His
                325

<210> SEQ ID NO 76
<211> LENGTH: 1291
<212> TYPE: DNA
<213> ORGANISM: Homo sapiens
<220> FEATURE:
<221> NAME/KEY: CDS
<222> LOCATION: (299)..(982)
<221> NAME/KEY: misc_feature
<222> LOCATION: (1143)..(1176)
<223> OTHER INFORMATION: an n may be any one of a or t or g or c
```

```
<400> SEQUENCE: 76
gcctccctga catgcagccc tctggacccc gaggttggac cctactgtga cacacctacc      60
atgcggacac tcttcaacct cctctggctt gccctggcct gcagccctgt tcacactacc     120
ctgtcaaagt cagatgccaa aaaagccgcc tcaaagacgc tgctggagaa gagtcagttt     180
tcagataagc cggtgcaaga ccggggtttg gtggtgacga acctcaaagc tgagagtgtg     240
gttcttgagc atcgcagcta ctgctcggca aggcccggg acagacactt tgctgggg       298 atg tac tgg gct atg tca ctc cac cag tgg aac agc cat ggc tac gat     346
Met Tyr Trp Ala Met Ser Leu His Gln Trp Asn Ser His Gly Tyr Asp
 1               5                  10                  15 gtc acc aag gtc ttt ggg agc aag ttc aca cag atc tca ccc gtc tgg     394
Val Thr Lys Val Phe Gly Ser Lys Phe Thr Gln Ile Ser Pro Val Trp
             20                  25                  30 ctg cag ctg aag aga cgt ggc cgt gag atg ttt gag gtc acg ggc ctc     442
Leu Gln Leu Lys Arg Arg Gly Arg Glu Met Phe Glu Val Thr Gly Leu
         35                  40                  45 cac gac gtg gac caa ggg tgg atg cga gct gtc agg aag cat gcc aag     490
His Asp Val Asp Gln Gly Trp Met Arg Ala Val Arg Lys His Ala Lys
     50                  55                  60 ggc ctg cac ata gtg cct cgg ctc ctg ttt gag gac tgg act tac gat     538
Gly Leu His Ile Val Pro Arg Leu Leu Phe Glu Asp Trp Thr Tyr Asp
 65                  70                  75                  80 gat ttc cgg aac gtc tta gac agt gag gat gag ata gag gag ctg agc     586
Asp Phe Arg Asn Val Leu Asp Ser Glu Asp Glu Ile Glu Glu Leu Ser
                 85                  90                  95 aag acc gtg gtc cag gtg gca aag aac cag cat ttc gat ggc ttc gtg     634
Lys Thr Val Val Gln Val Ala Lys Asn Gln His Phe Asp Gly Phe Val
            100                 105                 110 gtg gag gtc tgg aac cag ctg cta agc cag aag cgc gtg ggc ctc atc     682
Val Glu Val Trp Asn Gln Leu Leu Ser Gln Lys Arg Val Gly Leu Ile
        115                 120                 125 cac atg ctc acc cac ttg gcc gag gct ctg cac cag gcc cgg ctg ctg     730
His Met Leu Thr His Leu Ala Glu Ala Leu His Gln Ala Arg Leu Leu
    130                 135                 140 gcc ctc ctg gtc atc ccg cct gcc atc acc ccc ggg acc gac cag ctg     778
Ala Leu Leu Val Ile Pro Pro Ala Ile Thr Pro Gly Thr Asp Gln Leu
145                 150                 155                 160 ggc atg ttc acg cac aag gag ttt gag cag ctg gcc ccc gtg ctg gat     826
Gly Met Phe Thr His Lys Glu Phe Glu Gln Leu Ala Pro Val Leu Asp
                165                 170                 175 ggt ttc agc ctc atg acc tac gac tac gca aca ctg tcc tgg gtt cga     874
Gly Phe Ser Leu Met Thr Tyr Asp Tyr Ala Thr Leu Ser Trp Val Arg
            180                 185                 190 gcc tgc gtc cag gtc ctg gat ccc tgg ggc tca act tct atg gta tgg     922
Ala Cys Val Gln Val Leu Asp Pro Trp Gly Ser Thr Ser Met Val Trp
        195                 200                 205 act acg cga cct cca agg atg ccc gtg agc ctg ttg tcg ggg cca ggt     970
Thr Thr Arg Pro Pro Arg Met Pro Val Ser Leu Leu Ser Gly Pro Gly
    210                 215                 220 aca tcc aga cac tgaaggacca caggccccgg atggtgtggg acggccaggc        1022
Thr Ser Arg His
225 ctcagagcac ttcttcgagt acaagaagag ccgcagtggg aggcacgtcg tcttctaccc   1082 aaccctgaag tccctgcagg tgcggctgga gctggcccgg gagctgggcg ttggggtctc   1142 natntgggag ctgggccagg gcctggacta cttntacgac ctgctctagg tgggcattgc   1202
```

```
ggcctccgcg gtggacgtgt tcttttctaa gccatggagt gagtgagcag gtgtgaaata    1262
caggcctcca ctccgtttac aaaaaaaaa                                      1291

<210> SEQ ID NO 77
<211> LENGTH: 228
<212> TYPE: PRT
<213> ORGANISM: Homo sapiens

<400> SEQUENCE: 77

Met Tyr Trp Ala Met Ser Leu His Gln Trp Asn Ser His Gly Tyr Asp
  1               5                  10                  15

Val Thr Lys Val Phe Gly Ser Lys Phe Thr Gln Ile Ser Pro Val Trp
                 20                  25                  30

Leu Gln Leu Lys Arg Arg Gly Arg Glu Met Phe Glu Val Thr Gly Leu
             35                  40                  45

His Asp Val Asp Gln Gly Trp Met Arg Ala Val Arg Lys His Ala Lys
         50                  55                  60

Gly Leu His Ile Val Pro Arg Leu Leu Phe Glu Asp Trp Thr Tyr Asp
 65                  70                  75                  80

Asp Phe Arg Asn Val Leu Asp Ser Glu Asp Glu Ile Glu Glu Leu Ser
                 85                  90                  95

Lys Thr Val Gln Val Ala Lys Asn Gln His Phe Asp Gly Phe Val
                100                 105                 110

Val Glu Val Trp Asn Gln Leu Leu Ser Gln Lys Arg Val Gly Leu Ile
            115                 120                 125

His Met Leu Thr His Leu Ala Glu Ala Leu His Gln Ala Arg Leu Leu
        130                 135                 140

Ala Leu Leu Val Ile Pro Pro Ala Ile Thr Pro Gly Thr Asp Gln Leu
145                 150                 155                 160

Gly Met Phe Thr His Lys Glu Phe Glu Gln Leu Ala Pro Val Leu Asp
                165                 170                 175

Gly Phe Ser Leu Met Thr Tyr Asp Tyr Ala Thr Leu Ser Trp Val Arg
            180                 185                 190

Ala Cys Val Gln Val Leu Asp Pro Trp Gly Ser Thr Ser Met Val Trp
        195                 200                 205

Thr Thr Arg Pro Pro Arg Met Pro Val Ser Leu Leu Ser Gly Pro Gly
    210                 215                 220

Thr Ser Arg His
225

<210> SEQ ID NO 78
<211> LENGTH: 816
<212> TYPE: DNA
<213> ORGANISM: Homo sapiens
<220> FEATURE:
<221> NAME/KEY: CDS
<222> LOCATION: (2)..(628)

<400> SEQUENCE: 78 c cgc gtg ctg gtc ctg atg gtg ggc gcg gtg atg ttc acc cgg ggt tcg    49
  Arg Val Leu Val Leu Met Val Gly Ala Val Met Phe Thr Arg Gly Ser
    1               5                  10                  15 ccg gcc gcg tgg ggg cgc gcc agg gag aat atc tgc ttg ctc aac ttt      97
Pro Ala Ala Trp Gly Arg Ala Arg Glu Asn Ile Cys Leu Leu Asn Phe
             20                  25                  30 ttc tgt ggc acc atc gtg ctc atc ttc ttc ctg gag ctg gct gtg gcc     145
Phe Cys Gly Thr Ile Val Leu Ile Phe Phe Leu Glu Leu Ala Val Ala
         35                  40                  45
```

-continued

```
gtg ctg gcc ttc ctg ttc cag gac tgg gtg agg gac cgg ttc cgg gag        193
Val Leu Ala Phe Leu Phe Gln Asp Trp Val Arg Asp Arg Phe Arg Glu
 50                  55                  60 ttc ttc gag agc aac atc aag tcc tac cgg gac gat atc gat ctg caa        241
Phe Phe Glu Ser Asn Ile Lys Ser Tyr Arg Asp Asp Ile Asp Leu Gln
 65                  70                  75                  80 aac ctc atc gac tcc ctt cag aaa gct aac cag tgc tgt ggc gca tat        289
Asn Leu Ile Asp Ser Leu Gln Lys Ala Asn Gln Cys Cys Gly Ala Tyr
                 85                  90                  95 ggc cct gaa gac tgg gac ctc aac gtc tac ttc aat tgc agc ggt gcc        337
Gly Pro Glu Asp Trp Asp Leu Asn Val Tyr Phe Asn Cys Ser Gly Ala
            100                 105                 110 agc tac agc cga gag aag tgc ggg gtc ccc ttc tcc tgc tgc gtg cca        385
Ser Tyr Ser Arg Glu Lys Cys Gly Val Pro Phe Ser Cys Cys Val Pro
        115                 120                 125 gat cct gcg caa aaa gtt gtg aac aca cag tgt gga tat gat gtc agg        433
Asp Pro Ala Gln Lys Val Val Asn Thr Gln Cys Gly Tyr Asp Val Arg
    130                 135                 140 att cag ctg aag agc aag tgg gat gag tcc atc ttc acg aaa ggc tgc        481
Ile Gln Leu Lys Ser Lys Trp Asp Glu Ser Ile Phe Thr Lys Gly Cys
145                 150                 155                 160 atc cag gcg ctg gaa agc tgg ctc ccg cgg aac att tac att gtg gct        529
Ile Gln Ala Leu Glu Ser Trp Leu Pro Arg Asn Ile Tyr Ile Val Ala
                165                 170                 175 ggc gtc ttc atc gcc atc tcg ctg ttg cag ata ttt ggc atc ttc ctg        577
Gly Val Phe Ile Ala Ile Ser Leu Leu Gln Ile Phe Gly Ile Phe Leu
            180                 185                 190 gca agg acg ctg atc tca gac atc gag gca gtg aag gcc ggc cat cac        625
Ala Arg Thr Leu Ile Ser Asp Ile Glu Ala Val Lys Ala Gly His His
        195                 200                 205 ttc tgaggagcag agttgaggga gccgagctga gccacgctgg gaggccagag             678
Phe cctttctctg ccatcagccc tacgtccaga gggagaggag ccgacacccc cagagccagt      738
gccccatctt aagcatcagc gtgacgtgac ctctctgttt ctgcttgctg gtgctgaaga      798
ccaagggtcc cccttgtt                                                    816

<210> SEQ ID NO 79
<211> LENGTH: 209
<212> TYPE: PRT
<213> ORGANISM: Homo sapiens

<400> SEQUENCE: 79

Arg Val Leu Val Leu Met Val Gly Ala Val Met Phe Thr Arg Gly Ser
 1               5                  10                  15

Pro Ala Ala Trp Gly Arg Ala Arg Glu Asn Ile Cys Leu Leu Asn Phe
                20                  25                  30

Phe Cys Gly Thr Ile Val Leu Ile Phe Phe Leu Glu Leu Ala Val Ala
            35                  40                  45

Val Leu Ala Phe Leu Phe Gln Asp Trp Val Arg Asp Arg Phe Arg Glu
    50                  55                  60

Phe Phe Glu Ser Asn Ile Lys Ser Tyr Arg Asp Asp Ile Asp Leu Gln
65                  70                  75                  80

Asn Leu Ile Asp Ser Leu Gln Lys Ala Asn Gln Cys Cys Gly Ala Tyr
                85                  90                  95

Gly Pro Glu Asp Trp Asp Leu Asn Val Tyr Phe Asn Cys Ser Gly Ala
            100                 105                 110
```

```
Ser Tyr Ser Arg Glu Lys Cys Gly Val Pro Phe Ser Cys Cys Val Pro
        115                 120                 125

Asp Pro Ala Gln Lys Val Val Asn Thr Gln Cys Gly Tyr Asp Val Arg
        130                 135                 140

Ile Gln Leu Lys Ser Lys Trp Asp Glu Ser Ile Phe Thr Lys Gly Cys
145                 150                 155                 160

Ile Gln Ala Leu Glu Ser Trp Leu Pro Arg Asn Ile Tyr Ile Val Ala
                165                 170                 175

Gly Val Phe Ile Ala Ile Ser Leu Leu Gln Ile Phe Gly Ile Phe Leu
                180                 185                 190

Ala Arg Thr Leu Ile Ser Asp Ile Glu Ala Val Lys Ala Gly His His
        195                 200                 205

Phe

<210> SEQ ID NO 80
<211> LENGTH: 2574
<212> TYPE: DNA
<213> ORGANISM: Homo sapiens
<220> FEATURE:
<221> NAME/KEY: CDS
<222> LOCATION: (63)..(1022)

<400> SEQUENCE: 80
cgctccgtct ggaacggcgc aggtcccagc agctggggtt cccctcagc ccgtgagcag     60 cc atg tcc aac ccc agc gcc cca cca cca tat gaa gac cgc aac ccc     107
   Met Ser Asn Pro Ser Ala Pro Pro Pro Tyr Glu Asp Arg Asn Pro
     1               5                  10                  15 ctg tac cca ggc cct ctg ccc cct ggg ggc tat ggg cag cca tct gtc   155
Leu Tyr Pro Gly Pro Leu Pro Pro Gly Gly Tyr Gly Gln Pro Ser Val
                20                  25                  30 ctg cca gga ggg tat cct gcc tac cct ggc tac ccg cag cct ggc tac   203
Leu Pro Gly Gly Tyr Pro Ala Tyr Pro Gly Tyr Pro Gln Pro Gly Tyr
            35                  40                  45 ggt cac cct gct ggc tac cca cag ccc atg ccc ccc acc cac ccg atg   251
Gly His Pro Ala Gly Tyr Pro Gln Pro Met Pro Pro Thr His Pro Met
        50                  55                  60 ccc atg aac tac ggc cca ggc cat ggc tat gat ggg gag gag aga gcg   299
Pro Met Asn Tyr Gly Pro Gly His Gly Tyr Asp Gly Glu Glu Arg Ala
65                  70                  75 gtg agt gat agc ttc ggg cct gga gag tgg gat gac cgg aaa gtg cga   347
Val Ser Asp Ser Phe Gly Pro Gly Glu Trp Asp Asp Arg Lys Val Arg
 80                  85                  90                  95 cac act ttt atc cga aag gtt tac tcc atc atc tcc gtg cag ctg ctc   395
His Thr Phe Ile Arg Lys Val Tyr Ser Ile Ile Ser Val Gln Leu Leu
                100                 105                 110 atc act gtg gcc atc att gct atc ttc acc ttt gtg gaa cct gtc agc   443
Ile Thr Val Ala Ile Ile Ala Ile Phe Thr Phe Val Glu Pro Val Ser
            115                 120                 125 gcc ttt gtg agg aga aat gtg gct gtc tac tac gtg tcc tat gct gtc   491
Ala Phe Val Arg Arg Asn Val Ala Val Tyr Tyr Val Ser Tyr Ala Val
        130                 135                 140 ttc gtt gtc acc tac ctg atc ctt gcc tgc tgc cag gga ccc aga cgc   539
Phe Val Val Thr Tyr Leu Ile Leu Ala Cys Cys Gln Gly Pro Arg Arg
145                 150                 155 cgt ttc cca tgg aac atc att ctg ctg acc ctt ttt act ttt gcc atg   587
Arg Phe Pro Trp Asn Ile Ile Leu Leu Thr Leu Phe Thr Phe Ala Met
160                 165                 170                 175 ggc ttc atg acg ggc acc att tcc agt atg tac caa acc aaa gcc gtc   635
Gly Phe Met Thr Gly Thr Ile Ser Ser Met Tyr Gln Thr Lys Ala Val
```

-continued

|  | 180 | 185 | 190 |  |
|---|---|---|---|---|
| atc att gca atg atc atc act gcg gtg gta tcc att tca gtc acc atc<br>Ile Ile Ala Met Ile Ile Thr Ala Val Val Ser Ile Ser Val Thr Ile<br>            195                    200                  205 | | | 683 |
| ttc tgc ttt cag acc aag gtg agg gca tgg agg gcc ctt ccc tgg ccc<br>Phe Cys Phe Gln Thr Lys Val Arg Ala Trp Arg Ala Leu Pro Trp Pro<br>    210                          215                    220 | | | 731 |
| ccc gac tcc cct ttc tta tca ggc ccg gac ccc ggt aca cta ggg atg<br>Pro Asp Ser Pro Phe Leu Ser Gly Pro Asp Pro Gly Thr Leu Gly Met<br>225                        230                    235 | | | 779 |
| ttc cct aga gac ctg atc ccc ttc tcc tca tcc gca cct aca aaa ctg<br>Phe Pro Arg Asp Leu Ile Pro Phe Ser Ser Ser Ala Pro Thr Lys Leu<br>240                    245                    250           255 | | | 827 |
| tgt cct gtt tct gtc ctt aga atg ttg tgg aca ttc cca tac ccc cta<br>Cys Pro Val Ser Val Leu Arg Met Leu Trp Thr Phe Pro Tyr Pro Leu<br>                  260                    265                    270 | | | 875 |
| gga ggc agc act ggg act ccc tgg cag ggc cag tct gac tgg gct ggt<br>Gly Gly Ser Thr Gly Thr Pro Trp Gln Gly Gln Ser Asp Trp Ala Gly<br>            275                    280                    285 | | | 923 |
| tgt cac agc cat ctg aca ggt gcc tct ttc ttg ctt cct ggc agg tgg<br>Cys His Ser His Leu Thr Gly Ala Ser Phe Leu Leu Pro Gly Arg Trp<br>                290                    295                    300 | | | 971 |
| act tca cct cgt gca cag gcc tct tct gtg tcc tgg gaa ttg tgc tcc<br>Thr Ser Pro Arg Ala Gln Ala Ser Ser Val Ser Trp Glu Leu Cys Ser<br>305                        310                    315 | | | 1019 |
| tgg tgactgggat tgtcactagc attgtgctct tagcattgtg ctctacttcc<br>Trp<br>320 | | | 1072 |

| aatacgttta ctggctccac atgctctatg ctgctctggg ggccatttgt ttcaccctgt | 1132 |
|---|---|
| tcctggctta cgacacacag ctggtcctgg ggaaccggaa gcacaccatc agccccgagg | 1192 |
| actacatcac tggcgccctg cagatttaca cagacatcat ctacatcttc acctttgtgc | 1252 |
| tgcagctgat gggggatcgc aattaaggag caagccccca ttttcacccg atcctgggct | 1312 |
| ctcccttcca agctagaggg ctgggctcaa tgactgtggt ctgggcttta ggccccttc | 1372 |
| cttccccttg agtaacatgc ccagtttcct ttctgtcctg agacaggtg gcctctctgg | 1432 |
| ctatggatgt gtgggtactt ggtggggacg gaggagctag ggactaactg ttgctcttgg | 1492 |
| tgggcttggc agggactagg ctgaagatgt gtcttctccc cgccacctac tgtatgacac | 1552 |
| cacattcttc ctaacagctg gggttgtgag gaatatgaaa agagcctatt cgatagctag | 1612 |
| aagggaatat gaaaggtaga agtgacttca aggtcacgag gttcccctcc cacctctgtc | 1672 |
| acaggcttct tgactacgta gttggagcta tttcttcccc cagcaaagcc agagagcttt | 1732 |
| gtccccggcc tcctggacac ataggccatt atcctgtatt cctttggctt ggcatctttt | 1792 |
| agctcaggaa ggtagaagag atctgtgccc atgggtctcc ttgcttcaat cccttcttgt | 1852 |
| ttcagtgaca tatgtattgt ttatctgggt tagggatggg ggacagataa tagaacgagc | 1912 |
| aaagtaacct atacaggcca gcatggaaca gcatctcccc tgggcttgct cctggcttgt | 1972 |
| gacgctataa gacagagcag gccacatgtg gccattctgc tccccattct tgaaagctgc | 2032 |
| tggggcctcc ttgcaggctt ctggatctct ggtcagagtg aactcttgct tcctgtattc | 2092 |
| aggcagctca gagcagaaag taaggggcag agtcatacgt gtggccagga agtagccagg | 2152 |
| gtgaagagag actcggtgcg ggcagggaga atgcctgggg gtccctcacc tggctaggga | 2212 |
| gataccgaag cctactgtgg tactgaagac ttctgggttc tttccttctg ctaacccagg | 2272 |
| gagggtccta agaggaaggt gacttctctc tgtttgtctt aagttgcact gggggatttc | 2332 |

-continued

```
tgacttgagg cccatctctc cagccagcca ctgccttctt tgtaatatta agtgccttga    2392
gctggaatgg ggaaggggga caagggtcag tctgtcgggt gggggcagaa atcaaatcag    2452
cccaaggata tagttaggat taattactta atagagaaat cctaactata tcacacaaag    2512
ggatacaact ataaatgtaa taaaatttat gtctagaagt taaaaaaaaa aaaaaaaaa     2572 gt                                                                   2574
```

<210> SEQ ID NO 81
<211> LENGTH: 320
<212> TYPE: PRT
<213> ORGANISM: Homo sapiens

<400> SEQUENCE: 81

```
Met Ser Asn Pro Ser Ala Pro Pro Tyr Glu Asp Arg Asn Pro Leu
  1               5                  10                  15

Tyr Pro Gly Pro Leu Pro Pro Gly Gly Tyr Gly Gln Pro Ser Val Leu
                 20                  25                  30

Pro Gly Gly Tyr Pro Ala Tyr Pro Gly Tyr Pro Gln Pro Gly Tyr Gly
                 35                  40                  45

His Pro Ala Gly Tyr Pro Gln Pro Met Pro Thr His Pro Met Pro
     50                  55                  60

Met Asn Tyr Gly Pro Gly His Gly Tyr Asp Gly Glu Arg Ala Val
 65                  70                  75                  80

Ser Asp Ser Phe Gly Pro Gly Glu Trp Asp Asp Arg Lys Val Arg His
                 85                  90                  95

Thr Phe Ile Arg Lys Val Tyr Ser Ile Ile Ser Val Gln Leu Leu Ile
                100                 105                 110

Thr Val Ala Ile Ile Ala Ile Phe Thr Phe Val Glu Pro Val Ser Ala
                115                 120                 125

Phe Val Arg Arg Asn Val Ala Val Tyr Tyr Val Ser Tyr Ala Val Phe
                130                 135                 140

Val Val Thr Tyr Leu Ile Leu Ala Cys Cys Gln Gly Pro Arg Arg Arg
145                 150                 155                 160

Phe Pro Trp Asn Ile Ile Leu Leu Thr Leu Phe Thr Phe Ala Met Gly
                165                 170                 175

Phe Met Thr Gly Thr Ile Ser Ser Met Tyr Gln Thr Lys Ala Val Ile
                180                 185                 190

Ile Ala Met Ile Ile Thr Ala Val Val Ser Ile Ser Val Thr Ile Phe
                195                 200                 205

Cys Phe Gln Thr Lys Val Arg Ala Trp Arg Ala Leu Pro Trp Pro Pro
                210                 215                 220

Asp Ser Pro Phe Leu Ser Gly Pro Asp Pro Gly Thr Leu Gly Met Phe
225                 230                 235                 240

Pro Arg Asp Leu Ile Pro Phe Ser Ser Ala Pro Thr Lys Leu Cys
                245                 250                 255

Pro Val Ser Val Leu Arg Met Leu Trp Thr Phe Pro Tyr Pro Leu Gly
                260                 265                 270

Gly Ser Thr Gly Thr Pro Trp Gln Gly Gln Ser Asp Trp Ala Gly Cys
                275                 280                 285

His Ser His Leu Thr Gly Ala Ser Phe Leu Leu Pro Gly Arg Trp Thr
                290                 295                 300

Ser Pro Arg Ala Gln Ala Ser Ser Val Ser Trp Glu Leu Cys Ser Trp
305                 310                 315                 320
```

What is claimed is:

1. An isolated polypeptide comprising the amino acid sequence of SEQ ID NO:30.

2. A pharmaceutical composition comprising the polypeptide of claim 1 and a pharmaceutically acceptable carrier.

3. A kit comprising in one or more containers the pharmaceutical composition of claim 2.

4. An isolated polypeptide consisting of the amino acid sequence of residues 3–624 of SEQ ID NO:30, wherein the polypeptide has semaphorin-like activity.

* * * * *